US009802996B2

(12) United States Patent
Ochiai et al.

(10) Patent No.: US 9,802,996 B2
(45) Date of Patent: *Oct. 31, 2017

(54) GLYCOSYLATED POLYPEPTIDE AND DRUG COMPOSITION CONTAINING SAID POLYPEPTIDE

(71) Applicant: Glytech, Inc., Kyoto (JP)

(72) Inventors: Hirofumi Ochiai, Kyoto (JP); Taiji Shimoda, Kyoto (JP); Kazuhiro Fukae, Tokushima (JP); Masatoshi Maeda, Tokyo (JP); Keisuke Tazuru, Kyoto (JP); Kenta Yoshida, Hyogo (JP)

(73) Assignee: Glytech, Inc., Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/213,872

(22) Filed: Jul. 19, 2016

(65) Prior Publication Data

US 2016/0368961 A1 Dec. 22, 2016

Related U.S. Application Data

(63) Continuation of application No. 14/342,360, filed as application No. PCT/JP2012/072383 on Sep. 3, 2012, now Pat. No. 9,441,024.

(30) Foreign Application Priority Data

Sep. 4, 2011 (JP) ................. 2011-192203

(51) Int. Cl.
| *A61K 38/31* | (2006.01) |
| *A61P 5/02* | (2006.01) |
| *C07K 14/655* | (2006.01) |
| *A61K 47/48* | (2006.01) |
| *C07K 14/47* | (2006.01) |
| *A61K 38/00* | (2006.01) |

(52) U.S. Cl.
CPC ...... *C07K 14/655* (2013.01); *A61K 47/48092* (2013.01); *C07K 14/47* (2013.01); *C07K 14/6555* (2013.01); *A61K 38/00* (2013.01)

(58) Field of Classification Search
CPC .. A61K 38/00; A61K 47/48092; C07K 14/47; C07K 14/655; C07K 14/6555
See application file for complete search history.

(56) References Cited

U.S. PATENT DOCUMENTS

| 4,235,886 A | 11/1980 | Freidinger et al. |
| 4,280,953 A | 7/1981 | Guillemin et al. |
| 4,310,518 A | 1/1982 | Freidinger et al. |
| 4,316,891 A | 2/1982 | Guillemin et al. |
| 4,380,953 A | 4/1983 | Anderson et al. |
| 5,639,480 A | 6/1997 | Bodmer |
| 5,656,721 A | 8/1997 | Albert et al. |
| 5,750,499 A | 5/1998 | Hoeger et al. |
| 6,455,025 B1 | 9/2002 | Holmberg et al. |
| 9,422,357 B2* | 8/2016 | Ochiai ............... C07K 14/6555 |
| 9,441,024 B2* | 9/2016 | Ochiai ............... C07K 14/6555 |
| 2011/0195897 A1 | 8/2011 | Kajihara et al. |
| 2014/0336116 A1 | 11/2014 | Ochiai et al. |

FOREIGN PATENT DOCUMENTS

| CN | 201280053754.2 | 6/2015 |
| EP | 0157753 A1 | 3/1985 |
| JP | 03-014599 | 1/1991 |
| JP | 11-195897 | 7/1999 |
| JP | 11-514363 | 7/1999 |
| WO | WO 02/085418 | 10/2002 |
| WO | WO 2004/101619 | 11/2004 |
| WO | WO 2009/153960 A1 | 12/2009 |
| WO | WO 2009/156511 A2 | 12/2009 |

OTHER PUBLICATIONS

Cullen, J.J. et al., "Treatment of Acute Postoperative Ileus with Octreotide", *Am. J. Surg.*, 1993, vol. 165, No. 1, pp. 113-120.
Russian Office Action corresponding to Russian Application No. 2014112044, dated Aug. 12, 2016, 8 pages.
Johansson, S. "Design and Synthesis of Sialic Acid Conjugates as Inhibitors of EKC-causing Advenoviruses", 2008, Umea University: Doctoral Thesis. pp. 1-74.
Lavielle et al. "Synthesis and Biological Activity of Glycosylated Analgos of Somatostatin", *Biochem. Biophys. Res. Commun.*, 1979, vol. 91, No. 2, pp. 614-622.
Machine translation of Nishimura et al. WO 2004/101619, published on Nov. 2004. Machine translation date: May 1, 2015, 120 pages.
Pubchem Open Chemistry Database. "Compound Summary for CID 16129681", Accessed online at http://pubchem.ncbi.nlm.nih.gov/compound/16129681 on Apr. 18, 2015, 14 pages.
Schottelius et al. "N-Terminal Sugar Conjugation and C-Terminal Thr-for-Thr(ol) Exchange in Radioiodinated Tyr3-octreotide: Effect on Cellular Ligand Trafficking in Vitro and Tumor Accumulation in Vivo", *J. Med. Chem.*, 2005, vol. 48, pp. 2778-2789.
Shen et al. Human somatostatin I: Sequence of the cDNA. PNAS USA, 1982, vol. 79, pp. 4575-4579.
Cescato et al., "Agonist-Biased Signaling at the sst2A Receptor: The Multi-Somatostatin Analogs KE108 and SOM230 Activate and Antagonize Distinct Signaling Pathways," Mol Endocrinol, Jan. 2010, 24(1), pp. 240-249.
Erchegyi et al., "Novel sst$_4$-Selective Somatostatin (SRIF) Agonists. 2. Analogues with β-Methyl-3-(2-naphthyl)alanine Substitutions at Position 8," J. Med. Chem., 2003, 46, pp. 5587-5596.
International Preliminary Report on Patentability, PCT/JP2012/072380, Mar. 4, 2014, 9 pages.

(Continued)

*Primary Examiner* — Marcela M Cordero Garcia
(74) *Attorney, Agent, or Firm* — Myers Bigel, P.A.

(57) ABSTRACT

[Problem] To provide a glycosylated polypeptide having affinity to somatostatin receptors and, compared to somatostatins, having improved in-blood stability. [Solution] The glycosylated polypeptide is characterized by at least two amino acids in a somatostatin or an analog thereof being replaced by glycosylated amino acids.

18 Claims, 24 Drawing Sheets

(56) References Cited

OTHER PUBLICATIONS

International Search Report, PCT/JP2012/072380, Oct. 9, 2012, 4 pages.
Nishi et al., "Qualitative Improvement of Therapeutic Glycoproteins by Glycotechnology," Trends in Glycoscience and Glycotechnology, vol. 4, No. 18, Jul. 1992, pp. 336-344.
Pawlikowski et al., "Somatostatin analogs—from new molecules to new applications," Current Opinion in Pharmacology, 2004, 4, pp. 608-613.
Pradayrol et al., "N-Terminally Extended Somatostatin: The Primary Structure of Somatostatin-28," FEBS Letters, vol. 109, No. 1, Jan. 1980, pp. 55-58.
Saito, Haruhiko, "Atarashii Somatostatin Analog no Rinsho Oyo," Journal of Clinical and Experimental Medicine, 1987, vol. 141, No. 12, pp. 907-909.
Schmid, Herbert A., "Pasireotide (SOM230): Development, mechanism of action and potential applications," Molecular and Cellular Endocrinology, 286 (2008), pp. 69-74.
Written Opinion of the International Searching Authority, PCT/JP2012/072380, Oct. 9, 2012, 8 pages.
International Search Report Corresponding to International Application No. PCT/JP2012072380; Date of Mailing: Mar. 24, 2015; 10 Pages.
Lavielle et al., "Synthesis of a glycotripeptide and a glycosomatostatin containing the 3-O-(2-acetamido-2deoxy-beta-D-glucopyranosyl)-L-se rine residue", *Carbohydrate Research*, vol. 89, Jan. 1, 1981, pp. 229-236.
Andrews et al., "Structure of the 22-residue somatostatin from catfish an O-glycosylated peptide having multiple forms", The Journal of Biological Chemistry, Nov. 10, 1984, pp. 13267-13272.
Albert et al., "SDZ Co 611: a highly potent glycated analog of somatostatin with improved oral activity", Life Sciences, vol. 53, No. 6, Jan. 1, 1993, pp. 517-525.
Wang et al., "Neuroendocrine Peptides (NPY, GRP, VIP, Somotostatin) From the Brain and Stomach of the Alligator", *Peptide*, Oct. 1992, vol. 14(3), pp. 573-579.
Chinese Office Action corresponding to Chinese Application No. 201280053558.5, dated Apr. 14, 2016, 12 pages.

* cited by examiner

GLYCOSYLATED POLYPEPTIDE AND DRUG COMPOSITION CONTAINING SAID POLYPEPTIDE

STATEMENT OF PRIORITY

This application is a 35 U.S.C. §371 national phase application of International Application Serial No. PCT/JP2012/072383, filed Sep. 3, 2012, which claims the benefit, under 35 U.S.C. §119 (a) of Japanese Patent Application No. 2011-192203, filed Sep. 4, 2011, the entire contents of each of which are incorporated by reference herein.

STATEMENT REGARDING ELECTRONIC FILING OF A SEQUENCE LISTING

A Sequence Listing in ASCII text format, submitted under 37 C.F.R. §1.821, entitled 9778-9TS_ST25v2.txt, 99,959 bytes in size, generated on Sep. 11, 2015 and filed via EFS-Web, is provided in lieu of a paper copy. This Sequence Listing is hereby incorporated by reference into the specification for its disclosures.

TECHNICAL FIELD

The present invention relates to a glycosylated polypeptide and a pharmaceutical composition comprising said polypeptide.

BACKGROUND ART

Somatostatin is a cyclic peptide present in both the central nervous system and the surrounding tissue. Somatostatin was first isolated from mammalian hypothalamus, and was identified from anterior pituitary gland as an important inhibitor of growth hormone secretion. This peptide is widely distributed in e.g. the hypothalamus, the pancreas, and the gastrointestinal tract, and its action is exerted via binding to a somatostatin receptor. In addition, somatostatin is known for its secretory suppression of growth hormone (GH) and thyroid-stimulating hormone (TSH) in the pituitary gland, as well as secretion suppression of various hormones such as gastrin, selectin, cholecystokinin (CCK), and VIP (Vasoactive Intestinal Polypeptide) in the gastrointestinal tract, and glucagon and insulin in the pancreas. It is also known to have an action to suppress gastrointestinal motility.

Natural somatostatin having the structural formula: Ala-Gly-Cys-Lys-Asn-Phe-Phe-Trp-Lys-Thr-Phe-Thr-Ser-Cys (SEQ ID NO. 1) (also known as somatotropin release inhibiting factor (SRIF)) was first isolated by Guillemin and coworkers. This somatostatin exerts its effect by interacting with a family of receptors. Somatostatin receptor (SSTR) has 1 to 5 subtypes (SSTR1-SSTR5), and among these, SSTR2 is known to be distributed in each tissues of the GH-secreting human pituitary gland adenoma, the central nervous system, the anterior pituitary gland, the retina, the adrenal medulla, the stomach, the duodenal mucosa, the small intestines, and the colon, as well as in the glucagon-secreting A-cell of the pancreatic islet. Each of these receptors is also known to be expressed in various tumors. For example, it has been reported that SSTR1 and SSTR5 are expressed in a functional pituitary adenoma, SSTR2 as well as SSTR1 and SSTR3 are expressed in a gastrointestinal tumor, SSTR3 is expressed in a pheochromocytoma, SSTR1 and SSTR5 are expressed in a prostate cancer, and SSTR5 is expressed in a colorectal cancer (Non-Patent Literature 1).

Moreover, SSTR4 is reported in regards to its function as a receptor having an antagonistically modulating action and its possibility of being essential in the treatment of a glaucoma-related disease (Non-Patent Literature 2). As such, somatostatin and analogs thereof are potentially useful therapeutic drugs for somatostatin-related diseases or various types of tumors.

Meanwhile, because naturally-occurring somatostatin has a short half-life in blood of 2-3 minutes, it shows two undesirable properties of having low bioavailability and short duration of action, and thus its use or application as a therapeutic is limited. For this reason, various somatostatin analogs have been developed in order to find a somatostatin analog superior in any one of efficacy, biostability, duration of action, or selectivity considering the release suppression of growth hormone, insulin, or glucagon.

Octreotide (Patent Literatures 1 and 2) is reported as the first approved somatostatin analog that can be clinically utilized, and this octreotide is known to have affinity towards somatostatin receptors SSTR2, SSTR3, and SSTR5.

Octreotide has been developed as a cyclic peptide consisting of eight amino acids which has a sequence of four amino acids (Phe-Trp-Lys-Thr) (SEQ ID NO. 170) that is an important portion for showing the biological activity of somatostatin, Cys that forms a disulfide (S—S) bond at the two terminals of the sequence, and further D-Phe and Thr(ol) outside of the Cys at the two terminals. This octreotide can render persistence of action by improving the half-life in blood by its amino acid sequence, as well as has a higher selectivity towards growth hormone (GH) than somatostatin which enables it to have a strong action.

Such somatostatin analogs including octreotide can be used for treating patients who have a hormone-secreting and hormone-dependent tumor. Currently, symptoms related to metastatic carcinoid tumor which is a tumor of the neuroendocrine system (flushing, diarrhea, cardiac valve disease, and abdominal pain) and symptoms related to vasoactive intestinal peptide (VIP)-secreting adenoma (watery diarrhea) are treated with octreotide.

For example, in a carcinoid and VIP-producing tumor, octreotide inhibits both secretion and action of its active factor. Accordingly, in a VIP-producing tumor characterized in profusely-secreting diarrhea, a somatostatin analog can reduce its diarrhea by secretory inhibition of VIP as well as by directly influencing intestinal secretion.

On the other hand, however, many neuroendocrine tumors are reported to have resistance to somatostatin analogs such as octreotide (Non-Patent Literature 3). Moreover, although octreotide is used in the treatment of acromegaly, it is reported to have no effect on approximately one third of acromegaly patients. Further, it is reported that in majority of carcinoid tumor patients, octreotide exerts its effect only during initial administration, and tachyphylaxis is caused when the duration of administration is prolonged. Further, it is reported that octreotide does not show any effect on suppression of adrenocorticotropic hormone (ACTH) production in early Cushing's disease patients.

In light of the problems above, development of a somatostatin analog that binds to multiple receptor subtypes with high affinity like that of a natural somatostatin is desired for a tumor expressing multiple somatostatin receptors, and it is suggested that a somatostatin analog having such affinity towards somatostatin receptors may possibly also have effect on patients who were therapeutically ineffective with or patients who have resistance to past somatostatin analogs (Non-Patent Literature 4).

Accordingly, development of a somatostatin analog having a structure similar to a naturally-occurring somatostatin, similarly having affinity towards somatostatin receptors, and having extended half-life in blood compared to somatostatin has been desired.

Meanwhile, it has been becoming clear that sugar chains are responsible for various roles in vivo, and a method for adding a sugar chain to octreotide in order to extend the half-life in blood has also been proposed (such as Patent Literature 3).

However, research is delayed due to the complexity or diversity of its structure, and it cannot be said that the type of sugar chain or the position for adding a sugar chain is always optimized. A glycosylated polypeptide that has overcome the problems of past somatostatin analogs has not been reported.

CITATION LIST

Patent Literatures

[Patent Literature 1] U.S. Pat. No. 4,310,518
[Patent Literature 2] U.S. Pat. No. 4,235,886
[Patent Literature 3] Japanese Published Unexamined Patent Application Publication No. Hei 03 (1991)-014599

Non-Patent Literatures

[Non-Patent Literature 1] Current Opinion in Pharmacology, 2004, Vol. 4, pp. 608-613
[Non-Patent Literature 2] J. Med. Chem. 2003, Vol. 46, pp. 5587-5596
[Non-Patent Literature 3] Mol. Endocrinol., 2010, Vol. 24 (1), pp. 240-249
[Non-Patent Literature 4] Molecular and Cellular Endocrinology, Vol. 286, 2008, pp. 69-74

SUMMARY OF THE INVENTION

Problems to be Solved by the Invention

The object of the present invention is to provide a glycosylated polypeptide having affinity towards somatostatin receptors and improved stability in blood compared to somatostatin.

Means for Solving the Problems

As a result of repeated research to solve the above problems, the present inventors found a glycosylated polypeptide which maintains affinity towards somatostatin receptors and has improved stability in blood.

In other words, the present invention relates to a glycosylated polypeptide selected from the group consisting of: (A) SRIF14 consisting of the amino acid sequence represented by SEQ ID NO. 1; (B) a polypeptide having one or a few amino acids deleted, substituted, or added from/to SRIF14 consisting of the amino acid sequence represented by SEQ ID NO. 1; (C) a SRIF14 analog; (D) a polypeptide having 80% or more homology with SRIF14 consisting of the amino acid sequence represented by SEQ ID NO. 1; (E) a polypeptide further comprising N amino acids (wherein N is an integer from 1 or more to 20 or less) at the N-terminal side of (A)-(D); and (F) a polypeptide further comprising M amino acids (wherein M is an integer from 1 or more to 6 or less) at the C-terminal side of (A)-(D); characterized in that at least two amino acids are substituted with glycosylated amino acids, and the polypeptide has affinity towards somatostatin receptors.

Here, one embodiment of the glycosylated polypeptide of the present invention is characterized in that at least one of the amino acids substituted with said glycosylated amino acid is the amino acid corresponding to position 19 of SRIF14.

Moreover, in one embodiment of the glycosylated polypeptide of the present invention, said glycosylated polypeptide is characterized in that at least two amino acids are substituted with glycosylated amino acids in said polypeptide (E), and at least one of the amino acids substituted with said glycosylated amino acid is present at any of said N amino acids at the N-terminal side of said polypeptide (E).

Moreover, in one embodiment of the glycosylated polypeptide of the present invention, said glycosylated polypeptide is characterized in that at least two amino acids are substituted with glycosylated amino acids in said polypeptide (F), and at least one of the amino acids substituted with said glycosylated amino acid is present at any of said M amino acids at the C-terminal side of said polypeptide (F).

Moreover, in one embodiment of the glycosylated polypeptide of the present invention, said glycosylated polypeptide is characterized in that at least two amino acids are substituted with glycosylated amino acids in said polypeptide (E), and further the sequence of said N amino acids added onto the N-terminal side is represented by X—Y—, wherein X means a sequence of any L amino acids (wherein L is an integer from 1 or more to 6 or less), and Y is a sequence selected from the group consisting of: (1) Lys, (2) Arg-Lys, (3) Glu-Arg-Lys, (4) Arg-Glu-Arg-Lys (SEQ ID NO. 171), (5) Pro-Arg-Glu-Arg-Lys (SEQ ID NO. 172), (6) Ala-Pro-Arg-Glu-Arg-Lys (SEQ ID NO. 173), (7) Met-Ala-Pro-Arg-Glu-Arg-Lys (SEQ ID NO. 174), (8) Ala-Met-Ala-Pro-Arg-Glu-Arg-Lys (SEQ ID NO. 175), (9) Pro-Ala-Met-Ala-Pro-Arg-Glu-Arg-Lys (SEQ ID NO. 176), (10) Asn-Pro-Ala-Met-Ala-Pro-Arg-Glu-Arg-Lys (SEQ ID NO. 177), (11) Ser-Asn-Pro-Ala-Met-Ala-Pro-Arg-Glu-Arg-Lys (SEQ ID NO. 178), (12) Asn-Ser-Asn-Pro-Ala-Met-Ala-Pro-Arg-Glu-Arg-Lys (SEQ ID NO. 179), (13) Ala-Asn-Ser-Asn-Pro-Ala-Met-Ala-Pro-Arg-Glu-Arg-Lys (SEQ ID NO. 180), (14) Ser-Ala-Asn-Ser-Asn-Pro-Ala-Met-Ala-Pro-Arg-Glu-Arg-Lys (SEQ ID NO. 181), and (15) a sequence having one or a few amino acids deleted, substituted, or added from/to the above sequences (2)-(14).

Moreover, one embodiment of the glycosylated polypeptide of the present invention is characterized in that at least one of the amino acids substituted with said glycosylated amino acid is present in any of L amino acids which means X in X—Y-representing the sequence of said N amino acids added onto the N-terminal side of said polypeptide (E).

Moreover, one embodiment of the glycosylated polypeptide of the present invention is characterized in that the N amino acids added onto the N-terminal side are linked to said N-terminal side via a linker.

Moreover, in another embodiment of the glycosylated polypeptide of the present invention, a polypeptide selected from the group consisting of: (A) SRIF28 consisting of the amino acid sequence represented by SEQ ID NO. 2; (B) a polypeptide having one or a few amino acids deleted, substituted, or added from/to SRIF28 consisting of the amino acid sequence represented by SEQ ID NO. 2; (C) a SRIF28 analog; (D) a polypeptide having 80% or more homology with SRIF28 consisting of the amino acid sequence represented by SEQ ID NO. 2; (E) a polypeptide further comprising J amino acids (wherein J is an integer from 1 or more to 15 or less) at the N-terminal side of (A)-(D); and (F) a polypeptide further comprising K amino acids (wherein K is an integer from 1 or more to 6 or less) at the C-terminal side of (A)-(D); is characterized in that at least two amino acids are substituted with glycosylated amino acids, and the polypeptide has affinity towards somatostatin receptors.

Moreover, one embodiment of the glycosylated polypeptide of the present invention is characterized in that at least one of the amino acids substituted with said glycosylated amino acid is at least one amino acid selected from the group consisting of the amino acid corresponding to position 1, the amino acid corresponding to position 5, the amino acid corresponding to position 9, the amino acid corresponding to position, 12, the amino acid corresponding to position 13, the amino acid corresponding to position 14, and the amino acid corresponding to position 19 of SRIF28.

Moreover, in one embodiment of the glycosylated polypeptide of the present invention, said glycosylated polypeptide is characterized in that at least two amino acids are substituted with glycosylated amino acids in said polypeptide (E), wherein at least one of the amino acids substituted with said glycosylated amino acid is present in said J amino acids at the N-terminal side of said polypeptide (E).

Moreover, in one embodiment of the glycosylated polypeptide of the present invention, said glycosylated polypeptide Ls characterized in that at least two amino acids are substituted with glycosylated amino acids in said polypeptide (F), and at least one of the amino acids substituted with said glycosylated amino acid is present in said K amino acids of the C-terminal side of said polypeptide (F).

Moreover, in one embodiment of the glycosylated polypeptide of the present invention, said glycosylated polypeptide is characterized in that it has increased stability in blood compared to SRIF28.

Moreover, in one embodiment of the glycosylated polypeptide of the present invention, said glycosylated polypeptide is characterized in that it has increased half-life in blood by 10-fold or more compared to SRIF28.

Moreover, one embodiment of the glycosylated polypeptide of the present invention is characterized in that said affinity towards somatostatin receptors has affinity towards at least two or more receptors selected from the group consisting of SSTR1, SSTR2, SSTR3, SSTR4, and SSTR5.

Moreover, in one embodiment of the glycosylated polypeptide of the present invention, said glycosylated polypeptide is characterized in that it has affinity towards any one of at least SSTR1 and SSTR4.

Moreover, in one embodiment of the glycosylated polypeptide of the present invention, said glycosylated polypeptide is characterized in that it has affinity towards both SSTR1 and SSTR4.

Moreover, in one embodiment of the glycosylated polypeptide of the present invention, said glycosylated polypeptide is characterized in that it has affinity towards all of SSTR1, SSTR2, SSTR3, SSTR4, and SSTR5.

Moreover, one embodiment of the glycosylated polypeptide of the present invention is characterized in that each of said glycosylated amino acids is glycosylated Asn or glycosylated Cys.

Moreover, one embodiment of the glycosylated polypeptide of the present invention is characterized in that in each of said glycosylated amino acids, the sugar chain and the amino acid are linked without a linker.

Moreover, one embodiment of the glycosylated polypeptide of the present invention is characterized in that in each of said glycosylated amino acids, the sugar chain consists of 4 or more sugars.

Moreover, one embodiment of the glycosylated polypeptide of the present invention is characterized in that in each of said glycosylated amino acids, the sugar chain is a biantennary complex-type sugar chain, a triantennary complex-type sugar chain, or a tetraantennary complex-type sugar chain.

Moreover, one embodiment of the glycosylated polypeptide of the present invention is characterized in that in each of said glycosylated amino acids, the sugar chain is a biantennary complex-type sugar chain.

Moreover, one embodiment of the glycosylated polypeptide of the present invention is characterized in that said biantennary complex-type sugar chain is a sugar chain selected from the group consisting of a disialo sugar chain, a monosialo sugar chain, an asialo sugar chain, a diGlcNAc sugar chain, and a dimannose sugar chain.

Moreover, one embodiment of the glycosylated polypeptide of the present invention is characterized in that in each of said glycosylated amino acids, the sugar chain is a sugar chain represented by the following formula:

[Chemical Formula 1]

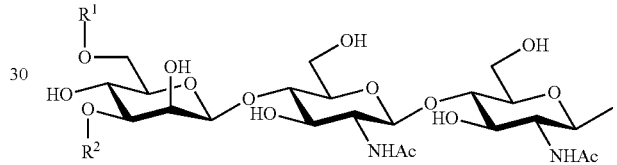

[wherein $R^1$ and $R^2$ are identical or different and are:

[Chemical Formula 2]

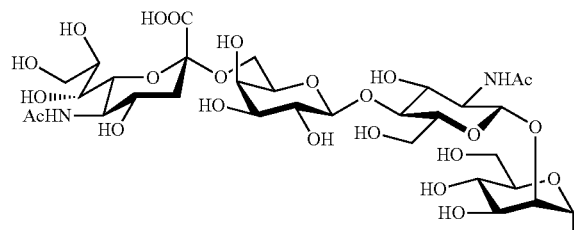

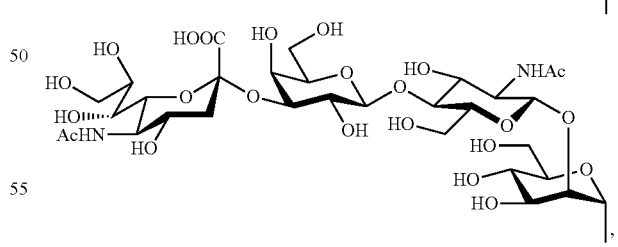

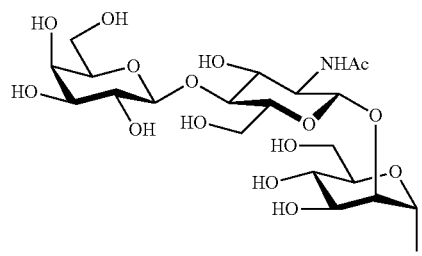

-continued

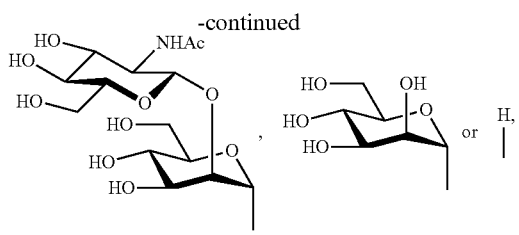

and Ac is an acetyl group].

Moreover, one embodiment of the glycosylated polypeptide of the present invention is characterized in that said sugar chain has at least one sialic acid at the non-reducing terminal, and the carboxy group of said sialic acid is modified by an alkylamino group, a benzyl group, an amino group, or an aminoethylamino group, having 1-30 carbons.

Moreover, in one embodiment of the glycosylated polypeptide of the present invention, said glycosylated polypeptide is characterized in that it has multiple glycosylated amino acids, wherein the sugar chains on each of said glycosylated amino acids are all identical.

Moreover, in one embodiment of the glycosylated polypeptide of the present invention, said glycosylated polypeptide is characterized in that it has Cys corresponding to Cys at position 17 and Cys at position 28 of SRIF28, and further these Cys are bound by a disulfide bond with each other.

Moreover, one embodiment of the glycosylated polypeptide of the present invention is characterized in that the C-terminal of said glycosylated polypeptide is amidated.

Moreover, one embodiment of the glycosylated polypeptide of the present invention is characterized in that an azido group is introduced at the N-terminal of said glycosylated polypeptide.

Moreover, one embodiment of the glycosylated polypeptide of the present invention is characterized in that it is labeled.

Moreover, another aspect of the present invention relates to a pharmaceutical composition characterized in that it comprises (I) the glycosylated polypeptide described above and/or a pharmaceutically acceptable salt thereof, and (II) a pharmaceutically acceptable carrier.

Moreover, one embodiment of the pharmaceutical composition of the present invention is characterized in that the sugar chains in said glycosylated polypeptide are substantially uniform.

Moreover, one embodiment of the pharmaceutical composition of the present invention is characterized in that it is employed for treatment or prevention of a somatostatin-related disease.

Moreover, one embodiment of the pharmaceutical composition of the present invention is characterized in that said somatostatin-related disease is at least one disease selected from the group consisting of acromegaly, gigantism, Alzheimer's disease and other forms of dementia, cancer, hormone-producing tumor, endocrine tumor, carcinoid, VIPoma, insulinoma, glucagonoma, Cushing's disease, hormone secretion defect, diabetes and complications thereof, pains, arthritis, diarrhea, gastric ulcer, inflammatory bowel disease, irritable bowel syndrome, gastrointestinal obstruction, ileus, postoperative restenosis, radiation damage, eye disease, dry eye, glaucoma, interstitial keratitis, iritis, cataract, and conjunctivitis.

Moreover, another aspect of the present invention relates to a method for treating or preventing a somatostatin-related disease, characterized in administering an effective amount of the glycosylated polypeptide described above.

Moreover, one embodiment of the treatment or prophylactic method of the present invention is characterized in that said somatostatin-related disease is at least one disease selected from the group consisting of acromegaly, gigantism, Alzheimer's disease and other forms of dementia, cancer, hormone-producing tumor, endocrine tumor, carcinoid, VIPoma, insulinoma, glucagonoma, Cushing's disease, hormone secretion defect, diabetes and complications thereof, pains, arthritis, diarrhea, gastric ulcer, inflammatory bowel disease, irritable bowel syndrome, gastrointestinal obstruction, ileus, postoperative restenosis, radiation damage, eye disease, dry eye, glaucoma, interstitial keratitis, iritis, cataract, and conjunctivitis.

Effects of the Invention

The glycosylated polypeptide of the present invention has affinity towards somatostatin receptors, and has significantly improved stability in blood compared to somatostatin by having at least two sugar chains in the polypeptide. Moreover, the glycosylated polypeptide of the present invention can be employed for treating a somatostatin-related disease by virtue of having the above characteristics.

Moreover, since the sugar chain added onto the glycosylated somatostatin of the present invention is easily degraded in vivo, no drug-induced suffering is caused to a living body by accumulation thereof.

Moreover, a part or all of the sugar chains added onto the glycosylated somatostatin of the present invention is a sugar chain present in the living body of e.g. mammals and birds including humans or a modified version thereof, and the possibility of showing side effects or antigenicity when administered in vivo is low. There is less concern for e.g. an allergic reactions or antibody production to occur and thereby losing drug effect.

Further, since many of the sugar chains employed herein are relatively short, those having uniform structure can be obtained without going through complex manufacturing steps. Accordingly, a pharmaceutical grade high quality glycosylated polypeptide having somatostatin activity can be stably obtained in a large scale.

BRIEF DESCRIPTION OF THE DRAWINGS

Figure 1A:
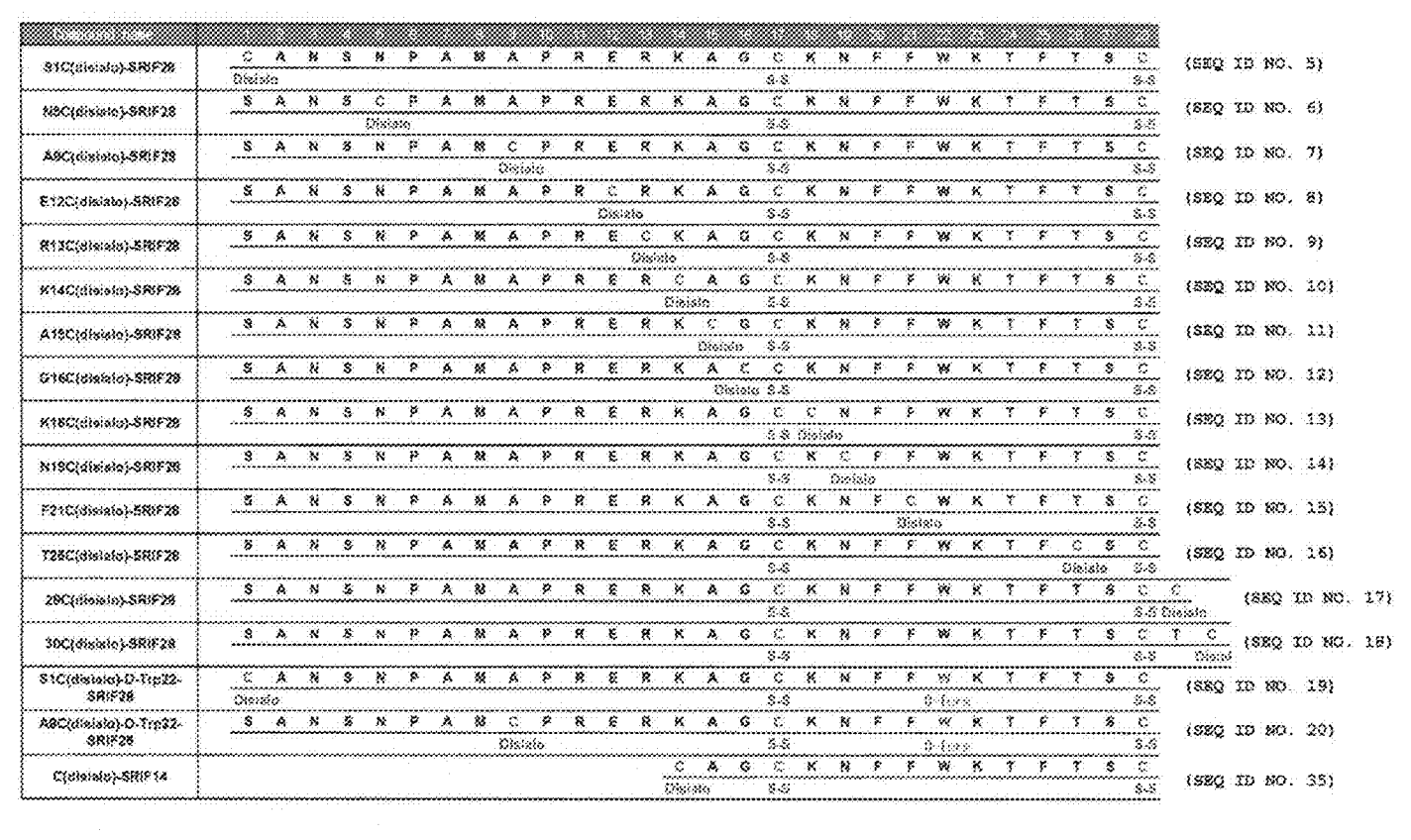
Figure 1B:
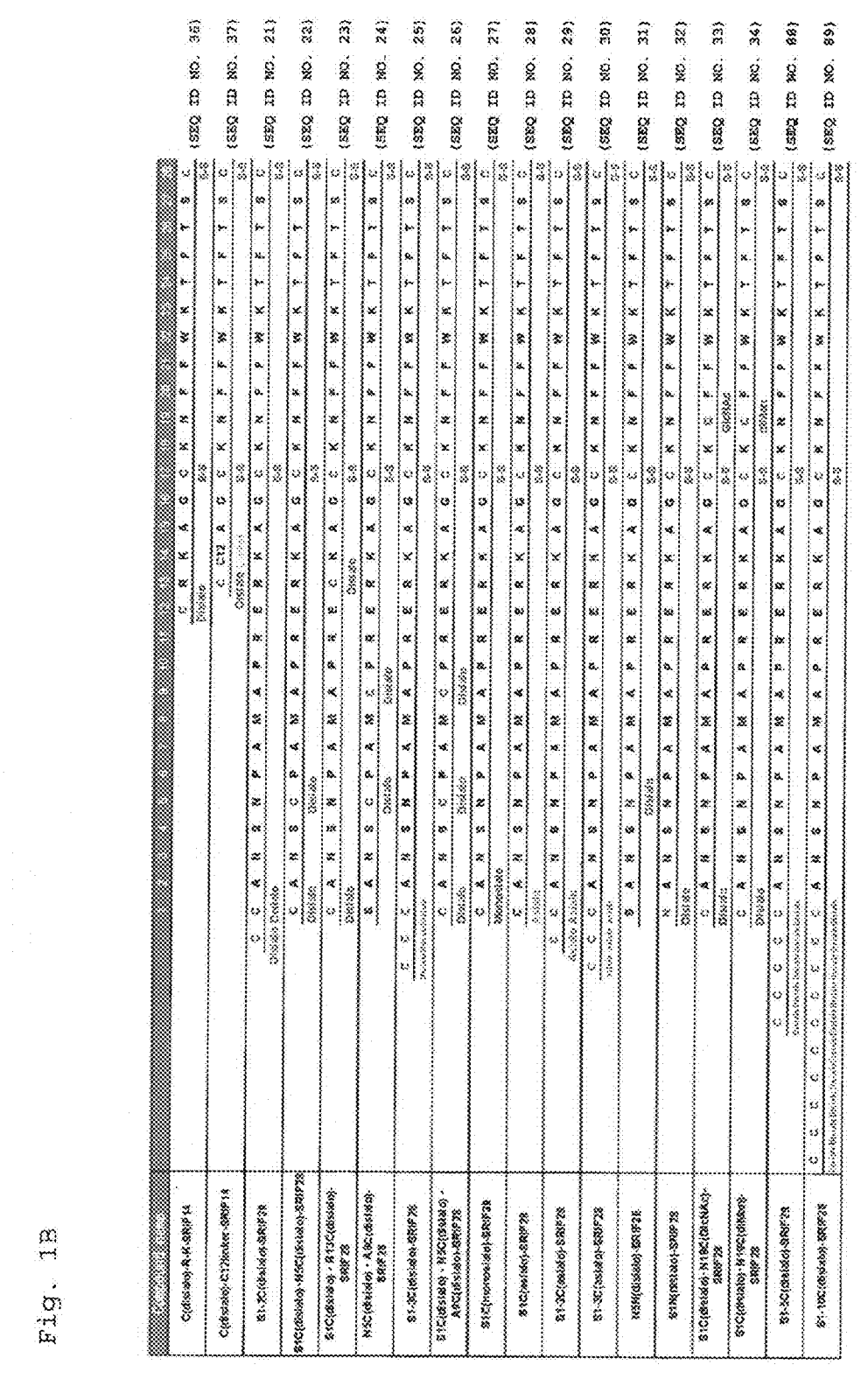
Figure 1C:
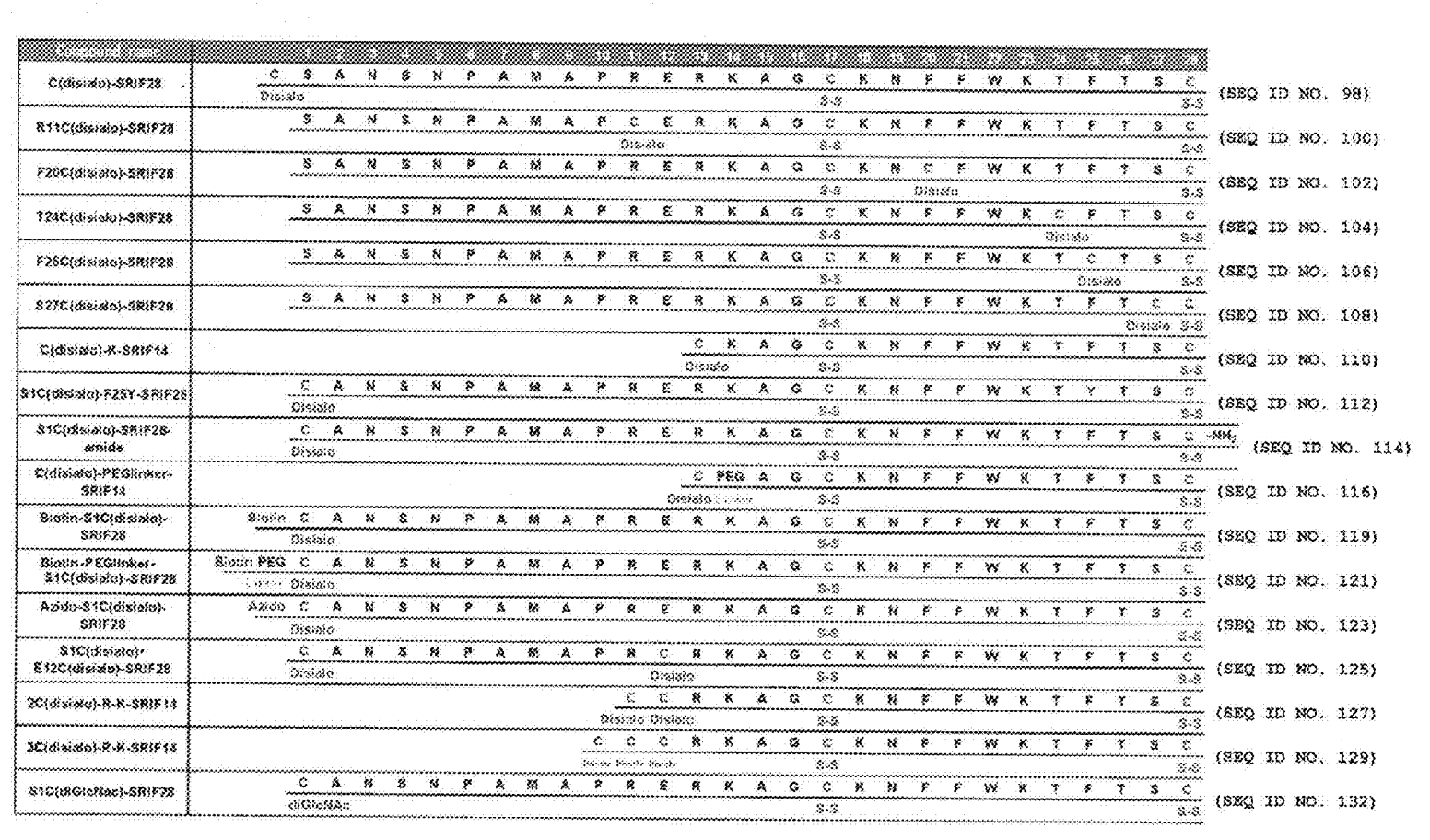
Figure 1D:
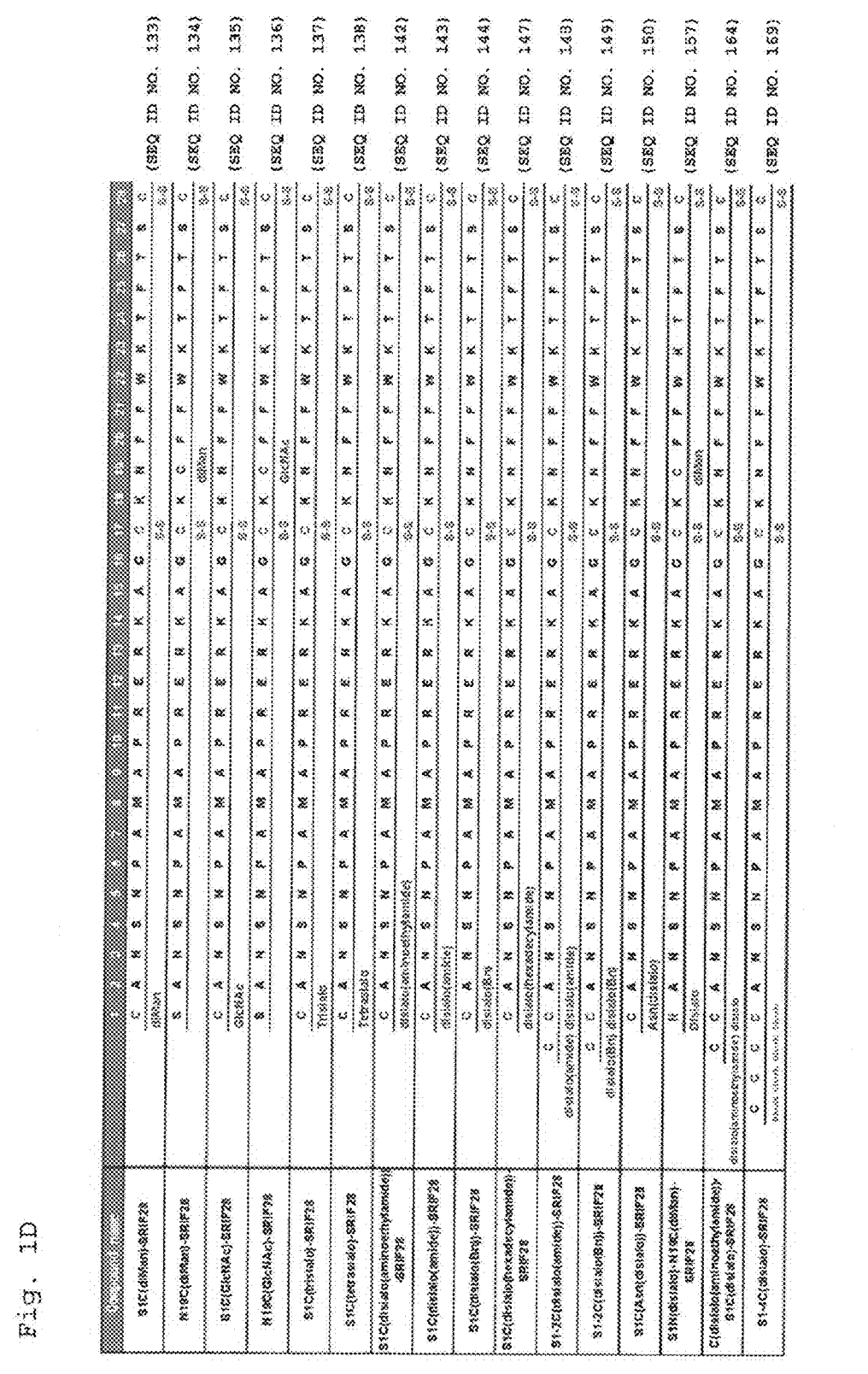

FIGS. 1A-1D show each compound name of the glycosylated polypeptides of an embodiment of the present invention and the amino acid sequence information of the glycosylated polypeptide having said compound name. Moreover.

In FIG. 2, the graph on the left is a graph showing the plasma concentration transition of each polypeptide when administered intravenously, and the graph on the right is a graph showing the plasma concentration transition of each polypeptide when administered subcutaneously.

In FIG. 3, the graph on the left is a graph showing the plasma concentration transition of each polypeptide when administered intravenously, and the graph on the right is a graph showing the plasma concentration transition of each polypeptide when administered subcutaneously.

In FIG. 4, the graph on the left is a graph showing the plasma concentration transition of each polypeptide when administered intravenously, and the graph on the right is a graph showing the plasma concentration transition of each polypeptide when administered subcutaneously.

In FIG. 5, the graph on the left is a graph showing the plasma concentration transition of each polypeptide when administered intravenously, and the graph on the right is a graph showing the plasma concentration transition of the polypeptides when administered subcutaneously.

In FIG. 6, the graph on the left is a graph showing the plasma concentration transition of each polypeptide when administered intravenously, and the graph on the right is a graph showing the plasma concentration transition of each polypeptide when administered subcutaneously.

In FIG. 7, the graph on the left is a graph showing the plasma concentration transition of each polypeptide when administered intravenously, and the graph on the right is a graph showing the plasma concentration transition of each polypeptide when administered subcutaneously.

In FIG. 8, the graph on the left is a graph showing the plasma concentration transition of each polypeptide when administered intravenously, and the graph on the right is a graph showing the plasma concentration transition of each polypeptide when administered subcutaneously.

In FIG. 9, the graph on the left is a graph showing the plasma concentration transition of each polypeptide when administered intravenously, and the graph on the right is a graph showing the plasma concentration transition of each polypeptide when administered subcutaneously.

In FIG. 10, the graph on the left is a graph showing the plasma concentration transition of each polypeptide when administered intravenously, and the graph on the right is a graph showing the plasma concentration transition of each polypeptide when administered subcutaneously.

In FIG. 11, the graph on the left is a graph showing the plasma concentration transition of each polypeptide when administered intravenously, and the graph on the right is a graph showing the plasma concentration transition of each polypeptide when administered subcutaneously.

In FIG. 12, the graph on the left is a graph showing the plasma concentration transition of each polypeptide when administered intravenously, and the graph on the right is a graph showing the plasma concentration transition of each polypeptide when administered subcutaneously.

In FIG. 13, the graph on the left is a graph showing the plasma concentration transition of each polypeptide when administered intravenously, and the graph on the right is a graph showing the plasma concentration transition of each polypeptide when administered subcutaneously.

In FIG. 14, the graph on the left is a graph showing the plasma concentration transition of each polypeptide when administered intravenously, and the graph on the right is a graph showing the plasma concentration transition of each polypeptide when administered subcutaneously.

In FIG. 15, the graph on the left is a graph showing the plasma concentration transition of each polypeptide when administered intravenously, and the graph on the right is a graph showing the plasma concentration transition of each polypeptide when administered subcutaneously.

In FIG. 16, the graph on the left is a graph showing the plasma concentration transition of each polypeptide when administered intravenously, and the graph on the right is a graph showing the plasma concentration transition of each polypeptide when administered subcutaneously.

In FIG. 17, the graph on the left is a graph showing the plasma concentration transition of each polypeptide when administered intravenously, and the graph on the right is a graph showing the plasma concentration transition of each polypeptide when administered subcutaneously.

In FIG. 18, the graph on the left is a graph showing the plasma concentration transition of each polypeptide when administered intravenously, and the graph on the right is a graph showing the plasma concentration transition of each polypeptide when administered subcutaneously.

In FIG. 19, the graph on the left is a graph showing the plasma concentration transition of each polypeptide when administered intravenously, and the graph on the right is a graph showing the plasma concentration transition of each polypeptide when administered subcutaneously.

DESCRIPTION OF EMBODIMENTS

Figure 1E:
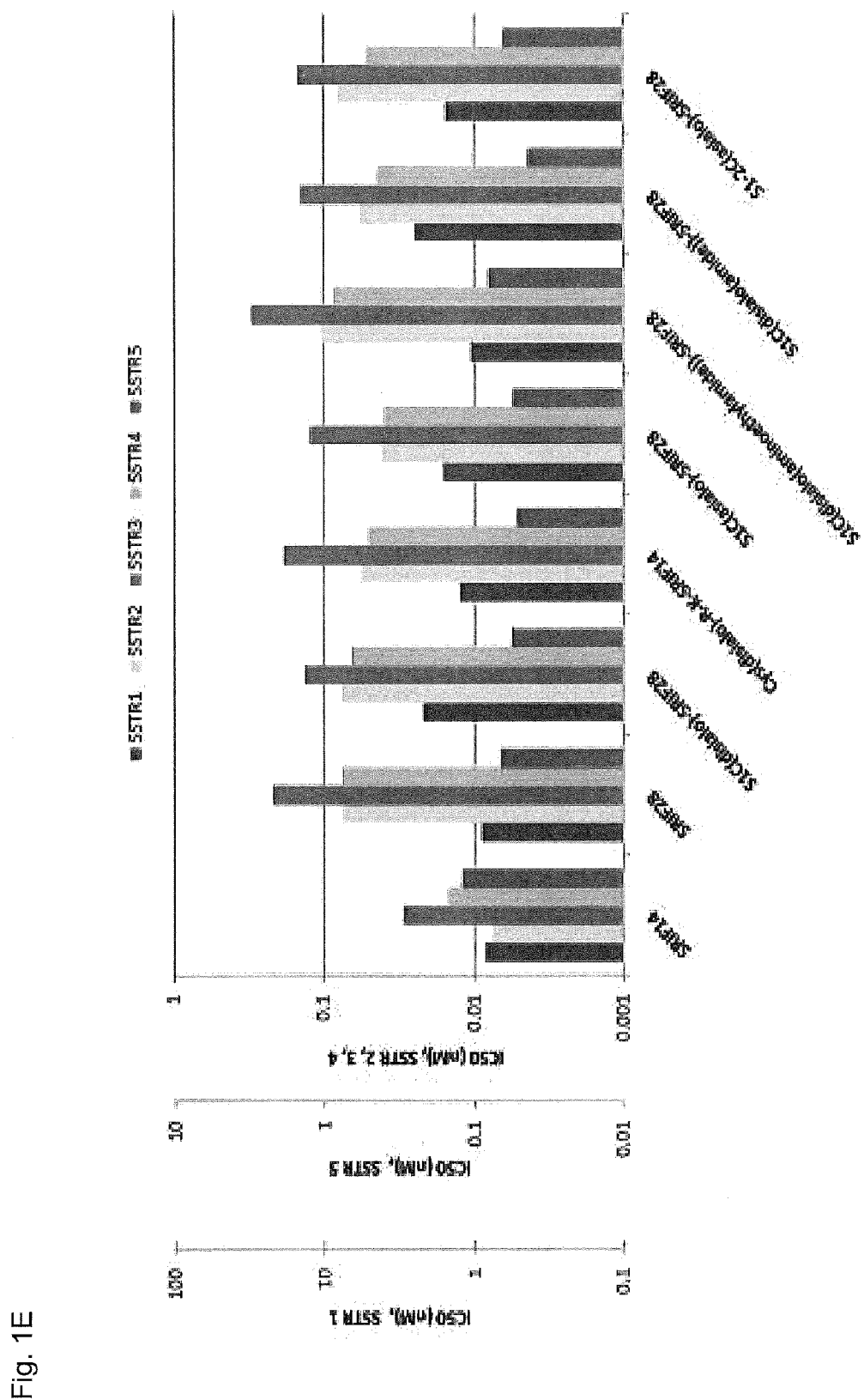
FIG. 1E is a graph showing the $IC_{50}$ value in regards to cAMP production suppressing action (agonist activity) when somatostatin receptor expression cells were treated with SRIF14, SRIF28, and the glycosylated polypeptides of an embodiment of the present invention.

A "Somatostatin" herein refers to SRIF14 consisting of a sequence of 14 amino acids or SRIF28 consisting of a sequence of 28 amino acids.

In the present specification, the N-terminal Ser in the SRIF28 amino acid sequence will be set to as position 1, and the C-terminal Cys as position 28. SRIF14 is in perfect match with the amino acid sequence of positions 15 to 28 in the SRIF28 amino acid sequence. Note that position 15 of the SRIF28 amino acid sequence is Ala, and the N-terminal Ala in the SRIF14 amino acid sequence (SEQ ID NO. 1) will be set as position 15 in correspondence with position 15 of SRIF28. SRIF14 and SRIF28 have a disulfide bond at Cys at position 17 and Cys at position 28.

SRIF14 has the amino acid sequence below (SEQ ID NO. 1). In the amino acid sequence below, 15 in "$Ala_{15}$" means Ala at position 15.

(SEQ ID NO. 1)
$Ala_{15}$-$Gly_{16}$-$Cys_{17}$-$Lys_{18}$-$Asn_{19}$-$Phe_{20}$-$Phe_{21}$-$Trp_{22}$-$Lys_{23}$-$Thr_{24}$-$Phe_{25}$-$Thr_{26}$-$Ser_{27}$-$Cys_{28}$

SRIF28 has the amino acid sequence below (SEQ ID NO. 2).

(SEQ ID NO. 2)
$Ser_1$-$Ala_2$-$Asn_3$-$Ser_4$-$Asn_5$-$Pro_6$-$Ala_7$-$Met_8$-$Ala_9$-$Pro_{10}$-$Arg_{11}$-$Glu_{12}$-$Arg_{13}$-$Lys_{14}$-$Ala_{15}$-$Gly_{16}$-$Cys_{17}$-$Lys_{18}$-$Asn_{19}$-$Phe_{20}$-$Phe_{21}$-$Trp_{22}$-$Lys_{23}$-$Thr_{24}$-$Phe_{25}$-$Thr_{26}$-$Ser_{27}$-$Cys_{28}$

An "amino acid" herein is employed in its broadest meaning, and includes not only natural amino acids but also non-natural amino acids such as amino acid variants and derivatives. Those skilled in the art will recognize in light of this broad definition that examples of amino acids herein include, e.g., natural proteinogenic L-amino acids; D-amino acids; chemically modified amino acids such as amino acid variants and derivatives; natural non-proteinogenic amino acids such as norleucine, β-alanine, and ornithine; and chemically synthesized compounds having properties well-known in the art characteristic of amino acids. Examples of non-natural amino acids include an α-methylamino acid (such as α-methylalanine), a D-amino acid, a histidine-like amino acid (such as 2-amino-histidine, β-hydroxy-histidine, homohistidine, α-fluoromethyl-histidine, and α-methyl-histidine), an amino acid having excess methylenes on the side chain ("homo" amino acid), and an amino acid in which the carboxylic functional group amino acid in the side chain is substituted with a sulfonate group (such as cysteic acid). Some of the somatostatin analogs having affinity towards somatostatin receptors are known to comprise a non-natural amino acid. In a preferred aspect, the amino acid contained in the compound of the present invention consists only of natural amino acids.

As used herein, when one of the amino acids or a few amino acids are said to be deleted, substituted, or added, the number of amino acids substituted etc. is not particularly limited as long as affinity towards somatostatin receptors is retained, but is 1-9, preferably 1-5, and more preferably approximately 1-3 amino acids, or 20% or less and preferably 10% or less of the entire length. The amino acid to be substituted or added may be a natural amino acid, a non-natural amino acid, or an amino acid analog, preferably a natural amino acid. Examples of somatostatin peptides having one of the amino acids or a few amino acids deleted, substituted, or added include, e.g., a somatostatin peptide having Trp at position 22 substituted with a D-form Trp (D-Trp), Asn at, position 19 deleted (J. Med. Chem., 2001, 44, 2238-2246), Phe at position 25 substituted with Tyr, and Met at position 8 substituted with Leu (Endocrinology, 1982, 10:1049-1051).

A "SRIF14 or SRIF28 analog" herein includes a polypeptide structurally similar to somatostatin and/or a polypeptide having an overlapping structure with somatostatin, e.g. a polypeptide having one of the amino acids or a few amino acids of somatostatin conservatively substituted, a modified somatostatin, a somatostatin fragment having affinity towards somatostatin receptors, and an elongated somatostatin having affinity towards somatostatin receptors.

"Having one of the amino acids or a few amino acids conservatively substituted" herein refers to an amino acid substitution in which the hydrophilicity and/or hydrophobicity index are similar between, the original amino acid and the amino acid to be substituted, and wherein apparent reduction or dissipation of affinity towards somatostatin receptors before and after such substitution is not caused.

A "modified somatostatin" herein is a modified version of somatostatin including a naturally-occurring variant of somatostatin or an artificially modified compound of somatostatin. Examples of such modifications include, e.g., alkylation, acylation (such as acetylation), amidation, carboxylation, ester formation, disulfide bond formation, glycosylation, lipidation, phosphorylation, hydroxylation, and binding of a labeling component of one or more amino acid residues of somatostatin.

A "somatostatin fragment having affinity towards somatostatin receptors" herein is a peptide having one or more amino acids deleted from the N- and/or C-terminals of somatostatin which maintains affinity towards somatostatin receptors.

An "elongated somatostatin having affinity towards somatostatin receptors" herein is a peptide having one or more amino acids added to the N- and/or C-terminals of SRIF28 or SRIF14 which maintains affinity towards somatostatin receptors.

The glycosylated polypeptide of the present invention comprises a glycosylated polypeptide which is a polypeptide consisting of an amino acid sequence having 80% or more homology with the amino acid sequence represented by SEQ ID NO. 1; a polypeptide consisting of an amino acid sequence having 80% or more homology with the amino acid sequence represented by SEQ ID NO. 2; or a polypeptide having an amino acid further added to the N- or C-terminal of these polypeptides; wherein at least one amino acid is substituted with a glycosylated amino acid, and the polypeptide has affinity towards somatostatin receptors.

A polypeptide having homology with SEQ ID NO. 1 or 2 can have preferably 80% or more, 85% or more, 90% or more, and 95% or more homology, as long as it has affinity towards somatostatin receptors.

The glycosylated polypeptide of the present invention also comprises a polypeptide having an amino acid further added to the N- and/or C-terminals of SRIF14 or SRIF28 as described above.

In the glycosylated polypeptide of the present invention, the amino acid further added to the N-terminal of SRIF14 is not particularly limited as long as it maintains affinity towards somatostatin receptors. For example, 1 or more to 20 or less amino acids can be added.

Here, the amino acid further added to the N-terminal of SRIF14 can be represented by X—Y—. Y is an amino acid that binds directly to the N-terminal amino acid of SRIF14 polypeptide, and Y consists of any of amino acid sequences (1)-(15) below:

(1) Lys,
(2) Arg-Lys,
(3) Glu-Arg-Lys,
(4) Arg-Glu-Arg-Lys (SEQ ID NO. 171),
(5) Pro-Arg-Glu-Arg-Lys (SEQ ID NO. 172),
(6) Ala-Pro-Arg-Glu-Arg-Lys (SEQ ID NO. 173),
(7) Met-Ala-Pro-Arg-Glu-Arg-Lys (SEQ ID NO. 174),
(8) Ala-Met-Ala-Pro-Arg-Glu-Arg-Lys (SEQ ID NO. 175),
(9) Pro-Ala-Met-Ala-Pro-Arg-Glu-Arg-Lys (SEQ ID NO. 176),
(10) Asn-Pro-Ala-Met-Ala-Pro-Arg-Glu-Arg-Lys (SEQ ID NO. 177),
(11) Ser-Asn-Pro-Ala-Met-Ala-Pro-Arg-Glu-Arg-Lys (SEQ ID NO. 178),
(12) Asn-Ser-Asn-Pro-Ala-Met-Ala-Pro-Arg-Glu-Arg-Lys (SEQ ID NO. 179),
(13) Ala-Asn-Ser-Asn-Pro-Ala-Met-Ala-Pro-Arg-Glu-Arg-Lys (SEQ ID NO. 180),
(14) Ser-Ala-Asn-Ser-Asn-Pro-Ala-Met-Ala-Pro-Arg-Glu-Arg-Lys (SEQ ID NO. 181), and
(15) a sequence having one or a few amino acids deleted, substituted, or added from/to the above sequences (2)-(14).

Moreover, X is any amino acid from 1 or more to 6 or less, and shows any 1, 2, 3, 4, 5, or 6 amino acids. Preferably, X is a glycosylated amino acid, and more preferably glycosylated Asn or glycosylated Cys.

In the glycosylated polypeptide of the present invention, the amino acid further added to the N-terminal of SRIF28 is not particularly limited as long as it maintains affinity towards somatostatin receptors. For example, any amino acids from 1 or more to 15 or less can be added, and any 1, 2, 3, 4, 5, 6, 7, 8, 9, 10, 11, 12, 13, 14, or 15 amino acids can be added. The amino acid further added to the N-terminal of SRIF28 is preferably a glycosylated amino acid, and more preferably glycosylated Asn or glycosylated Cys. Moreover, all of the any 1 or more to 15 or less amino acids can be glycosylated amino acids.

In the glycosylated polypeptide of the present invention, the amino acid further added to the C-terminal of SRIF14 or SRIF28 is not particularly limited as long as it maintains affinity towards somatostatin receptors. For example, any amino acids from 1 or more to 6 or less can be added, and any 1, 2, 3, 4, 5, or 6 amino acids can be added. The amino acid further added to the C-terminal of SRIF14 or SRIF28 is preferably a glycosylated amino acid, and more preferably glycosylated Asn or glycosylated Cys. Moreover, all of the any 1 or more to 6 or less amino acids can be glycosylated amino acids.

A "peptide having one or a few amino acids further added to the N-terminal side of somatostatin (position 1 of SRIF28 or position 15 of SRIF14)" herein refers to, in the case of SRIF28, those having any amino acid or glycosylated amino acid further added to the N-terminal Ser at position 1. Moreover, in the case of SRIF14, it refers to those having any amino acid or glycosylated amino acid further added to the N-terminal Ala at position 15.

Similarly, a "peptide having one or a few amino acids further added to the C-terminal side (position 28 of SRIF28 or SRIF14)" refers to those having any amino acid or glycosylated amino acid further added to Cys at position 28 of SRIF28 or SRIF14.

An amino acid can also be further added to the glycosylated polypeptide of the present invention at its N- or C-terminal via a linker. Examples of such linkers can include, e.g., an alkyl chain or a polyethylene glycol chain having amino and carboxy groups at the two terminals so that it can form a peptide bond with the amino acid. Examples of such linkers can include, e.g., —NH—(CH$_2$)$_n$—CO— (wherein n is an integer and is not limited as long as it does not inhibit the linker function of interest, but is preferably an integer from 1-15) or —NH—(CH$_2$CH$_2$O)$_m$—CH$_2$CH$_2$—CO— (wherein m is an integer and is not limited as long as it does not inhibit the linker function of interest, but is preferably an integer from 1-7). More specifically, examples can include —NH—(CH$_2$)$_{11}$—CO—(C12 linker) or —NH—(CH$_2$CH$_2$O)$_3$—CH$_2$CH$_2$—CO— (PEG linker). Moreover, the amino acid added to the glycosylated polypeptide via a linker is not particularly limited, but is preferably a glycosylated amino acid. Examples of a glycosylated amino acid can include glycosylated Asn or glycosylated Cys.

Moreover, in one embodiment of the present invention, an azido group can also be introduced into the glycosylated polypeptide at its N-terminal. Azidation of the N-terminal of the glycosylated polypeptide is preferred because it will allow various molecules to be selectively introduced by utilizing azide-alkyne [3+2] cycloaddition reaction or Staudinger reaction. The method for azidating the glycosylated polypeptide is not particularly limited, but it can be obtained by e.g. condensing the N-terminal of a glycopeptide synthesized on a resin in solid phase synthesis and an azido-substituted fatty acid with a condensation agent. Azido-substituted fatty acids can include 4-azidobutanoic acid, 5-azidopentanoic acid, and 6-azidohexanoic acid.

Moreover, in one embodiment of the present invention, a labeling compound can also be added to the glycosylated polypeptide at its N-terminal. Examples of the labeling compound used herein can include, but is not limited to, e.g. biotin, fluorescent dyes, and metal ion chelators. The labeling compound can be directly bound to the N-terminal of the glycopeptide, or it can also be bound to the N-terminal of the glycopeptide via a linker. For example, by adding biotin as the labeling compound to the N-terminal of the glycopeptide, strong binding with avidin can be utilized to enable application as research reagents, clinical test agents, or missile therapy.

The addition of a labeling compound to the glycosylated polypeptide of the present invention can be performed by a conventional method well-known to those skilled in the art. For example, the N-terminal of the glycosylated polypeptide on the resin in solid phase synthesis and a labeling compound can be condensed with a condensation agent.

The "glycosylated polypeptide" of the present invention is characterized in that at least two amino acids are substituted by glycosylated amino acids.

A "glycosylated polypeptide" herein includes e.g. a polypeptide having at least two amino acids of somatostatin substituted with glycosylated amino acids and a polypeptide having at least two amino acids substituted with glycosylated amino acids in the above somatostatin analog, each of which is included in the glycosylated polypeptide of the present invention even if one of the amino acids or a few amino acids other than the glycosylated amino acid is further deleted, substituted, or added. A peptide having at least two amino acids substituted with glycosylated amino acids in a peptide in which the C-terminal thereof is amidated (such as SRIF14NH$_2$ having the amino acid sequence of Ala-Gly-Cys-Lys-Asn-Phe-Phe-Trp-Lys-Thr-Phe-Thr-Ser-Cys-NH (SEQ ID NO. 3) or SRIF28NH$_2$ having the amino acid sequence of Ser-Ala-Asn-Ser-Asn-Pro-Ala-Met-Ala-Pro-Arg-Glu-Arg-Lys-Ala-Gly-Cys-Lys-Asn-Phe-Phe-Trp-Lys-Thr-Phe-Thr-Ser-Cys-NH$_2$ (SEQ ID NO. 4) is also included in the glycosylated polypeptide of the present invention. Further, a salt of these peptides is also included in glycosylated polypeptides.

A salt as used herein may be any of acid addition salts or base addition salts. Acids generally employed to form acid addition salts are inorganic acids such as hydrochloric acid, hydrobromic acid, hydroiodic acid, sulfuric acid, and phosphoric acid, as well as organic acids such as p-toluenesulfonic acid, methanesulfonic acid, oxalic acid, p-bromophenylsulfonic acid, carboxylic acid, succinic acid, citric acid, benzoic acid, and acetic acid. Base addition salts include salts derived from an inorganic base such as ammonium hydroxide or alkali or alkaline earth metal hydroxides, carbonates, and bicarbonates. In particular, pharmaceutically acceptable salts are preferred.

A "glycosylated (sugar chain attached) amino acid" herein is an, amino acid having a sugar chain bound thereto, and the sugar chain and the amino acid may be bound via a linker. The binding site of the sugar chain and the amino acid is not particularly restricted, but the amino acid is preferably bound to the reducing terminal of the sugar chain.

The type of amino acid to which the sugar chain binds is not particularly limited, and any of natural amino acids and non-natural amino acids can be employed. With respect to the glycosylated amino acids having identical or similar structure as those present as glycopeptides (glycoproteins) in vivo, the glycosylated amino acid is preferably glycosylated Asn, like N-linked sugar chain as well as glycosylated Ser and glycosylated Thr, and glycosylated Asn, like O-linked sugar, chain is particularly preferred.

Moreover, when the sugar chain and the amino acid are bound via a linker, with respect to easy binding with the linker, the amino acid of the glycosylated amino acid is preferably an amino acid having two or more carboxy groups in a molecule such as aspartic acid and glutamic acid, an amino acid having two or more amino groups in a molecule such as lysine, arginine, histidine, and tryptophan, an amino acid having a hydroxyl group in the molecule such as serine, threonine, and tyrosine, an amino acid having a thiol group in the molecule such as cysteine, and an amino acid having an amide group in the molecule such as asparagine and glutamine. In particular, with respect to reactivity, aspartic acid, glutamic acid, lysine, arginine, serine, threonine, cysteine, asparagine, and glutamine are preferred.

In any glycosylated polypeptide of the present invention, it is thought that if the sugar chain structure, the structure other than the sugar chain, the number of addition sites for the sugar chain, and the number of sugar chains added are identical, there is no major difference in the half-life in blood of the glycosylated polypeptide of the present invention whether the glycosylated amino acid is glycosylated Asn (without a linker) or glycosylated Cys (with a linker).

When the sugar chain and the amino acid are bound via a linker, linkers employed in the art can be widely used, examples of which can include, e.g., —NH—(CO)—(CH$_2$)$_a$—CH$_2$— (wherein a is an integer and is not limited as long as it does not inhibit the linker function of interest, but is preferably an integer from 0-4), C$_{1-10}$ polymethylene, —CH$_2$—R— (wherein R is a group produced by having one hydrogen atom detached from a group selected from the group consisting of an alkyl, a substituted alkyl, an alkenyl, a substituted alkenyl, an alkynyl, a substituted alkynyl, an aryl, a substituted aryl, a carbocyclic group, a substituted carbocyclic group, a heterocyclic group, and a substituted heterocyclic group), and —(CO)—(CH$_2$)$_a$—(CO)— (wherein a is an integer and is not limited as long as it does not inhibit the linker function of interest, but is preferably an integer from 0-4).

In the glycosylated amino acid, when the sugar chain and the amino acid on the somatostatin backbone are bound via a linker, it is preferred that the linker also comprises an amino acid at the sugar chain terminal. The type of amino acid is not particularly limited, but a preferred example can include Asn.

The manufacturing method of the glycosylated polypeptide of the present invention is not to be limited in any way by a description therefor (such as the description a "glycosylated polypeptide having an amino acid substituted with a glycosylated amino acid"), and a glycosylated polypeptide manufactured with any of methods A or B described below is included in the "glycosylated polypeptide having an amino acid substituted with a glycosylated amino acid". Moreover, for example, a glycosylated polypeptide in which a sugar chain without any amino acid bound thereto is bound directly or via a linker to an amino acid on a peptide; a glycosylated polypeptide in which a sugar or a sugar chain is further added to the sugar chain added in the glycosylated polypeptide in order to elongate the already added sugar chain; a glycosylated polypeptide in which one or a few amino acids are bound to the amino and/or carboxy group of a glycosylated amino acid, and further linked to one or more somatostatin fragments; and a glycosylated polypeptide in which a sugar chain having an amino acid bound thereto is bound via a linker to an amino acid on a peptide are also included in the glycosylated polypeptide of the present invention, as long as the final structure matches.

In the glycosylated polypeptide of the present invention, the number of amino acids to be substituted with a glycosylated amino acid may be appropriately adjusted by e.g. bioactivity such as stability in blood or secretory suppression of growth hormone etc., the number of amino acids present in the final glycosylated polypeptide, or the molecular weight of the glycosylated polypeptide before and after glycosylation. For example, the glycosylated polypeptide of the present invention can have 2-15 amino acids in its amino acid sequence substituted to glycosylated amino acids. With respect to stability in blood, as long as the desired activity is obtained, it is preferred to substitute 2 or more, e.g. it is preferred to substitute 2-10, and more preferably to substitute 2-3 amino acids. In general, in a glycosylated polypeptide having one amino acid of somatostatin substituted with a glycosylated amino acid, stability in blood will increase when one or more of amino acids other than the glycosylated amino acid are further substituted by glycosylated amino acids. On the other hand, although affinity towards somatostatin receptors will tend to decrease, the stability in blood of the glycosylated polypeptide will increase, and it is therefore possible to compensate for or increase the decreased somatostatin activity.

Moreover, when multiple sugar chains are present in a glycosylated polypeptide, the each sugar chains can be added to consecutive amino acids, or can be added to amino acids with intervals in the amino acid sequence of the glycosylated polypeptide. Placing the sugar chains densely is preferred because there is no rapid increase in plasma concentration. When the sugar chains are placed densely, for example, approximately 2-15 consecutive glycosylated amino acids can be added to the N-terminal of SRIF14 or SRIF28. Moreover, with respect to bioavailability, the preferred glycosylation position is adding multiple sugar chains with intervals rather than adding densely to consecutive amino acids.

In the glycosylated polypeptide of the present invention, the site for substituting an amino acid with a glycosylated amino acid can be appropriately adjusted with respect to having affinity towards at least one somatostatin receptor, and preferably, it can be appropriately adjusted with respect to having affinity towards multiple somatostatin receptors.

In one aspect of the present invention, the site for substituting an amino acid with a glycosylated amino acid can include, with respect to having affinity towards multiple receptors in SSTR1-SSTR5 among affinity of the glycosylated polypeptide towards somatostatin receptors, e.g., the amino acid corresponding to position 19 of SRIF14, the amino acids added at the 1st, 2nd, 3rd, 6th, 10th, and 14th positions from the N-terminal side among the amino acids further added to the N-terminal side of SRIF14, and the amino acids added at the 1st and 2nd positions from the C-terminal side among the amino acids further added to the C-terminal side of SRIF14. Preferably, it can include the amino acids added at the 3rd, 6th, 10th, and 14th positions from the N-terminal side among the amino acids further added to the N-terminal side of SRIF14.

Moreover, similarly with respect to having affinity towards multiple receptors in SSTR1-SSTR5, it can include the amino acids corresponding to positions 1, 5, 9, 12, 13, 14, and 19 of SRIF28, and the amino acids added at the 1st and 2nd positions from the C-terminal side among the amino acids further added to the C-terminal of SRIF28. Preferably, it can include the amino acids corresponding to positions 1, 5, 9, and 12 of SRIF28.

Moreover, particularly, examples of substitution of two or more amino acids of the glycosylated polypeptide of the present invention with glycosylated amino acids can include, with respect to the glycosylated polypeptide having affinity towards multiple somatostatin receptors, e.g., substitutions of the amino acids added at the 10th and 14th positions from the N-terminal side among the amino acids further added to the N-terminal side of SRIF14; the amino acids added at the 6th and 10th positions from the N-terminal side among the amino acids further added to the N-terminal side of SRIF14; the amino acids added at the 2nd and 14th positions from the N-terminal side among the amino acids further added to the N-terminal side of SRIF14; the amino acids added at the 14th and 15th positions from the N-terminal side among the amino acids further added to the N-terminal side of SRIF14; the amino acids added at the 14th, 15th, and 16th positions from the N-terminal side among the amino acids further added to the N-terminal side of SRIF14; and the amino acids added at the 6th, 10th, and 14th positions from the N-terminal side among the amino acids further added to the N-terminal side of SRIF14. Preferably, it can include, e.g., substitutions of the amino acids added at the 10th and 14th positions from the N-terminal side among the amino acids further added to the N-terminal side of SRIF14; the amino acids added at the 6th and 10th positions from the N-terminal side among the amino acids further added to the N-terminal side of SRIF14; the amino acids added at the 14th and 15th positions from the N-terminal side among the amino acids further added to the N-terminal side of SRIF14; the amino acids added at the 14th, 15th, and 16th positions from the N-terminal side among the amino acids further added to the N-terminal side of SRIF14; and the amino acids added at the 6th, 10th, and 14th positions from the N-terminal side among the amino acids further added to the N-terminal side of SRIF14.

Moreover, similarly, examples of substitution of two or more amino acids with glycosylated amino acids can include, with respect to the glycosylated polypeptide having affinity towards multiple somatostatin receptors, e.g., substitutions of the amino acids corresponding to positions 1 and 5; the amino acids corresponding to positions 5 and 9; the amino acids corresponding to positions 1 and 13; the amino acid corresponding to position 1 and the amino acid added at the 1st position from the N-terminal side among the amino acids further added to the N-terminal side of position 1; the amino acid corresponding to position 1 and the amino acids added at the 1st and 2nd positions from the N-terminal side among the amino acids further added to the N-terminal side of position 1; and the amino acids corresponding to positions 1, 5, and 9; preferably, substitutions of the amino acids corresponding to positions 1 and 5; substitutions of the amino acids corresponding to positions 5 and 9; substitution of the amino acid corresponding to position 1 and the amino acid added at the 1st position among the amino acids further added to the N-terminal side of position 1; the amino acid corresponding to position 1 and the amino acids added at the 1st and 2nd positions from the N-terminal side among the amino acids further added to the N-terminal side of position 1; and substitutions of the amino acids corresponding to positions 1, 5, and 9 of SRIF28.

In one aspect of the present invention, the site for substituting an amino acid with a glycosylated amino acid can include, with respect to the stability in blood of the glycosylated polypeptide, e.g., the amino acid corresponding to position 19 of SRIF14, the amino acids added at the 1st, 2nd, 3rd, 6th, 10th, 14th positions from the N-terminal side among the amino acids further added to the N-terminal side of SRIF14, and the amino acids added at the 1st and 2nd positions from the C-terminal side among the amino acids further added to the C-terminal side of SRIF14. Preferably, it can include the amino acid corresponding to position 19 of SRIF14, the amino acids added at the 1st and 2nd positions from the N-terminal side among the amino acids further added to the N-terminal side of SRIF14, and the amino acids added at the 1st and 2nd positions from the C-terminal side among the amino acids further added to the C-terminal side of SRIF14. More preferably, it is the amino acid corresponding to position 19 of SRIF14, the amino acid added at the 1st position from the N-terminal side among the amino acids further added to the N-terminal side of SRIF14, and the amino acid added at the 1st position from the C-terminal side among the amino acids further added to the C-terminal side of SRIF14.

Moreover, similarly with respect to the stability in blood of the glycosylated polypeptide, it is e.g. one or more amino acids selected from the group consisting of the amino acids corresponding to positions 1, 5, 9, 12, 13, 14, and 19 of SRIF28 and the amino acids added at the 1st and 2nd positions from the C-terminal side among the amino acids further added to the C-terminal side of SRIF28, preferably one or more amino acids selected from the group consisting of the amino acids corresponding to positions 13, 14, and 19 of SRIF28 and the amino acids added at the 1st and 2nd positions from the C-terminal side among the amino acids further added to the C-terminal side of SRIF28, and particularly preferably one or more amino acids selected from the group consisting of the amino acids corresponding to positions 14 and 19 of SRIF28 and the amino acid added at the 1st position from the C-terminal side among the amino acids further added to the C-terminal side of SRIF28. In particular, substitution of an amino acid at a distal site from the N-terminal side of SRIF28 is also preferred.

Here, an "amino acid corresponding to a particular amino acid" refers to an amino acid at the same position corresponding to the amino acid sequence of SRIF14 or SRIF28, as long as there is no addition or deletion etc. of an amino acid in the glycosylated polypeptide. Moreover, if an addition or deletion of an amino acid is present in the amino acid sequence of a glycosylated polypeptide, it refers to the amino acid at the position that takes into account the shift on the amino acid sequence by the addition or deletion of an amino acid. For example, in a glycosylated polypeptide having the sequence $Ser_1$-$Ala_2$-$Asn_3$-$Ser_4$-(SEQ ID NO:182) at positions 1 to 4, when one amino acid (Trp) is added between the amino acids at positions 2 and 3 (Ser-Ala-Trp-Asn-Ser-)(SEQ ID NO:183), the amino acid corresponding to the amino acid at position 3 (Asn) refers to the amino acid (Asn) in the glycosylated polypeptide which has been shifted one to the C-terminal side by the insertion of Trp.

In one aspect of the present invention, the amino acid substituted with an glycosylated amino acid is preferably one or more amino acids selected from an amino acid other than the amino acids corresponding to positions 17, 21, 22, 23, and 28 of SRIF28, and in particular, it is more preferably one or more amino acids selected from an amino acid other than the amino acids corresponding to positions 17, 22, 23, and 28 of SRIF28.

In one aspect of the present invention, when two or more amino acids are substituted with glycosylated amino acids, any combination above can be employed for the site for substituting an amino acid with a glycosylated amino acid but is not limited thereto. For example, a combination of one site being selected from the above preferred sites and other sites being selected from any site of SRIF14 or SRIF28; or a combination of one site being selected from the above preferred sites and other sites being selected from any of one or a few amino acids further added to the N-terminal (position of SRIF28 or position 15 of SRIF14) or C-terminal of somatostatin are also included in one preferred aspect of the present invention. Moreover, in a glycosylated polypeptide, it is more preferred that the two or more amino acids are substituted with glycosylated amino acids at the amino acids specified above. Moreover, it is further preferred that all the glycosylated amino acids included in the glycosylated polypeptide are substituted with glycosylated amino acids at the amino acids specified above.

Among the glycosylated polypeptides of the present invention, the combination of the two substituted amino acids in a glycosylated polypeptide having two amino acids substituted with glycosylated amino acids can be, e.g., two amino acids selected from the group consisting of the amino acid corresponding to position 19 of SRIF14, the 1st, 2nd, 3rd, 6th, 10th, and 14th amino acids from the N-terminal side among the amino acids further added to the N-terminal side of SRIF14, and the 1st and 2nd amino acids from the C-terminal side among the amino acids further added to the C-terminal side of SRIF14. Moreover, similarly, it can include two amino acids selected from the group consisting of the amino acids corresponding to positions 1, 5, 9, 12, 13, 14, and 19 of SRIF28, as well as the 1st amino acid further added to the C-terminal of SRIF28 and the 2nd amino acid further added to the C-terminal of SRIF28.

Similarly, substitution positions for a glycosylated polypeptide having three amino acids substituted with glycosylated amino acids or a glycosylated polypeptide having four or more amino acids substituted with glycosylated amino acids can include a combination of three or four or more amino acids selected from the group consisting of the amino acids specified above. However, the glycosylated polypeptide of the present invention is not limited to the combinations listed above, and comprises other combinations as long as it has affinity towards somatostatin receptors and improved stability in blood compared to a naturally-occurring somatostatin.

In one aspect of the present invention, the site where a deletion, substitution, or addition of an amino acid other than glycosylated amino acids occurs is preferably e.g. one or more amino acids selected from an amino acid other than the amino acids corresponding to positions 17, 22, 23, and 28 of SRIF28.

A "sugar chain" herein refers to a compound made from a string of one or more unit sugars (monosaccharides and/or derivatives thereof). When there is a string of two or more unit sugars, each unit sugar is bound with each other by a dehydration condensation with a glycoside bond in between. Such sugar chains include, but are not limited to e.g. a wide range such as monosaccharides and polysaccharides contained in vivo (glucose, galactose, mannose, fucose, xylose, N-acetylglucosamine (GlcNAc), N-acetylgalactosamine (GalNAc), sialic acid, and conjugates and derivatives thereof), as well as a sugar chain degraded or derived from conjugated biomolecules such as degraded polysaccharides, glycoproteins, proteoglycans, glycosaminoglycans, and glycolipids. The sugar chain may be linear or branched.

Moreover, a "sugar chain" herein also includes a sugar chain derivative, and examples of sugar chain derivatives include, but are not limited to, a sugar chain wherein the sugar constituting the sugar chain is e.g. a sugar having a carboxy group (such as aldonic acid in which C-position 1 is oxidized to become a carboxylic acid (such as D-gluconic acid which is oxidized D-glucose) and uronic acid in which the terminal C atom has become a carboxylic acid (D-glucuronic acid which is oxidized D-glucose)), a sugar having an amino group or an amino group derivative (such as acetylated amino group) (such as N-acetyl-D-glucosamine and N-acetyl-D-galactosamine), a sugar having both amino and carboxy groups (such as N-acetylneuraminic acid (sialic acid) and N-acetylmuramic acid), a deoxylated sugar (such as 2-deoxy-D-ribose), a sulfated sugar comprising a sulfate group, and a phosphorylated sugar comprising a phosphate group.

A preferred sugar chain herein is a sugar chain that increases the stability in blood of somatostatin and will not dissipate affinity towards somatostatin receptors when added to somatostatin (when substituted with an amino acid of somatostatin in the form of a glycosylated amino acid). In an aspect of the present invention, a preferred sugar chain is a sugar chain that can maintain affinity towards multiple receptors of somatostatin, and further preferably a sugar chain that can maintain affinity towards all the receptors of somatostatin when added to somatostatin (when substituted with an amino acid of somatostatin in the form of a glycosylated amino acid).

The sugar chain in the glycosylated polypeptide of the present invention is not particularly limited, and may be a sugar chain that exists as a glycoconjugate in vivo (such as a glycopeptide (or a glycoprotein), a proteoglycan, and a glycolipid), or it may be a sugar chain that does not exist as a glycoconjugate in vivo.

A sugar chain that exists as a glycoconjugate in vivo is preferred with respect to the fact that the glycosylated polypeptide of the present invention is administered in vivo. Examples of such sugar chains include N- or O-linked sugar chains which are sugar chains bound to a peptide (or a protein) in vivo as a glycopeptide (or a glycoprotein). An N-linked sugar chain is preferably employed. N-linked sugar chains can include, e.g., a high-mannose form, a complex form, or a hybrid form, particularly preferably a complex form.

Examples of preferred complex-type sugar chains used herein include, e.g., a sugar chain represented by the following general formula:

[Chemical Formula 3]

[wherein $R^1$ and $R^2$ are identical or different and are:

[Chemical Formula 4]

and Ac is an acetyl group].

In the glycosylated polypeptide of the present invention, the sugar chain may be bound to the somatostatin peptide with a method other than O- and N-linking, even if it is a sugar chain that exists as a glycoconjugate in vivo. For example, as described above, those in which the sugar chain is bound to Cys or Lys via a linker are also included in the glycosylated polypeptide of the present invention.

In one aspect of the present invention, it is preferred that the sugar chain in the glycosylated polypeptide of the present invention is a sugar chain consisting of 4 or more, for example, 5 or more, 7 or more, in particular 9 or more, or 11 or more sugars.

In one preferred aspect of the present invention, the sugar chain in the glycosylated polypeptide of the present invention is a sugar chain consisting of 5-11, 9-11, or 11 sugars.

In one preferred aspect of the present invention, the sugar chain in the glycosylated polypeptide of the present invention is a biantennary complex-type sugar chain. A complex-type sugar chain is characterized in that it comprises two or more types of monosaccharides, and has the basic structure shown below and a lactosamine structure shown by Galβ1-4GlcNAc.

[Chemical Formula 5]

A biantennary complex-type sugar chain refers to those having a monoantennary sugar chain consisting of 0-3 sugars bound to each of the two mannoses at the end of the basic structure. Examples of biantennary complex-type sugar chains are preferably e.g. a disialo sugar chain as shown below:

[Chemical Formula 6]
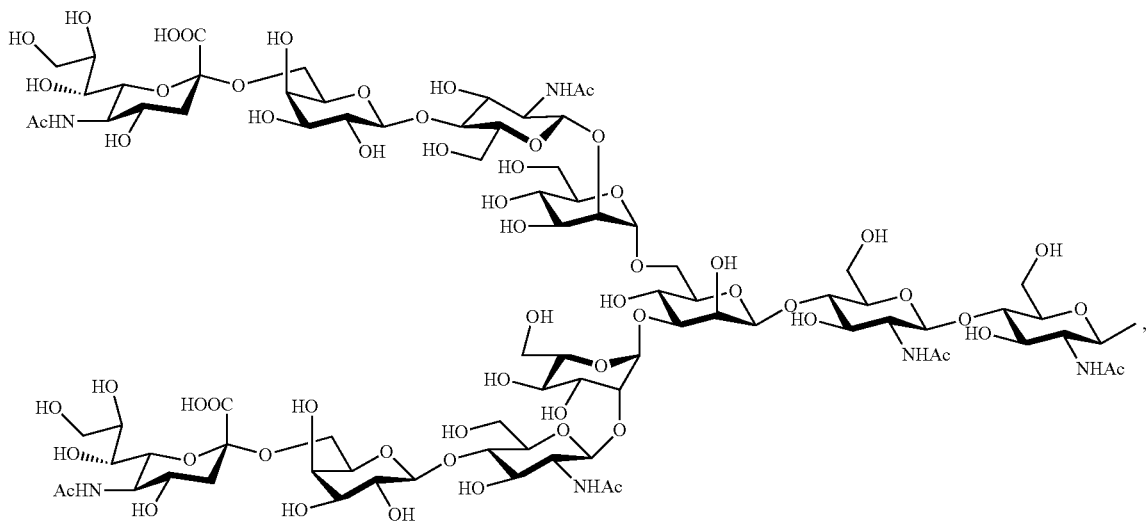
a monosialo sugar chain:
[Chemical Formula 7]
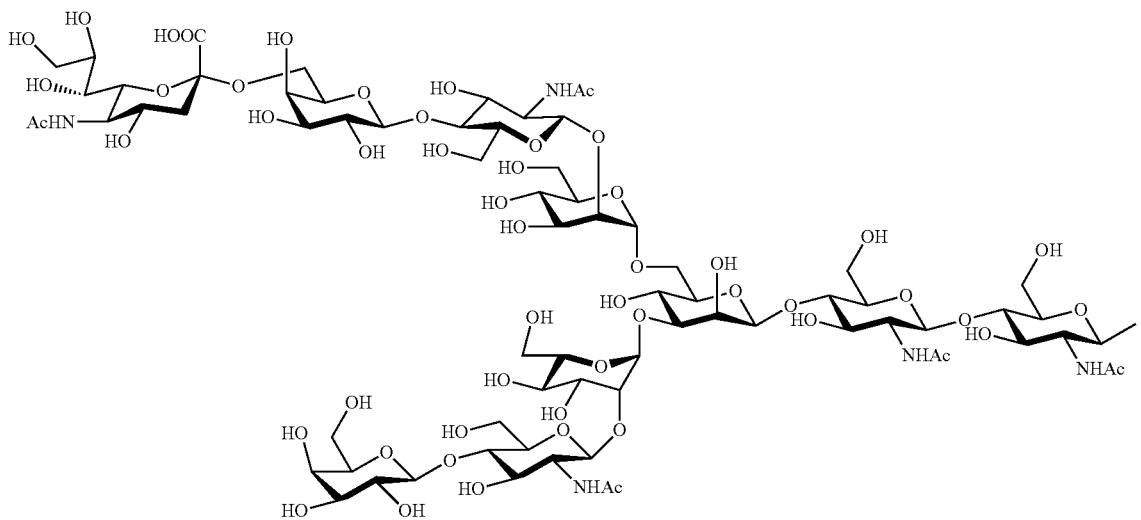

[Chemical Formula 7A]
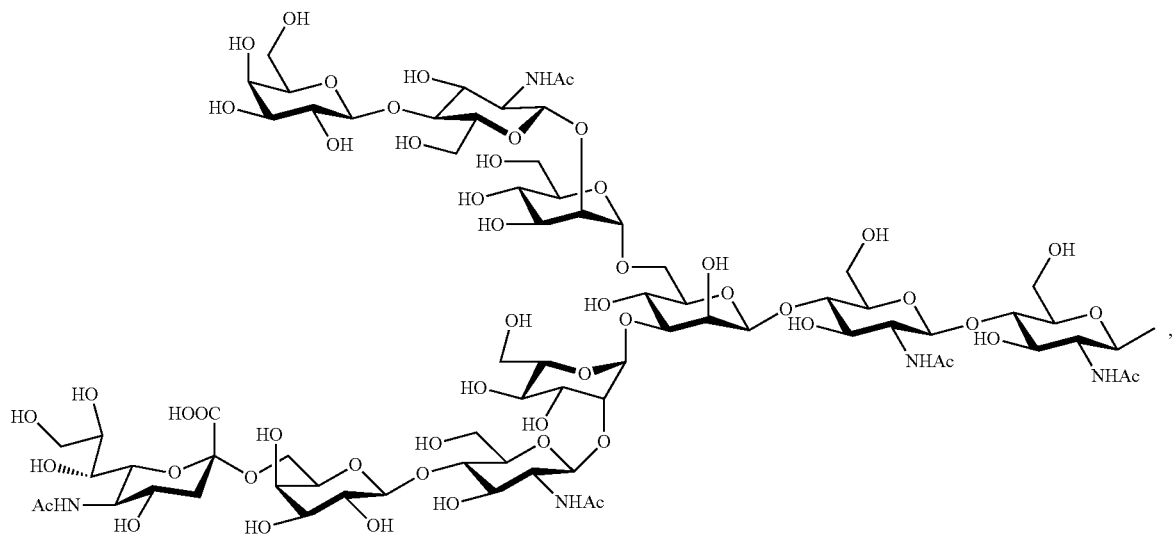
an asialo sugar chain:
[Chemical Formula 8]
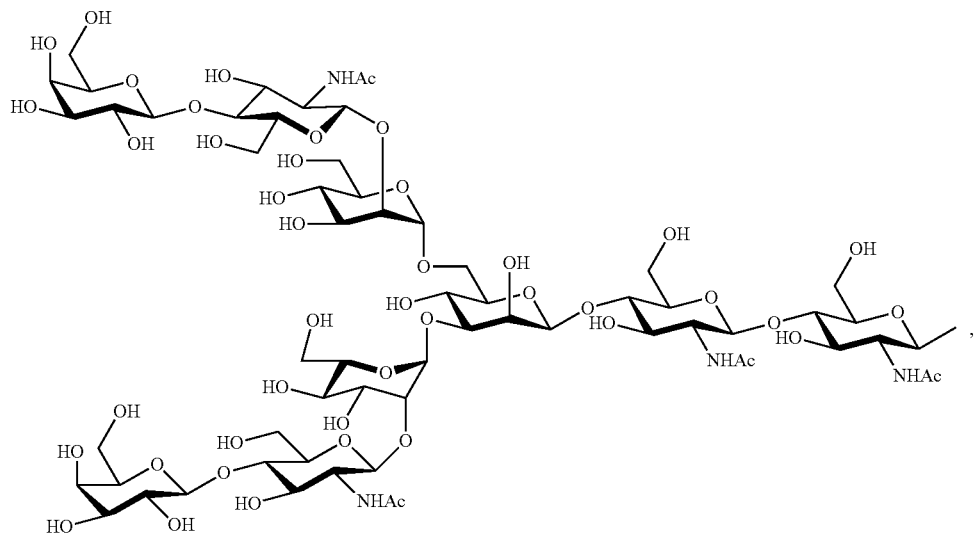

a diGlcNAc sugar chain:

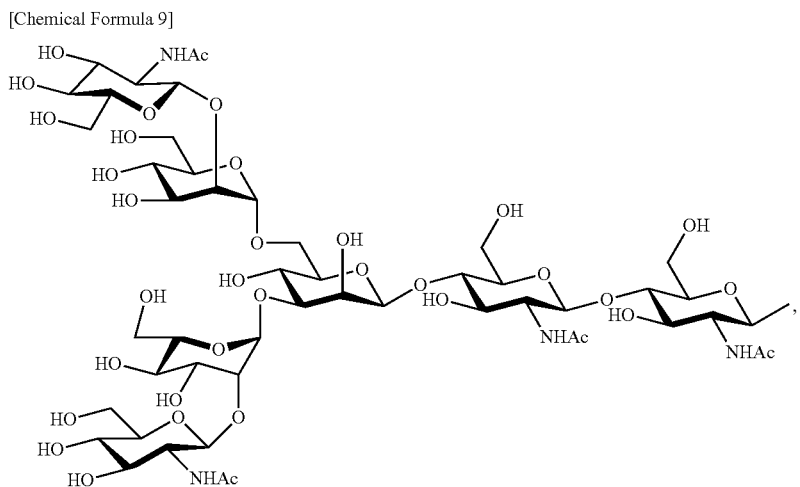

and a dimannose sugar chain:

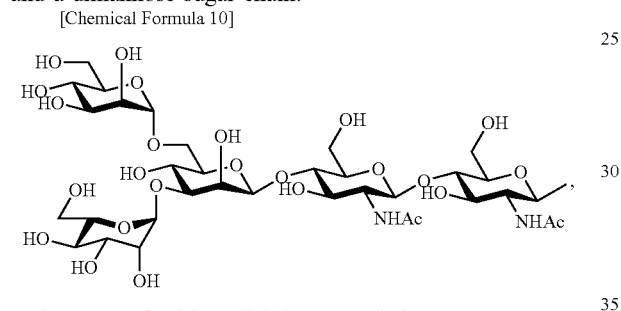

and more preferably a disialo sugar chain.

Moreover, the complex-type sugar chain of the present invention includes not only the above biantennary complex-type sugar chains, but also a triantennary complex-type sugar chain (triple-branched complex-type sugar chain) and a tetraantennary complex-type sugar chain (quadruple-branched complex-type sugar chain). For example, triantennary and tetraantennary complex-type sugar chains can include a trisialo sugar chain represented by the structural formula below:

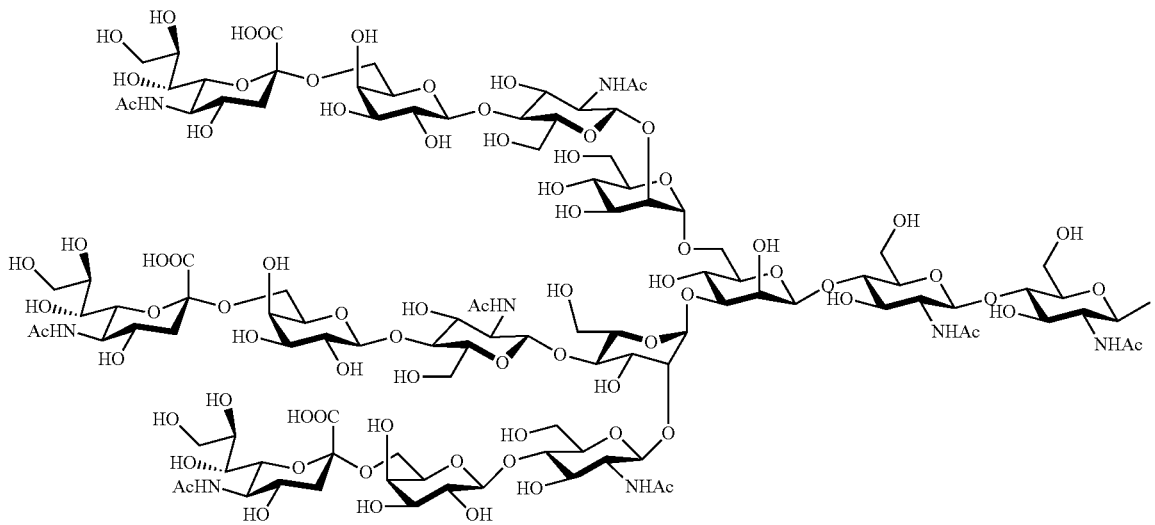

[Chemical Formula-2]

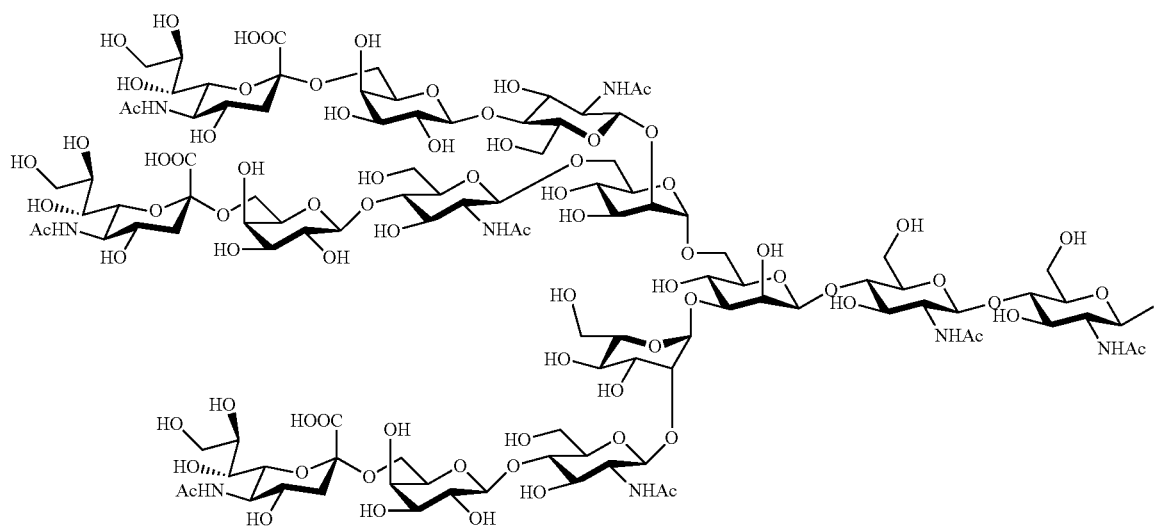

and a tetrasialo sugar chain represented by the structural formula below:

[Chemical Formula-3]

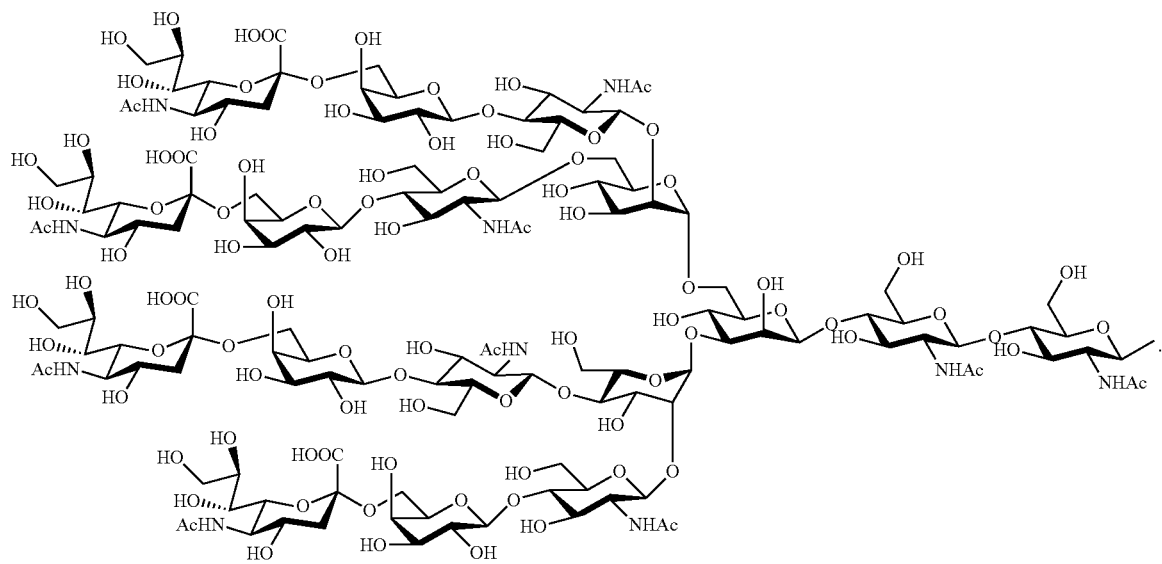

Moreover, triantennary and tetraantennary complex-type sugar chains can also include a sugar chain having one or more sugars deleted from the non-reducing terminal of these trisialo or tetrasialo sugar chains.

Further, the complex-type sugar chain of the present invention includes those with a fucose added. Complex-type sugar chains with a fucose added can include fucose-containing complex-type sugar chains represented by the structural formula below:

[Chemical Formula-4]
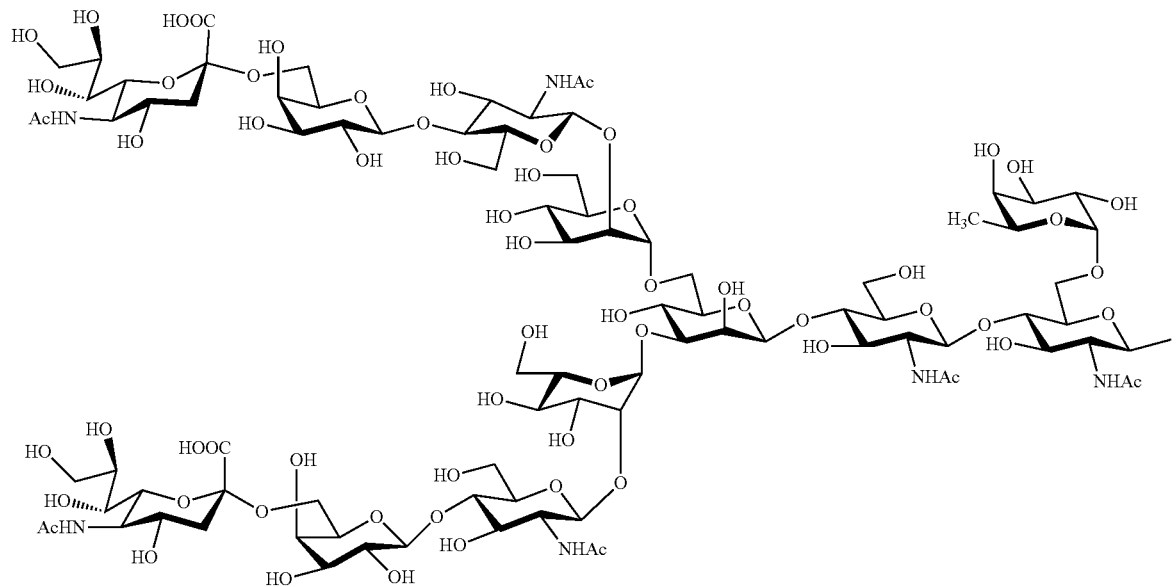
[Chemical Formula-5]
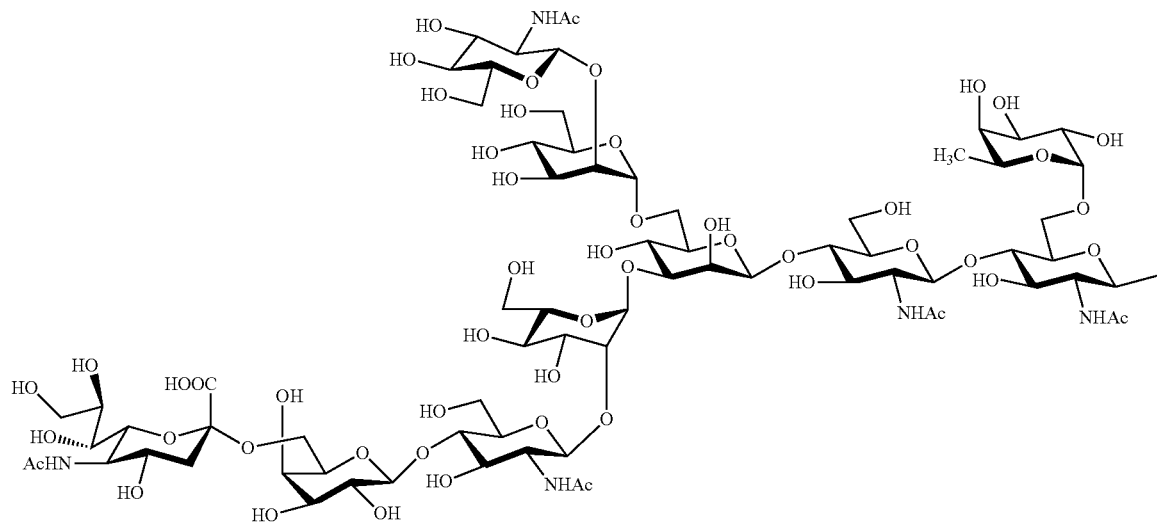

[Chemical Formula-6]
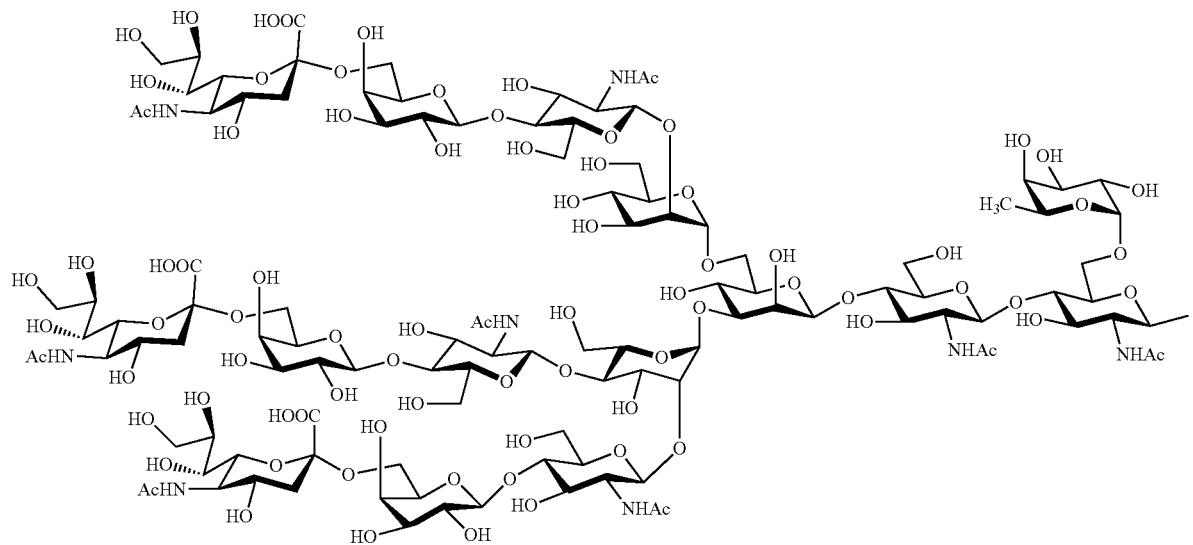
[Chemical Formula-7]
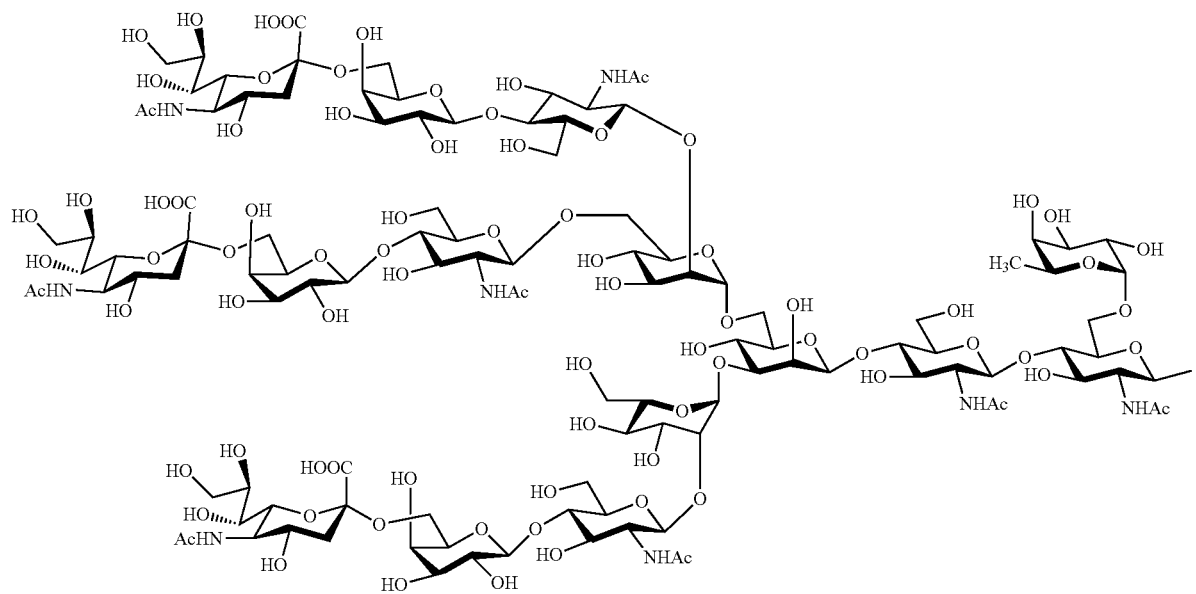

[Chemical Formula-8]

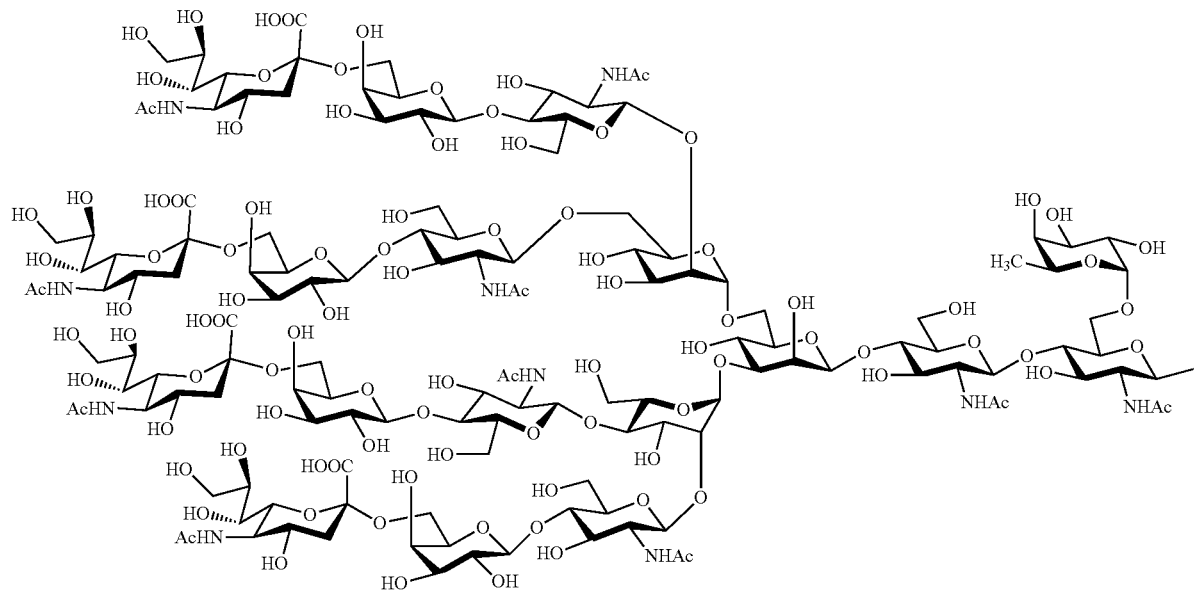

Moreover, a sugar chain having one or more sugars deleted from the non-reducing terminal of these fucose-containing complex-type sugar chains can also be included.

Moreover, a "disialo sugar chain," a "biantennary complex-type sugar chain," a "monosialo sugar chain," an "asialo sugar chain," a "diGlcNAc sugar chain," a "dimannose sugar chain," a "triantennary complex-type sugar chain," a "tetraantennary complex-type sugar chain," and a "fucose-containing complex-type sugar chain" herein include not only those shown in the above chemical formulae, but also those with a binding mode different from examples shown in the chemical formulae, and such sugar chains are also preferably employed as a sugar chain of the present invention. Examples of such sugar chains include, e.g., a disialo or monosialo sugar chain, in which sialic acid and galactose are bound with an (α2→3) bond.

Moreover, when the sugar chain is one having a sialic acid at the non-reducing terminal of the sugar chain, a sugar chain having the carboxy group of the sialic acid modified can also be employed. The modification of the carboxy group of the sialic acid is preferably a group capable of dissipating the negative charge of the carboxy group or converting it into positive charge, examples of which can include, e.g., an alkylamino group, a benzyl group, an amino group, and an aminoethylamino group, having 1-30 carbons. The introduction of these modifying groups will dissipate the negative charge of the carboxyl group of the sialic acid (such as benzyl or amino group) or convert it into positive charge (such as aminoethylamino group), and it is thus possible to contemplate blood clearance or control of body distribution of glycosylated polypeptide.

Moreover, the high-mannose sugar chain employed herein is a sugar chain having 2 or more mannoses further bound to the basic structure of the complex-type sugar chain described above. Because high-mannose sugar chains are bulky, stability in blood may become higher by binding a high-mannose sugar chain to the peptide. A sugar chain comprising 5-9 mannoses such as a mammalian high-mannose sugar chain is preferred, but it may be a sugar chain comprising more mannoses such as a yeast high-mannose sugar chain. Examples of high-mannose sugar chains preferably employed herein can include, e.g., high-mannose-5 (M-5):

[Chemical Formula 11]

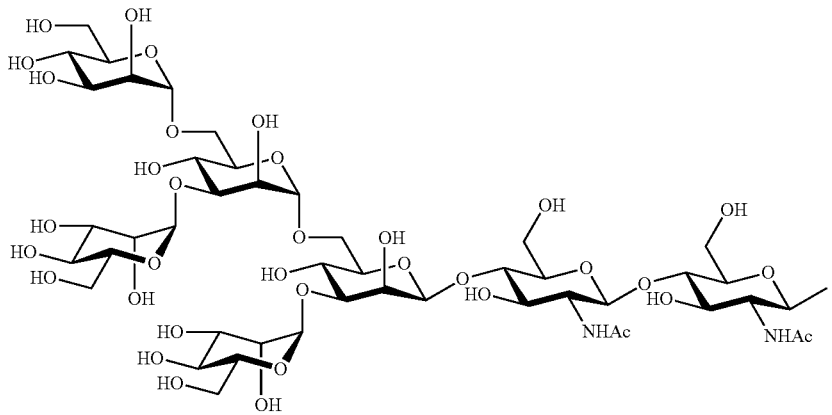

and high-mannose-9 (M-9):

[Chemical Formula 12]

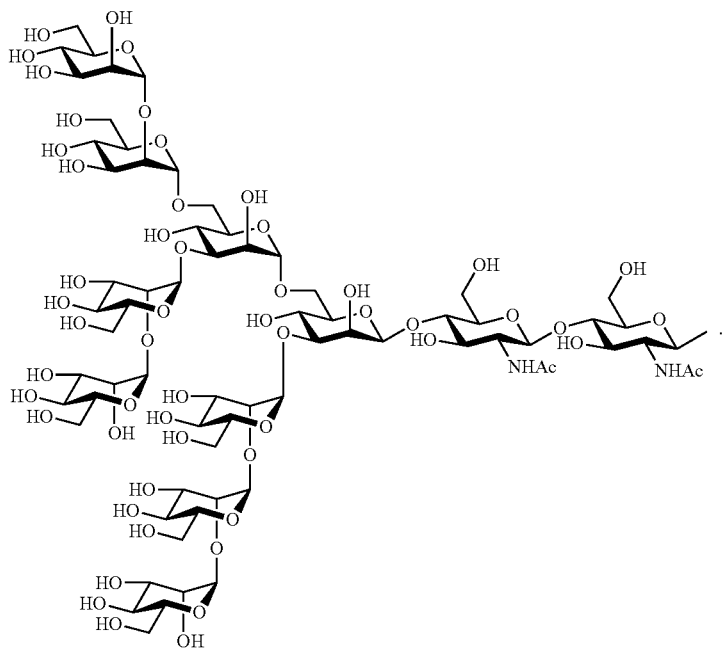

30

Preferred sugar chains herein can include, e.g., the sugar chains described below which are a sugar chain having an identical structure (a sugar chain in which the type of constituent sugar and the binding mode thereof are identical) with a sugar chain that exists in a human body as a glycoprotein bound to a protein (such as a, sugar chain described in "FEBS LETTERS Vol. 50, No. 3, February 1975"), or a sugar chain having one or more sugars deleted from the non-reducing terminal of the same.

[Chemical Formula 13]

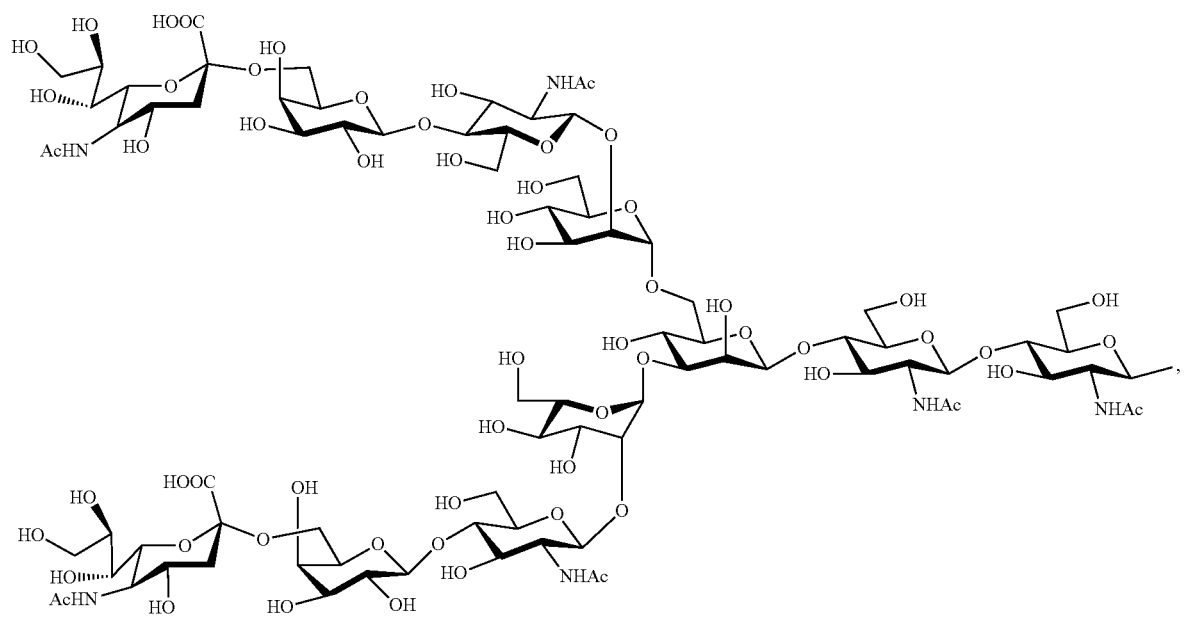

1

IS2S-11NC

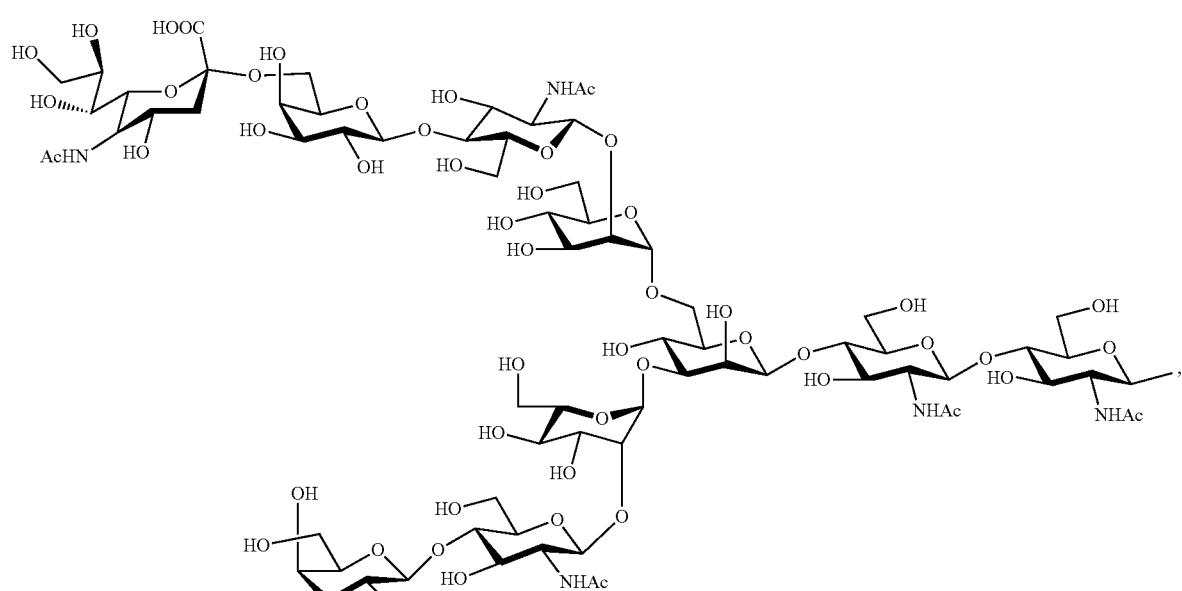
IS2G-10NC
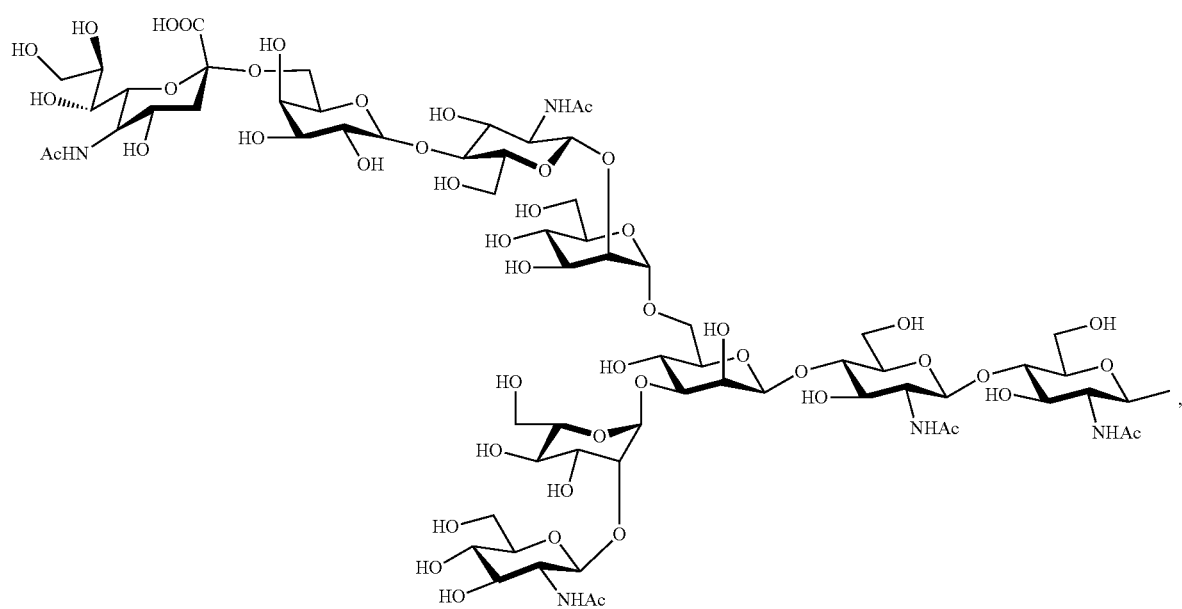
1S2GN-9NC

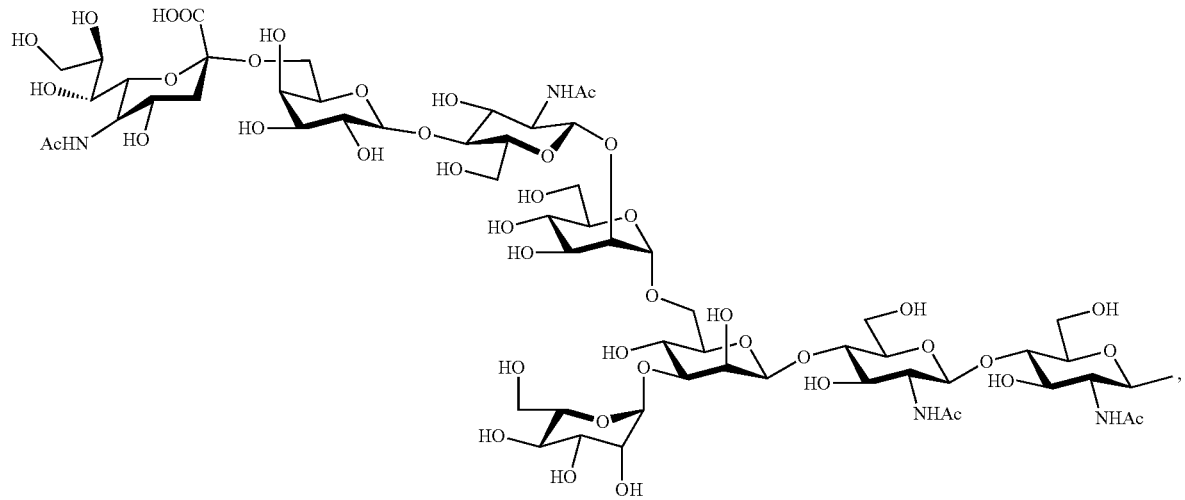
1S2M-8NC
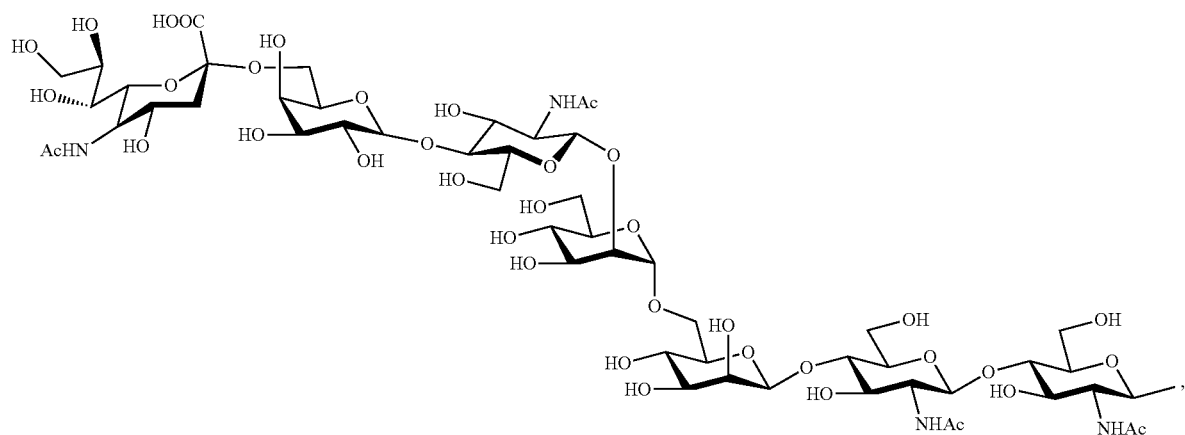
1S-7NC

-continued
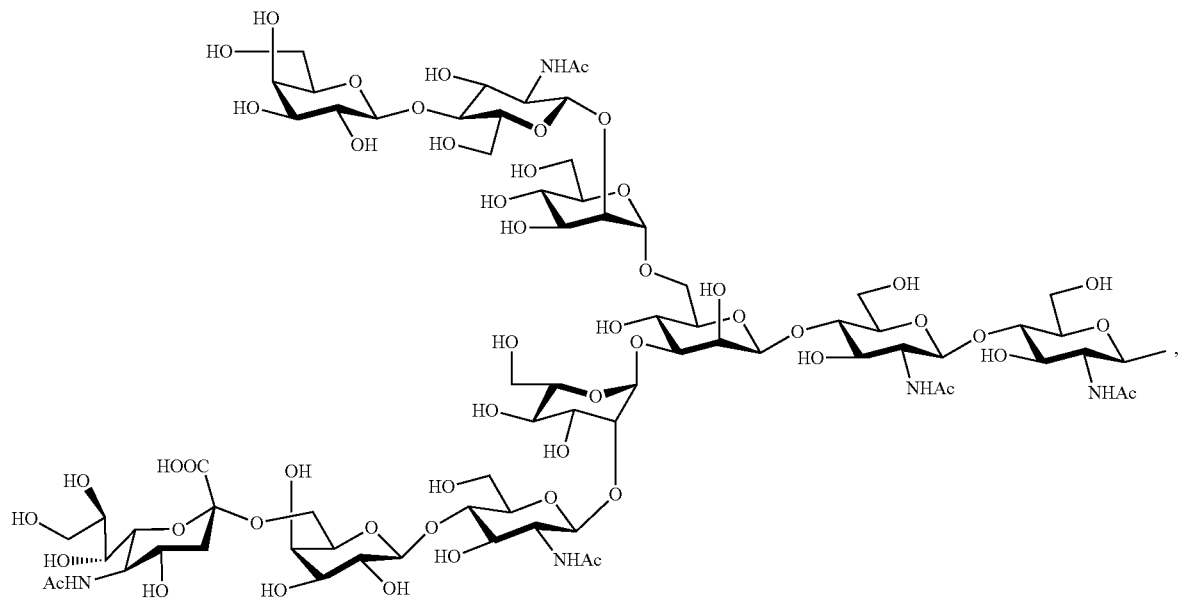
1G2S-10NC
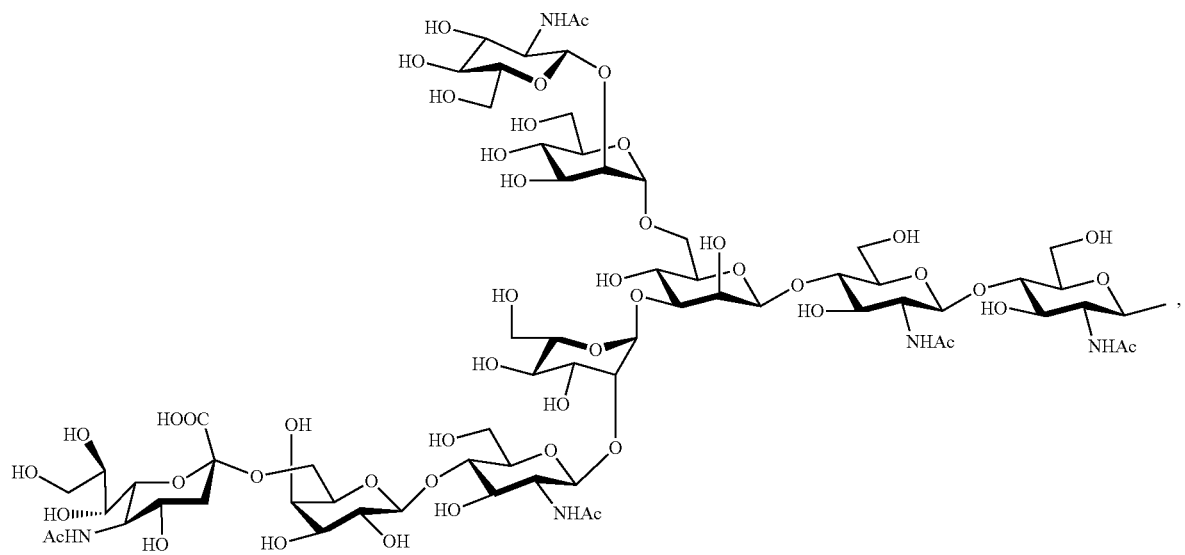
1GN2S-9NC

-continued
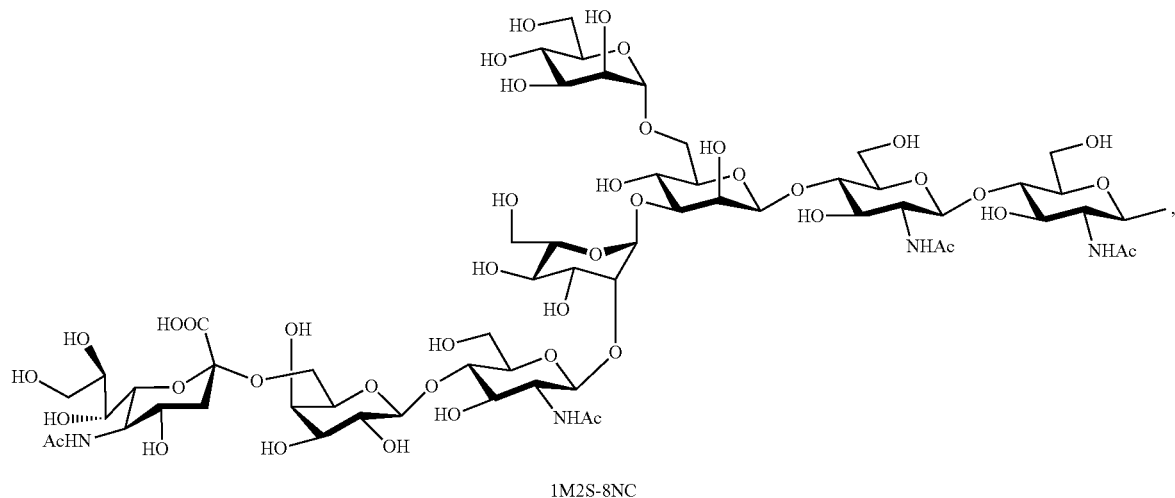
1M2S-8NC
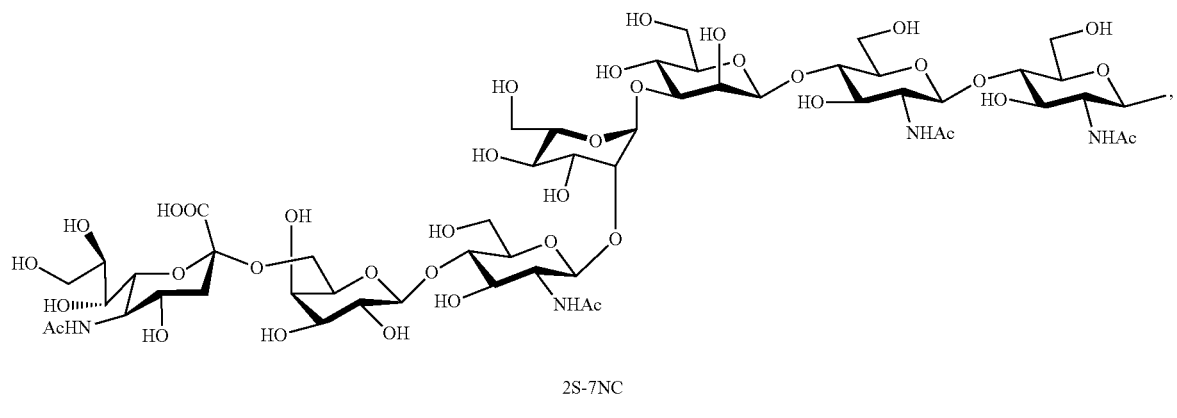
2S-7NC
[Chemical Formula 14]
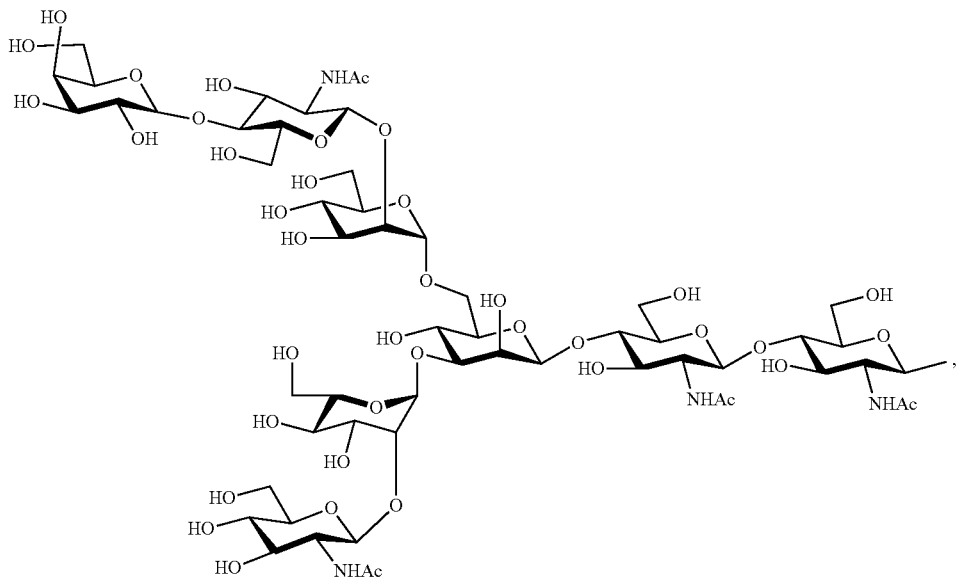
1G2GN-8NC -continued
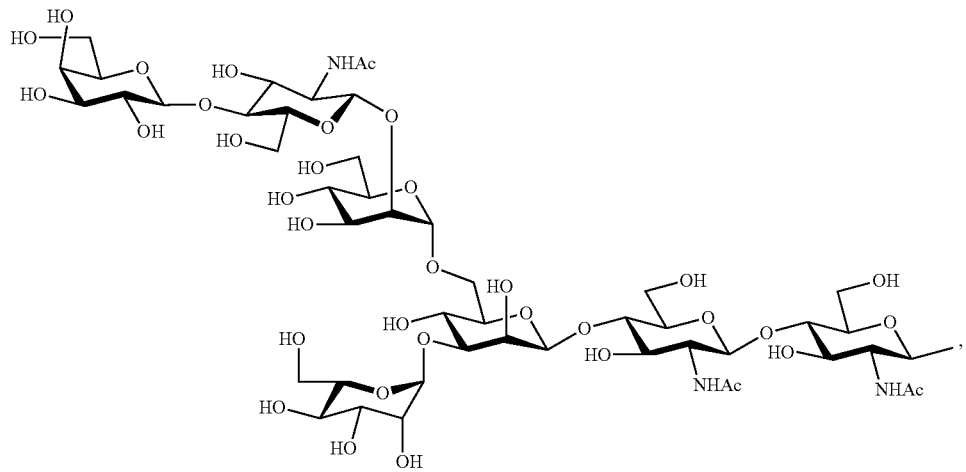
1G2M-7NC
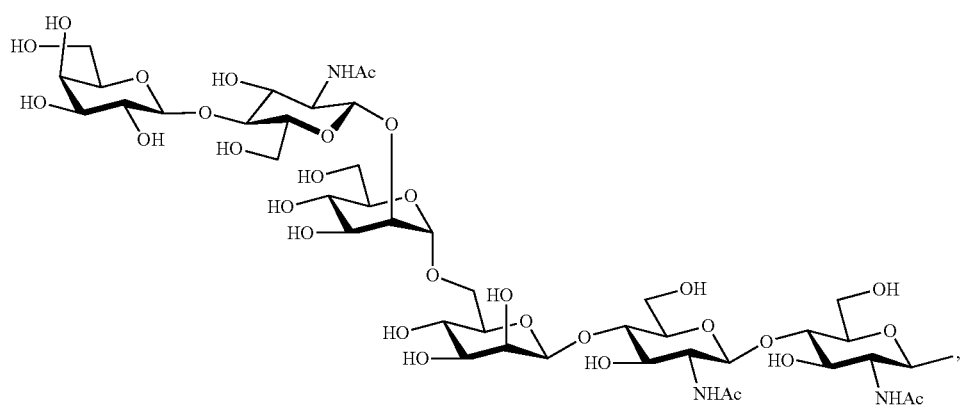
1G-6NC
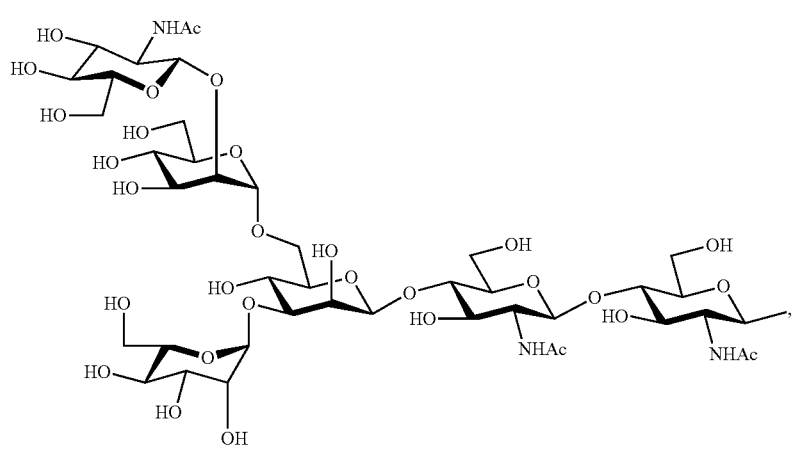
1GN2M-6NC -continued
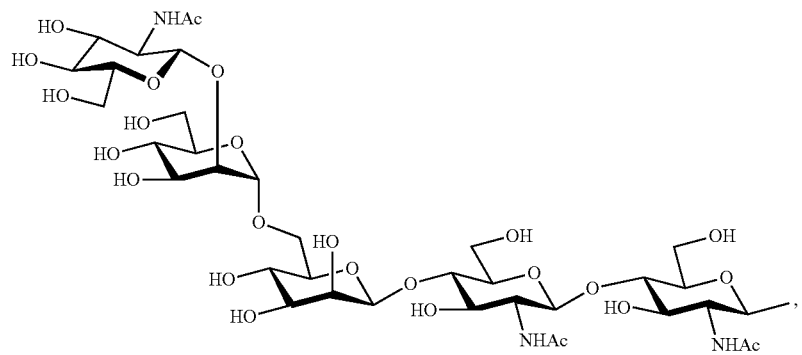
1GN-5NC
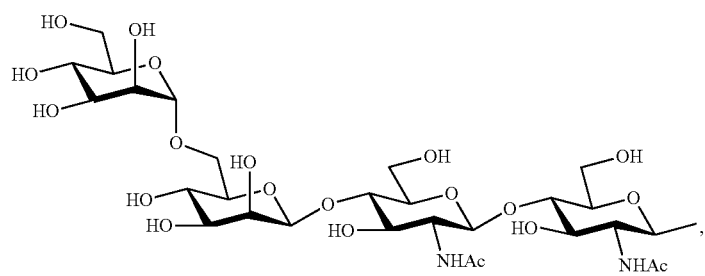
1M-4NC
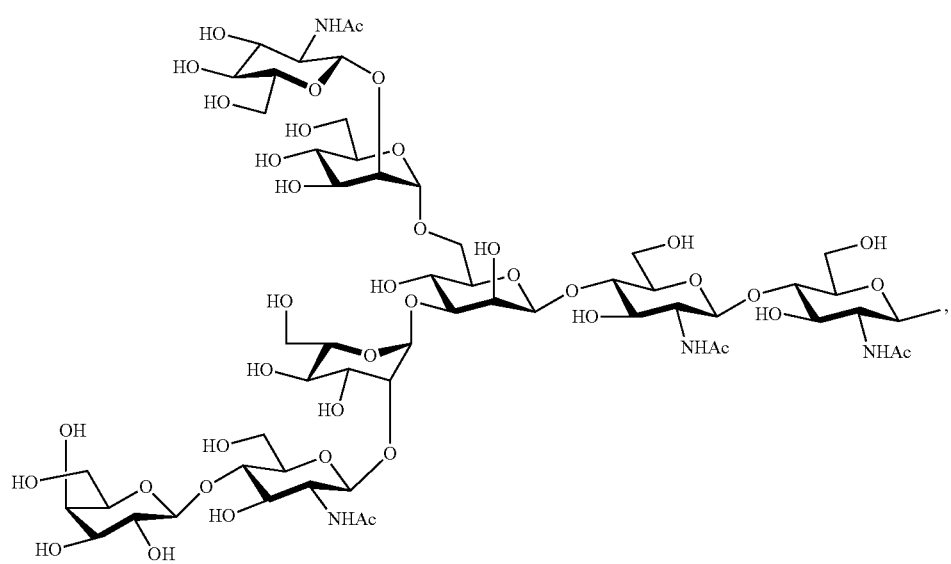
1GN2G-8NC -continued
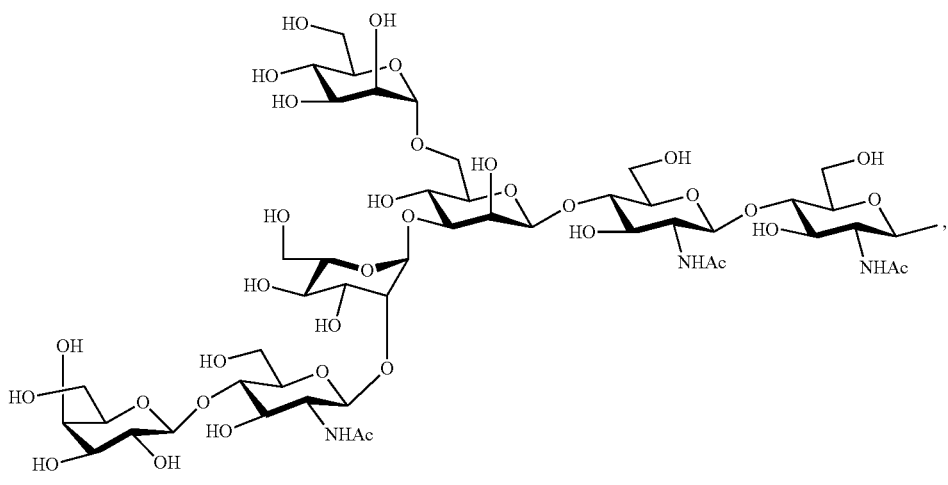
1M2G-7NC
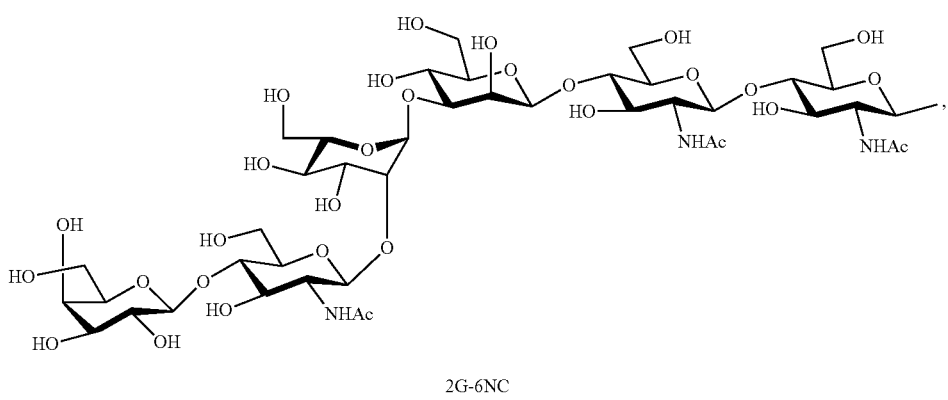
2G-6NC
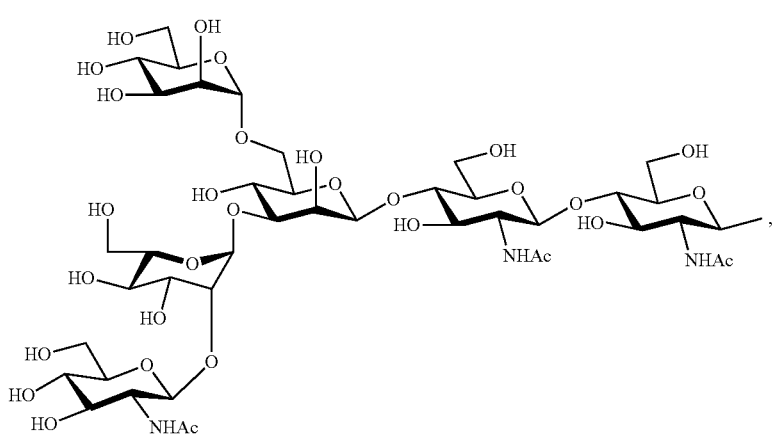
1M2GN-5NC -continued
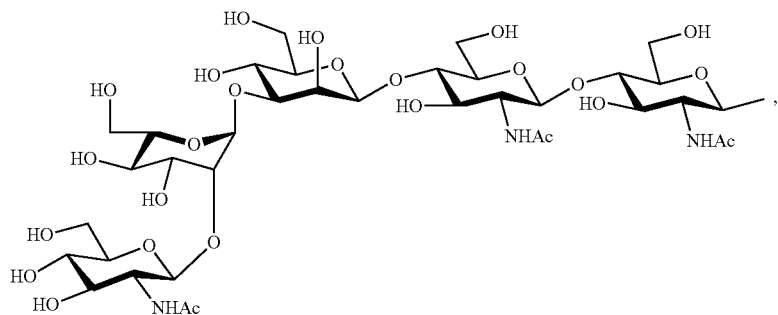
2GN-5NC
20
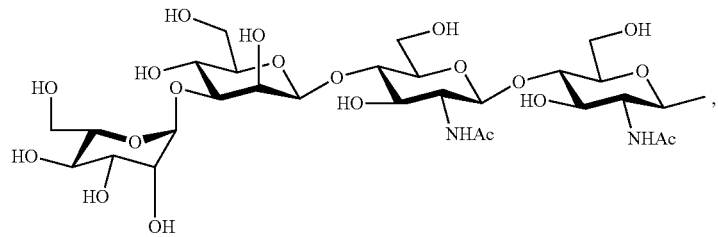
2M-4NC
21
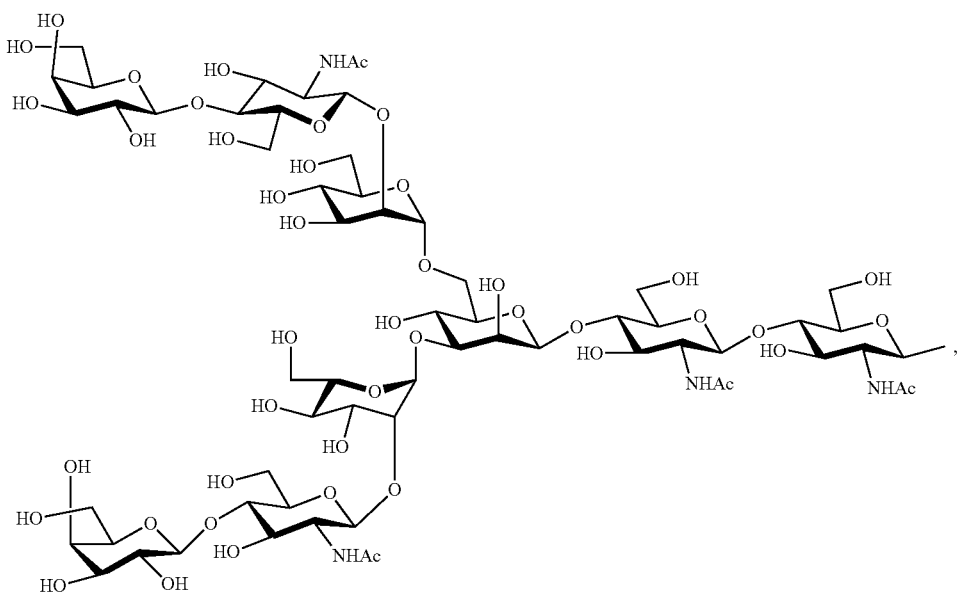
1G2G-9NC
22

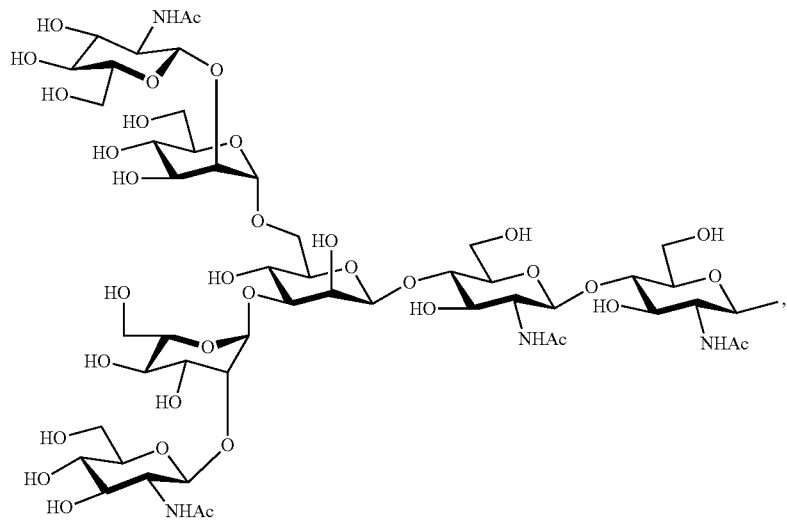
1GN2GN-7NC
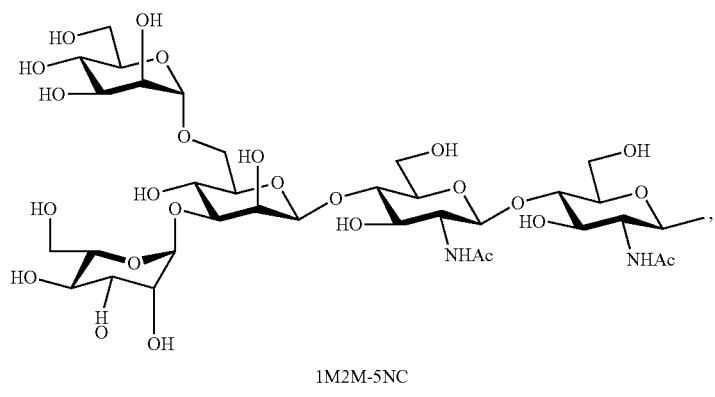
1M2M-5NC
[Chemical Formula 15]
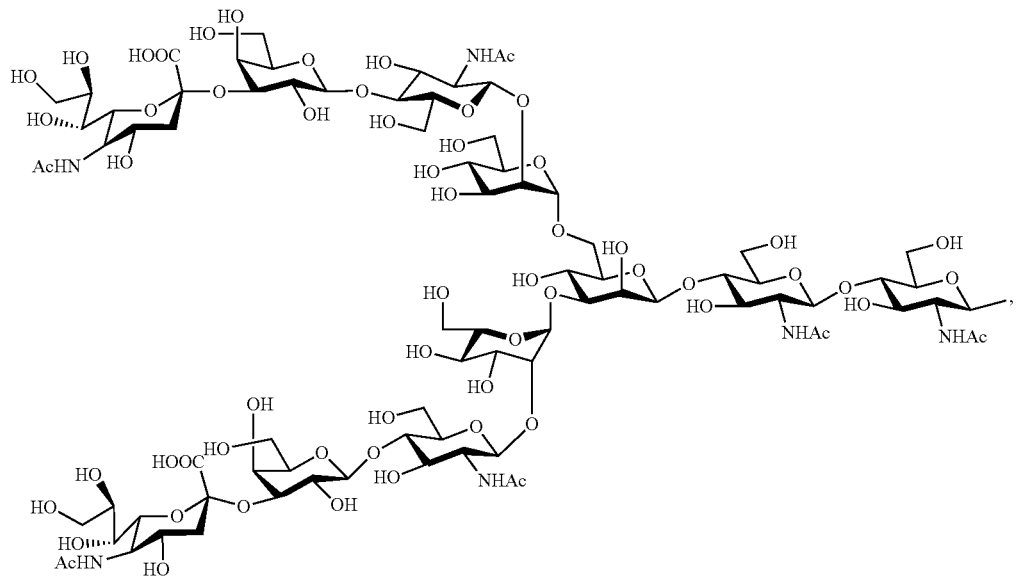
1S(3)2S(3)-11NC

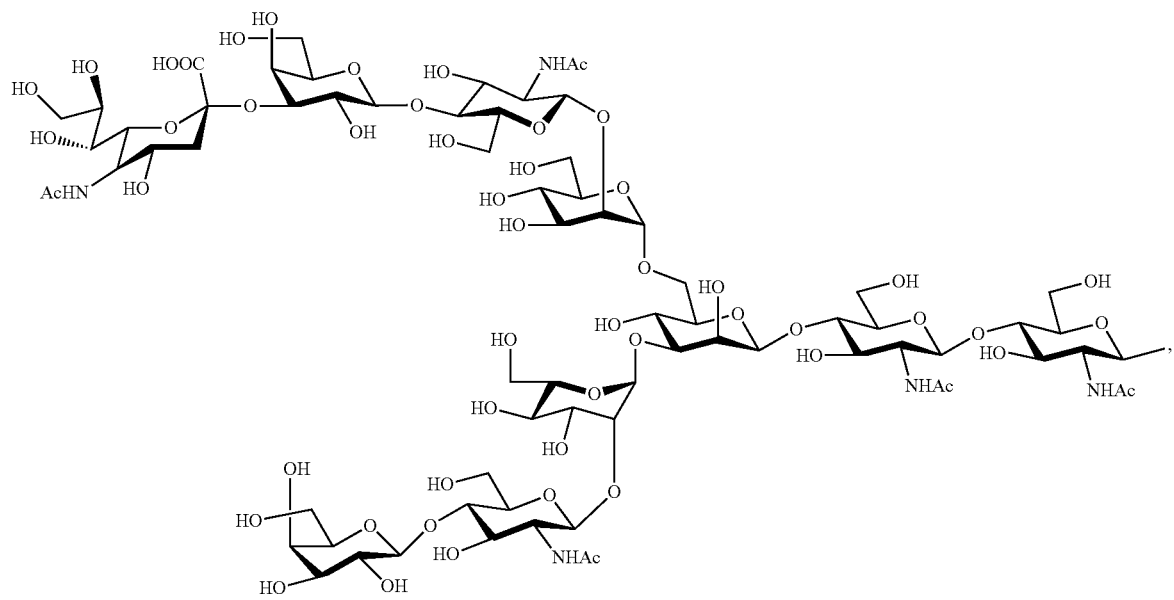
1S(3)2G-10NC
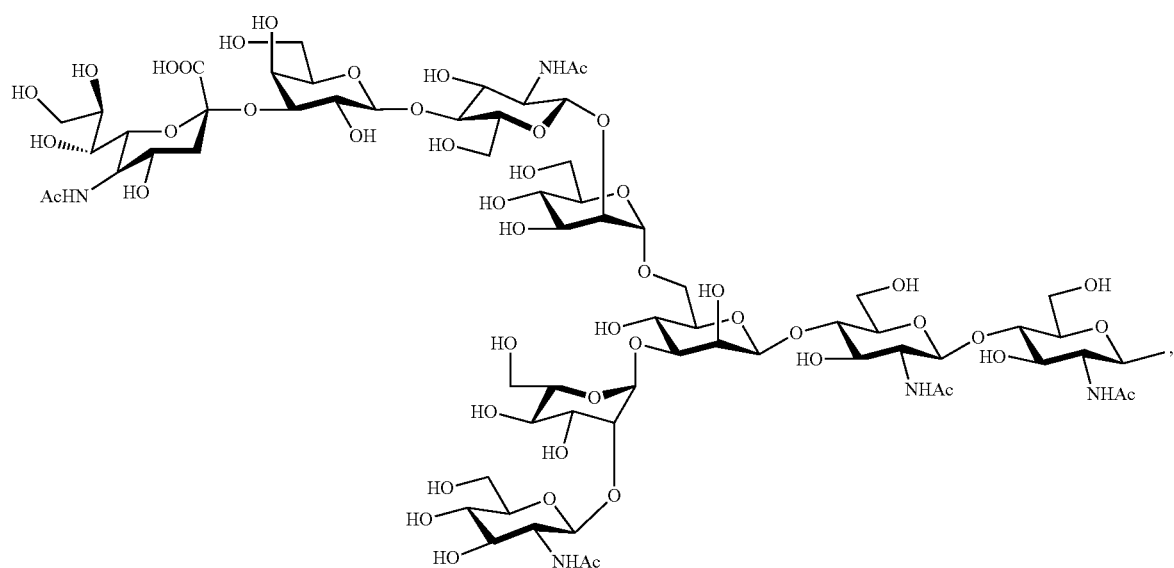
1S(3)2GN-9NC

-continued
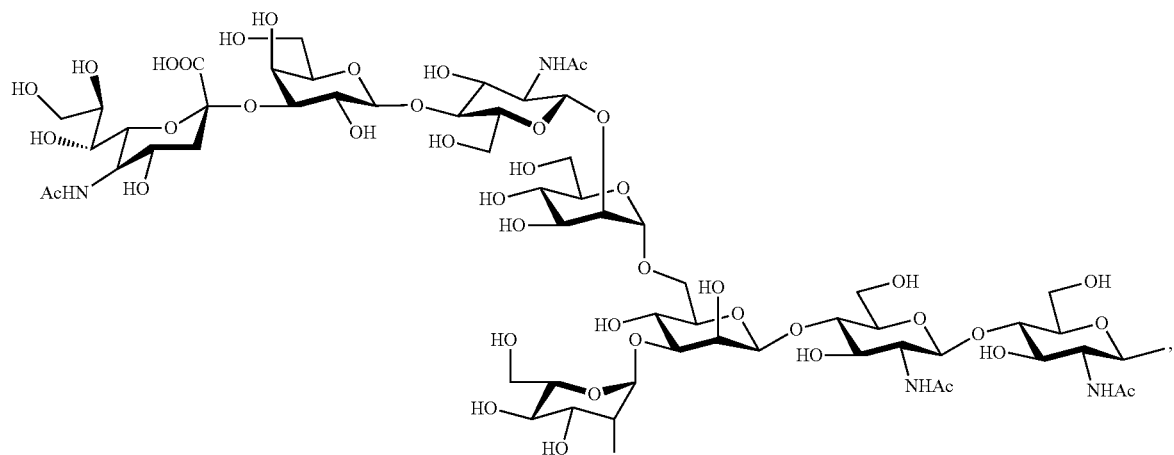
1S(3)2M-8NC
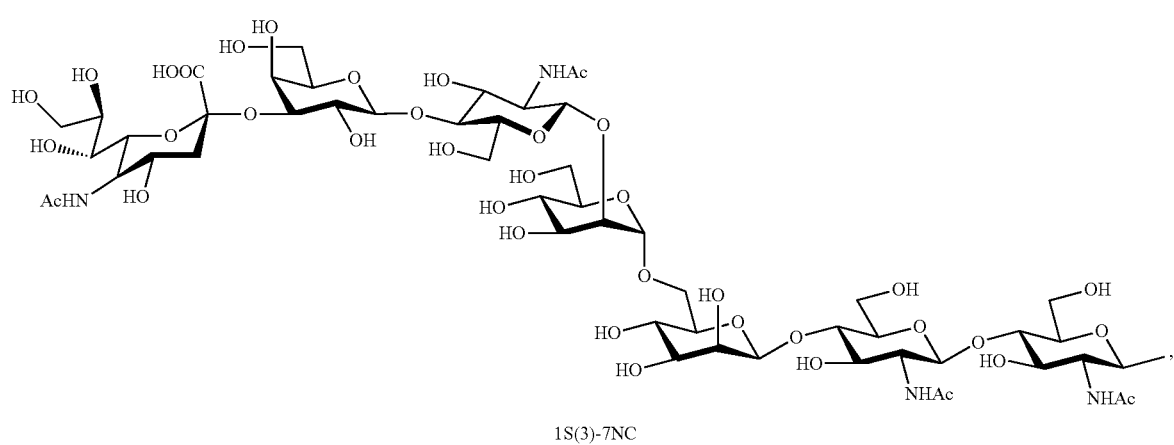
1S(3)-7NC
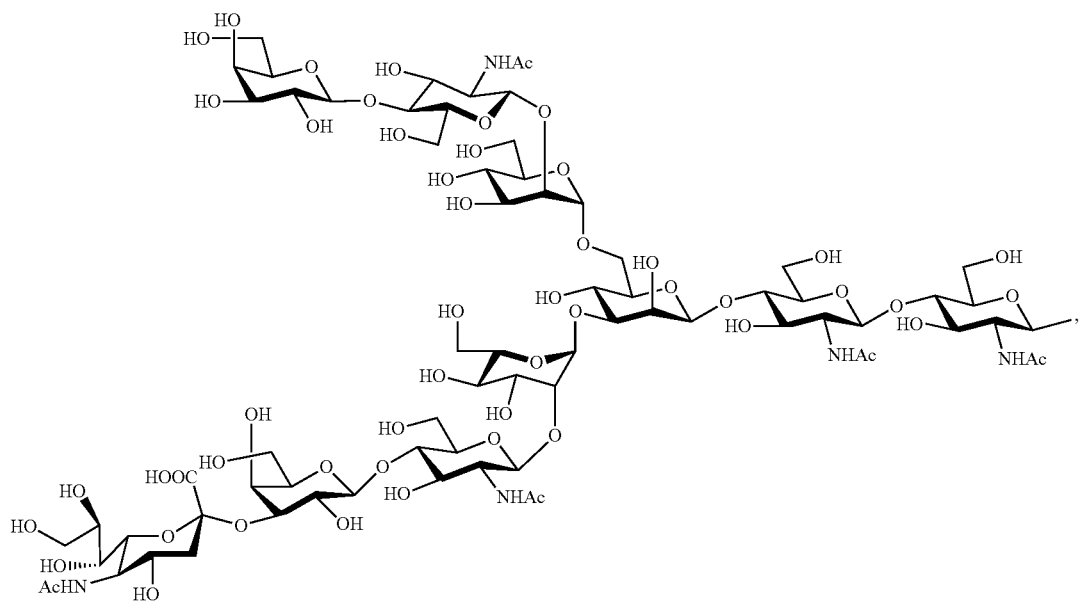
1G2S(3)-10NC

-continued
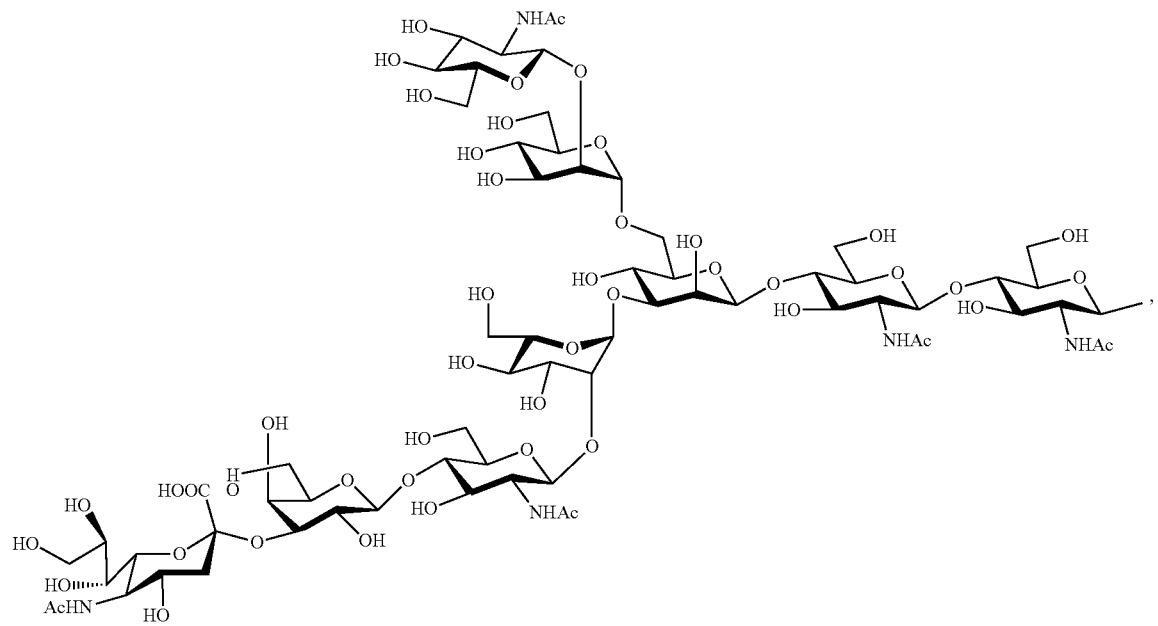
1GN2S(3)-9NC
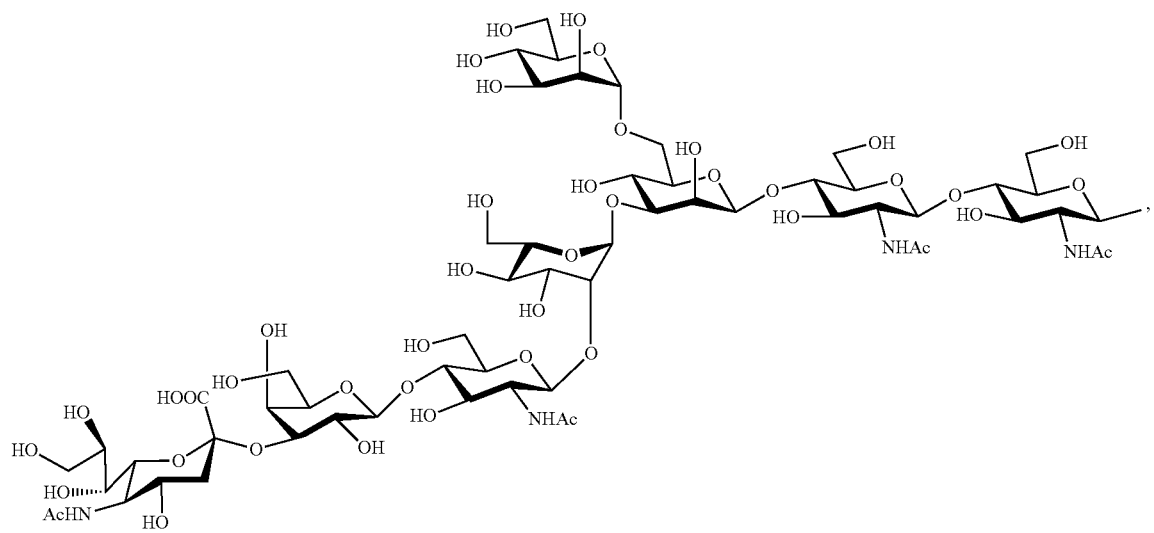
1M2S(3)-8NC

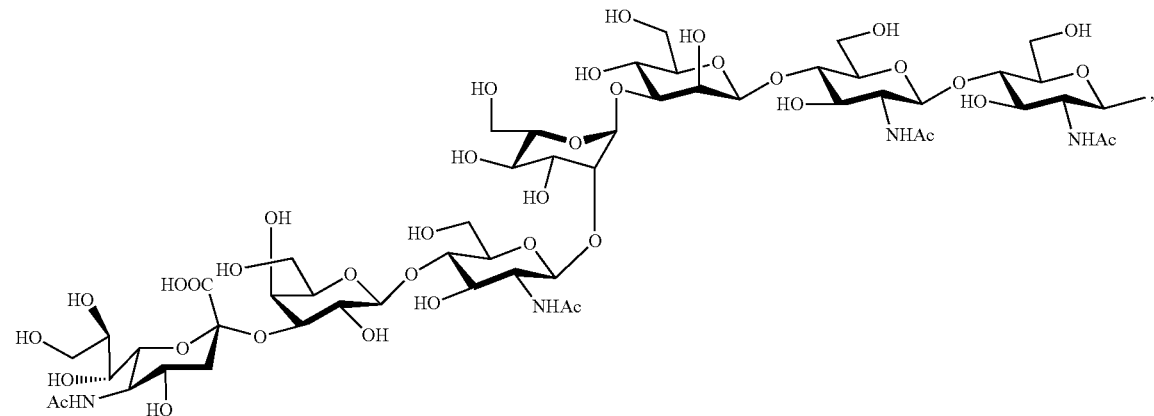
33
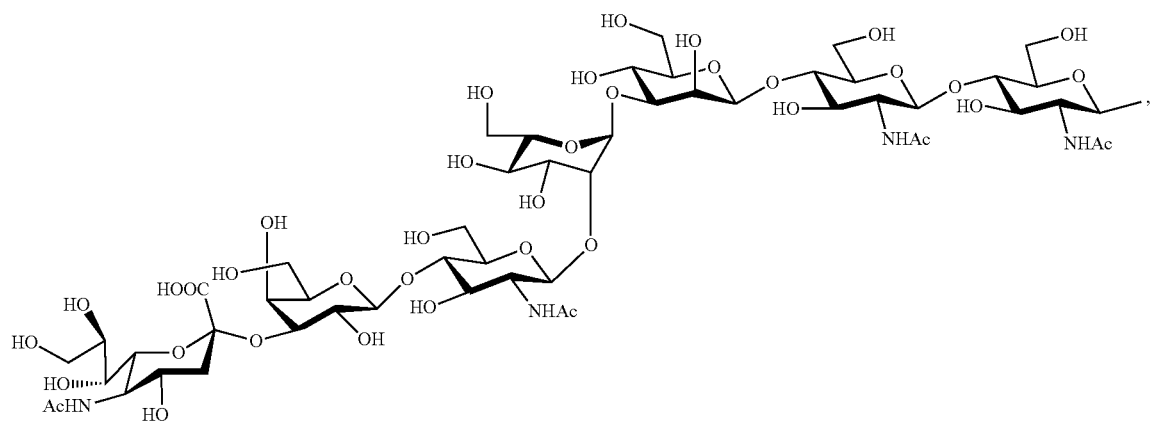
2S(3)-7NC
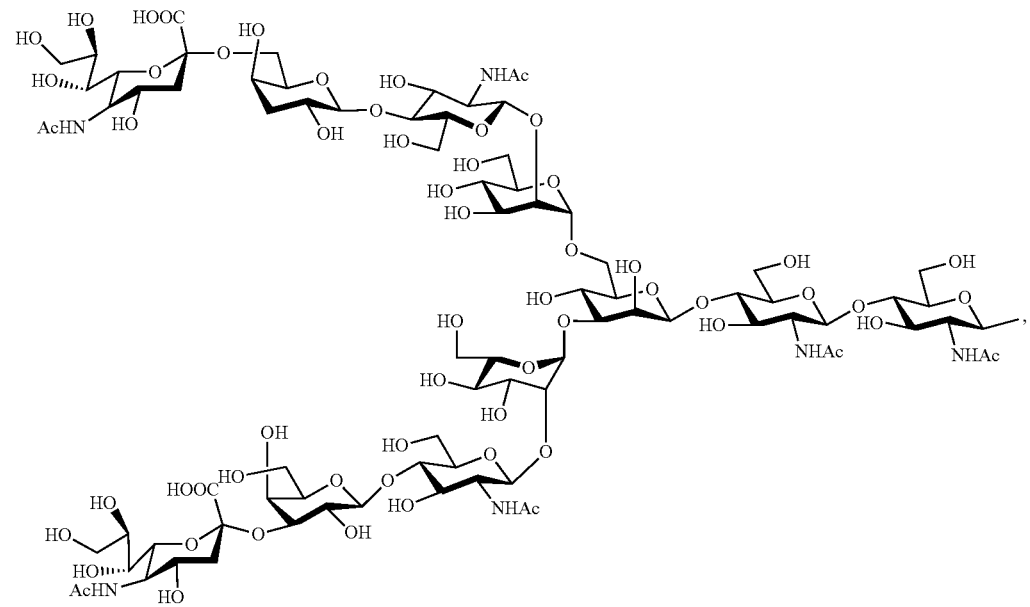
34
1S2S(3)-11NC

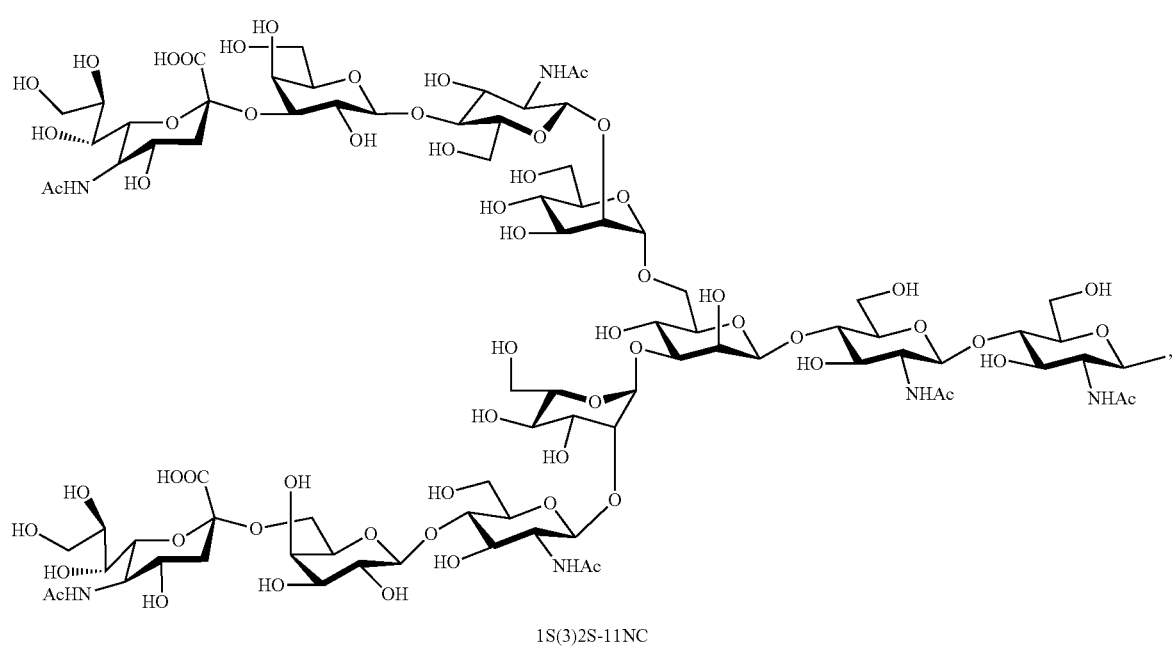

1S(3)2S-11NC

In one preferred aspect of the present invention, the sugar chain structure of the glycosylated amino acids in the glycosylated polypeptide of the present invention can be substantially identical, or they may have different sugar chain structures. When the sugar chain structure in the glycosylated polypeptide is substantially identical, they are preferably e.g. 90% or more identical or 99% or more identical, and it is most preferable that the sugar chain structure is completely identical. As used herein, the sugar chain structure in the glycopeptide is identical refers to the fact that in a glycosylated polypeptide having two or more sugar chains added, the type of sugar constituting the sugar chain, the binding order, and the binding mode are identical in the glycopeptide when said sugar chains are compared with each other. Moreover, in one preferred aspect of the present invention, it is preferred that the sugar chains of the glycosylated polypeptide of the present invention are uniform. As used herein, the sugar chains in the glycosylated polypeptide are uniform refers to the fact that the glycosylation sites in the peptide, the type of each sugar constituting the sugar chain, the binding order, and the binding mode between sugars are identical between glycopeptides when sugar chains are compared between glycosylated polypeptides, and that at least 90% or more, preferably 95% or more, and more preferably 99% or more of the sugar chain structure is uniform. In particular, a composition etc. comprising a glycopeptide in which the sugar chains are uniform between glycopeptides has a constant quality, and is preferred particularly in fields such as pharmaceuticals manufacture or assays. The proportion of the uniform sugar chain can be measured for example by a method employing e.g. HPLC, capillary electrophoresis, NMR, and mass spectrometry.

The preferred glycosylated polypeptides herein are the glycosylated polypeptides (SEQ ID NOs. 21-26, 29, 30, 33, 34, 88, 89, 125, 127, 129, 148, 149, 157, 164, and 169) manufactured in Examples 20-25, 28, 29, 32-35, 49-51, 63-64, and 66-68 described below. In other words, in the following. SRIF28 amino acid sequence: $Ser_1$-$Ala_2$-$Asn_3$-$Ser_4$-$Asn_5$-$Pro_6$-$Ala_7$-$Met_8$-$Ala_9$-$Pro_{10}$-$Arg_{11}$-$Glu_{12}$-$Arg_{13}$-$Lys_{14}$-$Ala_{15}$-$Glyl_{16}$-$Cys_{17}$-$Lys_{18}$-$Asn_{19}$-$Phe_{20}$-$Phe_{21}$-$Trp_{22}$-$Lys_{23}$-$Thr_{24}$-$Phe_{25}$-$Thr_{26}$-$Ser_{27}$-$Cys_{28}$ (SEQ ID NO. 2), (a1) a glycosylated polypeptide having disialo sugar chain attached Cys substituted for Ser at position 1, and having one disialo sugar chain attached Cys further added at the N-terminal side (Example 20) (SEQ ID NO. 21);

(a2) a glycosylated polypeptide having disialo sugar chain attached Cys substituted for Ser at position 1 and Asn at position 5 (Example 21) (SEQ ID NO. 22);

(a3) a glycosylated polypeptide having disialo sugar chain attached Cys substituted for Ser at position 1 and Arg at position 13 (Example 22) (SEQ ID NO. 23);

(a4) a glycosylated polypeptide having disialo sugar chain attached Cys substituted for Asn at position 5 and Ala at position 9 (Example 23) (SEQ ID NO. 24);

(a5) a glycosylated polypeptide having disialo sugar chain attached Cys substituted for Ser at position 1, and having two disialo sugar chain attached Cys further added at the N-terminal side (Example 24) (SEQ ID NO. 25);

(a6) a glycosylated polypeptide having disialo sugar chain attached Cys substituted for Ser at position 1, Asn at position 5, and Ala at position 9 (Example 25) (SEQ ID NO. 26);

(a7) a glycosylated polypeptide having asialo sugar chain attached Cys substituted for Ser at position 1, and having one asialo sugar chain attached Cys further added at the N-terminal side (Example 28) (SEQ ID NO. 29);

(a8) a glycosylated polypeptide having asialo sugar chain attached Cys substituted for Ser at position 1, and having two asialo sugar chain attached Cys further added at the N-terminal side (Example 29) (SEQ ID NO. 30);

(a9) a glycosylated polypeptide having disialo sugar chain attached Cys substituted for Ser at position 1, and having GlcNAc-added Cys substituted for Asn at position 19 (Example 32) (SEQ ID NO. 33);

(a10) a glycosylated polypeptide having disialo sugar chain attached Cys substituted for Ser at position 1, and having dimannose glycosylated Cys substituted for Asn at position 19 (Example 33) (SEQ ID NO. 34);

(a11) a glycosylated polypeptide having disialo sugar chain attached Cys substituted for Ser at position 1, and having four disialo sugar chain attached Cys further added at the N-terminal side (Example 34) (SEQ ID NO. 88);

(a12) a glycosylated polypeptide having disialo sugar chain attached Cys substituted for Ser at position 1, and having nine disialo sugar chain attached Cys further added at the N-terminal side (Example 35) (SEQ ID NO. 89);

(a13) a glycosylated polypeptide having disialo sugar chain attached Cys substituted for Ser at position 1 and Glu at position 12 (Example 49) (SEQ ID NO. 125);

(a14) a glycosylated polypeptide having disialo sugar chain attached Cys substituted for Ser at position 1 in which the carboxy group of the sialic acid on the sugar chain is converted into carboxylic amide, and having one disialo sugar chain attached Cys further added at the N-terminal side in which the carboxy group of the sialic acid on the sugar chain is converted into carboxylic amide (Example 63) (SEQ ID NO. 148);

(a15) a glycosylated polypeptide having disialo sugar chain attached Cys substituted for Ser at position 1 in which the carboxy group of the sialic acid on the sugar chain is protected by a benzyl group, and having one disialo sugar chain attached Cys further added at the N-terminal side in which the carboxy group of the sialic acid on the sugar chain is protected by a benzyl group (Example 64) (SEQ ID NO. 149);

(a16) a glycosylated polypeptide having disialo sugar chain attached Asn substituted for Ser at position 1, and having dimannose glycosylated Cys substituted for Asn at position 19 (Example 66) (SEQ ID NO. 157);

(a17) a glycosylated polypeptide having disialo sugar chain attached Cys substituted for Ser at position 1, and having one disialo sugar chain attached Cys further added at the N-terminal side in which the carboxy group of the sialic acid on the sugar chain has formed an amide bond with one end of 1,2-ethylenediamine (Example 67) (SEQ ID NO. 164); and (a18) a glycosylated polypeptide having disialo sugar chain attached Cys substituted for Ser at position 1, and having three disialo sugar chain attached Cys further added at the N-terminal side (Example 68) (SEQ ID NO. 169) are preferred.

Moreover, in the SRIF14 amino acid sequence: $Ala_{15}$-$Gly_{16}$-$Cys_{17}$-$Lys_{18}$-$Asn_{19}$-$Phe_{20}$-$Phe_{21}$-$Trp_{22}$-$Lys_{23}$-$Thr_{24}$-$Phe_{25}$-$Thr_{26}$-$Ser_{27}$-$Cys_{28}$ (SEQ ID NO. 1).

(a19) a glycosylated polypeptide having disialo sugar chain attached Cys-disialo sugar chain attached Cys-Arg-Lys-further added at the N-terminal side of Ala at position 15 (Example 50) (SEQ ID NO. 127); and (a20) a glycosylated polypeptide having disialo sugar chain attached Cys-disialo sugar chain attached Cys-disialo sugar chain attached Cys-Arg-Lys- further added at the N-terminal side of Ala at position 15 (Example 51) (SEQ ID NO. 129) are preferred.

The glycosylated polypeptide of the present invention can be manufactured by integrating a glycosylation step into a peptide synthesis method well-known to those skilled in the art. A method utilizing an enzyme represented by transglutaminase can also be employed for glycosylation, but since there are problems in this case such as the need for a large amount of the sugar chain to be added, the complication of purification after the final step, and the restriction for glycosylation position and the sugar chain capable of addition, it cannot be said to be a practical method for large scale manufacturing such as pharmaceuticals manufacture though it is possible to employ for synthesis of a small amount such as for assays.

As specific examples of simple manufacturing methods of the glycosylated polypeptide of the present invention which are stable manufacturing methods of a glycosylated polypeptide having uniform sugar chain structure, a method for manufacturing a glycosylated polypeptide by using glycosylated Asn as the glycosylated amino acid and applying a well-known peptide synthesis method such as solid and liquid phase synthesis (method A), and a method for manufacturing a glycosylated polypeptide by manufacturing a peptide in which any amino acid of somatostatin is substituted with Cys according to a well-known peptide synthesis method, and then adding a sugar chain to Cys by chemical synthesis (method B) will be exemplified below. Those skilled in the art is able to manufacture various glycosylated polypeptides by referring to these manufacturing methods, and the glycosylated polypeptide obtained and the manufacturing method thereof are extremely useful especially in the field of pharmaceuticals manufacture.

Moreover, these methods A and B can be performed in a combination of two or more. If it is a synthesis of a small amount such as for assays, it is also possible to further combine the above method employing a sugar chain elongation reaction by a transferase. Method A is described in International Publication No. 2004/005330 (US 2005222382 (A1)) and method B is described in International Publication No. 2005/010053 (US 2007060543 (A1)), the disclosures of which are incorporated herein by reference in their entirety. Moreover, the manufacture of sugar chains having uniform sugar chain structure employed in methods A and B are described in e.g. International Publication No. 03/008431 (US 2004181054 (A1)), International Publication No. 2004/058984 (US 2006228784 (A1)), International Publication No. 2004/058824 (US 2006009421 (A1)), International Publication No. 2004/070046 (US 2006205039 (A1)), and International Publication No. 2007/011055, the disclosures of which are incorporated herein by reference in their entirety.

Method for Manufacturing Glycosylated Polypeptide (Method A)

The glycosylated polypeptide can be manufactured by for example a solid phase synthesis employing glycosylated Asn, the outline of which is shown below.

(1) The carboxy group of an amino acid having the amino group nitrogen protected with a lipophilic protecting group is bound to a resin. In this case, since the amino group nitrogen of the amino acid is protected with a lipophilic protecting group, self-condensation between amino acids is prevented, and the resin reacts with the amino acid to cause binding.

(2) The lipophilic protecting group of the reactant obtained is detached to form a free amino group.

(3) This free amino group and the carboxy group of any amino acid having the amino group nitrogen protected with a lipophilic protecting group are subjected to amidation reaction.

(4) The above lipophilic protecting group is detached to form a free amino group.

(5) By repeating the above steps (3) and (4) for once or more, a peptide in which any number of any amino acids are linked and having a resin bound at one end and a free amino group at the other end is obtained.

(6) Finally, by cleaving the resin with an acid, a peptide having the desired amino acid sequence can be obtained.

In (1), if glycosylated Asn having the amino group nitrogen protected with a lipophilic protecting group is employed instead of the amino acid having the amino group nitrogen protected with a lipophilic protecting group, and the carboxy group of said asparagine portion is reacted with the hydroxyl group of the resin, a peptide having a glycosylated Asn at the C-terminal can be obtained.

Moreover, after (2), or after repeating (3) and (4) for any number of times that is once or more, if glycosylated Asn having the amino group nitrogen protected with a lipophilic protecting group is employed instead of the amino acid having the amino group nitrogen protected with a lipophilic protecting group in (3), a sugar chain can be added at any position.

As such, by employing glycosylated Asn having the amino group nitrogen protected with a lipophilic protecting group instead of the amino acid having the amino group nitrogen protected with a lipophilic protecting group for twice or more times in any of steps (1) and (3), a peptide having a sugar chain added at any two or more positions can be obtained.

After binding the glycosylated amino acid, if the lipophilic protecting group is detached to form a free amino group, and step (6) is performed immediately thereafter, a peptide having a glycosylated Asn at the N-terminal can be obtained.

The resin may be a resin generally used in solid phase synthesis, and for example, 2-chlorotrityl chloride resin (from Merck) functionalized with chlorine, Amino-PEGA resin (from Merck) functionalized with an amino group, NovaSyn TGT alcohol resin (from Merck), Wang resin (from Merck), or HMPA-PEGA resin (from Merck) etc. having a hydroxyl group can be employed. Moreover, a linker may exist between the Amino-PEGA resin and the amino acid, and examples of such linkers can include, e.g., 4-hydroxymethylphenoxyacetic acid (HMPA) and 4-(4-hydroxymethyl-3-methoxyphenoxy)-butylacetic acid (HMPB). H-Cys(Trt)-Trityl NovaPEG resin (from Merck) etc. in which the C-terminal amino acid is bound to the resin in advance can also be employed.

Moreover, when the C-terminal is to be amidated, it is preferred to employ e.g. Rink-Amide-PEGA resin (from Merck) functionalized with an amino group. By cleaving this resin and the peptide with an acid, the C-terminal amino acid of the peptide can be amidated.

In the binding between the resin and the amino acid having the amino group nitrogen protected with a lipophilic protecting group, for example, in order to use a resin having a hydroxyl group or a resin functionalized with chlorine, the carboxy group of the amino acid is bound to the resin via an ester bond. Moreover, if a resin functionalized with an amino group is to be used, the carboxy group of the amino acid is bound to the resin via an amide bond.

The 2-chlorotrityl chloride resin is preferred in that it can prevent the racemization of the terminal Cys when elongating the peptide chain in solid phase synthesis.

Any amino acid can be employed as the amino acid, and examples can include the natural amino acids serine (Ser), asparagine (Asn), valine (Val), leucine (Leu), isoleucine (Ile), alanine (Ala), tyrosine (Tyr), glycine (Gly), lysine (Lys), arginine (Arg), histidine (His), aspartic acid (Asp), glutamic acid (Glu), glutamine (Gln), threonine (Thr), cysteine (Cys), methionine (Met), phenylalanine (Phe), tryptophan (Trp), and proline (Pro).

Moreover, the D-form of the above natural amino acid can also be used.

Examples of lipophilic protecting groups can include, e.g., carbonate- or amide-based protecting groups such as a 9-fluorenylmethoxycarbonyl (Fmoc) group, a t-butyloxycarbonyl (Boc) group, a benzyl group, an allyl group, an allyloxycarbonyl group, and an acetyl group. When introducing a lipophilic protecting group into an amino acid, e.g. when introducing an Fmoc group, introduction can be carried out by adding 9-fluorenylmethyl-N-succinimidyl carbonate and sodium hydrogen carbonate and allowing reaction. The reaction may be performed at 0-50° C., preferably at room temperature for approximately about 1-5 hours.

As the amino acid protected with a lipophilic protecting group, those commercially available can also be used. Examples can include Fmoc-Ser-OH, Fmoc-Asn-OH, Fmoc-Val-OH, Fmoc-Leu-OH, Fmoc-Ile-OH, Fmoc-Ala-OH, Fmoc-Tyr-OH, Fmoc-Gly-OH, Fmoc-Lys-OH, Fmoc-Arg-OH, Fmoc-His-OH, Fmoc-Asp-OH, Fmoc-Glu-OH, Fmoc-Gln-OH, Fmoc-Thr-OH, Fmoc-Cys-OH, Fmoc-Met-OH, Fmoc-Phe-OH, Fmoc-Trp-OH, and Fmoc-Pro-OH.

Moreover, an amino acid protected with a lipophilic protecting group wherein the protecting group is introduced into the side chain can include, e.g., Fmoc-Arg(Pbf)-OH, Fmoc-Asn(Trt)-OH, Fmoc-Asp(OtBu)-OH, Fmoc-Cys (Acm)-OH, Fmoc-Cys(StBu)-OH, Fmoc-Cys(tBu)-OH, Fmoc-Cys(Trt)-OH, Fmoc-Glu(OtBu)-OH, Fmoc-Gln(Trt)-OH, Fmoc-His(Trt)-OH, Fmoc-Lys(Boc)-OH, Fmoc-Ser (tBu)-OH, Fmoc-Thr(tBu)-OH, Fmoc-Trp(Boc)-OH, and Fmoc-Tyr(tBu)-OH.

Moreover, if it is desired to add a linker in the amino acid sequence of the glycosylated polypeptide, the linker can be inserted at a preferred position by using a linker protected with a lipophilic protecting group instead of the above amino acid protected with a lipophilic protecting group in the process of solid phase synthesis.

When employing a 2-chlorotrityl chloride resin, esterification can be performed with a base such as diisopropylethylamine (DIPEA), triethylamine, pyridine, and 2,4,6-collidine. Moreover, when employing a resin having a hydroxyl group, e.g. a well-known dehydration condensation agent such as 1-mesitylenesulfonyl-3-nitro-1,2,4-triazole (MSNT), dicyclohexylcarbodiimide (DCC), and diisopropylcarbodiimide (DIC) can be employed as the esterification catalyst. The proportion of the amino acid and the dehydration condensation agent used is 1 part by weight of the former to generally 1-10 parts by weight, preferably 2-5 parts by weight of the latter.

The esterification reaction is preferably performed by for example placing the resin in a solid phase column, washing this resin with a solvent, and then adding the amino acid solution. Examples of washing solvents can include, e.g., dimethylformamide (DMF), 2-propanol, and dichloromethane. Examples of solvents for dissolving the amino acid can include, e.g., dimethyl sulfoxide (DMSO), DMF, and dichloromethane. The esterification reaction may be performed at 0-50° C., preferably at room temperature for approximately about 10 minutes-30 hours, preferably for approximately 15 minutes-24 hours.

It is also preferred to acetylate and cap the unreacted hydroxyl groups on the solid phase at this time with e.g. acetic anhydride.

The detachment of the lipophilic protecting group can be performed by for example treatment with a base. Examples of bases can include, e.g., piperidine and morpholine. In such a case, it is preferred that this is performed in the presence of a solvent. Examples of solvents can include, e.g., DMSO, DMF, and methanol.

The amidation reaction of the free amino group with the carboxy group of any amino acid having the amino group nitrogen protected with a lipophilic protecting group is preferably performed in the presence of an activator and a solvent.

Examples of activators can include, e.g., dicyclohexylcarbodiimide (DCC), 1-ethyl-3-(3-dimethylaminopropyl) carbodiimide hydrochloride (WSC/HCl), diphenylphosphorylazide (DPPA), carbonyldiimidazole (CDI), diethylcyanophosphonate (DEPC), benzotriazol-1-yloxy-trispyrrolidinophosphonium (DIPCI), benzotriazol-1-yloxy-trispyrrolidinophosphonium hexafluorophosphate (PyBOP), 1-hydroxybenzotriazole (HOBt), hydroxysuccinimide (HOSu), dimethylaminopyridine (DMAP), 1-hydroxy-7-azabenzotriazole (HOAt), hydroxyphthalimide (HOPht), pentafluorophenol (Pfp-OH), 2-(1H-benzotriazol-1-yl)-1,1,3,3-tetramethyluronium hexafluorophosphate (HBTU), 1-[bis(dimethylamino)methylene]-5-chloro-1H-benzotriazolium 3-oxide hexafluorophosphate (HCTU), O-(7-azabenzotriazol-1-yl)-1,1,3,3-tetramethyluronium hexafluorophosphonate (HATU), O-benzotriazol-1-yl-1,1,3,3-tetramethyluronium tetrafluoroborate (TBTU), and 3,4-dihydro-3-hydrodi-4-oxa-1,2,3-benzotriazine (Dhbt).

The amount of the activator used is preferably 1-20 equivalents, preferably 1-10 equivalents, and further preferably 1-5 equivalents to any amino acid having the amino group nitrogen protected with a lipophilic protecting group.

Examples of solvents can include, e.g., DMSO, DMF, and dichloromethane. The reaction may be performed at 0-50° C., preferably at room temperature for approximately about 10-30 hours, preferably for approximately 15 minutes-24 hours. The detachment of the lipophilic protecting group can be performed similarly to the above.

Treatment with an acid is preferred in order to cleave the peptide chain from the resin. Examples of acids can include, e.g., trifluoroacetic acid (TFA) and hydrogen fluoride (HF).

In this way, a glycosylated polypeptide having the desired position substituted with glycosylated Asn can be obtained. Moreover, the glycosylated polypeptide purified as such allows formation of a disulfide bond between deprotected Cys as described below.

In one embodiment of the present invention, when sialic acid is contained in the non-reducing terminal on the sugar chain of glycosylated Asn employed in solid phase synthesis, the sialic acid is prevented from being cleaved by the acid treatment. It is therefore preferred that the carboxy group of said sialic acid is protected by a protecting group. Examples of protecting groups can include, e.g., a benzyl group, an allyl group, and a diphenylmethyl group. The method for introduction and detachment of the protecting group can be performed by a well-known method. Moreover, the detachment of the protecting group is preferably performed after the glycosylated polypeptide manufactured by solid phase synthesis is cleaved from the resin. After cleaving from the resin, if the glycosylated polypeptide is to be cyclized by allowing formation of a disulfide bond in the glycosylated polypeptide, the detachment of the protecting group may be before or after the step of forming a disulfide bond.

Method for Manufacturing Glycosylated Polypeptide (Method B)

The glycosylated polypeptide can also be manufactured by a method of first synthesizing a peptide chain, and then adding a sugar chain to the synthesized peptide chain. Specifically, a peptide comprising Cys at the position to be glycosylated is manufactured by e.g. a solid phase synthesis method, a liquid phase synthesis method, a method of synthesis by a cell, and a method of separating and extracting those that naturally exist. Here, Cys that will not be glycosylated such as Cys at a position planned to form a disulfide bond are protected with for example an acetamidomethyl (Acm) group. Moreover, if Cys that will neither be glycosylated nor be used in the formation of a disulfide bond is to be introduced into the glycosylated polypeptide, Cys can be introduced by protecting the Cys with a protecting group during the glycosylation and disulfide bond formation steps, and then deprotecting the same. Such protecting groups can include, e.g., tert-butyl (tBu) or 4-methoxybenzyl.

Moreover, when a different sugar chain is to be added to Cys in the glycosylated polypeptide, the different sugar chain can be introduced by first unprotecting the Cys where the sugar chain is to be introduced, and then protecting the Cys where a different sugar chain is to be introduced with e.g. StBu. Specifically, when synthesizing a peptide by e.g. solid phase synthesis, Cys where the first sugar chain is to be introduced is unprotected, and Cys where the second sugar chain is to be introduced is made into Cys having a protecting group with e.g. Fmoc-Cys(StBu)-OH. Then, the sugar chain is introduced to the unprotected Cys while retaining the protecting group such as StBu. Next, the StBu group etc. is deprotected to introduce a different sugar chain to the Cys that became unprotected. Note that Cys where the first sugar chain is to be introduced and Cys where the second sugar chain is to be introduced can be one or more Cys.

In the deprotection of the StBu group, the deprotection can be performed by reaction with a reductant such as tris(2-carboxyethyl)phosphine hydrochloride (TCEP), dithiothreitol (DTT), and tributylphosphine. The above reaction may be performed generally at 0-80° C., preferably at 5-60° C., and further preferably at 10-35° C. The reaction time is preferably approximately 30 minutes-5 hours in general. After completion of the reaction, it may be purified with a well-known method (such as high performance liquid column chromatography (HPLC)) as appropriate.

When introducing different sugar chains, it is preferred that the introduction starts from sugar chains more stable against the reduction condition in the deprotection step of Cys or the acidic condition in the purification step such as HPLC. In particular, when a sialic acid-containing sugar chain is to be introduced, it is preferred that a sugar chain that does not have a sialic acid or a sugar chain having fewer sialic acid residues is introduced first.

Moreover, if it is desired to add a linker in the amino acid sequence of the glycosylated polypeptide, for example, the linker can be inserted at a preferred position of the synthesized polypeptide by using a linker protected with a lipophilic protecting group instead of an amino acid protected with a lipophilic protecting group in the process of solid phase synthesis.

Next, by reacting a haloacetylated complex-type sugar chain derivative with the peptide comprising an unprotected Cys obtained above, the sugar chain is reacted with the thiol group of the unprotected Cys and bound to the peptide. The above reaction may be performed in a phosphate buffer, a Tris-hydrochloride buffer, a citrate buffer, or a mixed solution thereof, generally at 0-80° C., preferably at 10-60° C., and further preferably at 15-35° C. The reaction time is generally 10 minutes-24 hours, and preferably approximately 30 minutes-5 hours in general. After completion of the reaction, it may be purified with a well-known method (such as HPLC) as appropriate.

A haloacetylated complex-type sugar chain derivative is for example a compound wherein the hydroxyl group bound to the carbon at position 1 of a complex-type asparagine-linked sugar chain is substituted with —NH—$(CH_2)_a$—(CO)—$CH_2X$ (wherein X is a halogen atom, and a is an integer and is not limited as long as it does not inhibit the linker function of interest, but is preferably an integer from 0-4).

Specifically, a haloacetylated complex-type sugar chain derivative and a Cys-containing peptide are reacted in a phosphate buffer at room temperature. After completion of the reaction, a glycosylated polypeptide substituted with a glycosylated Cys can be obtained by purification with HPLC.

Moreover, the reaction can also be performed in a mixed solution of an organic solvent such as DMSO, DMF, methanol, and acetonitrile with the above buffer. Here, the organic solvent can be added to the above buffer at a proportion in the range of 0-99% (v/v). For a peptide comprising an unprotected Cys with low solubility to the buffer, addition of such an organic solvent can improve the solubility to the reaction solution and is thus preferred.

Alternatively, the reaction can also be performed in an organic solvent such as DMSO, DMF, methanol, and acetonitrile or a mixed solution thereof. In this case, it is preferably performed in the presence of a base. Examples of bases can include, e.g., DIPEA, triethylamine, pyridine, and 2,4,6-collidine. Moreover, the reaction can also be performed in a mixed solution of guanidine hydrochloride or urea added to the buffer solution. Guanidine hydrochloride or urea can be added to the above buffer so that the final concentration will be 1 M-8 M. The solubility of a peptide with low solubility in the buffer can also be improved by addition of guanidine hydrochloride or urea and is thus preferred.

Further, in order to prevent the peptide comprising an unprotected Cys from forming a dimer via a disulfide bond, tris(2-carboxyethyl)phosphine hydrochloride (TCEP) or dithiothreitol (DTT) can also be added to the buffer for reaction. TCEP or DTT can be added to the buffer so that the final concentration will be 10 μM-10 mM.

Moreover, after binding the sugar chain to the Cys of interest, the protecting group of Cys protected with Acm etc. is deprotected. When the protecting group is an Acm group, it can be deprotected by subjecting to reaction with e.g. iodine, mercury acetate (II), silver nitrate (I), or silver(I) acetate in water, methanol, acetic acid, or a mixed solution thereof.

The above reaction may be performed generally at 0-80° C., preferably at 5-60° C., and further preferably at 10-35° C. The reaction time is preferably approximately 5 minutes-24 hours in general. After completion of the reaction, it may be treated with DTT or hydrochloric acid etc., and then purified with a well-known method (such as HPLC) as appropriate.

In this way, a glycosylated polypeptide having the desired position substituted with glycosylated Cys can be obtained. Moreover, the glycosylated polypeptide purified as such allows formation of a disulfide bond between deprotected Cys as described below.

Moreover, when manufacturing a glycosylated polypeptide having multiple sialic acid-containing sugar chains such as disialo or monosialo sugar chain in the peptide sequence, a sialic acid-containing sugar chain in which the carboxy group of the sialic acid on the sugar chain to be introduced is protected by e.g. a benzyl (Bn) group, an allyl group, a diphenylmethyl group, and a phenacyl group can be employed.

When a sugar chain having the carboxy group of the sialic acid protected is introduced, a step of deprotecting the sialic acid protecting group can be carried out after a step of forming a disulfide bond in the glycosylated polypeptide described below.

Accordingly, by protecting the carboxy group of the sialic acid with a benzyl group etc., a separation and purification step by e.g. HPLC in the manufacturing step will be facilitated. Moreover, the protection of the carboxy group of the sialic acid will also enable the prevention of detachment of an acid-labile sialic acid.

The protection reaction of the carboxy group of the sialic acid on the sugar chain can be performed by a method well-known to those skilled in the art. Moreover, in a glycosylated polypeptide in which a disulfide bond was formed, the protecting group of the carboxy group of the sialic acid can be deprotected by hydrolysis under basic conditions. The above reaction may be performed generally at 0-50° C., preferably at 0-40° C., and further preferably at 0-30° C. The reaction time is preferably approximately 5 minutes-5 hours in general. After completion of the reaction, it may be neutralized with a weak acid such as phosphoric or acetic acid, and then purified with a well-known method (such as HPLC) as appropriate.

Moreover, in the glycosylated polypeptide prepared by the above methods A and B, a disulfide bond between Cys can be formed with a method well-known to those skilled in the art employing e.g. air and/or oxygen, iodine, DMSO, a mixture of oxidized and reduced glutathione, potassium ferricyanide, Ellman's reagent (5,5'-dithiobis(2-nitrobenzoic acid)), thallium(III) trifluoroacetate, and alkyltrichlorosilane sulfoxide.

When forming a disulfide bond between Cys-Cys, Cys in the glycosylated polypeptide which desirably do not form a disulfide bond is to be protected with a protecting group. As such protecting groups, a protecting group which is stable under oxidizing conditions such as Acm, tBu, 4-methoxybenzyl, and 4-methylbenzyl can be employed.

Moreover, in method B, it is also possible to perform the formation of disulfide bond before the introduction of the sugar chain. However, if a protecting group is introduced to Cys that is to be subject to disulfide bonding, the deprotection step will come before the disulfide bond formation step.
(Activity)

The glycosylated polypeptide of the present invention has affinity towards somatostatin receptors. Having "affinity towards somatostatin receptors" herein means having affinity towards at least one of somatostatin receptors SSTR1, SSTR2, SSTR3, SSTR4, and SSTR5.

The glycosylated polypeptide of the present invention preferably has affinity towards two or more somatostatin receptors, more preferably has affinity towards three or more receptors, further preferably has affinity towards four or more receptors, and most preferably has affinity towards all five receptors SSTR1-SSTR5 similarly to a natural somatostatin (SRIF28 and SRIF14). In particular, it is preferred that it has affinity towards any one of at least SSTR1 and SSTR4 and affinity towards other SSTRs.

As such, the glycosylated polypeptide of the present invention has somatostatin activity (agonist activity) and antagonist activity towards a somatostatin receptor by having affinity towards a somatostatin receptor.

For example, affinity towards each somatostatin receptor can be measured with e.g. competitive binding experiment in vitro.

In the measurement of affinity by competitive binding experiment, the affinity of the test substance (such as 50% inhibitory concentration: $IC_{50}$ value or binding inhibition constant: Ki value) can be measured by competitively binding a labeled ligand and the test substance to the receptor and seeking the release of the labeled ligand when the test substance is administered.

For example, somatostatin activity (agonist activity) can be evaluated by a cAMP production suppression test in vitro employing somatostatin receptor expression cells as shown in Examples 69-3 and 69-4.

The cAMP production suppression test can be evaluated by treating somatostatin receptor expression cells with the glycosylated polypeptide or the control compounds SRIF14 or SRIF28, measuring the amount of cAMP accumulated in the cell after culturing for a certain amount of time, and comparing with the control compound. The amount of cAMP can be measured by a well-known method such as the enzyme immunoassay method (EIA).

For example, somatostatin activity (agonist activity) can be evaluated by a GH production suppression test in vivo as shown in Examples 89 and 90.

The GH production suppression test can be carried out for example as follows. The glycosylated polypeptide is subcutaneously administered to non-fasted rats. Rats are administered a GH release enhancer under general anesthesia, and then blood is collected in approximately 5 minutes. The collected blood is the plasma sample, and GH concentration is measured by a well-known method such as the enzyme immunoassay method (EIA). Moreover, as a control, plasma samples are obtained from rats which were administered with saline that does not contain glycosylated polypeptide, and somatostatin activity can be evaluated by comparing the GH concentrations measured.

In the glycosylated polypeptide of the present invention, even if some extent of attenuation in affinity towards each receptor is triggered by glycosylating its structure, the half-life in blood is extended and as a result, somatostatin activity equivalent to a naturally-occurring somatostatin that is not glycosylated (hereinafter may be referred to as "non-glycosylated somatostatin") can be maintained, and it can preferably have increased somatostatin activity. In light of this extension of half-life in blood, the ratio between the Ki value of the glycosylated polypeptide of the present invention against each receptor and the Ki value of unglycosylated SRIF14 is preferably in the range of 1000:1-0.3:1, more preferably in the range of 100:1-0.3:1, and further preferably in the range of 10:1-0.3:1, as measured in e.g. the method described in Example 69-1.

The stability in blood of the glycosylated polypeptide of the present invention is preferably equivalent to a naturally-occurring somatostatin (non-glycosylated somatostatin) or more. Stability in blood can be measured with a method well-known to those skilled in the art, and can be decided with e.g. stability in plasma, half-life in blood, and AUC (drug plasma concentration—area under the time curve) as indicators. Moreover, decrease in renal or hepatic clearance also contributes to an increase in stability in blood.

The glycosylated polypeptide of the present invention has increased half-life in blood compared to an non-glycosylated SRIF28, and its half-life is increased by 4-folds or more, preferably 10-fold or more, more preferably 20-folds or more, and further preferably 30-folds or more compared to SRIF28, as measured in e.g. the experimental method shown in Example 70.

Moreover, the glycosylated polypeptide of the present invention has preferably 4-folds or more, more preferably 10-fold or more, and further preferably 20-folds or more stability in blood compared to SRIF28, as measured in e.g. the experimental method shown in Example 88.

(Pharmaceutical Composition)

Next, a pharmaceutical composition containing the glycosylated polypeptide of the present invention as the active ingredient will be described.

The pharmaceutical composition containing the glycosylated polypeptide of the present invention as the active ingredient is effective for the treatment or prevention of somatostatin-related diseases. As described above, various actions are known for somatostatin, and diseases related to these actions also vary. For example, examples of somatostatin-related diseases include, e.g., acromegaly, gigantism, Alzheimer's disease and other forms of dementia, cancer, hormone-producing tumor, endocrine tumor (such as carcinoid, VIPoma, insulinoma, and glucagonoma), Cushing's disease, hormone secretion defect, diabetes and complications thereof, pains, arthritis, diarrhea, gastric ulcer, inflammatory bowel disease, irritable bowel syndrome, gastrointestinal obstruction, ileus, postoperative restenosis, radiation damage, and eye disease (such as dry eye, glaucoma, interstitial keratitis, iritis, cataract, and conjunctivitis). The pharmaceutical composition containing the glycosylated polypeptide of the present invention as the active ingredient is effective for the treatment or prevention of the above diseases, in particular, acromegaly, dementia, cancer, hormone-producing tumor, endocrine tumor, Cushing's disease, hormone secretion defect, diabetes complication, diarrhea, gastrointestinal obstruction, ileus, radiation damage, eye disease, various tumors or gut-associated disease, and gastrointestinal symptoms accompanying excess hormone production.

The above pharmaceutical composition is one formulated into the form of an ordinary pharmaceutical composition with a diluent or an excipient such as a generally used filler, expander, binder, moisturizer, disintegrant, surfactant, and lubricant.

Examples of such pharmaceutical compositions include, e.g., tablets, pills, powders, liquids, suspensions, emulsions, granules, capsules, suppositories, inhalants, ophthalmic solutions, and injections.

The amount of the glycosylated polypeptide of the present invention contained in the pharmaceutical composition is not particularly limited and can be selected as appropriate from a broad range, but in general 1-70% by weight of the glycosylated polypeptide of the present invention is preferably contained in the pharmaceutical composition.

The pharmaceutical composition containing the glycosylated polypeptide of the present invention as the active ingredient can either further contain other active ingredients, or it can be employed in combination with a pharmaceutical composition containing other active ingredients. Moreover, the pharmaceutical composition containing the glycosylated polypeptide of the present invention as the active ingredient can either comprise the glycosylated polypeptide as a pharmaceutically acceptable salt, or further contain one or more different glycosylated polypeptides of the present invention as active ingredients. Moreover, it can also be employed in combination with the pharmaceutical composition containing one or more different glycosylated polypeptides of the present invention as the active ingredient. Moreover, Examples of other ingredients that can be contained in the pharmaceutical composition can include a pharmaceutically acceptable carrier known to those skilled in the art.

Moreover, a treatment using the glycosylated polypeptide of the present invention may include e.g. radiation therapy, and it is also useful in scintigraphy for measuring the distribution of cells and tissues expressing any of SSTR1-SSTR5 throughout the body. The use of extracorporeal imaging by radiation scanning or magnetic resonance will enable in vivo semiquantitative detection.

A radiolabeled glycosylated polypeptide is useful for therapeutic treatment of a malignant tumor expressing any of SSTR1-SSTR5, for example in a human body in a tissue that does not comprise a substantial amount of SSTR1-SSTR5 in a healthy state. Moreover, the labeled glycosylated polypeptide can be administered for scintigraphy, or as a composition containing an effective amount to suppress a tumor. Examples of such labels are different isotopes such as iodine ($^{123}$I, $^{125}$I, and $^{131}$I) indium ($^{111}$In) carbon ($^{11}$C), fluorine ($^{18}$F), technetium ($^{99m}$Tc), and yttrium ($^{90}$Y), or a fluorescent label. The labeling can be carried out by a method well-known to those skilled in the art, and the label can be contained in the glycosylated polypeptide, bound directly thereto, or bound to an appropriate compound and then bound to the glycosylated polypeptide. For example, in iodization of tyrosine, the labeling can be performed by e.g. a method employing chloramine-T etc.

The method for administering the pharmaceutical composition according to the present invention is not particularly restricted, and it is administered with a method according to various drug formulations, age, sex, and the disease condition of the patient, and other conditions. The method of administration for tablets, pills, liquids, suspensions, emulsions, granules, and capsules include e.g. oral administration. Moreover, in case of injections, it can be intravenously, intramuscularly, intradermally, subcutaneously, or intraperitoneally administered alone or mixed with an ordinary fluid replacement such as glucose or amino acid. In case of suppositories, it is intrarectally administered. In case of ophthalmic solutions, it is applied to an eye tissue such as the conjunctival sac. In case of inhalants, it is applied to the bronchial tube or the lung.

The administration dose of the above pharmaceutical composition may be selected as appropriate according to usage, age, sex, and the disease extent of the patient, and other conditions, and for example can be an administration dose that will be 0.1-900 nmol, preferably 1-100 nmol, and more preferably 1-10 nmol of the glycosylated polypeptide of the present invention per 1 kg of body weight.

The administration frequency of the above pharmaceutical composition may be selected as appropriate according to usage, age, sex, and the disease extent of the patient, and other conditions, and 3 times/day, twice/day, once/day, and further at a less frequent administration frequency according to stability in blood thereof (such as once/week and once/month) may be selected. Preferably, the administration frequency of the above pharmaceutical composition is once or less per day.

The sugar chain added to the glycosylated polypeptide of the present invention is easily degraded by the metabolic system in the body. Moreover, in one aspect of the present invention, said sugar chain has a structure that exists as bound to a glycopeptide (or a glycoprotein) in vivo. Accordingly, a pharmaceutical composition comprising the glycosylated polypeptide of the present invention and said peptide as active ingredients has advantages such as not showing side effects or antigenicity when administered in vivo and less concern for losing drug effect by allergic reactions or antibody production.

Further, the glycosylated polypeptide of the present invention can be stably and easily supplied in large amounts, and it is extremely useful with respect to providing pharmaceuticals having stable and high quality.

Moreover, the present invention also provides a method for treating or preventing a somatostatin-related disease, characterized in administering an effective amount of the glycosylated polypeptide of the present invention.

The terms used herein are to be employed to describe particular embodiments, and do not intend to limit the invention.

Moreover, the term "comprising" as used herein, unless the content clearly indicates to be understood otherwise, intends the presence of the described items (such as components, steps, elements, and numbers), and does not exclude the presence of other items (such as components, steps, elements, and numbers).

Unless otherwise defined, all terms used herein (including technical and scientific terms) have the same meanings as those broadly recognized by those skilled in the art of the technology to which the present invention belongs. The terms used herein, unless explicitly defined otherwise, are to be construed as having consistent meanings with the meanings herein and related technical fields, and shall not be construed as having idealized or excessively formal meanings.

The embodiments of the present invention may be described referring to schematic diagrams. In case of schematic diagrams, they may be exaggerated in presentation in order to allow clear description.

Terms such as first and second are employed to express various elements, and it should be recognized that these elements are not to be limited by these terms. These terms are employed solely for the purpose of discriminating one element from another, and it is for example possible to describe a first element as a second element, and similarly, to describe a second element as a first element without departing from the scope of the present invention.

The present invention will now be described in further detail referring to Examples. However, the present invention can be embodied by various aspects, and shall not be construed as being limited to the Examples described herein.

EXAMPLES

The notation system of the glycosylated polypeptides herein will be described below.

For example, S1C(disialo)•N5C(disialo)-SRIF28 shows that Ser at position 1 (S1) and Asn at position 5 of polypeptide SRIF28 are both substituted by disialo sugar chain attached Cys (C(disialo)).

Moreover, S1C(disialo)-D-Trp22-SRIF28 shows that Ser at position 1 (S1) of polypeptide SRIF28 is substituted by disialo sugar chain attached Cys (C(disialo)), and further Trp at position 22 is substituted with D-Trp.

Moreover, C(disialo)-R-K-SRIF14 shows that glycosylated Cys-Arg-Lys- is added at the N-terminal side of SRIF14.

Moreover, 29C(disialo)-SRIF28 or 30C(disialo)-SRIF28 shows peptides having one disialo sugar chain attached Cys further added to Cys at position 28 which is the C-terminal of SRIF28 (29C(disialo)-SRIF28), or having -W-disialo sugar chain attached Cys (W is any amino acid that binds to Cys at position 28) further added to Cys at position 28 which is the C-terminal of SRIF28 (30C(disialo)-SRIF28).

Moreover, S1-2C(disialo)-SRIF28 shows that Ser at position 1 present at the N-terminal of polypeptide SRIF28 is substituted with two consecutive disialo sugar chain attached Cys.

In the meantime, "disialo" means a disialo sugar chain, "monosialo" means a monosialo sugar chain, "asialo" means an asialo sugar chain, "diGlcNAc" means a diGlcNAc sugar chain, "GlcNAc" means an N-acetylglucosamine, "diMan" means a dimannose sugar chain, "trisialo" means a trisialo sugar chain, and "tetrasialo" means a tetrasialo sugar chain. Moreover, (disialo(aminoethylamide)) means that the carboxy group of the sialic acid of the disialo sugar chain is modified by an aminoethylamino group. "Bn," "amide," or "hexadecylamide" instead of "aminoethylamide" each mean that the carboxy group of the sialic acid on the sugar chain is protected by a benzyl group, an amino group, hexadecylamino group.

Example 1 Synthesis of S1C(Disialo)-SRIF28

1-1 Glycosylation Reaction of Thiol

Peptide 1 (SEQ ID NO. 38) represented by the following formula (1) (from APC, Inc.) (60.6 mg, 18.3 μmol) and compound a represented by the following formula (a) (bromoacetamidated oligosaccharide: from Otsuka Chemical Co., Ltd.) (85.8 mg, 36.6 μmol, 2.0 equivalents to peptide 1) were dissolved in 33 mM phosphate buffer (pH 7.4, 5.5 mL), and reacted at room temperature for 30 minutes.

[Chemical Formula 17]

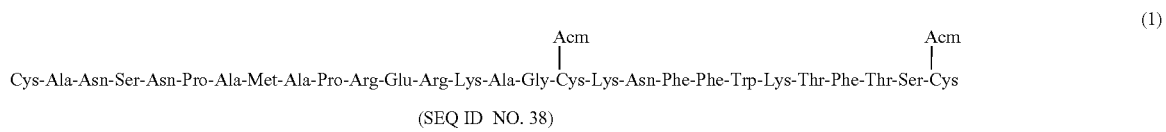

(SEQ ID NO. 38)

[Chemical Formula 18]

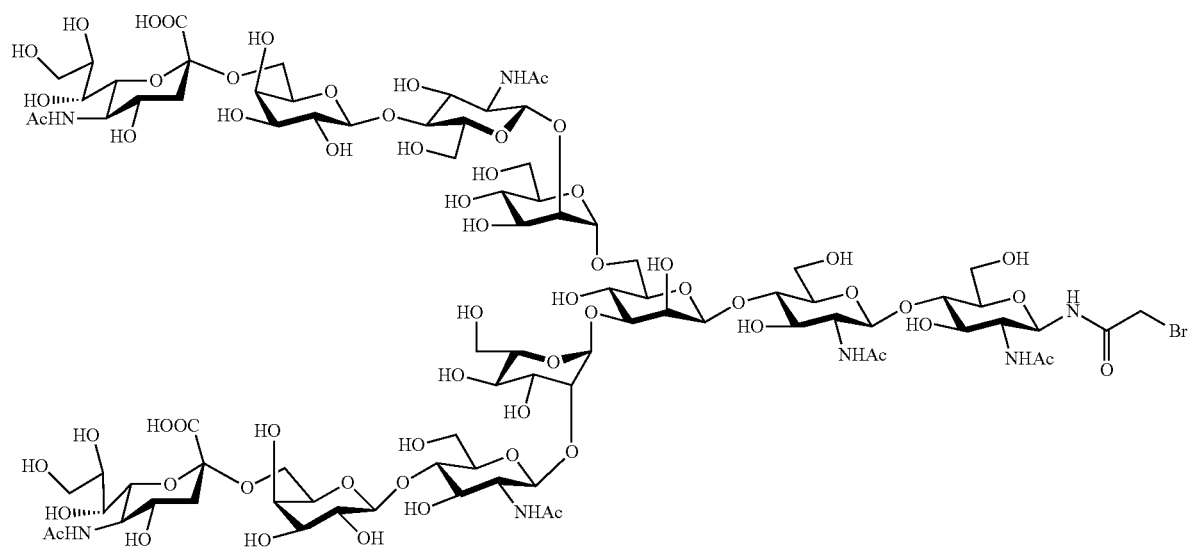

(a)

The reaction solution was purified with HPLC [column: SHISEIDO CAPCELL PAK C18 UG-120 (5 μm), φ20×250 mm, flow rate: 7.0 mL/min, eluent A: 0.1% aqueous acetic acid (AcOH), B: 0.09% AcOH/10% water/90% acetonitrile, gradient A:B=90:10→75:25, 15 minutes, linear gradient elution] to obtain glycopeptide 2 (SEQ ID NO. 39) represented by the following formula (2) (60.5 mg, 10.9 μmol, yield 59%).

[Chemical Formula 19]

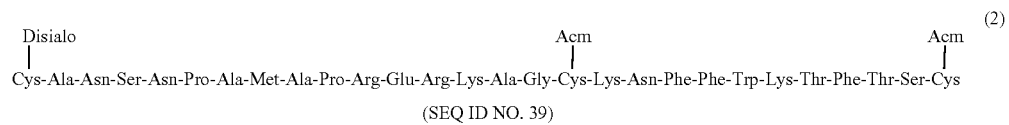

(SEQ ID NO. 39)

ESI-MS: (m/z) calcd for $C_{229}H_{358}N_{50}O_{102}S_4$: $[M+3H]^{3+}$ 1858.3, $[M+4H]^{4+}$ 1394.0, $[M+5H]^{5+}$ 1115.4. found 1858.1, 1393.8, 1115.2.

1-2 Deprotection of Acm Group

To glycopeptide 2 obtained in the method described in the above 1-1 (51.2 mg, 9.19 μmol) was added an aqueous solution (3.7 mL) of silver(I) acetate (18.8 mg, 113 μmol), and reacted at room temperature for 40 minutes DTT (43.6 mg, 282 μmol) dissolved in 200 mM Tris-HCl buffer (pH 7.4, 3.7 mL) and 100 mM ascorbic acid aqueous solution (0.92 mL) were added, and this was promptly filtered with a filter. The filtrate was purified with HPLC [column: SHISEIDO CAPCELL PAK C18 UG-120 (5 μm), φ20×250 mm, flow rate: 7.0 mL/min, eluent A: 0.1% aqueous AcOH, B: 0.09% AcOH/10% water/90% acetonitrile, gradient A:B=90:10→75:25, 15 minutes, linear gradient elution] to obtain glycopeptide 3 (SEQ ID NO. 40) represented by the following formula (3) (29.2 mg, 5.38 μmol, yield 58%).

[Chemical Formula 20]

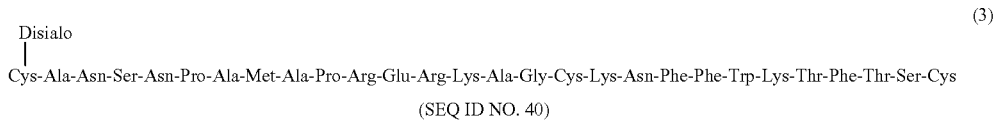

(SEQ ID NO. 40)

(3)

ESI-MS: (m/z) calcd for $C_{223}H_{348}N_{48}O_{100}S_4$: $[M+3H]^{3+}$ 1810.9, $[M+4H]^{4+}$ 1358.4, $[M+5H]^{5+}$ 1086.9, $[M+6H]^{6+}$ 906.0. found 1810.7, 1358.3, 1086.6, 905.7.

1-3 Formation of Disulfide Bond

Glycopeptide 3 obtained in the method described in the above 1-2 (29.2 mg, 5.38 μmol) was dissolved in 100 mM Tris-HCl buffer (pH 8.0)-DMSO (1/1, v/v, 10.8 mL), and reacted at room temperature for 2 days. The reaction solution was purified with HPLC [column: SHISEIDO CAPCELL PAK C18 UG-120 (5 μm), φ20×250 mm, flow rate: 7.0 mL/min, eluent A: 0.1% aqueous TFA, B: 0.09% TFA/10% water/90% acetonitrile, gradient A:B=77:23→64:36, 17 minutes, linear gradient elution] to obtain a fraction containing compound (S1C(disialo)-SRIF28) represented by the following formula (4) (SEQ ID NO. 5).

[Chemical Formula 21]

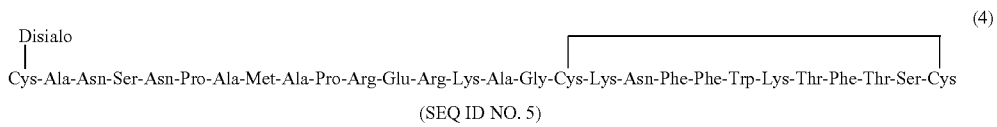

(SEQ ID NO. 5)

(4)

This fraction was further purified with HPLC [column: SHISEIDO CAPCELL PAK C18 UG-120 (5 μm), φ20×250 mm, flow rate: 7.0 mL/min, eluent A: 0.1% aqueous AcOH, B: 0.09% AcOH/10% water/90% acetonitrile, gradient A:B=90:10→75:25, 15 minutes, linear gradient elution] to obtain S1C(disialo)-SRIF28 (17.2 mg, 3.17 μmol, yield 59%).

ESI-MS: (m/z) calcd for $C_{223}H_{346}N_{48}O_{100}S_4$: $[M+3H]^{3+}$ 1810.2, $[M+4H]^{4+}$ 1357.9, $[M+5H]^{5+}$ 1086.5. found 1810.0, 1357.5, 1086.4.

Example 2 Synthesis of N5C(Disialo)-SRIF28

A compound represented by the following formula (6) (N5C(disialo)-SRIF28) (SEQ ID NO. 6) was synthesized similarly to Example 1, except that a compound represented by the following formula (5) (peptide 5) (SEQ ID NO. 41) was employed instead of peptide 1.

[Chemical Formula 22]

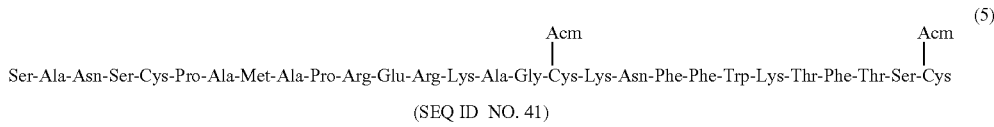

(SEQ ID NO. 41)

[Chemical Formula 23]

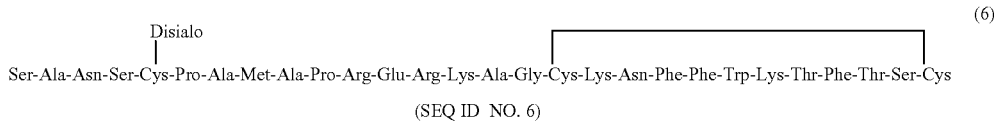

(SEQ ID NO. 6)

Example 3 Synthesis of A9C(Disialo)-SRIF28

A compound represented by the following formula (8) (A9C(disialo)-SRIF28) (SEQ ID NO. 7) was synthesized similarly to Example 1, except that a compound represented by the following formula (7) (peptide 7) (SEQ ID NO. 42) was employed instead of peptide 1.

[Chemical Formula 24]

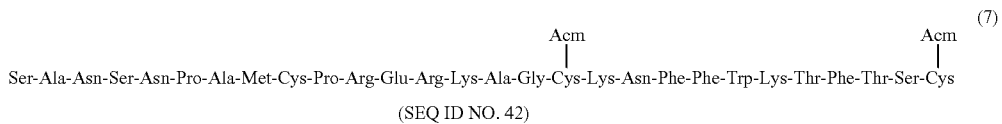

(SEQ ID NO. 42)

[Chemical Formula 25]

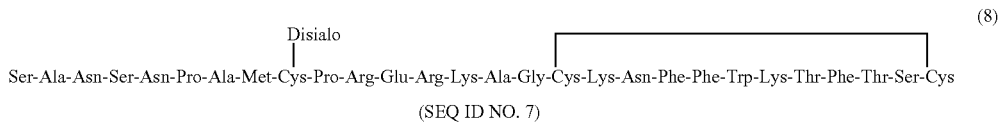

(SEQ ID NO. 7)

Example 4 Synthesis of E12C(Disialo)-SRIF28

A compound represented by the following formula (10) (E12C(disialo)-SRIF28) (SEQ ID NO. 8) was synthesized similarly to Example 1, except that a compound represented by the following formula (9) (peptide 9) (SEQ ID NO. 43) was employed instead of peptide 1.

[Chemical Formula 26]

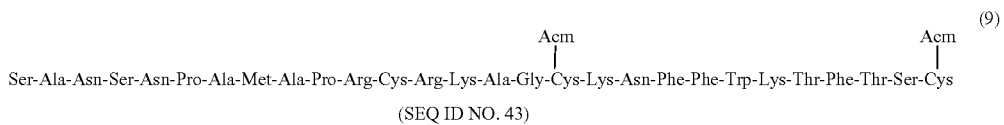

(SEQ ID NO. 43)

[Chemical Formula 27]

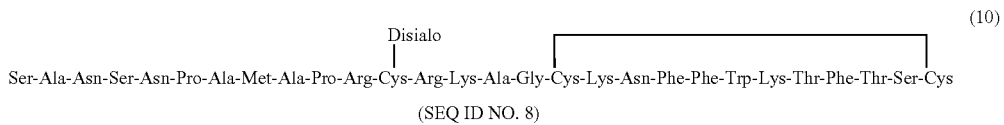

(SEQ ID NO. 8)

Example 5 Synthesis of R13C(Disialo)-SRIF28

A compound represented by the following formula (12) (R13C(disialo)-SRIF28) (SEQ ID NO. 9) was synthesized similarly to Example 1, except that a compound represented by the following formula (11) (peptide 11) (SEQ ID NO. 44) was employed instead of peptide 1.

[Chemical Formula 28]

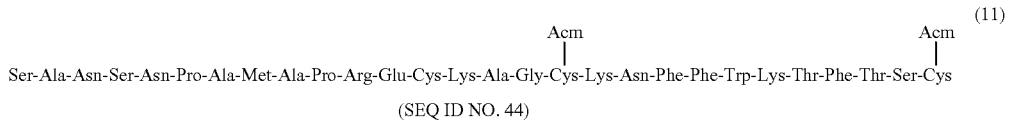

(SEQ ID NO. 44)

[Chemical Formula 29]

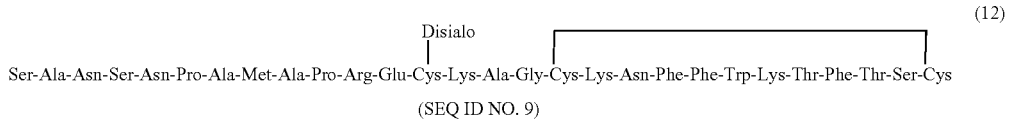

(SEQ ID NO. 9)

Example 6 Synthesis of K14C(Disialo)-SRIF28

A compound represented by the following formula (14) (K14C(disialo)-SRIF28) (SEQ ID NO. 10) was synthesized similarly to Example 1, except that a compound represented by the following formula (13) (peptide 13) (SEQ ID NO. 45) was employed instead of peptide 1.

[Chemical Formula 30]

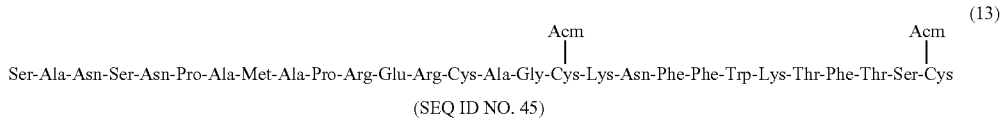

(SEQ ID NO. 45)

[Chemical Formula 31]

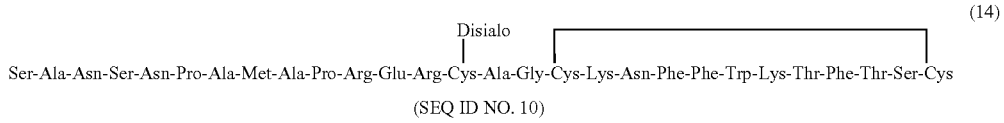

(SEQ ID NO. 10)

Example 7 Synthesis of A15C(Disialo)-SRIF28

A compound represented by the following formula (16) (A15C(disialo)-SRIF28) (SEQ ID NO. 11) was synthesized similarly to Example 1, except that a compound represented by the following formula (15) (peptide 15) (SEQ ID NO. 46) was employed instead of peptide 1.

[Chemical Formula 32]

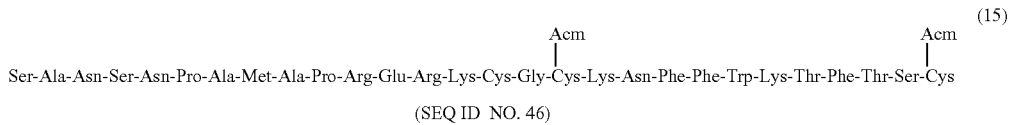

(SEQ ID NO. 46)

[Chemical Formula 33]

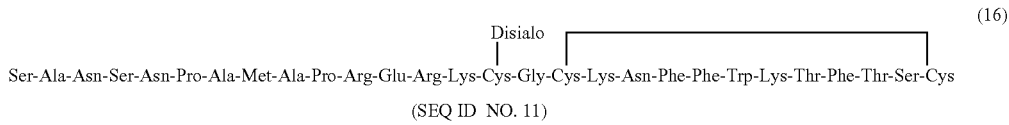

(SEQ ID NO. 11)

Example 8 Synthesis of G16C(Disialo)-SRIF28

A compound represented by the following formula (18) (G16C(disialo)-SRIF28) (SEQ ID NO. 12) was synthesized similarly to Example 1, except that a compound represented by the following formula (17) (peptide 17) (SEQ ID NO. 47) was employed instead of peptide 1.

[Chemical Formula 34]

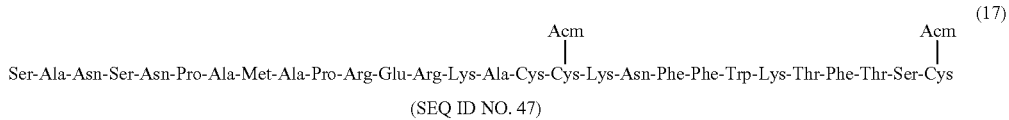

(17)

(SEQ ID NO. 47)

[Chemical Formula 35]

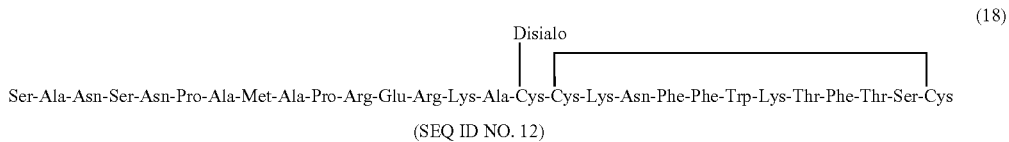

(18)

(SEQ ID NO. 12)

Example 9 Synthesis of K18C(Disialo)-SRIF28

A compound represented by the following formula (20) (K18C(disialo)-SRIF28) (SEQ ID NO. 13) was synthesized similarly to Example 1, except that a compound represented by the following formula (19) (peptide 19) (SEQ ID NO. 48) was employed instead of peptide 1.

[Chemical Formula 36]

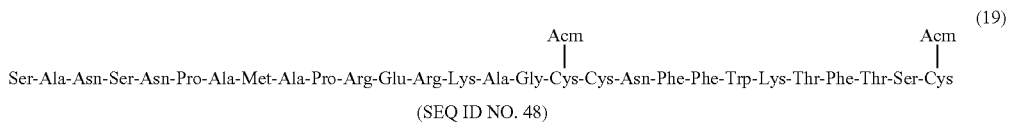

(19)

(SEQ ID NO. 48)

[Chemical Formula 37]

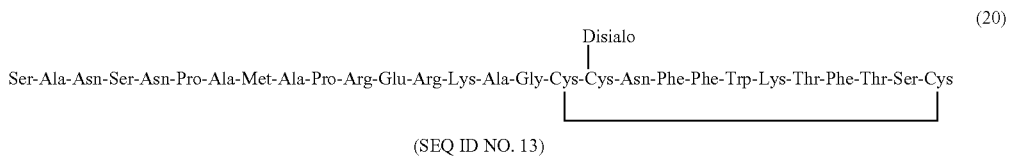

(20)

(SEQ ID NO. 13)

Example 10 Synthesis of N19C(Disialo)-SRIF28

A compound represented by the following formula (22) (N19C(disialo)-SRIF28) (SEQ ID NO. 14) was synthesized similarly to Example 1, except that a compound represented by the following formula (21) (peptide 21) (SEQ ID NO. 49) was employed instead of peptide 1.

[Chemical Formula 38]

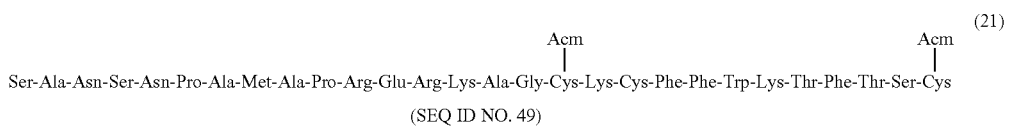

(21)

(SEQ ID NO. 49)

[Chemical Formula 39]

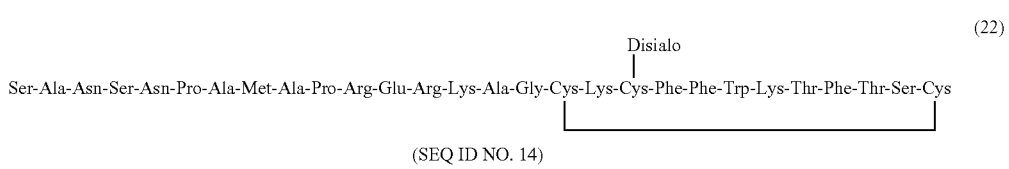

(22)

(SEQ ID NO. 14)

Example 11 Synthesis of F21C(Disialo)-SRIF28

A compound represented by the following formula (24) (F21C(disialo)-SRIF28) (SEQ ID NO. 15) was synthesized similarly to Example 1, except that a compound represented by the following formula (23) (peptide 23) (SEQ ID NO. 50) was employed instead of peptide 1.

[Chemical Formula 40]

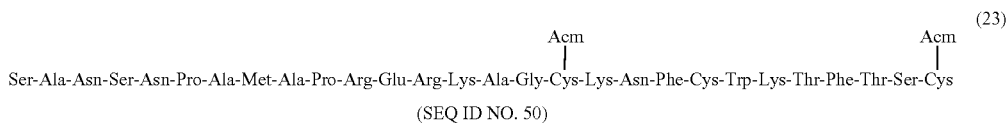

(SEQ ID NO. 50)

[Chemical Formula 41]

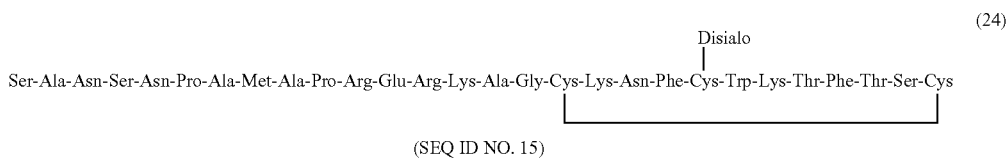

(SEQ ID NO. 15)

Example 12 Synthesis of T26C(Disialo)-SRIF28

A compound represented by the following formula (26) (T26C(disialo)-SRIF28) (SEQ ID NO. 16) was synthesized similarly to Example 1, except that a compound represented by the following formula (25) (peptide 25) (SEQ ID NO. 51) was employed instead of peptide 1.

[Chemical Formula 432]

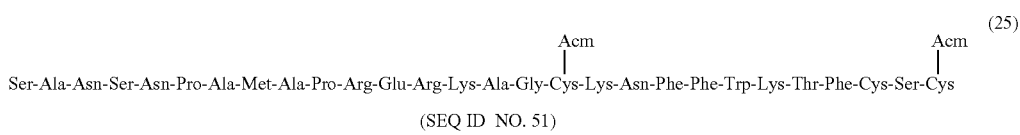

(SEQ ID NO. 51)

[Chemical Formula 43]

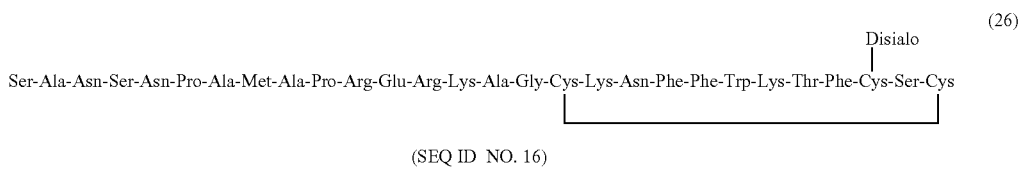

(SEQ ID NO. 16)

Example 13 Synthesis of 29C(Disialo)-SRIF28

A compound represented by the following formula (28) (29C(disialo)-SRIF28) (SEQ ID NO. 17) was synthesized similarly to Example 1, except that a compound represented by the following formula (27) (peptide 27) (SEQ ID NO. 52) was employed instead of peptide 1.

[Chemical Formula 44]

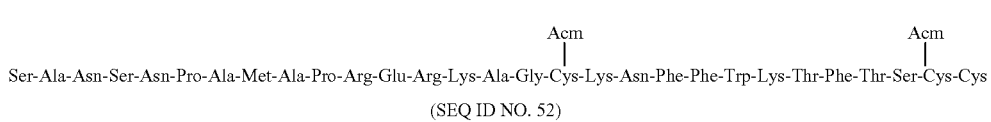

(27)

(SEQ ID NO. 52)

[Chemical Formula 45]

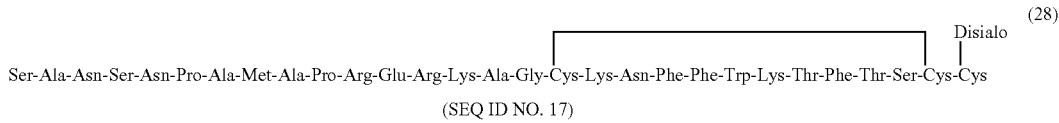

(28)

(SEQ ID NO. 17)

Example 14 Synthesis of 30C(Disialo)-SRIF28

A compound represented by the following formula (30) (30C(disialo)-SRIF28) (SEQ ID NO. 18) was synthesized similarly to Example 1, except that a compound represented by the following formula (29) (peptide 29) (SEQ ID NO. 53) was employed instead of peptide 1.

[Chemical Formula 46]

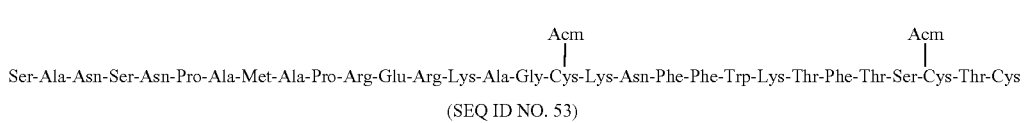

(29)

(SEQ ID NO. 53)

[Chemical Formula 47]

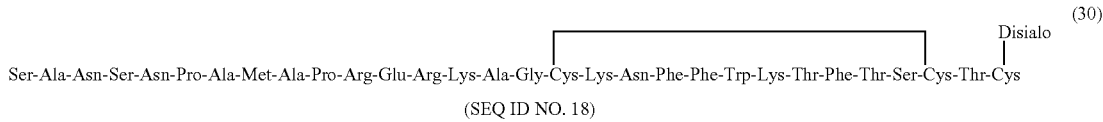

(30)

(SEQ ID NO. 18)

Example 15 Synthesis of S1C(Disialo)-D-Trp22-SRIF28

A compound represented by the following formula (32) (S1C(disialo)-D-Trp22-SRIF28) (SEQ ID NO. 19) was synthesized similarly to Example 1, except that a compound represented by the following formula (31) (peptide 31) (SEQ ID NO. 54) was employed instead of peptide 1.

[Chemical Formula 48]

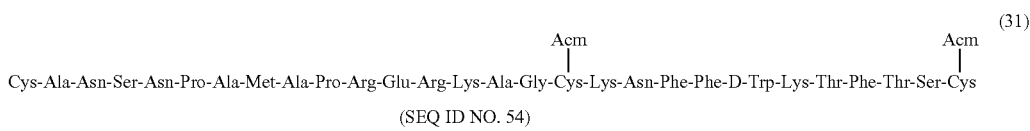

(31)

(SEQ ID NO. 54)

[Chemical Formula 49]

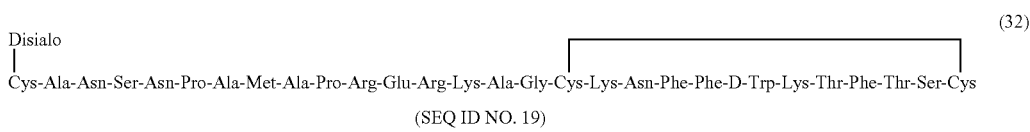

(32)

(SEQ ID NO. 19)

Example 16 Synthesis of A9C(Disialo)-D-Trp22-SRIF28

A compound represented by the following formula (34) (A9C(disialo)-D-Trp22-SRIF28) (SEQ ID NO. 20) was synthesized similarly to Example 1, except that a compound represented by the following formula (33) (peptide 33) (SEQ ID NO. 55) was employed instead of peptide 1.

[Chemical Formula 50]

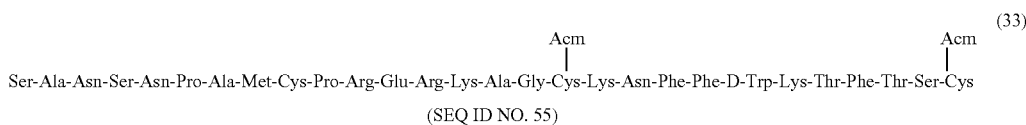

(SEQ ID NO. 55)

[Chemical Formula 51]

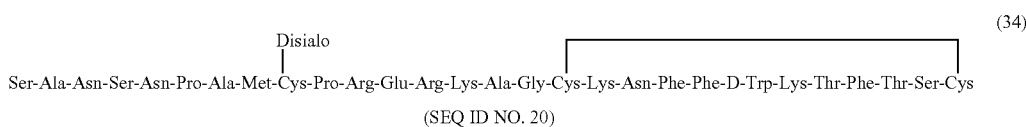

(SEQ ID NO. 20)

Example 17 Synthesis of C(Disialo)-SRIF14

A compound represented by the following formula (36) (C(disialo)-SRIF14) (SEQ ID NO. 35) was synthesized similarly to Example 1, except that a compound represented by the following formula (35) (peptide 35) (SEQ ID NO. 56) was employed instead of peptide 1.

[Chemical Formula 52]

(35)

Acm                 Acm
|                  |
Cys-Ala-Gly-Cys-Lys-Asn-Phe-Phe-Trp-Lys-Thr-Phe-Thr-Ser-Cys (SEQ ID NO. 56)

[Chemical Formula 53]

(36)

Disialo
|   ⎡⎯⎯⎯⎯⎯⎯⎯⎯⎯⎯⎯⎯⎯⎯⎯⎯⎯⎯⎯⎯⎯⎯⎤
Cys-Ala-Gly-Cys-Lys-Asn-Phe-Phe-Trp-Lys-Thr-Phe-Thr-Ser-Cys (SEQ ID NO. 35)

Example 18 Synthesis of C(Disialo)-R-K-SRIF14

A compound represented by the following formula (38) (C(disialo)-R-K-SRIF14) (SEQ ID NO. 36) was synthesized similarly to Example 1, except that a compound represented by the following formula (37) (peptide 37) (SEQ ID NO. 57) was employed instead of peptide 1.

[Chemical Formula 54]

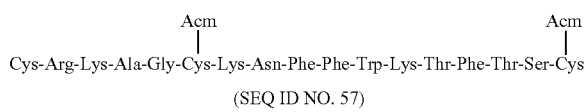

(SEQ ID NO. 57)

[Chemical Formula 55]

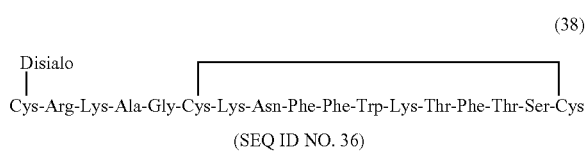

(SEQ ID NO. 36)

Example 19 Synthesis of C(Disialo)-C12 Linker-SRIF14

19-1 Synthesis of Peptide 2-chlorotrityl chloride resin (100 μmol) was taken in a column for solid phase synthesis, and after washing with DMF and dichloromethane, a solution of Fmoc-Cys(Acm)-OH (49.7 mg, 120 μmol) and DIPEA (104.5 μL, 600 μmol) in dichloromethane (3.0 mL) was added, and this was shaken for 1 hour. After washing with dichloromethane and DMF, the Fmoc protecting group was removed by treating with 20% piperidine in DMF. After washing with DMF, in a peptide solid phase synthesis method with Fmoc strategy employing a Prelude™ peptide synthesizer, a protected peptide 39 (SEQ ID NO. 58) represented by the following formula (39) was synthesized in a state bound to the resin. The condensation reaction was performed in DMF using HCTU as the condensation agent.

[Chemical Formula 56]

(39)

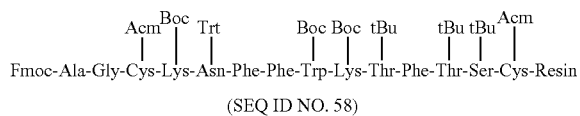

(SEQ ID NO. 58)

The Fmoc protecting group was removed by treating with 20% piperidine in DMF. After washing with DMF and dichloromethane, employing HCTU as the condensation agent, Fmoc-12-aminododecanoic acid and Fmoc-Cys(Trt)-OH were condensed in sequence. After condensation, the Fmoc protecting group was removed by treating with 20% piperidine in DMF. After washing with DMF and dichloromethane, TFA:water:triisopropylsilane:ethanedithiol (=90:2.5:5:2.5) was added, and this was shaken for 3 hours at room temperature. This leads to the detachment of the protecting group of the amino acid side chain (other than the Acm group), as well as cleaving between the peptide and the resin. The resin was filtered off, cold diethyl ether was added to the filtrate, and crude peptide was obtained as precipitate. A part of the crude peptide was purified with HPLC [column: SHISEIDO CAPCELL PAK C18 UG-120 (5 μm), φ20×250 mm, flow rate: 7.0 mL/min, eluent A: 0.1% aqueous TFA, B: 0.09% TFA/10% water/90% acetonitrile, gradient A:B=60:40→36.2:63.8, 20 minutes, linear gradient elution] to obtain a compound represented by the following formula (40) (peptide 40) (SEQ ID NO. 59) (11.2 mg).

[Chemical Formula 57]

(40)

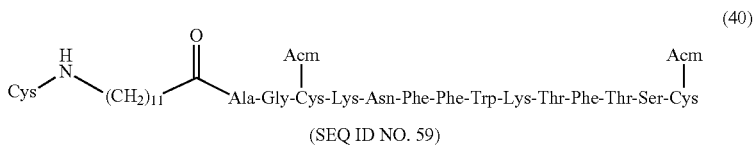

(SEQ ID NO. 59)

ESI-MS: (m/z) calcd for $C_{97}H_{144}N_{22}O_{23}S_3$: $[M+2H]^{2+}$ 1042.3, $[M+3H]^{3+}$ 695.2. found 1042.0, 695.0.

19-2 Glycosylation Reaction of Thiol

Peptide 40 obtained in the method described in the above 19-1 (6.8 mg, 3.3 μmol) and compound a represented by the above formula (a) (19.1 mg, 8.15 μmol) were dissolved' in 0.2 M phosphate buffer (pH 7.4, 0.96 mL) containing 7 M guanidine hydrochloride and 330 μM TCEP, and reacted at room temperature for 2 hours. After confirming the disappearance of raw materials with HPLC, the reaction solution was purified with HPLC [column: SHISEIDO CAPCELL PAK C18 UG-120 (5 μm), 920×250 mm, flow rate: 7.0 mL/min, eluent A: 0.1% aqueous AcOH, B: 0.09% AcOH/10% water/90% acetonitrile, gradient A:B=80:20→50:50, 25 minutes, linear gradient elution] to obtain a compound represented by the following formula (41) (glycopeptide 41) (SEQ ID NO. 60) (7.1 mg, 1.6 μmol, yield 50%).

[Chemical Formula 58]

(41)

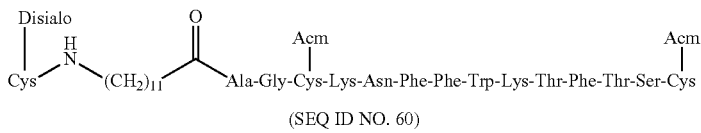

(SEQ ID NO. 60)

ESI-MS: (m/z) calcd for $C_{183}H_{283}N_{29}O_{85}S_3$: $[m+3H]^{3+}$ 1449.5, $[M+4H]^{4+}$ 1087.4, $[M+5H]^{5+}$ 870.1. found 1449.3, 1087.2, 870.0.

19-3 Deprotection of Acm Group

To glycopeptide 41 obtained in the method described in the above 19-2 (10.3 mg, 2.37 μmol) was added an aqueous solution (0.95 mL) of silver(I) acetate (9.7 mg, 58 μmol), and reacted at room temperature for 30 minutes. DTT (22.3 mg, 145 μmol) dissolved in 100 mM phosphate buffer (pH 7.4, 0.95 mL) and 100 mM ascorbic acid aqueous solution (0.95 mL) were added, and this was promptly filtered with a filter. The filtrate was purified with HPLC [column: SHISEIDO CAPCELL PAK C18 UG-120 (5 μm), φ20×250 mm, flow rate: 7.0 mL/min, eluent A: 0.1% aqueous AcOH, B: 0.09% AcOH/10% water/90% acetonitrile, gradient A:B=80:20→50:50, 25 minutes, linear gradient elution] to obtain glycopeptide 42 represented by the following formula 42 (SEQ ID NO. 61) (5.8 mg, 1.4 μmol, yield 59%).

[Chemical Formula 59]

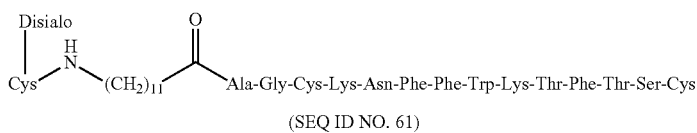

(42)

(SEQ ID NO. 61)

ESI-MS: (m/z) calcd for $C_{177}H_{273}N_{27}O_{83}S_3$: $[M+3H]^{3+}$ 1402.1, $[M+4H]^{4+}$ 1051.8, $[M+5H]^{5+}$ 841.7. found 1401.9, 1051.7, 841.5.

19-4 Formation of Disulfide Bond

Glycopeptide 42 obtained in the method described in the above 19-3 (5.8 mg, 1.4 μmol) was dissolved in 100 mM Tris-HCl buffer (pH 8.0)-DMSO (1/1, v/v, 3.5 mL), and reacted at room temperature for 30 hours. The reaction solution was purified with HPLC [column: SHISEIDO CAPCELL PAK C18 UG-120 (5 μm), φ20×250 mm, flow rate: 7.0 mL/min, eluent A: 0.1% aqueous TFA, B: 0.09% TFA/10% water/90% acetonitrile, gradient A:B=70:30→50:50%, 25 minutes, linear gradient elution] to obtain a fraction containing compound (C(disialo)-C12 linker-SRIF14) represented by the following formula 43 (SEQ ID NO. 37).

[Chemical Formula 60]

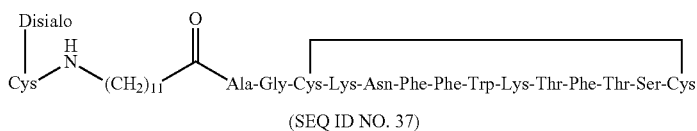

(43)

(SEQ ID NO. 37)

This fraction was further purified with HPLC [column: SHISEIDO CAPCELL PAK C18 UG-120 (5 μm), φ20×250 mm, flow rate: 7.0 mL/min, eluent A: 0.1% aqueous AcOH, B: 0.09% AcOH/10% water/90% acetonitrile, gradient A:B=80:20→50:50, 25 minutes, linear gradient elution] to obtain C(disialo)-C12 linker-SRIF14 (3.6 mg, 0.86 μmol, yield 61%).

ESI-MS: (m/z) calcd for $C_{177}H_{271}N_{27}O_{83}S_3$: $[M+3H]^{3+}$ 1401.5, $[M+4H]^{4+}$ 1051.3, $[M+5H]^{5+}$ 841.3. found 1401.2, 1051.2, 841.1.

Example 20 Synthesis of S1-2C(Disialo)-SRIF28

20-1 Synthesis of Peptide 2-chlorotrityl chloride resin (100 μmol) was taken in a column for solid phase synthesis, and after washing with DMF and dichloromethane, a solution of Fmoc-Cys(Acm)-OH (49.7 mg, 120 μmol) and DIPEA (104.5 μL, 600 μmol) in dichloromethane (3.0 mL) was added, and this was shaken for 1 hour. After washing with dichloromethane and DMF, the Fmoc protecting group was removed by treating with 20% piperidine in DMF. After washing with DMF and dichloromethane, in a peptide solid phase synthesis method with Fmoc strategy employing a Prelude™ peptide synthesizer, a protected peptide was synthesized on a resin. The condensation reaction was performed in DMF using HCTU as the condensation agent.

The Fmoc protecting group was removed by treating with 20% piperidine in DMF. After washing with DMF and dichloromethane, TFA:water:triisopropylsilane:ethanedithiol (=90:2.5:5:2.5) was added, and this was shaken for 3 hours at room temperature. The resin was filtered off, cold diethyl ether was added to the filtrate, and crude peptide was obtained as precipitate. A part of the crude peptide was purified with HPLC [column: SHISEIDO CAPCELL PAK C18 UG-120 (5 μm), φ20×250 mm, flow rate: 7.0 mL/min, eluent A: 0.1% aqueous TFA, B: 0.09% TFA/10% water/90% acetonitrile, gradient A:B=72:28→68.5:31.5, 20 minutes, linear gradient elution] to obtain peptide 44 (SEQ ID NO. 62) represented by the following formula (44) (30.7 mg).

[Chemical Formula 61]

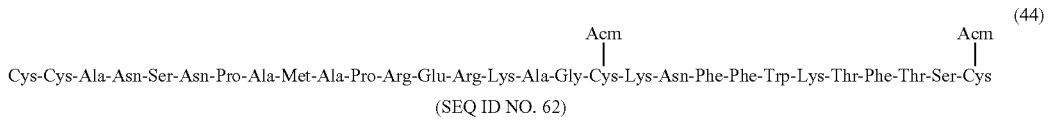

(SEQ ID NO. 62)

ESI-MS: (m/z) calcd for $C_{146}H_{224}N_{44}O_{41}S_5$: $[M+3H]^{3+}$ 1138.3, $[M+4H]^{4+}$ 854.0, $[M+5H]^{5+}$ 683.4. found 1138.2, 853.9, 683.1.

20-2 Glycosylation Reaction of Thiol

Peptide 44 obtained in the method described in the above 20-1 (45.8 mg, 13.4 μmol) and compound a represented by the above formula (a) (125.8 mg, 53.7 μmol, 4.0 equivalents to peptide 44) were dissolved in 33 mM phosphate buffer (pH 7.4, 4.0 mL), and reacted at room temperature for 30 minutes. The reaction solution was purified with HPLC [column: SHISEIDO CAPCELL PAK C18 UG-120 (5 μm), φ20×250 mm, flow rate: 7.0 mL/min, eluent A: 0.1% aqueous AcOH, B: 0.09% AcOH/10% water/90% acetonitrile, gradient A:B=83:17→72:28, 15 minutes, linear gradient elution] to obtain glycopeptide 45 represented by the following formula 45 (SEQ ID NO. 63) (44.5 mg, 5.61 μmol, yield 42%).

[Chemical Formula 62]

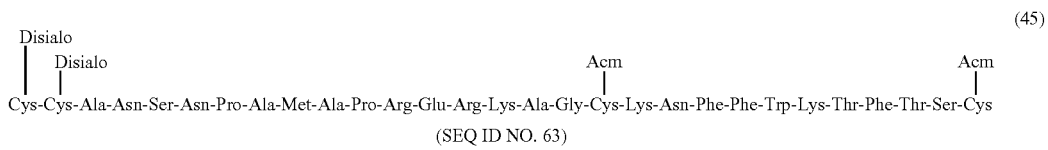

(SEQ ID NO. 63)

ESI-MS: (m/z) calcd for $C_{318}H_{502}N_{58}O_{165}S_5$: $[M+5H]^{5+}$ 1588.6, $[M+6H]^{6+}$ 1324.0, $[M+7H]^{7+}$ 1135.0, $[M+8H]^{8+}$ 993.3, $[M+9H]^{9+}$ 883.0. found 1588.6, 1324.0, 1135.0, 993.2, 883.0.

20-3 Deprotection of Acm Group

To glycopeptide 45 obtained in the method described in the above 20-2 (44.5 mg, 5.61 μmol) was added an aqueous solution (2.2 mL) of silver(I) acetate (14.8 mg, 88.7 μmol), and reacted at room temperature for 30 minutes. DTT (33.2 mg, 215 μmol) dissolved in 200 mM phosphate buffer (pH 7.4, 2.2 mL) and 100 mM ascorbic acid aqueous solution (561 μL) were added, and this was promptly filtered with a filter. The filtrate was purified with HPLC [column: SHISEIDO CAPCELL PAK C18 UG-120 (5 μm), φ20×250 mm, flow rate: 7.0 mL/min, eluent A: 0.1% aqueous AcOH, B: 0.09% AcOH/10% water/90% acetonitrile, gradient A:B=83:17→72:28, 15 minutes, linear gradient elution] to obtain glycopeptide 46 (SEQ ID NO. 64) represented by the following formula (46) (34.4 mg, 4.41 μmol, yield 79%).

[Chemical Formula 63]

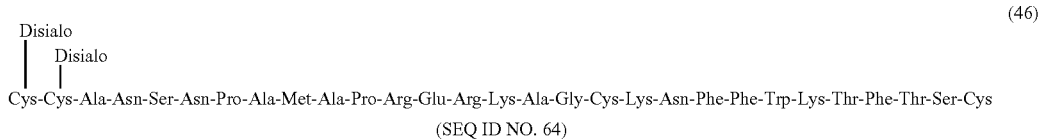

(SEQ ID NO. 64)

ESI-MS: (m/z) calcd for $C_{312}H_{492}N_{56}O_{163}S_5$: $[M+4H]^{4+}$ 1950.0, $[M+5H]^{5+}$ 1560.2, $[M+6H]^{6+}$ 1300.3. found 1949.8, 1560.1, 1300.2.

20-4 Formation of Disulfide Bond

Glycopeptide 46 obtained in the method described in the above 20-3 (34.4 mg, 4.41 μmol) was dissolved in 100 mM Tris-HCl buffer (pH 8.0)-DMSO (1/1, v/v, 8.8 mL), and reacted at room temperature for 2 days. The reaction solution was purified with HPLC [column: SHISEIDO CAPCELL PAK C18 UG-120 (5 μm), φ20×250 mm, flow rate: 7.0 mL/min, eluent A: 0.1% aqueous TFA, B: 0.09% TFA/10% water/90% acetonitrile, gradient A:B=77:23→65:35, 16 minutes, linear gradient elution] to obtain a fraction containing compound (S1-2C(disialo)-SRIF28) represented by the following formula (47) (SEQ ID NO. 21).

[Chemical Formula 64]

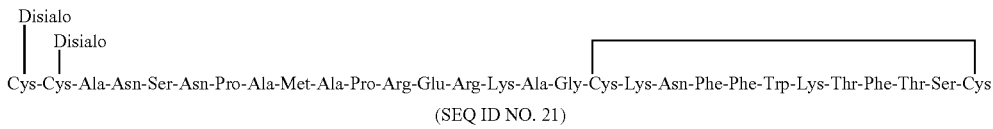

(SEQ ID NO. 21)

This fraction was further purified with HPLC [column: SHISEIDO CAPCELL PAK C18 UG-120 (5 μm), φ20×250 mm, flow rate: 7.0 mL/min, eluent A: 0.1% aqueous AcOH, B: 0.09% AcOH/10% water/90% acetonitrile, gradient A:B=83:17→72:28, 15 minutes, linear gradient elution] to obtain S1-2C(disialo)-SRIF28 (20.1 mg, 2.58 μmol, yield 58%).

ESI-MS: (m/z) calcd for $C_{312}H_{490}N_{56}O_{163}S_5$: $[M+4H]^{4+}$ 1949.5, $[M+5H]^{5+}$ 1559.8, $[M+6H]^{6+}$ 1300.0. found 1949.4, 1559.7, 1299.9.

Example 21 Synthesis of S1C(Disialo)•N5C(Disialo)-SRIF28

A compound represented by the following formula (49) (S1C(disialo)•N5C(disialo)-SRIF28) (SEQ ID NO. 22) was synthesized similarly to Example 20, except that a compound represented by the following formula (48) (peptide 48) (SEQ ID NO. 65) was employed instead of peptide 44.

[Chemical Formula 65]

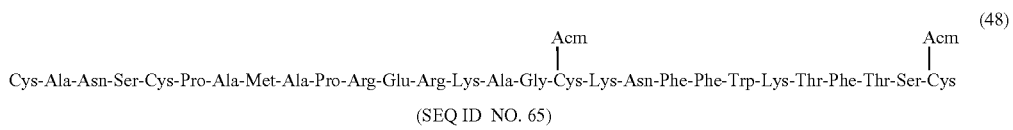

(SEQ ID NO. 65)

[Chemical Formula 66]

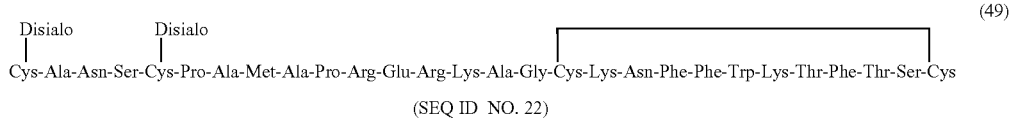

(SEQ ID NO. 22)

Example 22 Synthesis of S1C(Disialo)•R13C(Disialo)-SRIF28

A compound represented by the following formula (51) (S1C(disialo)•R13C(disialo)-SRIF28) (SEQ ID NO. 23) was synthesized similarly to Example 20, except that a compound represented by the following formula (50) (peptide 50) (SEQ ID NO. 66) was employed instead of peptide 44.

[Chemical Formula 67]

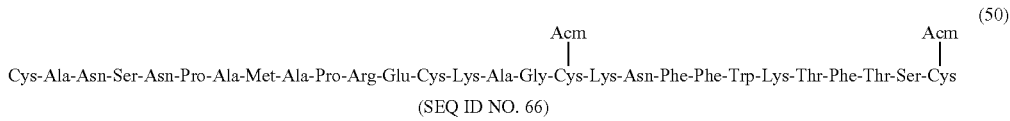

(SEQ ID NO. 66)

[Chemical Formula 68]

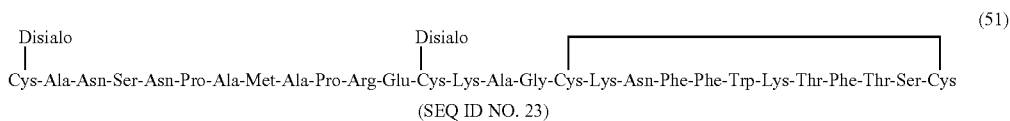

(SEQ ID NO. 23)

Example 23 Synthesis of N5C(Disialo)•A9C(Disialo)-SRIF28

A compound represented by the following formula (53) (N5C(disialo)•A9C(disialo)-SRIF28) (SEQ ID NO. 24) was synthesized similarly to Example 20, except that a compound represented by the following formula (52) (peptide 52) (SEQ ID NO. 67) was employed instead of peptide 44.

[Chemical Formula 69]

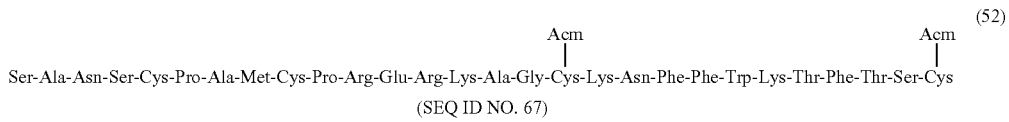

(SEQ ID NO. 67)

[Chemical Formula 70]

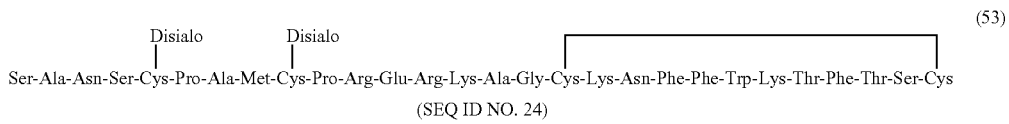

(SEQ ID NO. 24)

Example 24 Synthesis of S1-3C(Disialo)-SRIF28

24-1 Synthesis of Peptide 2-chlorotrityl chloride resin (100 μmol) was taken in a column for solid phase synthesis, and after washing with DMF and dichloromethane, a solution of Fmoc-Cys(Acm)-OH (49.7 mg, 120 μmol) and DIPEA (104.5 μL, 600 μmol) in dichloromethane (3.0 mL) was added, and this was shaken for 1 hour. After washing with dichloromethane and DMF, the Fmoc protecting group was removed by treating with 20% piperidine in DMF. After washing with DMF, in a peptide solid phase synthesis method with Fmoc strategy employing a Prelude™ peptide synthesizer, a protected peptide was synthesized on the resin. The condensation reaction was performed in DMF using HCTU as the condensation agent.

The Fmoc protecting group was removed by treating with 20% piperidine in DMF. After washing with DMF and dichloromethane, TFA:water:triisopropylsilane:ethanedithiol (=90:2.5:5:2.5) was added, and this was shaken at room temperature for 3 hours. The resin was filtered off, cold diethyl ether was added to the filtrate, and crude peptide was obtained as precipitate. A part of the crude peptide was purified with HPLC [column: SHISEIDO CAPCELL PAK C18 UG-120 (5 μm), φ50×250 mm, flow rate: 43.7 mL/min, eluent A: 0.1% aqueous TFA, B: 0.09% TFA/10% water/90% acetonitrile, gradient A:B=73:27→65:35, 14 minutes, linear gradient elution] to obtain peptide 54 (SEQ ID NO. 68) represented by the following formula (54) (41.7 mg).

[Chemical Formula 71]

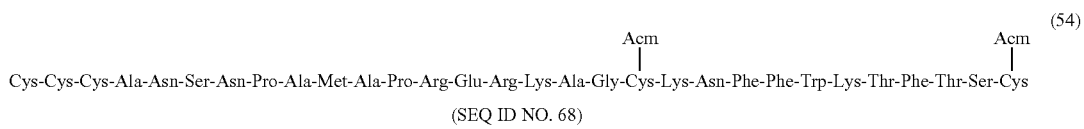

(SEQ ID NO. 68)

ESI-MS: (m/z) calcd for $C_{149}H_{229}N_{45}O_{42}S_6$: $[M+3H]^{3+}$ 1172.7, $[M+4H]^{4+}$ 879.8, $[M+5H]^{5+}$ 704.0. found 1172.5, 879.4, 703.9.

24-2 Glycosylation Reaction of Thiol

Peptide 54 obtained in the method described in the above 24-1 (10.7 mg, 3.04 μmol) and compound a represented by the above formula (a) (36.6 mg, 15.6 μmol, 5.2 equivalents to peptide 54) were dissolved in 33 mM phosphate buffer (pH 7.4, 0.91 mL) containing 10 μM TCEP, and reacted at room temperature for 100 minutes. The reaction solution was purified with HPLC [column: SHISEIDO CAPCELL PAK C18 UG-120 (5 μm), ϕ20×250 mm, flow rate: 7.0 mL/min, eluent A: 0.1% aqueous AcOH, B: 0.09% AcOH/10% water/90% acetonitrile, gradient A:B=80:20→70:30, 5 minutes, then A:B=70:30→65:35, 12 minutes, linear gradient elution] to obtain glycopeptide 55 (SEQ ID NO. 69) represented by the following formula (55) (11.7 mg, 1.14 μmol, yield 38%).

[Chemical Formula 72]

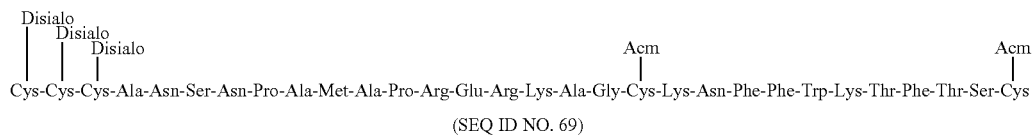

(55)

(SEQ ID NO. 69)

ESI-MS: (m/z) calcd for $C_{407}H_{646}N_{66}O_{228}S_6$: $[M+5H]^{5+}$ 2061.8, $[M+6H]^{6+}$ 1718.4, $[M+7H]^{7+}$ 1473.0, $[M+8H]^{8+}$ 1289.0, $[M+9H]^{9+}$ 1145.9, $[M+10H]^{10+}$ 1031.4. found 2061.8, 1718.2, 1472.9, 1289.0, 1145.8, 1031.3.

24-3 Deprotection of Acm Group

To glycopeptide 55 obtained in the method described in the above 24-2 (11.7 mg, 1.14 μmol) was added an aqueous solution (0.46 mL) of silver(I) acetate (4.7 mg, 28 μmol), and reacted at room temperature for 2 hours. DTT (11.3 mg, 73 μmol) dissolved in 200 mM Tris-HCl buffer (pH 7.4, 0.46 mL) and 100 mM ascorbic acid aqueous solution (0.11 mL) were added, and this was promptly filtered with a filter. The filtrate was purified with HPLC [column: SHISEIDO CAPCELL PAK C18 UG-120 (5 μm), ϕ20×250 mm, flow rate: 7.0 mL/min, eluent A: 0.1% aqueous AcOH, B: 0.09% AcOH/10% water/90% acetonitrile, gradient A:B=80:20→70:30, 5 minutes, then 70:30→55:45, 15 minutes, linear gradient elution] to obtain glycopeptide 56 (SEQ ID NO. 70) represented by the following formula (56) (7.4 mg, 0.73 μmol, yield 64%).

[Chemical Formula 73]

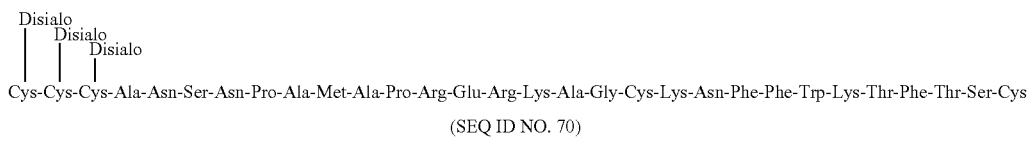

(56)

(SEQ ID NO. 70)

ESI-MS: (m/z) calcd for $C_{401}H_{636}N_{64}O_{226}S_6$: $[M+6H]^{6+}$ 1694.7, $[M+7H]^{7+}$ 1452.7, $[M+8H]^{8+}$ 1271.3, $[M+9H]^{9+}$ 1130.1, $[M+10H]^{10+}$ 1017.2. found 1694.6, 1452.5, 1271.4, 1130.0, 1017.2.

24-4 Formation of Disulfide Bond

Glycopeptide 56 obtained in the method described in the above 24-3 (7.4 mg, 0.73 μmol) was dissolved in 100 mM Tris-HCl buffer (pH 8.0)-DMSO (1/1, v/v, 1.8 mL), and reacted at room temperature for 25 hours. The reaction solution was purified with HPLC [column: SHISEIDO CAPCELL PAK C18 UG-120 (5 μm), ϕ20×250 mm, flow rate: 7.0 mL/min, eluent A: 0.1% aqueous TFA, B: 0.09% TFA/10% water/90% acetonitrile, gradient A:B=80:20→70:30, 5 minutes, then 70:30→69.3:30.7, 5 minutes, linear gradient elution] to obtain a fraction containing compound (S1-3C(disialo)-SRIF28) represented by the following formula (57) (SEQ ID NO. 25).

[Chemical Formula 74]

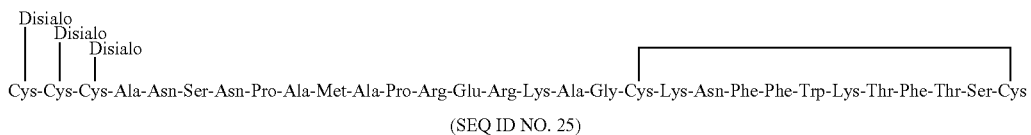

(57)

(SEQ ID NO. 25)

This fraction was further purified with HPLC [column: SHISEIDO CAPCELL PAK C18 UG-120 (5 μm), φ20×250 mm, flow rate: 7.0 mL/min, eluent A: 0.1% aqueous AcOH, B: 0.09% AcOH/10% water/90% acetonitrile, gradient A:B=80:20→40:60, 20 minutes, linear gradient elution] to obtain S1-3C(disialo)-SRIF28 (4.7 mg, 0.46 μmol, yield 63%).

ESI-MS: (m/z) calcd for $C_{401}H_{634}N_{64}O_{226}S_6$: $[M+3H]^{3+}$ 3387.7, $[M+4H]^{4+}$ 2541.0, $[M+5H]^{5+}$ 2033.0, $[M+6H]^{6+}$ 1694.3, $[M+7H]^{7+}$ 1452.4. found 3387.6, 2540.9, 2032.7, 1694.2, 1452.3.

Example 25 Synthesis of S1C(disialo) N5C(disialo) A9C(disialo)-SRIF28

A compound represented by the following formula (59) (S1C(disialo)•N5C(disialo)•A9C(disialo)-SRIF28) (SEQ ID NO. 26) was synthesized similarly to Example 24, except that peptide 58 (SEQ ID NO. 71) represented by the following formula (58) was employed instead of peptide 54.

[Chemical Formula 75]

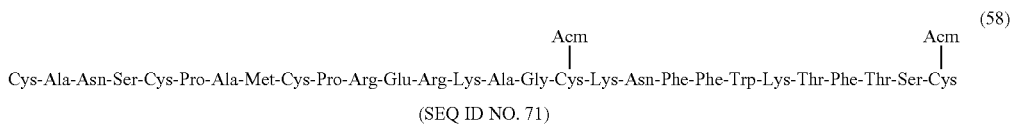

(58)

(SEQ ID NO. 71)

[Chemical Formula 76]

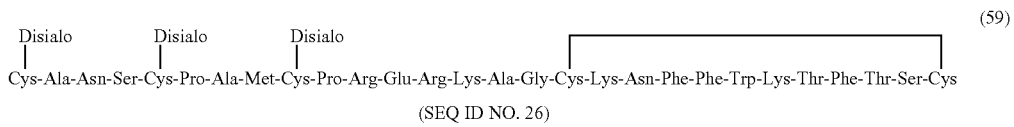

(59)

(SEQ ID NO. 26)

Example 26 Synthesis of S1C(Monosialo)-SRIF28

A compound represented by the following formula (60) (S1C(monosialo)-SRIF28) (SEQ ID NO. 27) was synthesized similarly to Example 1, except that compound b represented by the following formula (b) (bromoacetamidated oligosaccharide: from Otsuka Chemical Co, Ltd.) was employed instead of compound a.

[Chemical Formula 77]

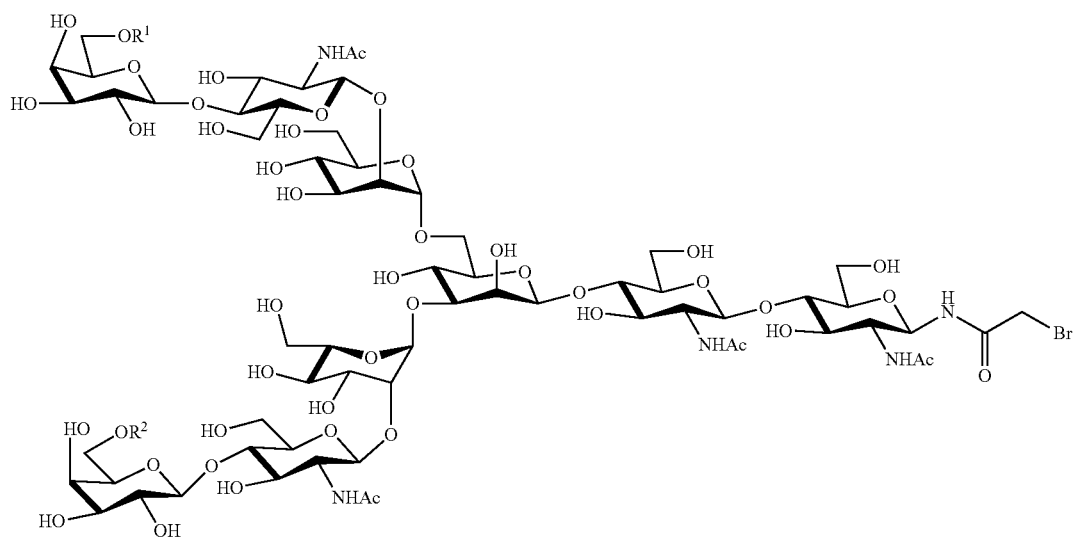

(b)

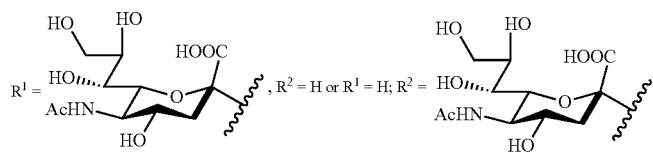

, $R^2$ = H or $R^1$ = H; $R^2$ =

[Chemical Formula 78]

(60)

Monosialo
|
Cys-Ala-Asn-Ser-Asn-Pro-Ala-Met-Ala-Pro-Arg-Glu-Arg-Lys-Ala-Gly-Cys-Lys-Asn-Phe-Phe-Trp-Lys-Thr-Phe-Thr-Ser-Cys (SEQ ID NO. 27)

In the final product, the ratio between the glycosylated polypeptide having the sugar chain of the following formula b1 and the glycosylated polypeptide having the sugar chain of the following formula b2 was 45:55. Note that it is possible to manufacture a glycosylated polypeptide having substantially uniform sugar chain structure by using monosialo sugar chain derivatives having identical structure.

[Chemical Formula 79]
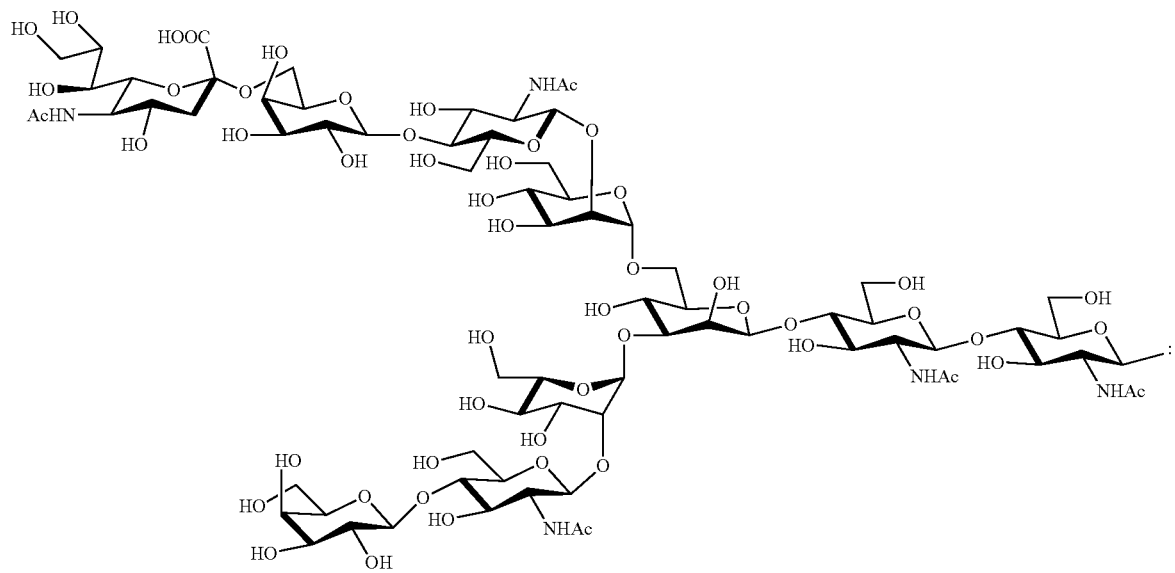
(b1)
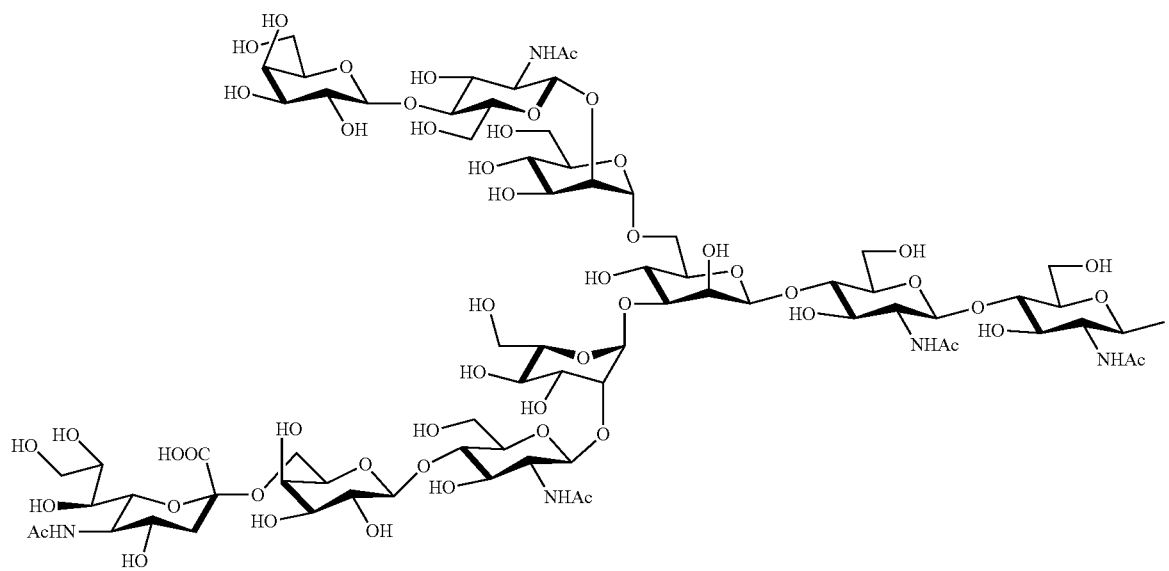
(b2)
Example 27 Synthesis of S1C(Asialo)-SRIF28
A compound represented by the following formula (61) (S1C(asialo)-SRIF28) (SEQ ID NO. 28) was synthesized similarly to Example 1, except that compound c represented by the following formula (c) (bromoacetamidated oligosaccharide: from Otsuka Chemical Co., Ltd.) was employed instead of compound a.

[Chemical Formula 80]

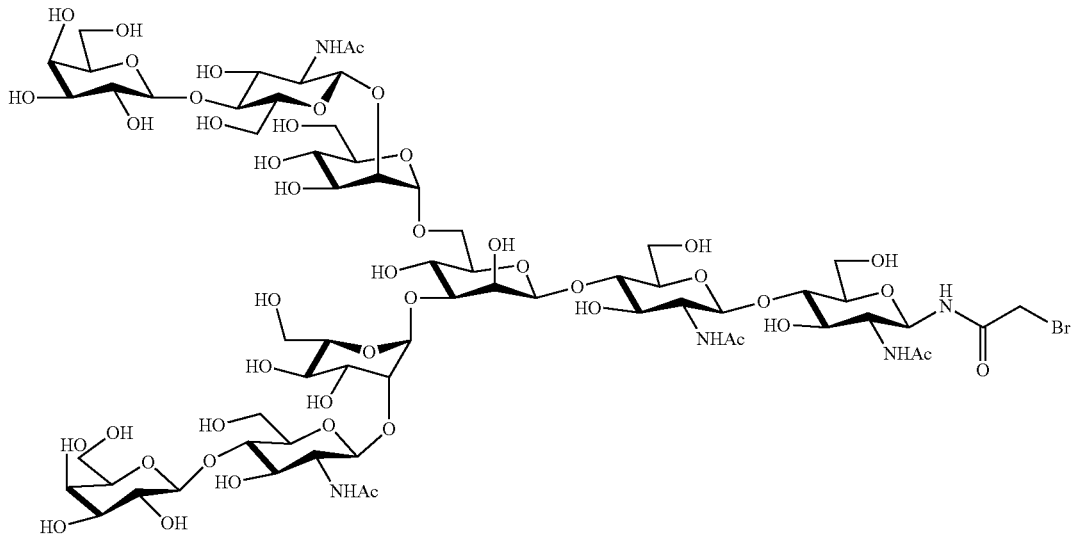

(c)

[Chemical Formula 81]

(61)

Asialo
|
Cys-Ala-Asn-Ser-Asn-Pro-Ala-Met-Ala-Pro-Arg-Glu-Arg-Lys-Ala-Gly-Cys-Lys-Asn-Phe-Phe-Trp-Lys-Thr-Phe-Thr-Ser-Cys (SEQ ID NO. 28)

Example 28 Synthesis of S1-2C(Asialo)-SRIF28

28-1 Glycosylation Reaction of Thiol

Peptide 44 (21.2 mg, 6.21 μmol) and compound c (44.5 mg, 25.3 μmol, 4.1 equivalents to peptide 44) were dissolved in 33 mM phosphate buffer (pH 7.4, 1.9 mL), and reacted at room temperature for 1 hour. The reaction solution was purified with HPLC [column: SHISEIDO CAPCELL PAK C18 UG-120 (5 μm), φ20×250 mm, flow rate: 7.0 mL/min, eluent A: 0.1% aqueous TEA, B: 0.09% TFA/10% water/90% acetonitrile, gradient A:B=77:23→62:38, 15 minutes, linear gradient elution] to obtain glycopeptide 62 (SEQ ID NO. 72) represented by the following formula (62) (24.0 mg, 3.54 μmol, yield 57%).

[Chemical Formula 82]

(62)

Asialo
| Asialo              Acm              Acm
|  |                   |                |
Cys-Cys-Ala-Asn-Ser-Asn-Pro-Ala-Met-Ala-Pro-Arg-Glu-Arg-Lys-Ala-Gly-Cys-Lys-Asn-Phe-Phe-Trp-Lys-Thr-Phe-Thr-Ser-Cys (SEQ ID NO. 72)

ESI-MS: (m/z) calcd for $C_{274}H_{434}N_{54}O_{133}S_5$: $[M+4H]^{4+}$ 1694.3, $[M+5H]^{5+}$ 1355.6, $[M+6H]^{6+}$ 1129.8. found 1694.3, 1355.6, 1130.0.

28-2 Deprotection of Acm Group

To glycopeptide 62 obtained in the method described in the above 28-1 (24.0 mg, 3.54 µmol) was added an aqueous solution (1.4 mL) of silver(I) acetate (6.0 mg, 36 µmol), and reacted at room temperature for 3 hours. DTT (14.0 mg, 90.8 µmol) dissolved in 500 mM phosphate buffer (pH 7.4, 0.57 mL) and 100 mM ascorbic acid aqueous solution (0.35 mL) were added, and this was promptly filtered with a filter. The filtrate was purified with HPLC [column: SHISEIDO CAPCELL PAK C18 UG-120 (5 µm), φ20×250 mm, flow rate: 7.0 mL/min, eluent A: 0.1% aqueous TFA, B: 0.09% TFA/10% water/90% acetonitrile, gradient A:B=75:25→65:35, 15 minutes, linear gradient elution] to obtain glycopeptide 63 (SEQ ID NO. 73) represented by the following formula (63) (20.1 mg, 3.03 µmol, yield 86%).

[Chemical Formula 83]

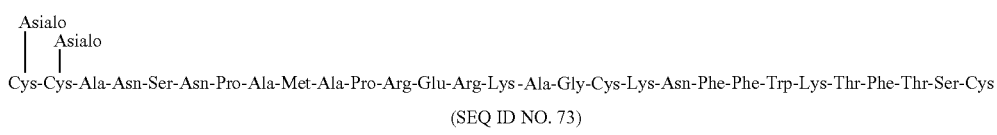

(63)

(SEQ ID NO. 73)

ESI-MS: (m/z) calcd for $C_{268}H_{424}N_{52}O_{131}S_5$: $[M+4H]^{4+}$ 1658.7, $[M+5H]^{5+}$ 1327.2. found 1658.8, 1327.0.

28-3 Formation of Disulfide Bond

Glycopeptide 63 obtained in the method described in the above 28-2 (20.1 mg, 3.03 µmol) was dissolved in 100 mM Tris-HCl buffer (pH 8.0)-DMSO (1/1, v/v, 6.1 mL), and reacted at room temperature for 2 days. The reaction solution was purified with HPLC [column: SHISEIDO CAPCELL PAK C18 UG-120 (5 µm), φ20×250 mm, flow rate: 7.0 mL/min, eluent A: 0.1% aqueous TFA, B: 0.09% TFA/10% water/90% acetonitrile, gradient A:B=77:23→65:35, 16 minutes, linear gradient elution] to obtain a fraction containing compound (S1-2C(asialo)-SRIF28) represented by the following formula (64) (SEQ ID NO. 29).

This fraction was further purified with HPLC [column: SHISEIDO CAPCELL PAK C18 UG-120 (5 µm), φ20×250 mm, flow rate: 7.0 mL/min, eluent A: 0.1% aqueous AcOH, B: 0.09% AcOH/10% water/90% acetonitrile, gradient A:B=92:8→80:20, 16 minutes, linear gradient elution] to obtain S1-2C(asialo)-SRIF28 (11.0 mg, 1.66 µmol, yield 55%).

ESI-MS: (m/z) calcd for $C_{268}H_{422}N_{52}O_{131}S_5$: $[M+4H]^{4+}$ 1658.2, $[M+5H]^{5+}$ 1326.8, $[M+6H]^{6+}$ 1105.8, $[M+7H]^{7+}$ 948.0, $[M+8H]^{8+}$ 829.6. found 1658.1, 1326.7, 1105.6, 947.8, 829.4.

Example 29 Synthesis of S1-3C(Asialo)-SRIF28

29-1 Glycosylation Reaction of Thiol

Peptide 54 (21.3 mg, 6.06 µmol) and compound c (53.4 mg, 30.3 µmol, 5.0 equivalents to peptide 54) were dissolved in 33 mM phosphate buffer (pH 7.4, 1.8 mL), and reacted at room temperature for 1 hour. The reaction solution was purified with HPLC [column: SHISEIDO CAPCELL PAK C18 UG-120 (5 µm), φ20×250 mm, flow rate: 7.0 mL/min, eluent A: 0.1% aqueous TFA, B: 0.09% TFA/10% water/90% acetonitrile, gradient A:B=75:25→70:30, 20 minutes, linear gradient elution] to obtain glycopeptide 65 (SEQ ID NO. 74) represented by the following formula (65) (39.3 mg, 4.59 µmol, yield 76%).

[Chemical Formula 84]

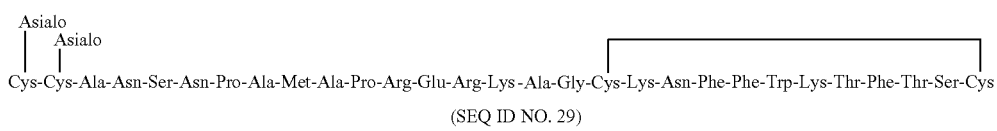

(64)

(SEQ ID NO. 29)

[Chemical Formula 85]

(65)

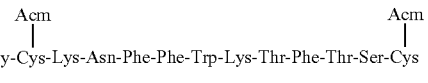
Cys-Cys-Cys-Ala-Asn-Ser-Asn-Pro-Ala-Met-Ala-Pro-Arg-Glu-Arg-Lys-Ala-Gly-Cys-Lys-Asn-Phe-Phe-Trp-Lys-Thr-Phe-Thr-Ser-Cys (SEQ ID NO. 74)

ESI-MS: (m/z) calcd for $C_{341}H_{544}N_{60}O_{180}S_6$: $[M+4H]^{4+}$ 2140.2, $[M+5H]^{5+}$ 1712.3, $[M+6H]^{6+}$ 1427.1. found 2140.2, 1712.4, 1427.2.

29-2 Deprotection of Acm Group

To glycopeptide 65 obtained in the method described in the above 29-1 (39.3 mg, 4.59 μmol) was added an aqueous solution (1.8 mL) of silver(I) acetate (18.7 mg, 112 μmol), and reacted at room temperature for 90 minutes. DTT (43.4 mg, 28.1 μmol) dissolved in 200 mM phosphate buffer (pH 7.4, 1.8 mL) and 100 mM ascorbic acid aqueous solution (0.46 mL) were added, and this was promptly filtered with a filter. The filtrate was purified with HPLC [column: SHISEIDO CAPCELL PAK C18 UG-120 (5 μm), φ20×250 mm, flow rate: 7.0 mL/min, eluent A: 0.1% aqueous TFA, B: 0.09% TFA/10% water/90% acetonitrile, gradient A:B=75:25→68:32, 18 minutes, linear gradient elution] to obtain glycopeptide 66 (SEQ ID NO. 75) represented by the following formula (66) (27.6 mg, 3.28 μmol, yield 71%).

This fraction was further purified with HPLC [column: SHISEIDO CAPCELL PAK C18 UG-120 (5 μm), φ20×250 mm, flow rate: 7.0 mL/min, eluent A: 0.1% aqueous AcOH, B: 0.09% AcOH/10% water/90% acetonitrile, gradient A:B=96:4→82:18, 20 minutes, linear gradient elution] to obtain S1-3C(asialo)-SRIF28 (14.5 mg, 1.72 μmol, yield 52%).

ESI-MS: (m/z) calcd for $C_{335}H_{532}N_{58}O_{178}S_6$: $[M+4H]^{4+}$ 2104.1, $[M+5H]^{5+}$ 1683.5, $[M+6H]^{6+}$ 1403.1. found 2103.7, 1683.3, 1403.0.

Example 30 Synthesis of N5N(Disialo)-SRIF28

30-1 Solid Phase Synthesis of Glycopeptide 2-chlorotrityl chloride resin (100 μmol) was taken in a column for solid phase synthesis, and after washing with

[Chemical Formula 86]

(66)

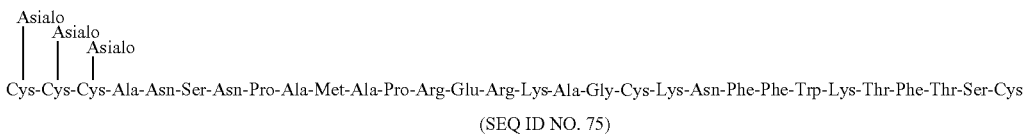
Cys-Cys-Cys-Ala-Asn-Ser-Asn-Pro-Ala-Met-Ala-Pro-Arg-Glu-Arg-Lys-Ala-Gly-Cys-Lys-Asn-Phe-Phe-Trp-Lys-Thr-Phe-Thr-Ser-Cys (SEQ ID NO. 75)

ESI-MS: (m/z) calcd for $C_{335}H_{534}N_{58}O_{178}S_6$: $[M+4H]^{4+}$ 2104.6, $[M+5H]^{5+}$ 1683.9, $[M+6H]^{6+}$ 1403.4. found 2104.6, 1684.0, 1403.3.

29-3 Formation of Disulfide Bond

Glycopeptide 66 obtained in the method described in the above 29-2 (27.6 mg, 3.28 μmol) was dissolved in 100 mM Tris-HCl buffer (pH 8.0)-DMSO (1/1, v/v, 8.2 mL), and reacted at room temperature for 2 days. The reaction solution was purified with HPLC [column: SHISEIDO CAPCELL PAK C18 UG-120 (5 μm), φ20×250 mm, flow rate: 7.0 mL/min, eluent A: 0.1% aqueous TFA, B: 0.09% TFA/10% water/90% acetonitrile, gradient A:B=72:28→70.5:29.5, 15 minutes, linear gradient elution] to obtain a fraction containing compound (S1-3C(asialo)-SRIF28) represented by the following formula (67) (SEQ ID NO. 30).

DMF and dichloromethane, a solution of Fmoc-Cys(Trt)-OH (72.5 mg, 120 μmol) and DIPEA (104.6 μL, 600 μmol) in dichloromethane (3.0 mL) was added, and this was shaken for 1 hour. After washing with dichloromethane and DMF, the Fmoc protecting group was removed by treating with 20% piperidine in DMF. After washing with DMF, in a peptide solid phase synthesis method with Fmoc strategy employing a Prelude™ peptide synthesizer, a protected peptide 68 (SEQ ID NO 76) represented by the following formula (68) was synthesized in a state bound to the resin. The condensation reaction was performed in DMF using HCTU as the condensation agent.

[Chemical Formula 87]

(67)

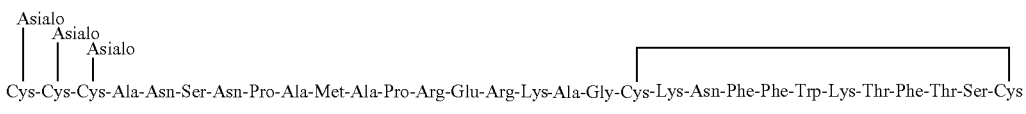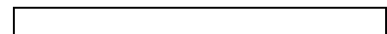
Cys-Cys-Cys-Ala-Asn-Ser-Asn-Pro-Ala-Met-Ala-Pro-Arg-Glu-Arg-Lys-Ala-Gly-Cys-Lys-Asn-Phe-Phe-Trp-Lys-Thr-Phe-Thr-Ser-Cys (SEQ ID NO. 30)

[Chemical Formula 88]

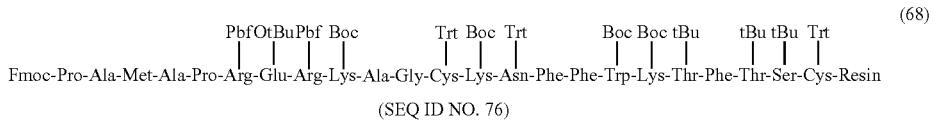

(68)

(SEQ ID NO. 76)

Next, the Fmoc protecting group was removed by treating with 20% piperidine in DMF. After washing with DMF, compound d represented by the following formula (d) (from Otsuka Chemical Co., Ltd.) (411.9 mg, 150.4 μmol), DMSO-DMF (1/1, v/v, 871 μL) solution, TBTU (64.2 mg, 200 μmol), and DIPEA (52.3 μL, 300 μmol) were sequentially added to the resin, and this was shaken at room temperature for 3 hours to allow condensation.

To this resin, employing HOBt/DIC as the condensation agent, Fmoc-Ser(tBu)-OH, Fmoc-Asn(Trt)-OH, Fmoc-Ala, and Fmoc-Ser(tBu)-OH were condensed in sequence. After condensation, the Fmoc protecting group was removed by treating with 20% piperidine in DMF. After washing with DMF and dichloromethane, TFA:water:triisopropylsilane:ethanedithiol (=90:2.5:5:2.5) was added, and this was

[Chemical Formula 89]

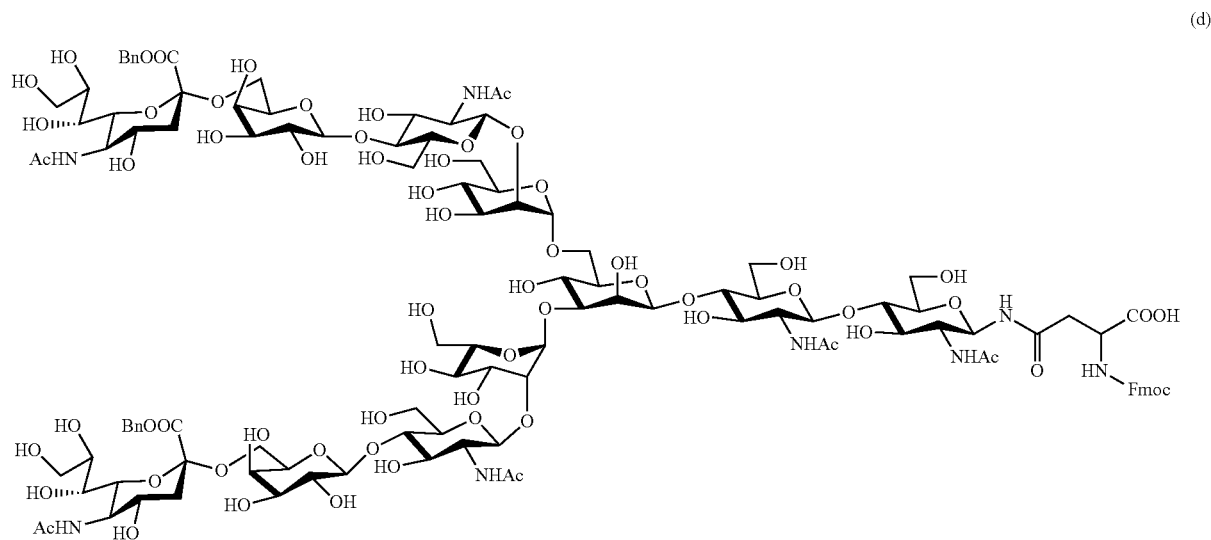

(d)

After washing with DMF, this condensation operation was repeated once. After washing the resin with DMF and dichloromethane, this was shaken with 20% piperidine in DMF for 20 minutes to deprotect the Fmoc group, and the resin was washed with DMF to synthesize a protected compound represented by the following formula (69) (peptide 69) (SEQ ID NO. 77) on the resin.

shaken at room temperature for 3 hours. Cold diethyl ether was added to the filtrate, and crude peptide was obtained as precipitate. This crude peptide was purified with HPLC [column: SHISEIDO CAPCELL PAK C18 UG-120 (5 μm), φ20×250 mm, flow rate: 7.0 mL/min, eluent A: 0.1% aqueous TFA, B: 0.09% TFA/10% water/90% acetonitrile,

[Chemical Formula 90]

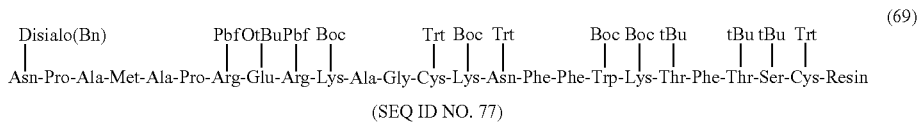

(69)

(SEQ ID NO. 77)

A:B=70:30] to obtain glycopeptide 70 (SEQ ID NO. 78) represented by the following formula (70) (29.1 mg, 5.26 µmol).

[Chemical Formula 91]

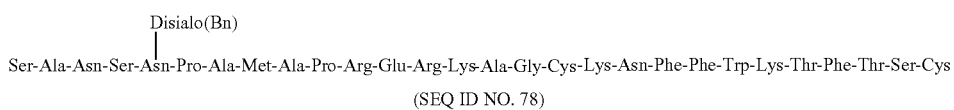

(70)

(SEQ ID NO. 78)

ESI-MS: (m/z) calcd for $C_{235}H_{357}N_{47}O_{100}S_3$: $[M+3H]^{3+}$ 1846.6, $[M+4H]^{4+}$ 1385.2, $[M+5H]^{5+}$ 1108.4. found 1846.5, 1385.1, 1108.3.

30-2 Formation of Disulfide Bond

Glycopeptide 70 obtained in the method described in the above 30-1 (12.2 mg, 2.20 µmol) was dissolved in 100 mM Tris-HCl buffer (pH 8.0)-DMSO (1/1, v/v, 5.5 mL), and reacted at room temperature for 2 days. The reaction solution was purified with HPLC [column: SHISEIDO CAPCELL PAK C18 UG-120 (5 µm), φ20×250 mm, flow rate: 7.0 mL/min, eluent A: 0.1% aqueous TFA, B: 0.09% TFA/10% water/90% acetonitrile, gradient A:B=80:20→66:35, 30 minutes, linear gradient elution] to obtain glycopeptide 71 (SEQ ID NO. 79) represented by the following formula (71) (8.3 mg, 1.5 µmol, yield 68%).

[Chemical Formula 92]

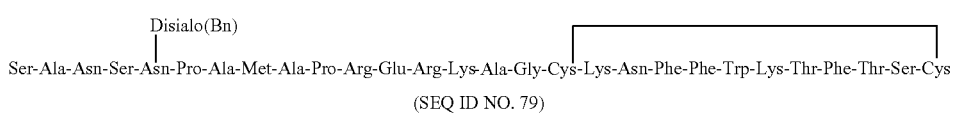

(71)

(SEQ ID NO. 79)

ESI-MS: (m/z) calcd for $C_{235}H_{355}N_{47}O_{100}S_3$: $[M+3H]^{3+}$ 1846.5, $[M+4H]^{4+}$ 1384.7, $[M+5H]^{5+}$ 1108.0. found 1846.5, 1384.7, 1108.1.

30-3 Deprotection of Benzyl Group

Glycopeptide 71 obtained in the method described in the above 30-2 (7.5 mg, 1.4 µmol) was dissolved in 50 mM sodium hydroxide aqueous solution (20.6 mL), and reacted at 0° C. for 80 minutes. 200 mM acetic acid aqueous solution (5.1 mL) was added, and the mixed solution was purified with HPLC [column: SHISEIDO CAPCELL PAK C18 UG-120 (5 µm), φ20×250 mm, flow rate: 7.0 mL/min, eluent A: 0.1% aqueous TFA, B: 0.09% TFA/10% water/90% acetonitrile, gradient A:B=73:27→66.3:33.7, 20 minutes, linear gradient elution] to obtain a fraction containing compound (N5N(disialo)-SRIF28) represented by the following formula (72) (SEQ ID NO. 31).

This fraction was further purified with HPLC [column: SHISEIDO CAPCELL PAK C18 UG-120 (5 µm), φ20×250 mm, flow rate: 7.0 mL/min, eluent A: 0.1% aqueous AcOH, B: 0.09% AcOH/10% water/90% acetonitrile, gradient A:B=80:20→60:40, 30 minutes, linear gradient elution] to obtain N5N(disialo)-SRIF28 (1.4 mg, yield 19%).

ESI-MS: (m/z) calcd for $C_{221}H_{343}N_{47}O_{100}S_3$: $[M+3H]^{3+}$ 1785.9, $[M+4H]^{4+}$ 1339.6, $[M+5H]^{5+}$ 1071.9. found 1785.7, 1339.5, 1071.8.

Example 31 Synthesis of S1N(Disialo)-SRIF28

31-1 Solid Phase Synthesis of Glycopeptide 2-chlorotrityl chloride resin (100 µmol) was taken in a column for solid phase synthesis, and after washing with DMF and dichloromethane, a solution of Fmoc-Cys(Trt)-OH (72.5 mg, 120 µmol) and DIPEA (104.6 µL, 600 µmol) in dichloromethane (3.0 mL) was added, and this was shaken for 1 hour. After washing with dichloromethane and DMF, the Fmoc protecting group was removed by treating with 20% piperidine in DMF. After washing with DMF, in a peptide solid phase synthesis method with Fmoc strategy employing a Prelude™ peptide synthesizer, a protected peptide 73 (SEQ ID NO. 80) represented by the following formula (73) was synthesized in a state bound to the resin. The condensation reaction was performed in DMF using HCTU as the condensation agent.

[Chemical Formula 93]

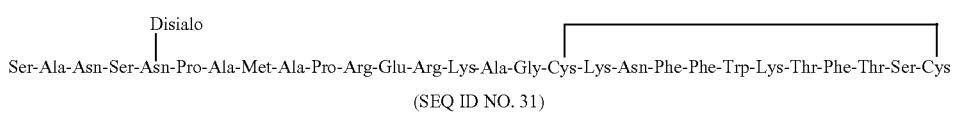

(72)

(SEQ ID NO. 31)

[Chemical Formula 94]

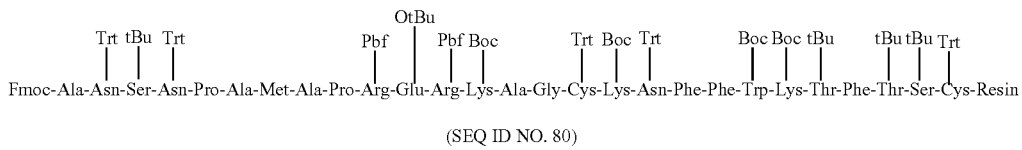

(73)

(SEQ ID NO. 80)

Next, the Fmoc protecting group was removed by treating with 20% piperidine in DMF. After washing with DMF, compound d (420.2 mg, 153.3 μmol), DMSO-DMF (1/1, v/v, 871 μL) solution, TBTU (64.2 mg, 200 μmol), and DIPEA (52.3 μL, 300 μmol) were sequentially added to the resin, and this was shaken at room temperature for 2 hours to allow condensation. After washing with DMF, this condensation operation was repeated once. After washing the resin with DMF and dichloromethane, this was shaken with 20% piperidine in DMF for 20 minutes to deprotect the Fmoc group, and the resin was washed with DMF to synthesize a protected peptide 74 (SEQ ID NO. 81) represented by the following formula (74) on the resin.

[Chemical Formula 95]

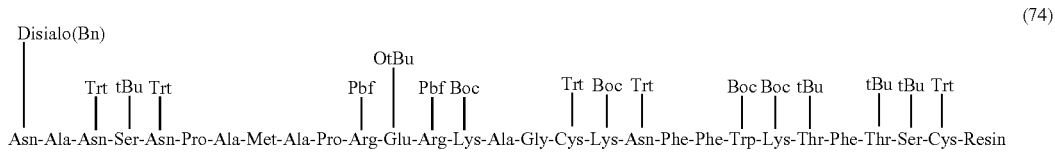

(74)

(SEQ ID NO. 81)

After washing with DMF and dichloromethane, TFA:water:triisopropylsilane:ethanedithiol (=90:2.5:5:2.5) was added, and this was shaken at room temperature for 3 hours. Cold diethyl ether was added to the filtrate, and crude peptide was obtained as precipitate. This crude peptide was purified with HPLC [column: SHISEIDO CAPCELL PAK C18 UG-120 (5 μm), ϕ20×250 mm, flow rate: 7.0 mL/min, eluent A: 0.1% aqueous TFA, B: 0.09% TFA/10% water/90% acetonitrile, A:B=71:29] to obtain glycopeptide 75 (SEQ ID NO. 82) represented by the following formula (75) (65.7 mg, 11.8 μmol).

[Chemical Formula 96]

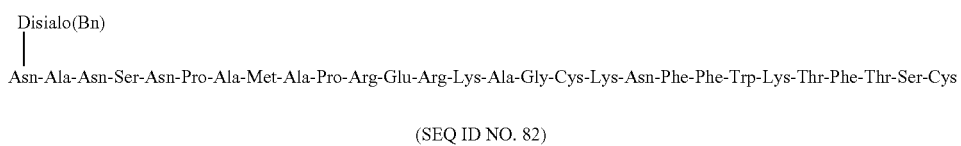

(75)

(SEQ ID NO. 82)

ESI-MS: (m/z) calcd for $C_{236}H_{358}N_{48}O_{100}S_3$: $[M+4H]^{4+}$ 1392.0, $[M+5H]^{5+}$ 1113.8. found 1391.9, 1113.8.

31-2 Formation of Disulfide Bond

Glycopeptide 75 obtained in the method described in the above 31-1 (20.3 mg, 3.65 μmol) was dissolved in 100 mM Tris-HCl buffer (pH 8.0)-DMSO (1/1, v/v, 9.0 mL), and reacted at room temperature for 2 days. The reaction solution was purified with HPLC [column: SHISEIDO CAPCELL PAK C18 UG-120 (5 μm), ϕ20×250 mm, flow rate: 7.0 mL/min, eluent A: 0.1% aqueous TFA, B: 0.09% TFA/10% water/90% acetonitrile, gradient A:B=72:28→67:33, 30 minutes, linear gradient elution] to obtain glycopeptide 76 (SEQ ID NO. 83) represented by the following formula (76) (17.0 mg, 3.06 μmol, yield 84%).

[Chemical Formula 97]

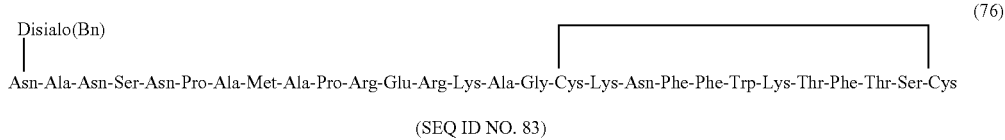

(76)

(SEQ ID NO. 83)

ESI-MS: (m/z) calcd for $C_{236}H_{356}N_{48}O_{100}S_3$: $[M+4H]^{4+}$ 1391.5, $[M+5H]^{5+}$ 1113.4. found 1391.3, 1113.2.

31-3 Deprotection of Benzyl Group

Glycopeptide T6 obtained in the method described in the above 31-2 (7.0 mg, 1.3 μmol) was dissolved in 50 mM sodium hydroxide aqueous solution (19.1 mL), and reacted at 0° C. for 1 hour. 200 mM acetic acid aqueous solution (9.6 mL) was added, and the mixed solution was purified with HPLC [column: SHISEIDO CAPCELL PAK C18 UG-120 (5 μm), ϕ20×250 mm, flow rate: 7.0 mL/min, eluent A: 0.1% aqueous AcOH, B: 0.09% AcOH/10% water/90% acetonitrile, gradient A:B=85:15→77.5:22.5, 20 minutes, linear gradient elution] to obtain a compound represented by the following formula (77) (S1N(disialo)-SRIF28) (SEQ ID NO. 32) (2.7 mg, 0.50 μmol, yield 40%).

[Chemical Formula 98]

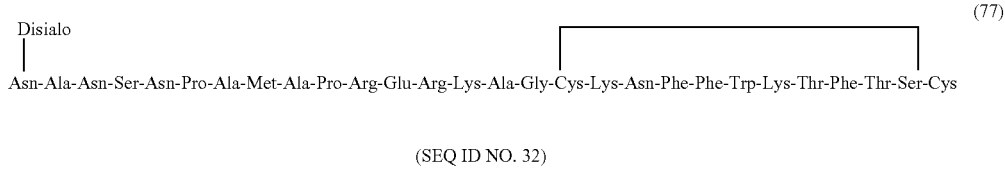

(77)

(SEQ ID NO. 32)

ESI-MS: (m/z) calcd for $C_{222}H_{344}N_{48}O_{100}S_3$: $[M+3H]^{3+}$ 1794.9, $[M+4H]^{4+}$ 1346.4, $[M+5H]^{5+}$ 1077.3, $[M+6H]^{6+}$ 897.9. found 1794.7, 1346.2, 1077.2, 897.7.

Example 32 Synthesis of S1C(Disialo)•N19C(GlcNAc)-SRIF28

32-1 Synthesis of Peptide 2-chlorotrityl chloride resin (100 μmol) was taken in a column for solid phase synthesis, and after washing with DMF and dichloromethane, a solution of Fmoc-Cys(Acm)-OH (49.7 mg, 120 μmol) and DIPEA (104.5 μL, 600 μmol) in dichloromethane (3.0 mL) was added, and this was shaken for 1 hour. After washing with dichloromethane and DMF, the Fmoc protecting group was removed by treating with 20% piperidine in DMF. After washing with DMF and dichloromethane, in a peptide solid phase synthesis method with Fmoc strategy employing a Prelude™ peptide synthesizer, a protected peptide was synthesized on a resin. The condensation reaction was performed in DMF using HCTU as the condensation agent.

The Fmoc protecting group was removed by treating with 20% piperidine in DMF. After washing with DMF and dichloromethane, TFA:water:triisopropylsilane:ethanedithiol (=90:2.5:5:2.5) was added, and this was shaken at room temperature for 3 hours. The resin was filtered off, cold diethyl ether was added to the filtrate, and crude peptide was obtained as precipitate. A part of the crude peptide was purified with HPLC [column: SHISEIDO CAPCELL PAK C18 UG-120 (5 μm), ϕ20×250 mm, flow rate: 7.0 mL/min, eluent A: 0.1% aqueous TFA, B: 0.09% TFA/10% water/90% acetonitrile, gradient A:B=72:28→64:36, 20 minutes, linear gradient elution] to obtain peptide 78 (SEQ ID NO. 84) represented by the following formula (78) (28.9 mg).

[Chemical Formula 99]

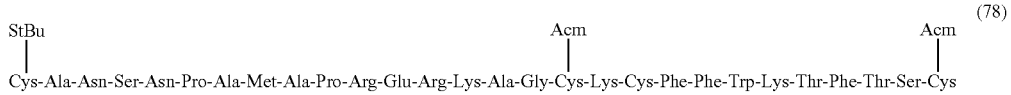

(78)

(SEQ ID NO. 84)

ESI-MS: (m/z) calcd for $C_{146}H_{226}N_{42}O_{39}S_{6}$: $[M+3H]^{3+}$ 1129.7, $[M+4H]^{4+}$ 847.5. found 1129.5, 847.4.

32-2 Glycosylation of Thiol and Deprotection of StBu Group

Peptide 78 obtained in the method described in the above 32-1 (10.0 mg, 2.95 µmol) and compound e represented by the following formula (e) (bromoacetamidated monosaccharide: from Otsuka Chemical Co., Ltd.) (2.0 mg, 5.90 µmol, 2.0 equivalents to peptide 78) were dissolved in 33 mM phosphate buffer (pH 7.4, 0.89 mL) containing 20 µM TCEP, and reacted at room temperature for 2 hours.

[Chemical Formula 100]

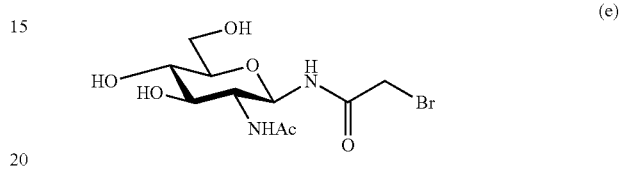

(e)

After the reaction, DTT (45.5 mg, 295 µmol) dissolved in 0.1 M phosphate buffer (pH 7.4, 3.0 mL) was added, and reacted at room temperature for 3 hours. The reaction solution was purified with HPLC [column: SHISEIDO CAPCELL PAK C18 UG-120 (5 µm), φ20×250 mm, flow rate: 7.0 mL/min, eluent A: 0.1% aqueous TFA, B: 0.09% TFA/10% water/90% acetonitrile, gradient A:B=75:25→65:35, 20 minutes, linear gradient elution] to obtain glycopeptide 79 (SEQ ID NO. 85) represented by the following formula (79) (6.8 mg, 1.9 µmol, yield 64%).

[Chemical Formula 101]

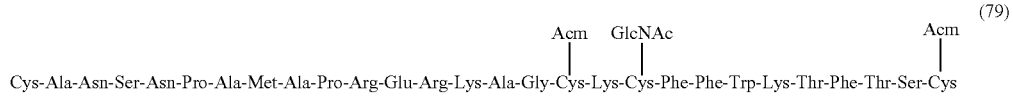

(79)

(SEQ ID NO. 85)

ESI-MS: (m/z) calcd for $C_{152}H_{234}N_{44}O_{45}S_{5}[M+3H]^{3+}$ 1187.0, $[M+4H]^{4+}$ 890.5. found 1187.0, 890.5.

32-3 Glycosylation Reaction of Thiol

Peptide 79 obtained in the method described in the above 32-2 (6.8 mg, 1.9 µmol) and compound a represented by the above formula (a) (22.4 mg, 9.56 µmol, 5.0 equivalents to peptide 79) were dissolved in 0.1 M phosphate buffer (pH 7.4, 2.0 mL) containing 7.6 mM DTT, and reacted at room temperature for 2 hours. The reaction solution was purified with HPLC [column: SHISEIDO CAPCELL PAK C18 UG-120 (5 µm), φ20×250 mm, flow rate: 7.0 mL/min, eluent A: 0.1% aqueous AcOH, B: 0.09% AcOH/10% water/90% acetonitrile, gradient A:B=85:15→65:35, 20 minutes, linear gradient elution] to obtain glycopeptide 80 (SEQ ID NO. 86) represented by the following formula (80) (3.4 mg, 0.58 µmol, yield 31%).

[Chemical Formula 102]

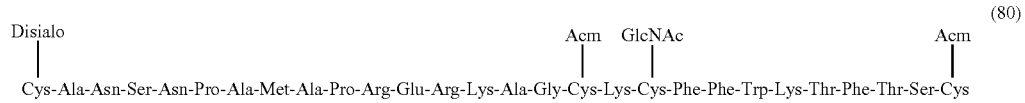

(80)

(SEQ ID NO. 86)

ESI-MS: (m/z) calcd for $C_{238}H_{373}N_{51}O_{107}S_5$: $[M+5H]^{5+}$ 1165.2, $[M+6H]^{6+}$ 971.2, $[M+7H]^{7+}$ 832.6, $[M+8H]^{8+}$ 728.6. found 1165.2, 971.1, 832.6, 728.6.

32-4 Deprotection of Acm Group

To glycopeptide 80 obtained in the method described in the above 32-3 (3.8 mg, 0.65 μmol) was added an aqueous solution (262 μL) of silver(I) acetate (2.7 mg, 16 μmol), and reacted at room temperature for 1 hour. DTT (10.0 mg, 64.8 μmol) dissolved in 100 mM phosphate buffer (pH 7.4, 426 μL) and 100 mM ascorbic acid aqueous solution (66 μL) were added, and this was promptly filtered with a filter. The filtrate was purified with HPLC [column: SHISEIDO CAPCELL PAK C18 UG-120 (5 μm), ϕ20×250 mm, flow rate: 7.0 mL/min, eluent A: 0.1% aqueous AcOH, B: 0.09% AcOH/10% water/90% acetonitrile, gradient A:B=90:10→60:40, 30 minutes, linear gradient elution] to obtain glycopeptide 81 (SEQ ID NO. 87) represented by the following formula (81) (2.5 mg, 0.44 μmol, yield 67%).

[Chemical Formula 103]

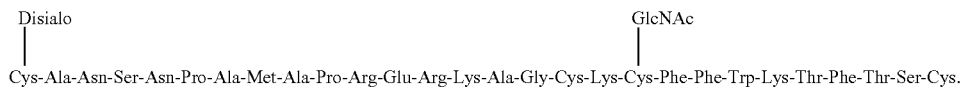

(81)

(SEQ ID NO. 87)

ESI-MS: (m/z) calcd for $C_{232}H_{363}N_{49}O_{105}S_5$: $[M+3H]^{3+}$ 1894.0, $[M+4H]^{4+}$ 1420.7, $[M+5H]^{5+}$ 1136.8. found 1893.8, 1420.6, 1136.7.

32-4 Formation of Disulfide Bond

Glycopeptide 81 obtained in the method described in the above 32-3 (2.5 mg, 0.44 μmol) was dissolved in 100 mM Tris-HCl buffer (pH 8.0)-DMSO (1/1, v/v, 1.1 mL), and reacted overnight at room temperature. The reaction solution was purified with HPLC [column: SHISEIDO CAPCELL PAK C18 UG-120 (5 μm), ϕ20×250 mm, flow rate: 7.0 mL/min, eluent A: 0.1% aqueous AcOH, B: 0.09% AcOH/10% water/90% acetonitrile, gradient A:B=90:10→70:30, 30 minutes, linear gradient elution] to obtain a compound represented by the following formula (82) (S1C(disialo)•N19C(GlcNAc)-SRIF28) (SEQ ID NO. 33) (1.5 mg, 0.26 μmol, yield 59%).

[Chemical Formula 104]

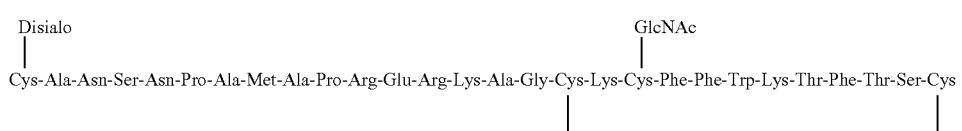

(82)

(SEQ ID NO. 33)

ESI-MS: (m/z) calcd for $C_{232}H_{361}N_{49}O_{105}S_5$: $[M+3H]^{3+}$ 1893.3, $[M+4H]^{4+}$ 1420.2, $[M+5H]^{5+}$ 1136.4. found 1893.5, 1420.1, 1136.3.

Example 33 Synthesis of S1C(Disialo)•N19C(diMan)-SRIF28

A compound represented by the following formula (83) (S1C(disialo)•N19C(diMan)-SRIF28) (SEQ ID NO. 34) was synthesized similarly to Example 32, except that compound f represented by the following formula (f) (bromoacetamidated oligosaccharide: from Otsuka Chemical Co., Ltd.) was employed instead of compound e.

[Chemical Formula 105]

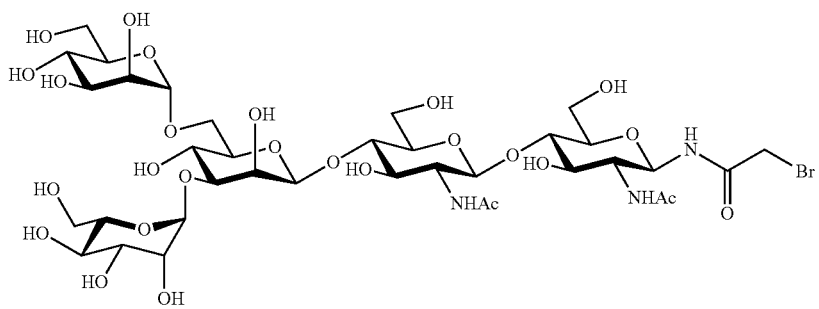

(f)

[Chemical Formula 106]

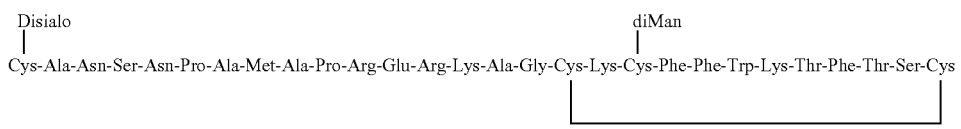

(83)

(SEQ ID NO. 34)

Example 34 Synthesis of S1-5C(Disialo)-SRIF28

34-1 Synthesis of Peptide 2-chlorotrityl chloride resin (100 μmol) was taken in a column for solid phase synthesis, and after washing with DMF and dichloromethane, a solution of Fmoc-Cys(Acm)-OH (49.7 mg, 120 μmol) and DIPEA (104.5 μL, 600 μmol) in dichloromethane (3.0 mL) was added, and this was shaken for 1 hour. After washing with dichloromethane and DMF, the Fmoc protecting group was removed by treating with 20% piperidine in DMF. After washing with DMF, in a peptide solid phase synthesis method with Fmoc strategy employing a Prelude™ peptide synthesizer, a protected peptide was synthesized on the resin. The condensation reaction was performed in DMF using HCTU as the condensation agent.

The Fmoc protecting group was removed by treating with 20% piperidine in DMF. After washing with DMF and dichloromethane, TFA:water:triisopropylsilane:ethanedithiol (=90:2.5:5:2.5) was added, and this was shaken at room temperature for 3 hours. The resin was filtered off, cold diethyl ether was added to the filtrate, and crude peptide was obtained as precipitate. The crude peptide was purified with HPLC [column: SHISEIDO CAPCELL PAK C18 UG-120 (5 μm), ϕ50×250 mm, flow rate: 43.7 mL/min, eluent A: 0.1% aqueous TFA, B: 0.09% TFA/10% water/90% acetonitrile, gradient A:B=73:27→65:35, 35 minutes, linear gradient elution] to obtain peptide 84 (SEQ ID NO. 90) represented by the following formula (84).

[Chemical Formula 107]

(84)

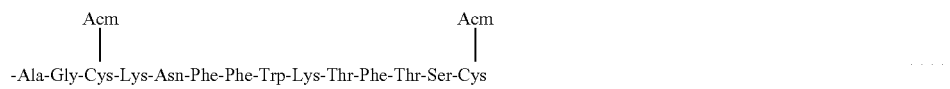

(SEQ ID NO. 90)

ESI-MS: (m/z) calcd for $C_{155}H_{239}N_{47}O_{44}S_8$: $[M+3H]^{3+}$ 1241.5, $[M+4H]^{4+}$ 931.3, $[M+5H]^{5+}$ 745.3. found 1241.2, 931.2, 745.1.

34-2 Glycosylation Reaction of Thiol

Peptide 84 obtained in the method described in the above 34-1 (33.7 mg, 9.06 μmol) and compound a represented by the above formula (a) (bromoacetamidated oligosaccharide: from Otsuka Chemical Co., Ltd.) (160.9 mg, 68.6 μmol, 7.5 equivalents to peptide 84) were dissolved in 33 mM phosphate buffer (pH 7.4, 2.7 mL) containing 10 μM TCEP, and reacted overnight at room temperature. The reaction solution was purified with HPLC [column: SHISEIDO Proteonavi (5 μm), ϕ20×250 mm, flow rate: 7.0 mL/min, eluent A: 0.1% aqueous AcOH, B: 0.09% AcOH/10% water/90% acetonitrile, gradient A:B=80:20→78.4:21.6, 20 minutes, linear gradient elution] to obtain glycopeptide 85 (SEQ ID NO. 91) represented by the following formula (85) (35.1 mg, 2.33 μmol, yield 26%).

ESI-MS: (m/z) calcd for $C_{585}H_{934}N_{82}O_{354}S_8$: $[M+6H]^{6+}$ 2507.1, $[M+7H]^{7+}$ 2149.1, $[M+8H]^{8+}$ 1880.6. found 2506.9, 2149.0, 1880.6.

[Chemical Formula 108]

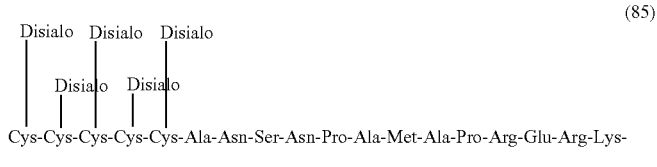

(85)

(SEQ ID NO. 91)

34-3 Deprotection of Acm Group

To glycopeptide 85 obtained in the method described in the above 34-2 (20.6 mg, 1.37 µmol) was added an aqueous solution (0.55 mL) of silver(I) acetate (5.6 mg, 34 µmol), and reacted at room temperature for 50 minutes. Then, DTT (13.8 mg, 89 µmol) dissolved in 200 mM phosphate buffer (pH 7.4, 0.55 mL) and 100 mM ascorbic acid aqueous solution (137 µL) were added, and this was promptly filtered with a filter. The filtrate was purified with HPLC [column: SHISEIDO Proteonavi (5 µm), ϕ20×250 mm, flow rate: 7.0 mL/min, eluent A: 0.1% aqueous AcOH, B: 0.09% AcOH/10% water/90% acetonitrile, gradient A:B=80:20→73.6:26.4, 16 minutes, linear gradient elution] to obtain glycopeptide 86 (SEQ ID NO. 92) represented by the following formula (86) (13.6 mg, 0.913 µmol, yield 67%).

[Chemical Formula 109]

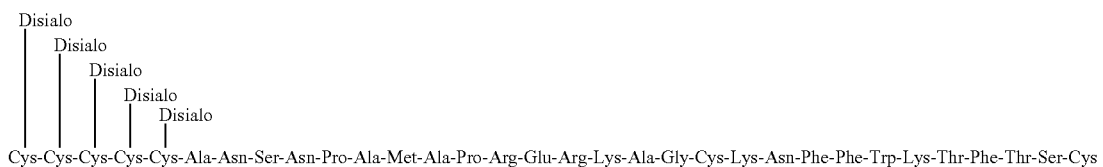

(86)

(SEQ ID NO. 92)

ESI-MS: (m/z) calcd for $C_{579}H_{924}N_{80}O_{352}S_8$: $[M+6H]^{6+}$ 2483.4, $[M+7H]^{7+}$ 2128.8, $[M+8H]^{8+}$ 1862.8. found 2483.2, 2128.8, 1862.9.

34-4 Formation of Disulfide Bond

Glycopeptide 86 obtained in the method described in the above 34-3 (13.6 mg, 0.913 µmol) was dissolved in 100 mM Tris-HCl buffer (pH 8.0)-DMSO (1/1, v/v, 2.2 mL), and reacted at room temperature for 2 days. Then, the reaction solution was purified with HPLC [column: Proteonavi (5 µm), ϕ20×250 mm, flow rate: 7.0 mL/min, eluent A: 10 mM ammonium acetate aqueous solution, B: 10 mM ammonium acetate-acetonitrile (1/9, v/v), gradient A:B=78:22→70.8:29.2, 15 minutes, linear gradient elution] to obtain S1-5C (disialo)-SRIF28 (SEQ ID NO. 88) represented by the following formula (87) (10.4 mg, 0.698 µmol, yield 76%).

[Chemical Formula 110]

(87)

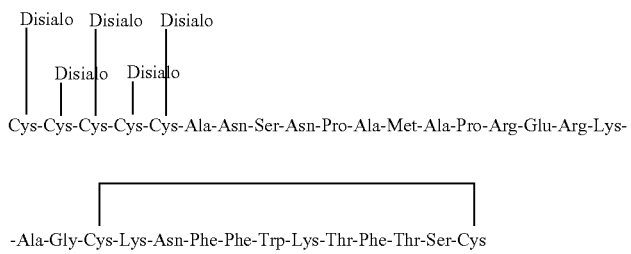

(SEQ ID NO. 88)

ESI-MS: (m/z) calcd for $C_{579}H_{922}N_{30}O_{352}S_8$: $[M+4H]^{5+}$ 3724.1, $[M+5H]^{5+}$ 2979.5, $[M+6H]^{6+}$ 2483.1, $[M+7H]^{7+}$ 2128.5, $[M+8H]^{8+}$ 1862.6. found 3723.7, 2979.1, 2482.9, 2128.2, 1862.4.

Example 35 Synthesis of S1-10C(Disialo)-SRIF28

35-1 Synthesis of Peptide 2-chlorotrityl chloride resin (100 μmol) was taken in a column for solid phase synthesis, and after washing with DMF and dichloromethane, a solution of Fmoc-Cys(Acm)-OH (49.7 mg, 120 μmol) and DIPEA (104.5 μL, 600 μmol) in dichloromethane (3.0 mL) was added, and this was shaken for 1 hour. After washing with dichloromethane and DMF, the Fmoc protecting group was removed by treating with 20% piperidine in DMF. After washing with DMF, in a peptide solid phase synthesis method with Fmoc strategy employing a Prelude™ peptide synthesizer, a protected peptide was synthesized on the resin. The condensation reaction was performed in DMF using HCTU as the condensation agent.

The Fmoc protecting group was removed by treating with 20% piperidine in DMF. After washing with DMF and dichloromethane, TFA:water:triisopropylsilane:ethanedithiol (=90:2.5:5:2.5) was added, and this was shaken at room temperature for 3 hours. The resin was filtered off, cold diethyl ether was added to the filtrate, and crude peptide was obtained as precipitate. The crude peptide was purified with HPLC [column: SHISEIDO CAPCELL PAK C18 UG-120 (5 μm), φ20×250 mm, flow rate: 7.0 mL/min, eluent A: 0.1% aqueous TFA, B: 0.09% TFA/10% water/90% acetonitrile, gradient A:B=69:31→66.6:33.4, 15 minutes, linear gradient elution] to obtain peptide 88 (SEQ ID NO. 93) represented by the following formula (88) (16.8 mg).

[Chemical Formula 111]

(88)

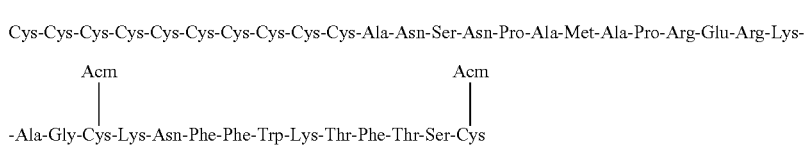

(SEQ ID NO. 93)

ESI-MS: (m/z) calcd for $C_{170}H_{264}N_{52}O_{49}S_{13}$: $[M+3H]^{3+}$ 1413.4, $[M+4H]^{4+}$ 1060.3, $[M+5H]^{5+}$ 848.4. found 1412.9, 1060.2, 848.1.

35-2 Synthesis of Disialo Sugar Chain Having Bromoacetamidated Benzyl Protecting Group To compound a (28.9 mg, 12.3 μmol) were sequentially added DMF (0.58 mL), lithium bromide (21.5 mg, 248 μmol), and benzyl bromide (14.6 μL, 122 μmol), and reacted at 30° C. for 20 hours. Benzyl bromide (14.6 μL, 122 μmol) was further added and reacted for 20 hours. To the reaction solution was added toluene (30 mL), and after centrifugal separation (10,000×g, 10 minutes), the precipitate was dissolved in water (100 μL) and purified with HPLC [column: SHISEIDO CAPCELL PAK C18 UG-120 (5 μm), φ20×250 mm, flow rate: 8.0 mL/min, eluent: water:acetonitrile=95:5→70:30, 20 minutes, linear gradient elution] to obtain compound g represented by the following formula (g) (bromoacetamidated disialo sugar chain: 7.6 mg, 3.0 μmol, yield 24%).

[Chemical Formula 112]

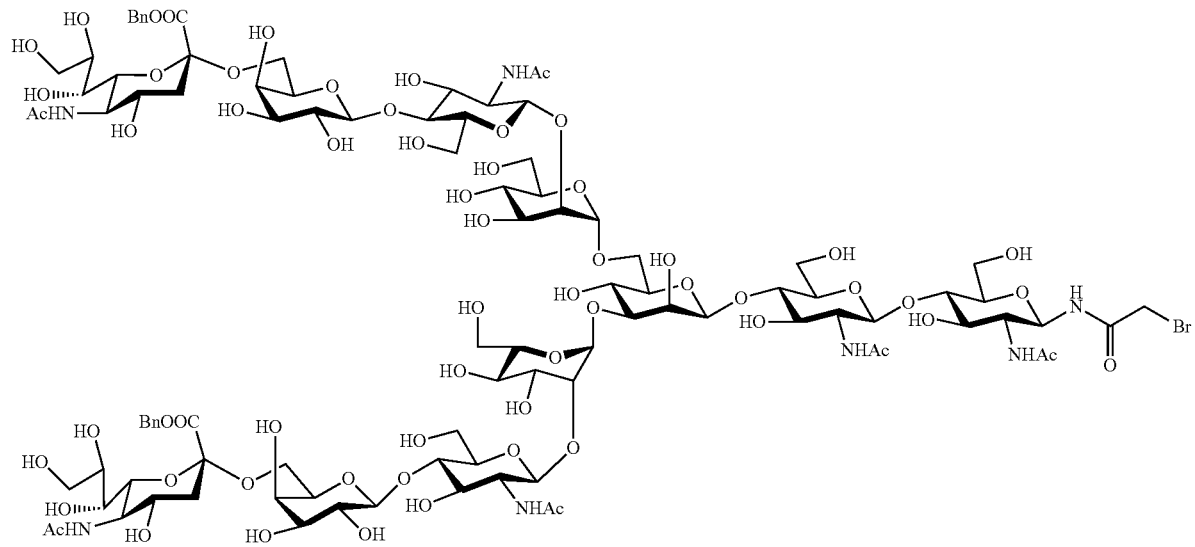

(g)

MALDI-MS: (m/z) calcd for $C_{100}H_{152}BrN_7O_{62}$: [M+Na]$^+$ 2544.8. found 2544.4.

35-3 Glycosylation Reaction of Thiol

Peptide 88 obtained in the method described in the above 35-1 (8.1 mg, 1.9 μmol) and compound g obtained in the method described in the above 35-2 (58.0 mg) were dissolved in 66 mM phosphate buffer (pH 6.8, 0.57 mL) containing 2.3 M guanidine hydrochloride, and reacted overnight at room temperature. The reaction solution was purified with HPLC [column: SHISEIDO CAPCELL PAK C18 UG-120 (5 μm), φ20×250 mm, flow rate: 7.0 mL/min, eluent A: 0.1% aqueous AcOH, B: 0.09% AcOH/10% water/ 90% acetonitrile, gradient A:B=80:20→74.7:25.3, 30 minutes, linear gradient elution] to obtain glycopeptide 89 (SEQ ID NO. 94) represented by the following formula (89) (12.3 mg, 0.429 μmol, yield 23%).

ESI-MS: (m/z) calcd for $C_{1170}H_{1774}N_{122}O_{669}S_{13}$: [M+8H]$^{8+}$ 3584.7, [M+9H]$^{9+}$ 3186.5, [M+10H]$^{10+}$ 2868.0, [M+11H]$^{11+}$ 2607.4, [M+12H]$^{12+}$ 2390.2, [M+13H]$^{13+}$ 2206.4, [M+14H]$^{14+}$ 2048.9. found 3585.0, 3186.6, 2867.9, 2607.6, 2390.1, 2206.4, 2048.9.

35-4 Deprotection of Acm Group

To glycopeptide 89 obtained in the method described in the above 35-3 (49.8 mg, 1.74 μmol) was added an aqueous solution (0.70 mL) of silver(I) acetate (10.2 mg), and reacted at room temperature for 1 hour. A solution of DTT (16.6 mg) in 200 mM phosphate buffer (pH 7.4, 0.70 mL) and 100 mM ascorbic acid aqueous solution (0.17 mL) were added, and this was promptly filtered with a filter. The filtrate was purified with HPLC [column: SHISEIDO CAPCELL PAK C18 UG-120 (5 μm), φ20×250 mm, flow rate: 7.0 mL/min, eluent A: 0.1% aqueous AcOH, B: 0.09% AcOH/10% water/

[Chemical Formula 113]

(89)

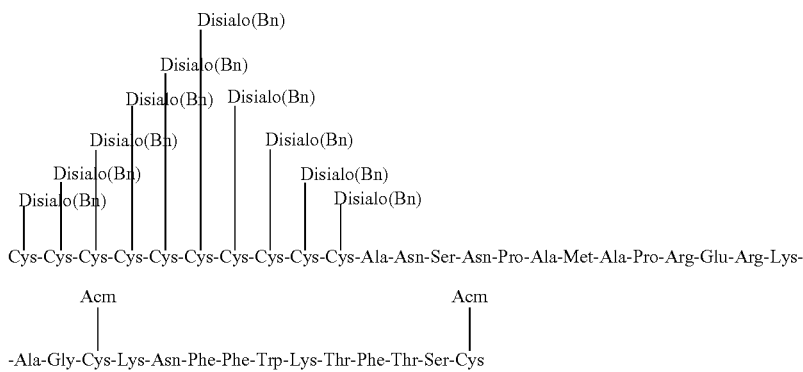

(SEQ ID NO. 94)

90% acetonitrile, gradient A:B=78:22→73:27, 20 minutes, linear gradient elution] to obtain glycopeptide 90 (SEQ ID NO. 95) represented by the following formula (90) (33.0 mg, 1.16 μmol, yield 67%).

ESI-MS: (m/z) calcd for $C_{1164}H_{1762}N_{120}O_{667}S_{13}$: $[M+8H]^{8+}$ 3566.7, $[M+9H]^{9+}$ 3170.5, $[M+10H]^{10+}$ 2853.6. found 3566.6, 3170.4, 2853.6.

[Chemical Formula 114]

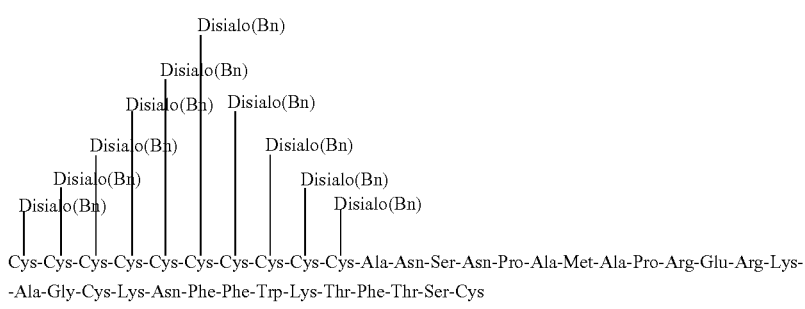

(90)

(SEQ ID NO. 95)

ESI-MS: (m/z) calcd for $C_{1164}H_{1764}N_{120}O_{867}S_{13}$: $[M+9H]^{9+}$ 3170.8, $[M+10H]^{10+}$ 2853.8, $[M+11H]^{11+}$ 2594.4, $[M+12H]^{12+}$ 2378.3, $[M+13H]^{13+}$ 2195.4, $[M+14H]^{14+}$ 2038.7, $[M+15H]^{15+}$ 1902.9. found 3170.9, 2853.7, 2594.4, 2378.3, 2195.4, 2038.7, 1902.9.

35-5 Formation of Disulfide Bond

Glycopeptide 90 obtained in the method described in the above 35-4 (2.1 mg, 0.074 μmol) was dissolved in 100 mM Tris-HCl buffer (pH 8.0)-DMSO (1/1, v/v, 185 μL), and reacted at room temperature for 2 days. Then, the reaction solution was purified with HPLC [column: SHISEIDO CAPCELL PAK C18 UG-120 (5 μm), ϕ4.6×250 mm, flow rate: 0.7 mL/min, eluent A: 10 mM ammonium acetate aqueous solution, B: 10 mM ammonium acetate-acetonitrile (1/9, v/v), gradient A:B=69:31→65:35, 20 minutes, linear gradient elution] to obtain glycopeptide 91 (SEQ ID NO. 96) represented by the following formula (91) (1.0 mg, 0.035 μmol, yield 47%).

35-6 Deprotection of Benzyl Group

Glycopeptide 91 obtained in the method described in the above 35-5 (17.1 mg, 0.599 μmol) was dissolved in 50 mM sodium hydroxide aqueous solution (12 mL), and reacted at 0° C. for 90 minutes. 100 mM acetic acid aqueous solution 12 mL was added, and the mixed solution was purified with HPLC [column: SHISEIDO Proteonavi, ϕ4.6×250 mm, flow rate: 0.7 mL/min, eluent A: 10 mM ammonium acetate aqueous solution, B: 10 mM ammonium acetate-acetonitrile (1/9, v/v), gradient A:B=72:18→80:20, 20 minutes, linear gradient elution] to obtain glycopeptide 92 (SEQ ID NO. 89) represented by the following formula (92) (5.8 mg, 0.22 μmol, yield 37%).

[Chemical Formula 115]

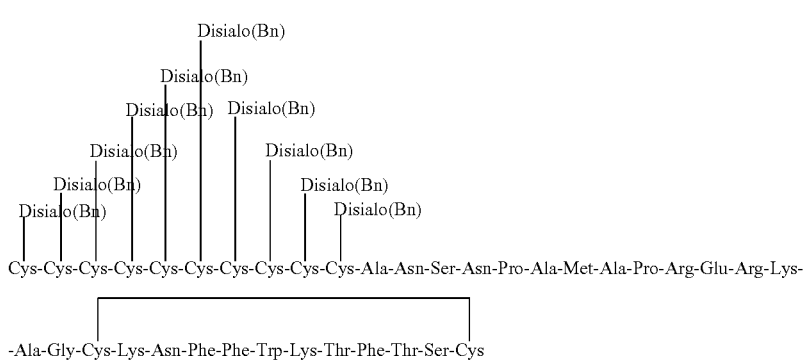

(91)

(SEQ ID NO. 96)

[Chemical Formula 116]

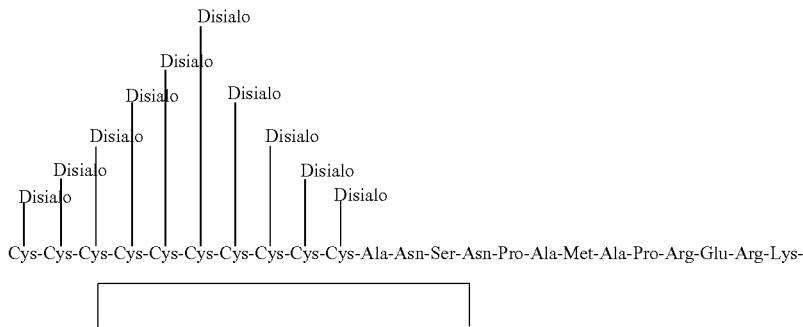

(92)

(SEQ ID NO. 89)

ESI-MS: (m/z) calcd for $C_{1024}H_{1642}N_{120}O_{667}S_{13}$: $[M+7H]^{7+}$ 3818.6, $[M+8H]^{8+}$ 3341.4, $[M+9H]^{9+}$ 2970.3, $[M+10H]^{10+}$ 2673.3. found 3818.3, 3341.0, 2970.1, 2673.1.

Example 36 Synthesis of C(Disialo)-SRIF28

A compound represented by the following formula (94) (C(disialo)-SRIF28) (SEQ ID NO. 98) was synthesized similarly to Example 1, except that a compound represented by the following formula (93) (peptide 93) (SEQ ID NO. 97) was employed instead of peptide 1.

[Chemical Formula 117]

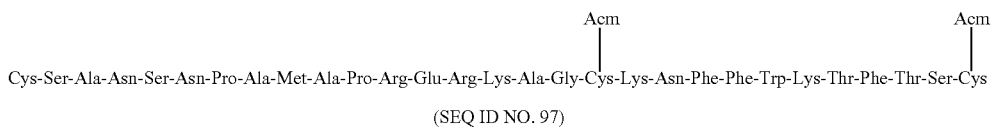

(93)

(SEQ ID NO. 97)

[Chemical Formula 118]

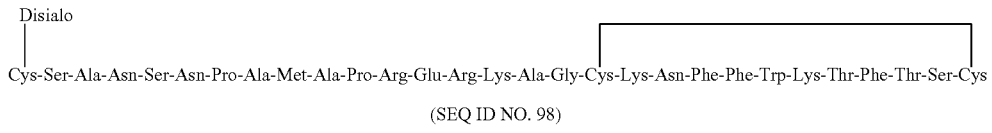

(94)

(SEQ ID NO. 98)

Example 37 Synthesis of R11C(Disialo)-SRIF28

A compound represented by the following formula (96) (R11C(disialo)-SRIF28) (SEQ ID NO. 100) was synthesized similarly to Example 1, except that a compound represented by the following formula (95) (peptide 95) (SEQ ID NO. 99) was employed instead of peptide 1.

[Chemical Formula 119]

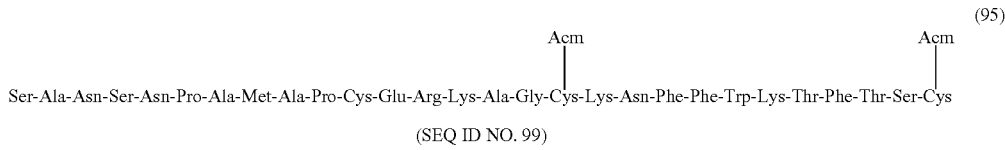

(95)

(SEQ ID NO. 99)

[Chemical Formula 120]

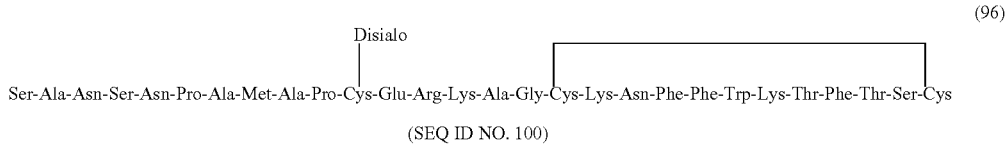

(96)

(SEQ ID NO. 100)

Example 38 Synthesis of F20C(Disialo)-SRIF28

A compound represented by the following formula (98) (F20C(disialo)-SRIF28) (SEQ ID NO. 102) was synthesized similarly to Example 1, except that a compound represented by the following formula (97) (peptide 97) (SEQ ID NO. 101) was employed instead of peptide 1.

[Chemical Formula 121]

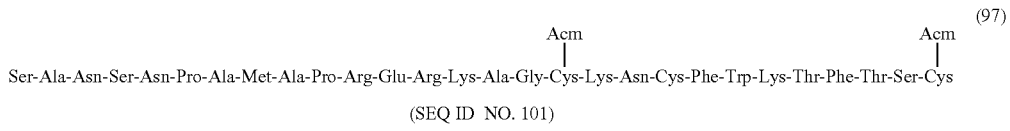

(97)

(SEQ ID NO. 101)

[Chemical Formula 122]

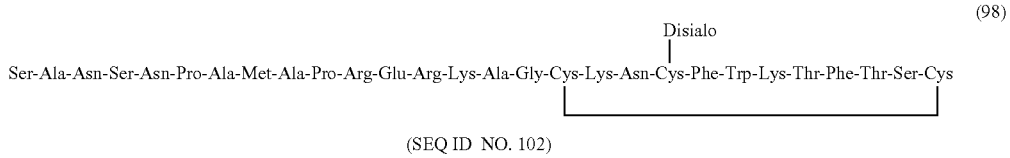

(98)

(SEQ ID NO. 102)

Example 39 Synthesis of T24C(Disialo)-SRIF28

A compound represented by the following formula (100) (T24C(disialo)-SRIF28) (SEQ ID NO. 104) was synthesized similarly to Example 1, except that a compound represented by the following formula (99) (peptide 99) (SEQ ID NO. 103) was employed instead of peptide 1.

[Chemical Formula 123]

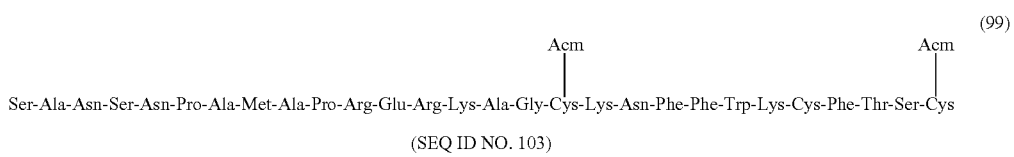

(99)

(SEQ ID NO. 103)

[Chemical Formula 124]

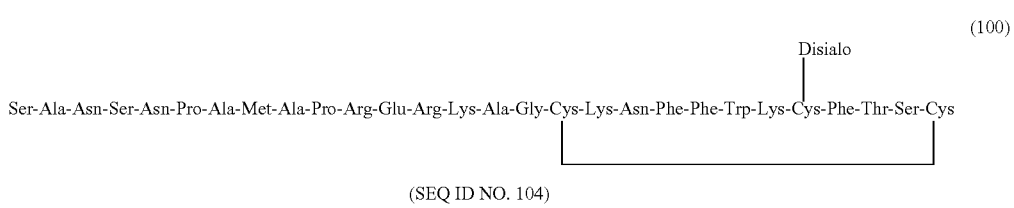

(100)

(SEQ ID NO. 104)

Example 40 Synthesis of F25C(Disialo)-SRIF28

A compound represented by the following formula (102) (F25C(disialo)-SRIF28) (SEQ ID NO. 106) was synthesized similarly to Example 1, except that a compound represented by the following formula (101) (peptide 101) (SEQ ID NO. 105) was employed instead of peptide 1.

[Chemical Formula 125]

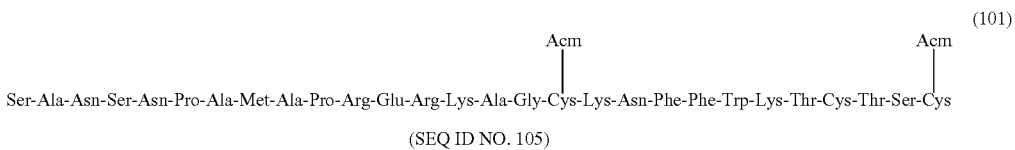

(SEQ ID NO. 105)

[Chemical Formula 126]

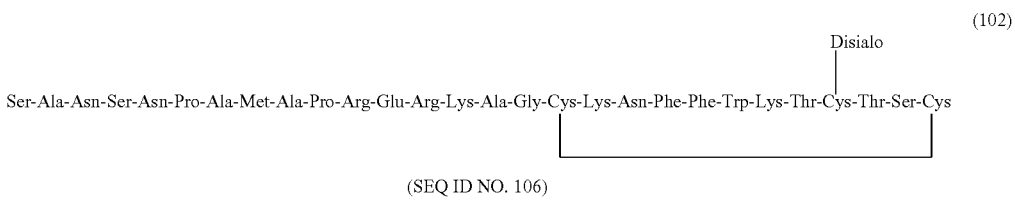

(SEQ ID NO. 106)

Example 41 Synthesis of S27C(Disialo)-SRIF28

A compound represented by the following formula (104) (S27C(disialo)-SRIF28) (SEQ ID NO. 108) was synthesized similarly to Example 1, except that a compound represented by the following formula (103) (peptide 103) (SEQ ID NO. 107) was employed instead of peptide 1.

[Chemical Formula 127]

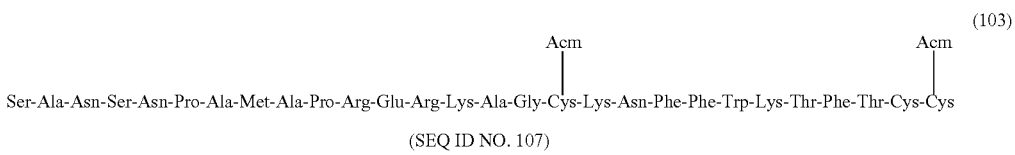

(SEQ ID NO. 107)

[Chemical Formula 128]

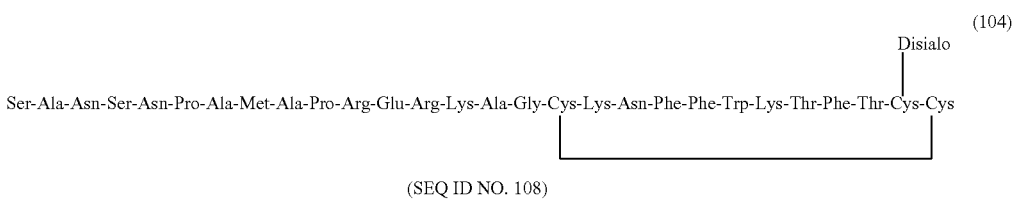

(SEQ ID NO. 108)

Example 42 Synthesis of C(Disialo)-K-SRIF14

A compound represented by the following formula (106) (C(disialo)-K-SRIF14) (SEQ ID NO. 110) was synthesized similarly to Example 1, except that a compound represented by the following formula (105) (peptide 105) (SEQ ID NO. 109) was employed instead of peptide 1.

[Chemical Formula 129]

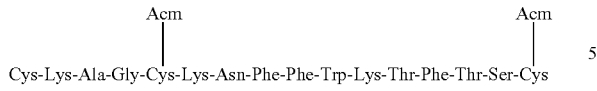

(SEQ ID NO. 109)

[Chemical Formula 130]

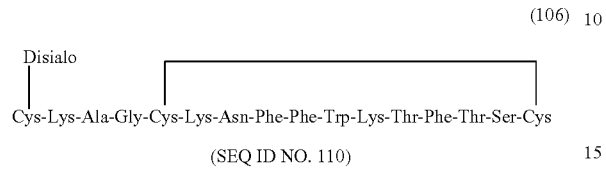

(106)

(SEQ ID NO. 110)

Example 43 Synthesis of S1C(Disialo)-F25Y-SRIF28

A compound represented by the following formula (108) (S1C(disialo)-F25Y-SRIF28) (SEQ ID NO. 112) was synthesized similarly to Example 1, except that a compound represented by the following formula (107) (peptide 107) (SEQ ID NO. 111) was employed instead of peptide 1.

[Chemical Formula 131]

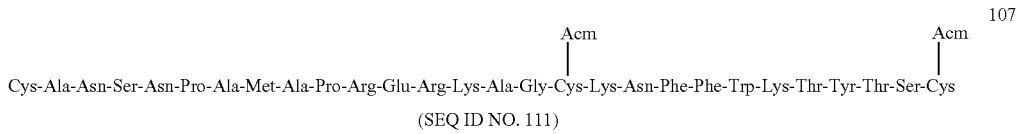

(107)

(SEQ ID NO. 111)

[Chemical Formula 132]

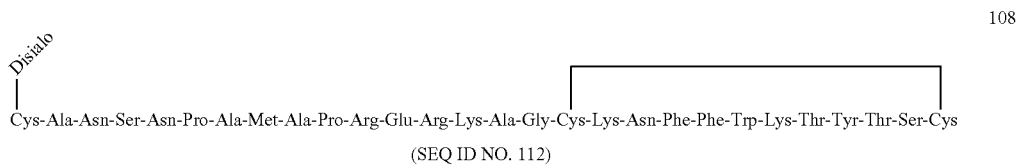

108

(SEQ ID NO. 112)

Example 44 Synthesis of S1C(Disialo)-SRIF28-Amide

A compound represented by the following formula (110) (S1C(disialo)-SRIF28-amide) (SEQ ID NO. 114) was synthesized similarly to Example 1, except that a compound represented by the following formula (109) (peptide 109) (SEQ ID NO. 113) was employed instead of peptide 1.

[Chemical Formula 133]

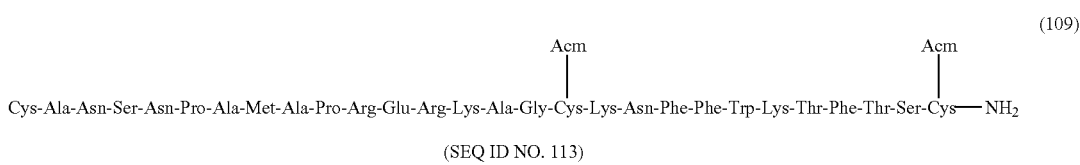

(109)

(SEQ ID NO. 113)

[Chemical Formula 134]

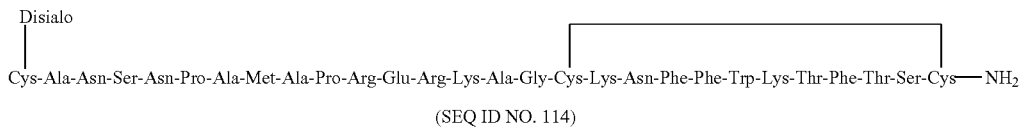

(110)

(SEQ ID NO. 114)

Example 45 Synthesis of C(Disialo)-PEG Linker-SRIF14

45-1 Synthesis of Peptide

The Fmoc protecting group of the protected peptide 39 (SEQ ID NO. 58) (50 μmol) bound to the resin, obtained in the method described in the above 19-1, was removed by treating with 20% piperidine in DMF. After washing with DMF, employing HCTU as the condensation agent, Fmoc-NH-(PEG)$_2$-COOH (from Merck) and Fmoc-Cys(Trt)-OH were condensed in sequence. The Fmoc protecting group was removed by treating with 20% piperidine in DMF. After washing with DMF and dichloromethane, TFA:water:triisopropylsilane:ethanedithiol (=90:2.5:5:2.5) was added, and this was shaken for 3 hours at room temperature. The resin was filtered off, cold diethyl ether was added to the filtrate, and crude peptide was obtained as precipitate. A part of the crude peptide was purified with HPLC [column: SHISEIDO CAPCELL PAK C18 UG-120 (5 μm), ϕ20×250 mm, flow rate: 7.0 mL/min, eluent A: 0.1% aqueous TFA, B: 0.09% TFA/10% water/90% acetonitrile, gradient A:B=74:26→69:31, 1 minute, then 69:31→62:38, 30 minutes, linear gradient elution] to obtain a compound represented by the following formula (111) (peptide 111) (SEQ ID NO. 115) (43.1 mg).

[Chemical Formula 135]

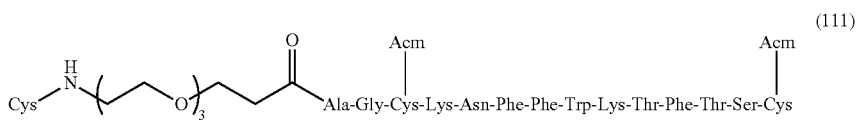

(111)

ESI-MS: (m/z) calcd for $C_{94}H_{138}N_{22}O_{26}S_3$: $[M+2H]^{2+}$ 1045.2, $[M+3H]^{3+}$ 697.1. found 1045.0, 697.0.

45-2 Synthesis of C(Disialo)-PEG Linker-SRIF14

A compound represented by the following formula (112) (C(disialo)-PEG linker-SRIF14) (SEQ ID NO. 116) was synthesized similarly to Example 1, except that peptide 111 obtained in the method described in the above 45-1 was employed instead of peptide 1.

[Chemical Formula 136]

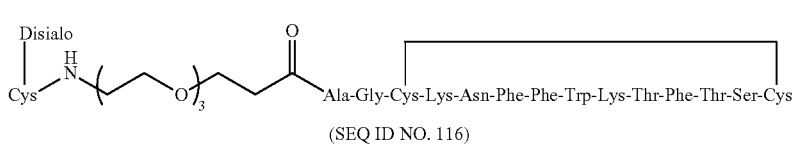

(112)

(SEQ ID NO. 116)

Example 46 Synthesis of Biotin-S1C(Disialo)-SRIF28

46-1 Synthesis of Peptide 2-chlorotrityl chloride resin (100 μmol) was taken in a column for solid phase synthesis, and after washing with DMF and dichloromethane, a dichloromethane (3.0 mL) solution containing Fmoc-Cys(Acm)-OH (49.7 mg, 120 μmol) and DIPEA (104.5 μL, 600 μmol) was added, and this was shaken for 1 hour. After washing with dichloromethane and DMF, the Fmoc protecting group was removed by treating with 20% piperidine in DMF. After washing with DMF, in a peptide solid phase synthesis method with Fmoc strategy employing a Prelude™ peptide synthesizer, a protected peptide 113 (SEQ ID NO. 117) represented by the following formula (113) was synthesized in a state bound to the resin. The condensation reaction was performed in DMF using HCTU as the condensation agent.

[Chemical Formula 137]

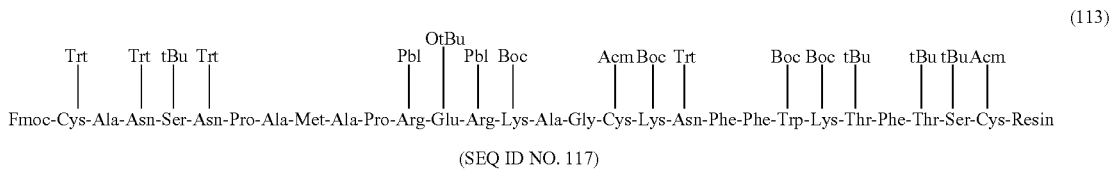

(113)

(SEQ ID NO. 117)

The Fmoc protecting group was removed by treating with 20% piperidine in DMF. After washing with DMF, employing HCTU as the condensation agent, biotin was condensed. After washing with DMF and dichloromethane, TFA:water:triisopropylsilane:ethanedithiol (=90:2.5:5:2.5) was added, and this was shaken at room temperature for 3 hours. This leads to the detachment of the protecting group of the amino acid side chain (other than the Acm group), as well as cleaving between the peptide and the resin. The resin was filtered off, cold diethyl ether was added to the filtrate, and crude peptide was obtained as precipitate. The crude peptide was purified with HPLC [column: SHISEIDO CAPCELL PAK C18 UG-120 (5 μm), ϕ20×250 mm, flow rate: 7.0 mL/min, eluent A: 0.1% aqueous TFA, B: 0.09% TFA/10% water/90% acetonitrile, gradient A:B=75:25→61:39, 18 minutes, linear gradient elution] to obtain peptide 114 (SEQ ID NO. 118) represented by the following formula (114).

[Chemical Formula 138]

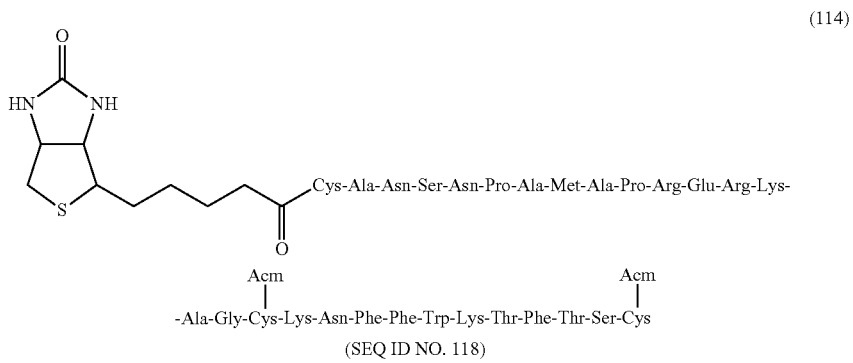

(114)

(SEQ ID NO. 118)

ESI-MS: (m/z) calcd for $C_{153}H_{233}N_{45}O_{42}S_5$: $[M+3H]^{3+}$ 1179.4, $[M+4H]^{4+}$ 884.8, $[M+5H]^{5+}$ 708.0. found 1179.2, 884.4, 707.9.

46-2 Synthesis of Biotin-S1C(Disialo)-SRIF28

A compound represented by the following formula (115) (Biotin-S1C(disialo)-SRIF28) (SEQ ID NO. 119) was synthesized similarly to Example 1, except that peptide 114 obtained in the method described in the above 46-1 was employed instead of peptide 1.

[Chemical Formula 139]

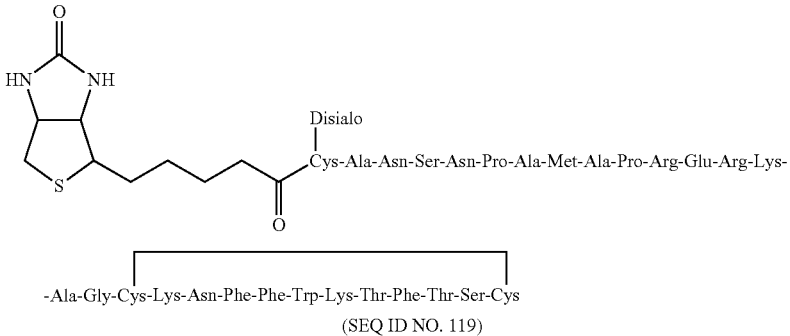

(115)

(SEQ ID NO. 119)

Example 47 Synthesis of Biotin-PEG Linker-S1C(Disialo)-SRIF28

47-1 Synthesis of Peptide

The Fmoc protecting group of the protected peptide 113 (SEQ ID NO. 117) bound to the resin, obtained in the above 46-1, was removed by treating with 20% piperidine in DMF. After washing with DMF, employing HCTU as the condensation agent, Fmoc-NH-(PEG)$_2$-COOH (from Merck) and biotin were condensed in sequence. After washing with DMF and dichloromethane, TFA:water:triisopropylsilane:ethanedithiol (=90:2.5:5:2.5) was added, and this was shaken at room temperature for 3 hours. The resin was filtered off, cold diethyl ether was added to the filtrate, and crude peptide was obtained as precipitate. The crude peptide was purified with HPLC [column: SHISEIDO CAPCELL PAK C18 UG-120 (5 μm), φ20×250 mm, flow rate: 7.0 mL/min, eluent A: 0.1% aqueous TFA, B: 0.09% TFA/10% water/90% acetonitrile, gradient A:B=75:25→61:39, 22 minutes, linear gradient elution] to obtain peptide 116 (SEQ ID NO. 120) represented by the following formula (116).

[Chemical Formula 140]

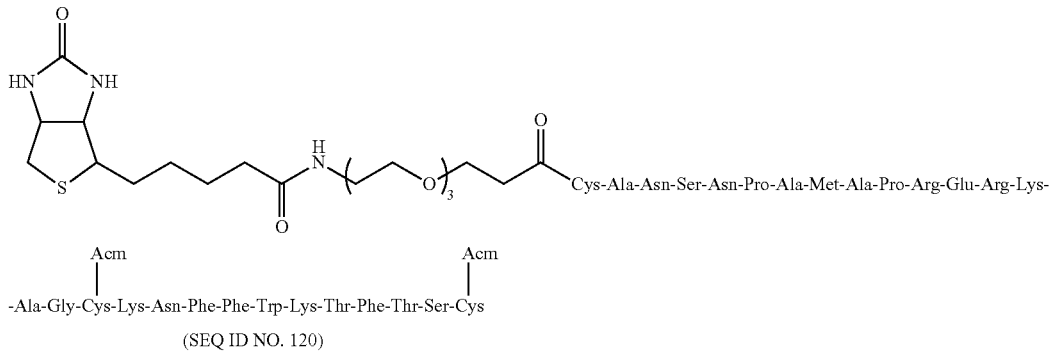

(116)

(SEQ ID NO. 120)

ESI-MS: (m/z) calcd for $C_{162}H_{250}N_{46}O_{46}S_5$: $[M+3H]^{3+}$ 1247.1, $[M+4H]^{4+}$ 935.6, $[M+5H]^{5+}$ 748.7. found 1246.9, 935.4, 748.6.

47-2 Synthesis of Biotin-PEG Linker-S1C(Disialo)-SRIF28

A compound represented by the following formula (117) (Biotin-PEG linker-S1C(disialo)-SRIF28) (SEQ ID NO. 121) was synthesized similarly to Example 1, except that peptide 116 obtained in the method described in the above 47-1 was employed instead of peptide 1.

[Chemical Formula 141]

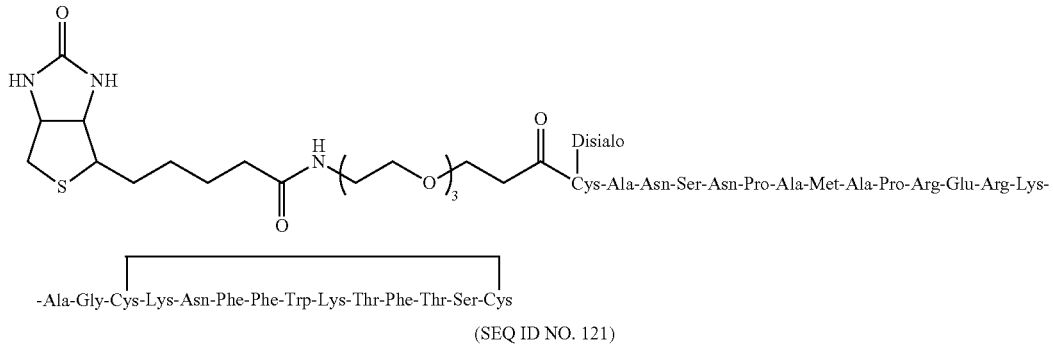

(117)

(SEQ ID NO. 121)

Example 48 Synthesis of Azido-S1C(Disialo)-SRIF28

48-1 Synthesis of Peptide

The Fmoc protecting group of the protected peptide 113 (SEQ ID NO. 117) bound to the resin, obtained in the above 46-1, was removed by treating with 20% piperidine in DMF. After washing with DMF, employing HCTU as the condensation agent, 5-Azido-pentanoic acid was condensed. After washing with DMF and dichloromethane, TFA:water:triisopropylsilane:ethanedithiol (=90:2.5:5:2.5) was added, and this was shaken at room temperature for 3 hours. The resin was filtered off, cold diethyl ether was added to the filtrate, and crude peptide was obtained as precipitate. The crude peptide was purified with HPLC [column: SHISEIDO CAPCELL PAK C18 UG-120 (5 μm), φ20×250 mm, flow rate: 7.0 mL/min, eluent A: 0.1% aqueous TFA, B: 0.09% TFA/10% water/90% acetonitrile, gradient A:B=70:30→60:40, 20 minutes, linear gradient elution] to obtain peptide 118 (SEQ ID NO. 122) represented by the following formula (118).

[Chemical Formula 142]

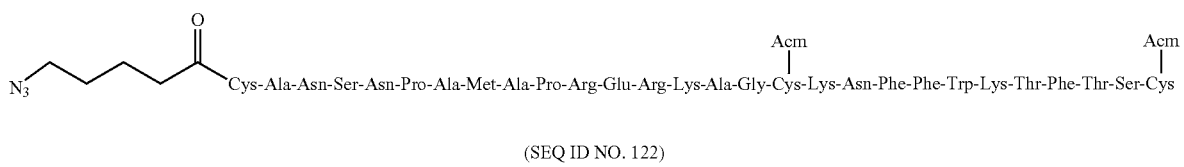

(118)

(SEQ ID NO. 122)

ESI-MS: (m/z) calcd for $C_{148}H_{226}N_{46}O_{41}S_4$: $[M+3H]^{3+}$ 1145.6, $[M+4H]^{4+}$ 859.5, $[M+5H]^{5+}$ 687.8. found 1145.5, 859.2, 687.5.

48-2 Synthesis of Azido-S1C(Disialo)-SRIF28

A compound represented by the following formula (119) (Azido-S1C(disialo)-SRIF28) (SEQ ID NO. 123) was synthesized similarly to Example 1, except that peptide 118 obtained in the method described in the above 48-1 was employed instead of peptide 1.

[Chemical Formula 143]

(119)

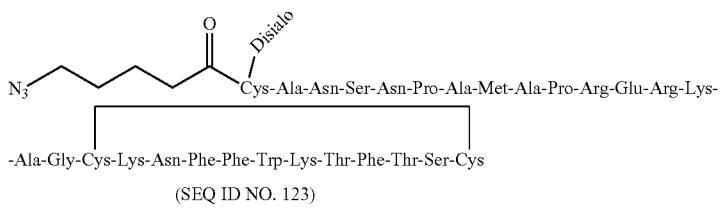

(SEQ ID NO. 123)

Example 49 Synthesis of S1C(Disialo)•E12C(Disialo)-SRIF28

A compound represented by the following formula (121) (S1C(disialo)•E12C(disialo)-SRIF28) (SEQ ID NO. 125) was synthesized similarly to Example 20, except that a compound represented by the following formula (120) (peptide 120) (SEQ ID NO. 124) was synthesized and employed instead of peptide 44.

[Chemical Formula 144]

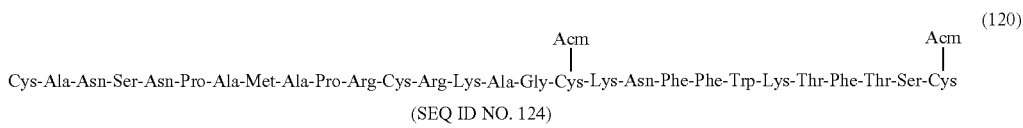

(120)

(SEQ ID NO. 124)

[Chemical Formula 145]

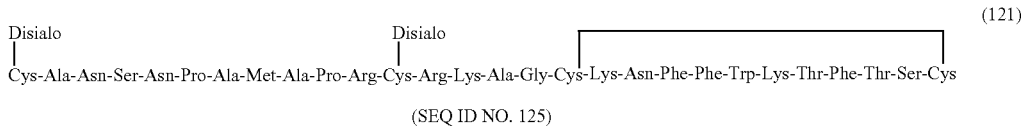

(121)

(SEQ ID NO. 125)

Example 50 Synthesis of 2C(Disialo)-R-K-SRIF14

A compound represented by the following formula (123) (2C(disialo)-R-K-SRIF14) (SEQ ID NO. 127) was synthesized similarly to Example 20, except that a compound represented by the following formula (122) (peptide 122) (SEQ ID NO. 126) was synthesized and employed instead of peptide 44.

[Chemical Formula 146]

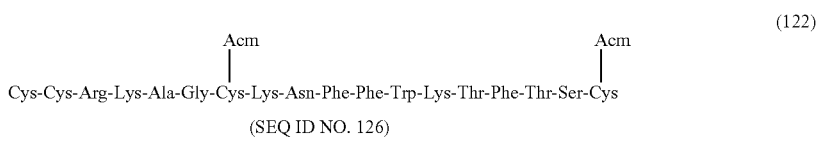

(122)

(SEQ ID NO. 126)

[Chemical Formula 147]

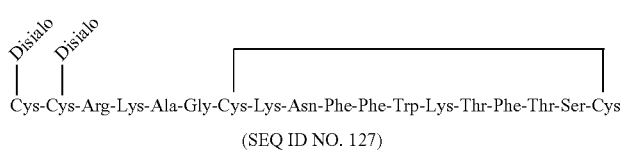

(123)

(SEQ ID NO. 127)

Example 51 Synthesis of 3C(Disialo)-R-K-SRIF14

A compound represented by the following formula (125) (3C(disialo)-R-K-SRIF14) (SEQ ID NO. 129) was synthesized similarly to Example 24, except that a compound represented by the following formula (124) (peptide 124) (SEQ ID NO. 128) was synthesized and employed instead of peptide 54.

[Chemical Formula 148]

(124)

Cys-Cys-Cys-Arg-Lys-Ala-Gly-Cys

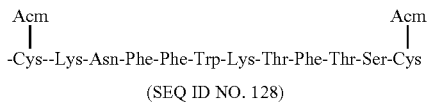

-Cys--Lys-Asn-Phe-Phe-Trp-Lys-Thr-Phe-Thr-Ser-Cys (SEQ ID NO. 128)

[Chemical Formula 149]

(125)

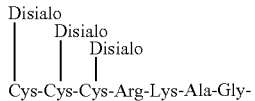

Cys-Cys-Cys-Arg-Lys-Ala-Gly-

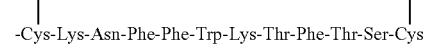

-Cys-Lys-Asn-Phe-Phe-Trp-Lys-Thr-Phe-Thr-Ser-Cys (SEQ ID NO. 129)

Example 52 Synthesis of S1C(diGlcNAc)-SRIF28

52-1 Glycosylation Reaction of Thiol

Peptide 1 (SEQ ID NO. 38) (from APC, Inc.) (25.0 mg, 7.56 μmol) and compound h represented by the following formula (h) (bromoacetamidated oligosaccharide: from Otsuka Chemical Co., Ltd.) (15.6 mg, 15.1 μmol, 2.0 equivalents to peptide 1) were dissolved in 33 mM phosphate buffer (pH 7.4, 2.3 mL), and reacted at room temperature for 30 minutes.

[Chemical Formula 150]

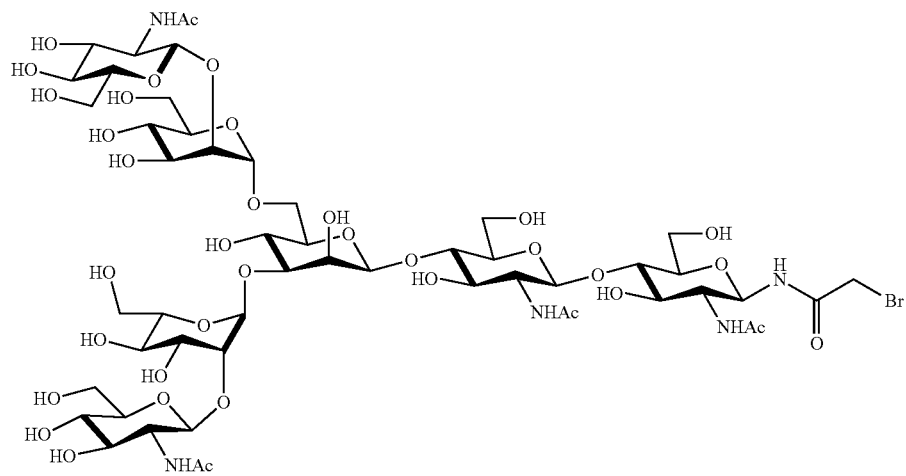

(h)

The reaction solution was purified with HPLC [column: SHISEIDO CAPCELL PAK C18 UG-120 (5 μm), ϕ20×250 mm, flow rate: 7.0 mL/min, eluent A: 0.1% aqueous TFA, B: 0.09% TFA/10% water/90% acetonitrile, A:B=75:25→62:38, 13 minutes, linear gradient elution] to obtain glycopeptide 126 (SEQ ID NO. 130) represented by the following formula (126) (25.6 mg, 6.01 μmol, yield 79%).

[Chemical Formula 151]

(126)

diGlcNAc | Acm | Acm
Cys-Ala-Asn-Ser-Asn-Pro-Ala-Met-Ala-Pro-Arg-Glu-Arg-Lys-Ala-Gly-Cys-Lys-Asn-Phe-Phe-Trp-Lys-Thr-Phe-Thr-Ser-Cys (SEQ ID NO. 130)

ESI-MS: (m/z) calcd for $C_{195}H_{304}N_{48}O_{76}S_4$: $[M+3H]^{3+}$ 1556.0, $[M+4H]^{4+}$ 1167.3. found 1555.7, 1167.0.

52-2 Deprotection of Acm Group

To glycopeptide 126 obtained in the method described in the above 52-1 (28.3 mg, 6.07 μmol) was added an aqueous solution (2.4 mL) of silver(I) acetate (12.5 mg, 74.5 μmol), and reacted at room temperature for 30 minutes. DTT (28.8 mg, 187 μmol) dissolved in 200 mM Tris-HCl buffer (pH 7.4, 2.4 mL) and 100 mM ascorbic acid aqueous solution (0.6 mL) were added, and this was promptly filtered with a filter. The filtrate was purified with HPLC [column: SHISEIDO CAPCELL PAK C18 UG-120 (5 μm), φ20×250 mm, flow rate: 7.0 mL/min, eluent A: 0.1% aqueous AcOH, B: 0.09% AcOH/10% water/90% acetonitrile, gradient A:B=73:27→60:40, 13 minutes, linear gradient elution] to obtain glycopeptide 127 (SEQ ID NO. 131) represented by the following formula (127) (19.8 mg, 4.38 μmol, yield 72%).

[Chemical Formula 152]

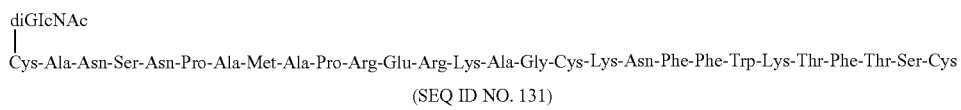

(127)

(SEQ ID NO. 131)

ESI-MS: (m/z) calcd for $C_{189}H_{294}N_{46}O_{74}S_4$: $[M+3H]^{3+}$ 1508.6, $[M+4H]^{4+}$ 1131.7, $[M+5H]^{5+}$ 905.6. found 1508.3, 1131.5, 905.4.

52-3 Formation of Disulfide Bond

Glycopeptide 127 obtained in the method described in the above 52-2 (19.8 mg, 4.38 μmol) was dissolved in 100 mM Tris-HCl buffer (pH 8.0)-DMSO (1/1, v/v, 8.8 mL), and reacted at room temperature for 2 days. The reaction solution was crudely purified with HPLC [column: SHISEIDO CAPCELL PAK C18 UG-120 (5 μm), φ20×250 mm, flow rate: 7.0 mL/min, eluent A: 0.1% aqueous TFA, B: 0.09% TFA/10% water/90% acetonitrile, gradient A:B=73:27→60:40, 13 minutes, linear gradient elution] to obtain a fraction containing compound (S1C(diGlcNAc)-SRIF28) represented by the following formula (128) (SEQ ID NO. 132).

[Chemical Formula 153]

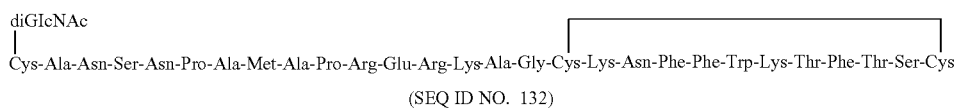

(128)

(SEQ ID NO. 132)

This fraction was further purified with HPLC [column: SHISEIDO CAPCELL PAK C18 UG-120 (5 μm), φ20×250 mm, flow rate: 7.0 mL/min, eluent A: 0.1% aqueous AcOH, B: 0.09% AcOH/10% water/90% acetonitrile, gradient A:B=90:10→78:22, 12 minutes, linear gradient elution] to obtain S1C(diGlNAc)-SRIF28 (11.9 mg, 2.63 μmol, yield 60%).

ESI-MS: (m/z) calcd for $C_{189}H_{292}N_{46}O_{74}S_4$: $[M+3H]^{3+}$ 1508.0, $[M+4H]^{4+}$ 1131.2, $[M+5H]^{5+}$ 905.2. found 1507.7, 1131.0, 905.0.

Example 53 Synthesis of S1C(diMan)-SRIF28

A compound represented by the following formula (129) (S1C(diMan)-SRIF28) (SEQ ID NO. 133) was, synthesized similarly to Example 52, except that compound f was employed instead of compound h.

[Chemical Formula 154]

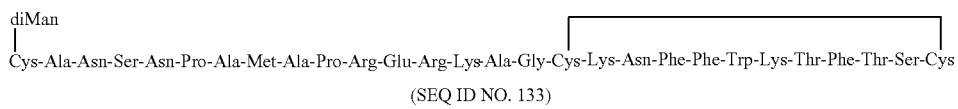

(129)

(SEQ ID NO. 133)

Example 54 Synthesis of N19C(diMan)-SRIF28

A compound represented by the following formula (130) (N19C(diMan)-SRIF28) (SEQ ID NO. 134) was synthesized similarly to Example 52, except that peptide 21 was employed instead of peptide 1 and compound f was employed instead of compound h.

[Chemical Formula 155]

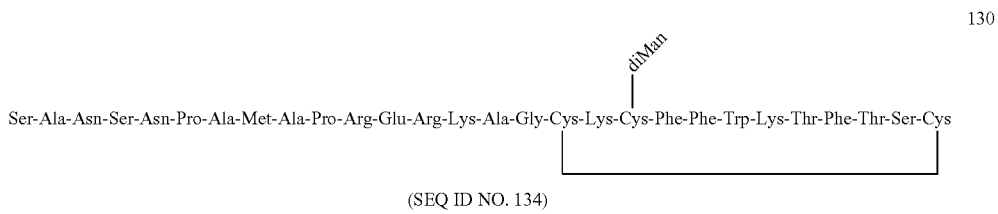

(SEQ ID NO. 134)

Example 55 Synthesis of S1C(GlcNAc)-SRIF28

A compound represented by the following formula (131) (S1C(GlcNAc)-SRIF28) (SEQ ID NO. 135) was synthesized similarly to Example 52, except that compound e was employed instead of compound h.

[Chemical Formula 156]

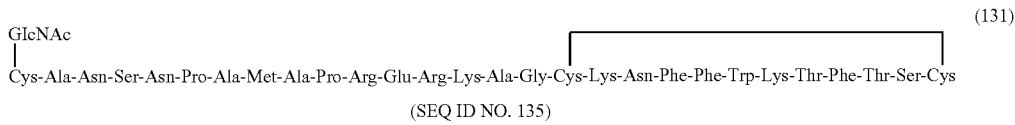

(SEQ ID NO. 135)

Example 56 Synthesis of N19C(GlcNAc)-SRIF28

A compound represented by the following formula (132) (N19C(GlcNAc)-SRIF28) (SEQ ID NO. 136) was synthesized similarly to Example 52, except that peptide 21 was employed instead of peptide 1 and compound e was employed instead of compound h.

[Chemical Formula 157]

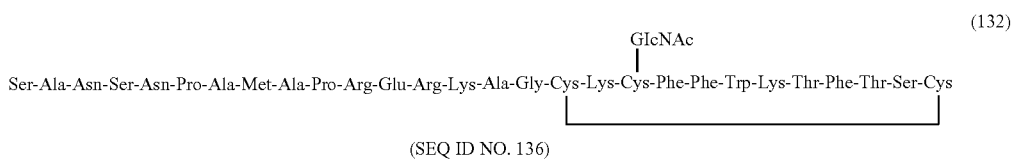

(SEQ ID NO. 136)

Example 57 Synthesis of S1C(Trisialo)-SRIF28

A compound represented by the following formula (133) (S1C(trisialo)-SRIF28) (SEQ ID NO. 137) was synthesized similarly to Example 1, except that compound i represented by the following formula (i) (bromoacetamidated oligosaccharide: from Otsuka Chemical Co., Ltd.) was employed instead of compound a.

[Chemical Formula 158]

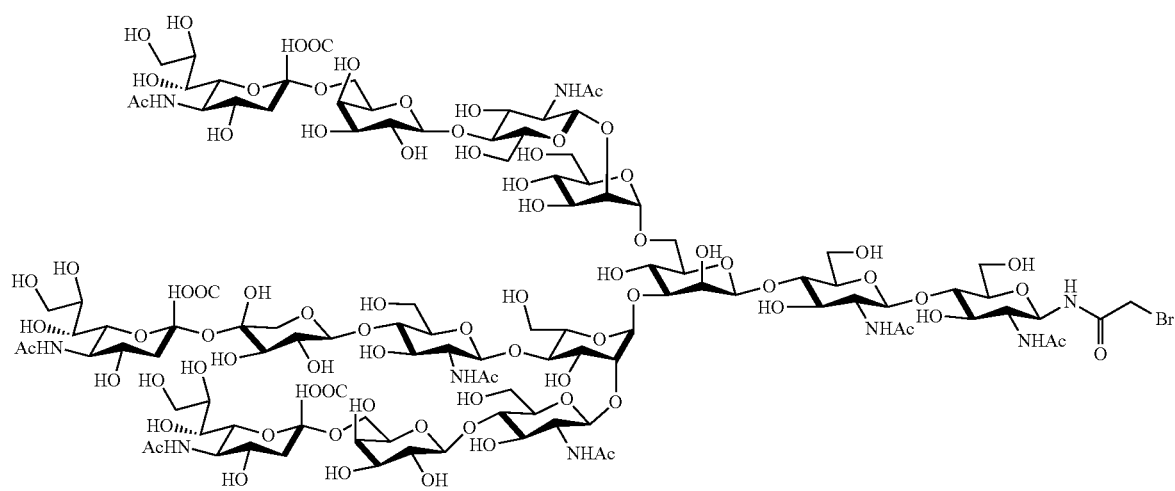

(i)

[Chemical Formula 159]

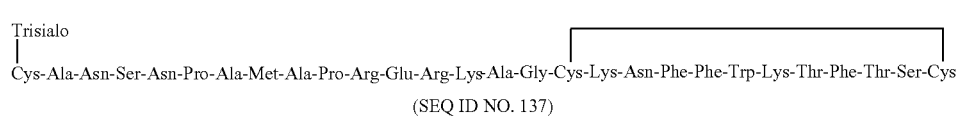

(133)

(SEQ ID NO. 137)

Example 58 Synthesis of S1C(Tetrasialo)-SRIF28

A compound represented by the following formula (134) (S1C(tetrasialo)-SRIF28) (SEQ ID NO. 138) was synthesized similarly to Example 1, except that compound j represented by the following formula (j) (bromoacetamidated oligosaccharide: from Otsuka Chemical Co., Ltd.) was employed instead of compound a.

[Chemical Formula 160]

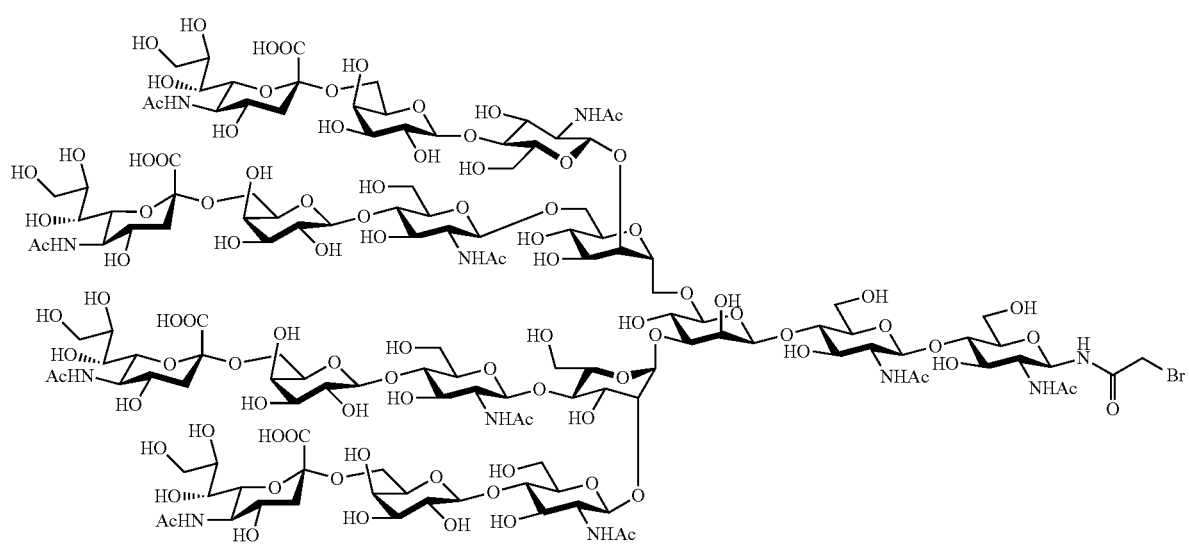

(j)

[Chemical Formula 161]

(134)

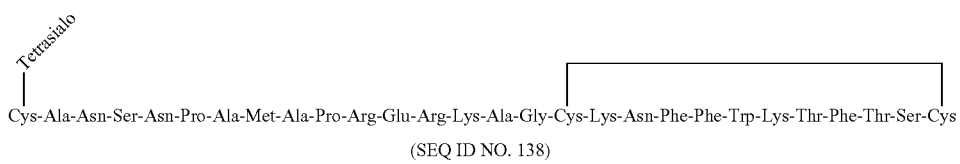

Cys-Ala-Asn-Ser-Asn-Pro-Ala-Met-Ala-Pro-Arg-Glu-Arg-Lys-Ala-Gly-Cys-Lys-Asn-Phe-Phe-Trp-Lys-Thr-Phe-Thr-Ser-Cys (SEQ ID NO. 138)

Example 59 Synthesis of S1C(Disialo(Aminoethylamide))-SRIF28

59-1 Synthesis of Bromoacetamidated Disialo Sugar Chain Derivative

To compound k represented by the following formula (k) (from Otsuka Chemical Co., Ltd.) (204.1 mg, 92.1 μmol) were added water (2 mL) and tert-butyl N-(2-aminoethyl) carbamate (0.29 mL, 0.18 mmol), and this was stirred at room temperature for 1 hour. After lyophilization, to the lyophilizate obtained were added DMF (5 mL), HATU (349 mg, 921 μmol), and DIPEA (161 μL, 921 μmol), and reacted at 37° C. for 18 hours. Toluene (50 mL) was added to the solution, and the deposited precipitate was collected by filtration. The precipitate was dissolved in DMF (5 mL), purified with gel filtration purification [column: Sephadex G-25, φ20×200 mm, flow rate: 30 mL/h], and the fraction of interest was collected and lyophilized to obtain compound l represented by the following formula (l) (152.4 mg, 60.8 μmol, yield 66%).

[Chemical Formula 162]

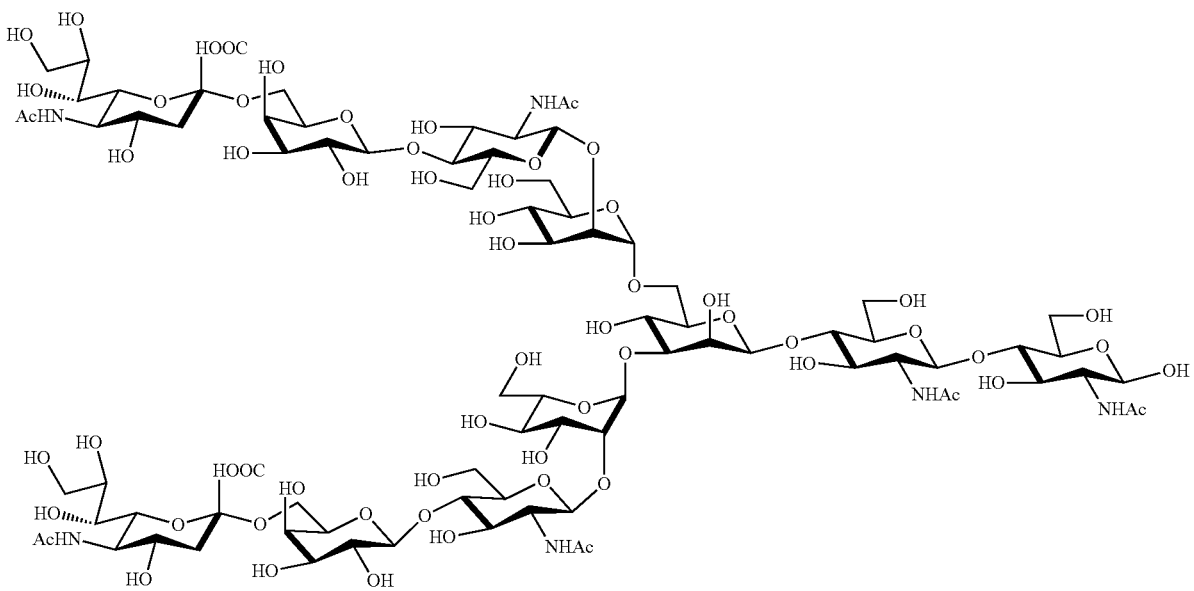

(k)

[Chemical Formula 163]

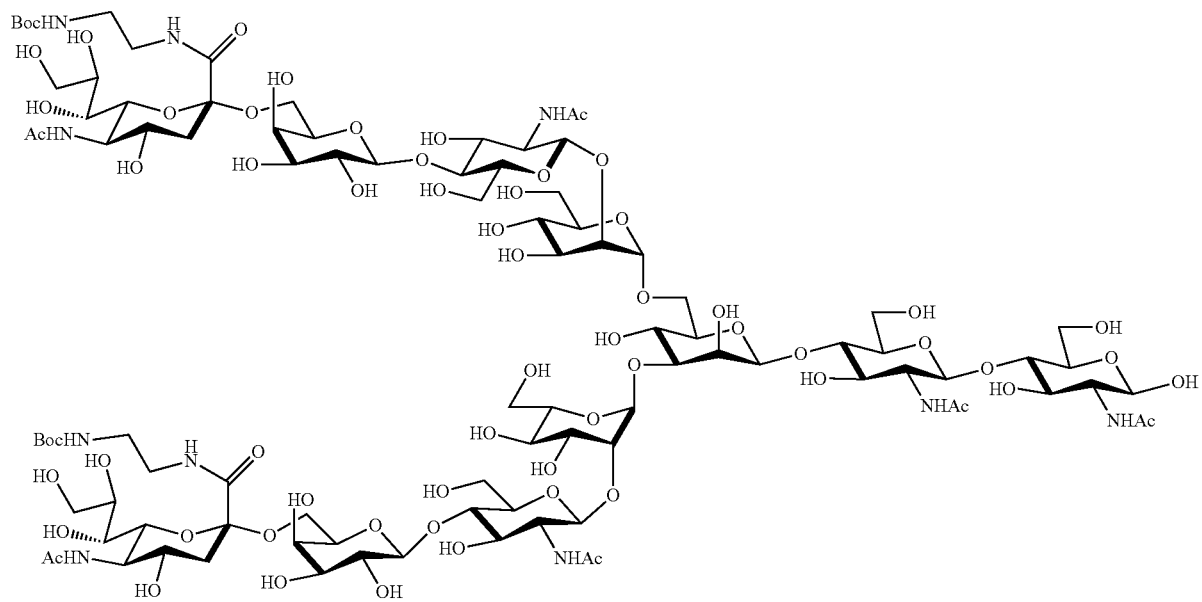

(l)

MALDI-MS: (m/z) calcd for $C_{98}H_{166}N_{10}O_{64}$: [M+Na]$^+$ 2530.0. found 2529.4.

Compound 1 (100 mg, 39.8 μmol) and ammonium hydrogen carbonate (31.4 mg, 398 μmol) were dissolved in water (1 mL), and reacted at room temperature for 7 days. After lyophilization, to the lyophilizate obtained were sequentially added water (1 mL), DCC (41.0 mg, 199 μmol), and bromoacetic acid (27.7 mg, 199 μmol) dissolved in DMF (1 mL). After 1 hour of reaction under ice cooling, the solution was purified with HPLC [column: SHISEIDO CAPCELL PAK C18 UG-120 (5 μm), φ20×250 mm, flow rate: 8.0 mL/min, eluent: water:acetonitrile=84:16] to obtain compound m represented by the following formula (m) (bromoacetamidated disialo sugar chain derivative: 100 mg, 38.2 μmol, yield 96%).

[Chemical Formula 164]

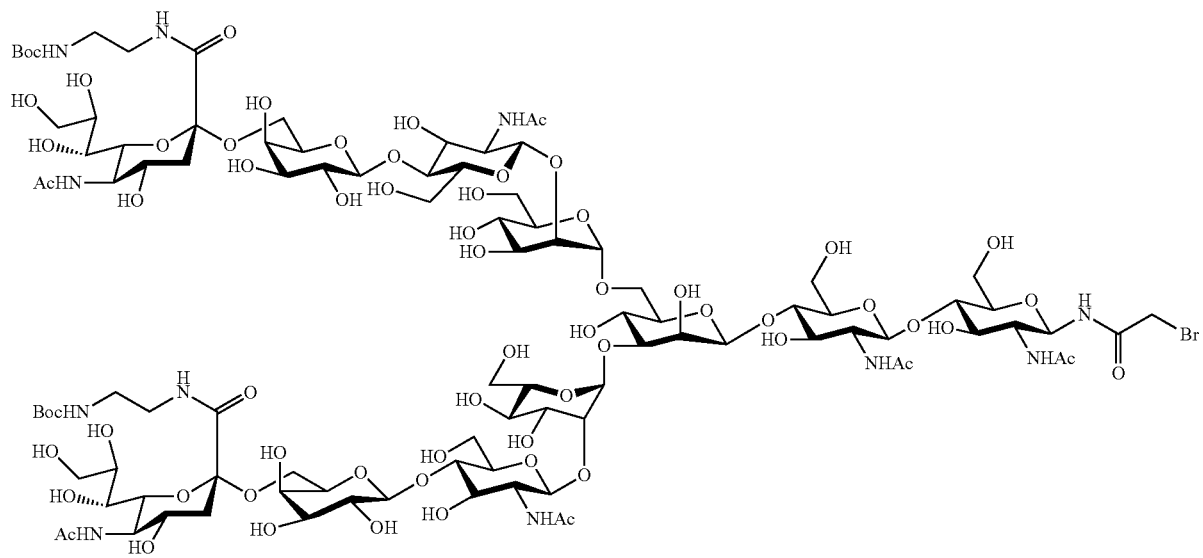

(m)

MALDI-MS: (m/z) (m/z) calcd for $C_{100}H_{168}BrN_{11}O_{64}$: [M+Na]$^+$ 2648.9. found 2648.5.

59-2 Glycosylation Reaction of Thiol

Compound m obtained in the method described in the above 59-1 (14.2 mg, 5.40 μmol) and peptide 1 (15.0 mg, 4.53 μmol were dissolved in 33 mM phosphate buffer (pH 7.4, 1.3 mL), and reacted at room temperature for 30 minutes. The reaction solution was purified with HPLC [column: SHISEIDO CAPCELL PAK C18 UG-120 (5 μm), ϕ20×250 mm, flow rate: 7.0 mL/min, eluent A: 0.1% acetic acid (AcOH) water, B: 0.09% AcOH/10% water/90% acetonitrile, gradient A:B=86:14→82:18, 20 minutes, linear gradient elution] to obtain glycopeptide 135 (SEQ ID NO. 139) represented by the following formula (135) (13.4 mg, 2.29 μmol, yield 51%).

ESI-MS: (m/z) calcd for $C_{243}H_{386}N_{54}O_{104}S_4$: $[M+4H]^{4+}$ 1465.1, $[M+5H]^{5+}$ 1172.2, $[M+6H]^{6+}$ 977.0. found 1464.9, 1172.1, 977.1.

[Chemical Formula 165]

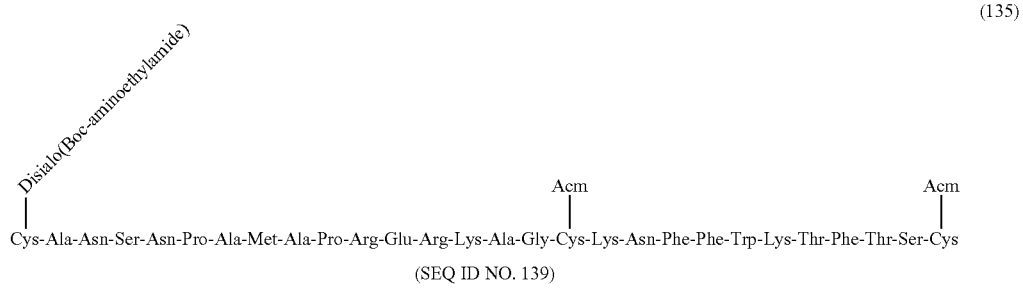

(135)

(SEQ ID NO. 139)

59-3 Deprotection of Boc Group

Glycopeptide 135 obtained in the method described in the above 59-2 (13.4 mg, 2.29 μmol) was dissolved in 95% TFA aqueous solution (458 μL), and this was shaken at room temperature for 5 minutes. After adding 50 mM ammonium acetate aqueous solution (pH 6.8, 33 mL), the reaction solution was purified with HPLC [column: SHISEIDO CAPCELL PAK C18 UG-120 (5 μm), ϕ20×250 mm, flow rate: 7.0 mL/min, eluent A: 0.1% aqueous TFA, B: 0.09% TFA/10% water/90% acetonitrile, gradient A:B=73:27→65:35, 10 minutes, linear gradient elution] to obtain glycopeptide 136 (SEQ ID NO. 140) represented by the following formula (136) (12.7 mg, 98 μmol, yield 98%).

[Chemical Formula 166]

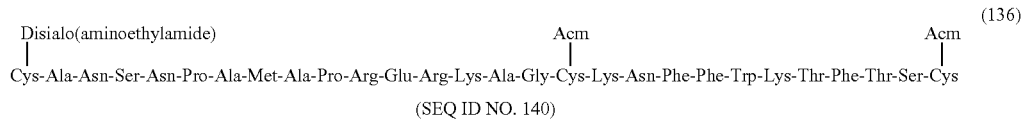

(136)

(SEQ ID NO. 140)

ESI-MS: (m/z) calcd for $C_{233}H_{370}N_{54}O_{100}S_4$: $[M+4H]^{4+}$ 1415.1, $[M+5H]^{5+}$ 1132.2, $[M+6H]^{6+}$ 943.7, $[M+7H]^{7+}$ 809.0. found 1414.9, 1132.1, 943.6, 808.9.

59-4 Deprotection of Acm Group

To glycopeptide 136 obtained in the method described in the above 59-3 (12.7 mg, 2.25 μmol) was added an aqueous solution (0.9 mL) of silver(I) acetate (9.2 mg, 55 μmol), and reacted at room temperature for 30 minutes. Then, DTT, (21.2 mg, 137 μmol) dissolved in 200 mM phosphate buffer (pH 7.4, 0.9 mL) and 100 mM ascorbic acid aqueous solution (225 μL) were added, and this was promptly filtered with a filter. The filtrate was purified with HPLC [column: SHISEIDO CAPCELL PAK C18 UG-120 (5 μm), φ20×250 mm, flow rate: 7.0 mL/min, eluent A: 0.1% aqueous TFA, B: 0.09% TFA/10% water/90% acetonitrile, gradient A:B=73:27→60:40, 13 minutes, linear gradient elution] to obtain glycopeptide 137 (SEQ ID NO. 141) represented by the following formula (136) (5.2 mg, 0.94 μmol, yield 42%).

[Chemical Formula 167]

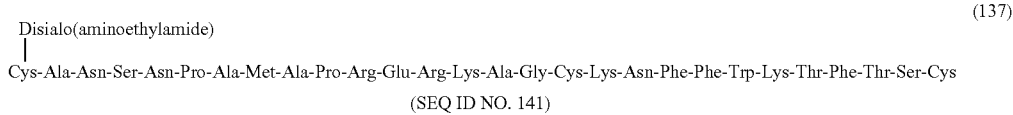

(SEQ ID NO. 141)

ESI-MS: (m/z) calcd for $C_{227}H_{360}N_{52}O_{98}S_4$: $[M+4H]^{4+}$ 1379.5, $[M+5H]^{5+}$ 1103.8, $[M+6H]^{6+}$ 920.0, $[M+7H]^{7+}$ 788.7. found 1379.4, 1103.7, 919.9, 788.6.

59-5 Formation of Disulfide Bond

Glycopeptide 137 obtained in the method described in the above 59-4 (5.2 mg, 0.94 μmol) was dissolved in 100 mM Tris-HCl buffer (pH 8.0)-DMSO (1/1, v/v, 1.9 mL), and reacted at room temperature for 2 days. The reaction solution was purified with HPLC [column: SHISEIDO CAPCELL PAK C18 UG-120 (5 μm), φ20×250 mm, flow rate: 7.0 mL/min, eluent A: 0.1% aqueous TFA, B: 0.09% TFA/10% water/90% acetonitrile, gradient A:B=70:30→65:35, 13 minutes, linear gradient elution] to obtain a fraction containing compound (S1C(disialo(aminoethylamide))-SRIF28) represented by the following formula (138) (SEQ ID NO. 142).

This fraction was further purified with HPLC [column: SHISEIDO CAPCELL PAK C18 UG-120 (5 μm), φ20×250 mm, flow rate: 7.0 mL/min, eluent A: 0.1% aqueous AcOH, B: 0.09% AcOH/10% water/90% acetonitrile, gradient A:B=92:8→85:15, minutes, linear gradient elution] to obtain S1C(disialo(aminoethylamide))-SRIF28 (3.8 mg, 0.69 μmol, yield 73%).

ESI-MS: (m/z) calcd for $C_{227}H_{358}N_{52}O_{98}S_4$: $[M+3H]^{3+}$ 1838.3, $[M+4H]^{4+}$ 1379.0, $[M+5H]^{5+}$ 1103.4, $[M+6H]^{6+}$ 919.6, $[M+7H]^{7+}$ 788.4. found 1838.0, 1378.5, 1103.2, 919.5, 788.2.

Example 60 Synthesis of S1C(Disialo(Amide))-SRIF28

60-1 Synthesis of Bromoacetamidated Disialo Sugar Chain Derivative

To compound k (from Otsuka Chemical Co., Ltd.) (152 mg, 68.6 μmol) were sequentially added DMF (1.9 mL), lithium bromide (357 mg, 4.12 mmol), and phenacyl chloride (273 mg, 1.37 mmol), and reacted at 37° C. After 10 hours, water (19 mL) was added and the precipitate was removed by filtration. To the filtrate was added 25% ammonium water (5 mL), and reacted at room temperature for 18 hours, and then 100 mM phosphate buffer (pH 7.4, 80 mL) was added to allow neutralization. The solution was purified with HPLC [column: YMC Hydrosphere C18 (5 μm), φ20×250 mm, flow rate: 8.0 mL/min, eluent: 0.1% aqueous TFA:acetonitrile=98:2→92:8, 30 minutes, linear gradient elution] and lyophilized to obtain compound n represented by the following formula (n) (60.9 mg, 27.4 μmol, yield 40%).

MALDI-MS: (m/z) calcd for $C_{84}H_{140}N_8O_{60}$: $[M+Na]^+$ 2243.8. found 2243.6.

[Chemical Formula 168]

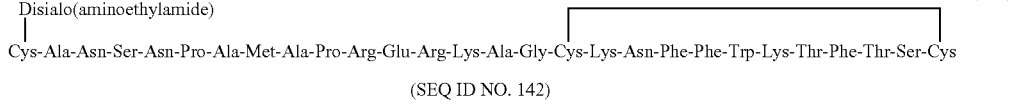

(SEQ ID NO. 142)

[Chemical Formula 164]

(n)

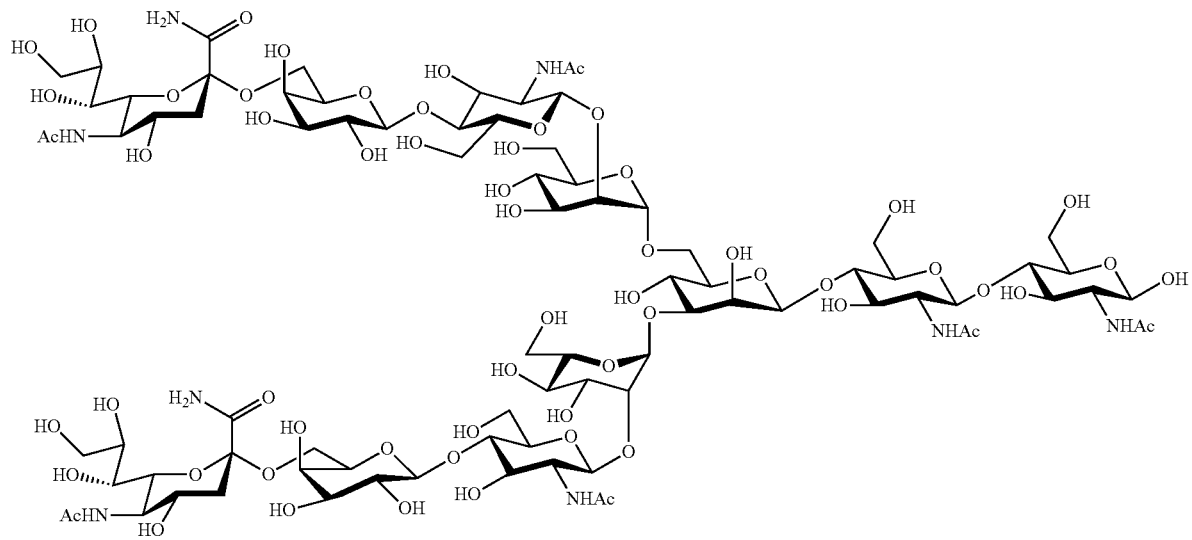

The obtained intermediate n (37.3 mg, 16.8 μmol) and ammonium hydrogen carbonate (13.3 mg, 168 μmol) were dissolved in water (0.37 mL), and reacted at room temperature for 7 days. After lyophilization, to the lyophilizate obtained were sequentially added water (0.37 mL), DCC (17.3 mg, 84 μmol), and bromoacetic acid (11.7 mg, 84 μmol) dissolved in DMF (0.37 mL). The solution after 1 hour of reaction under ice cooling was purified with HPLC [column: YMC Hydrosphere C18 (5 μm), ϕ20×250 mm, flow rate: 8.0 mL/min, eluent: 0.1% aqueous TFA:acetonitrile=98:2→92:8, 30 minutes, linear gradient elution] to obtain compound o represented by the following formula (o) (bromoacetamidated disialo sugar chain derivative: 29.0 mg, 12.4 μmol, yield 74%).

MALDI-MS: (m/z) calcd for $C_{86}H_{142}BrN_9O_{60}$: $[M+Na]^+$ 2362.7. found 2362.5.

60-2 Synthesis of S1C(Disialo(Amide))-SRIF28

A compound represented by the following formula (139) (S1C(disialo(amide))-SRIF28) (SEQ ID NO. 143) was synthesized similarly to Example 1, except that compound o obtained in the method described in the above 60-1 was employed instead of compound a.

[Chemical Formula 170]

(o)

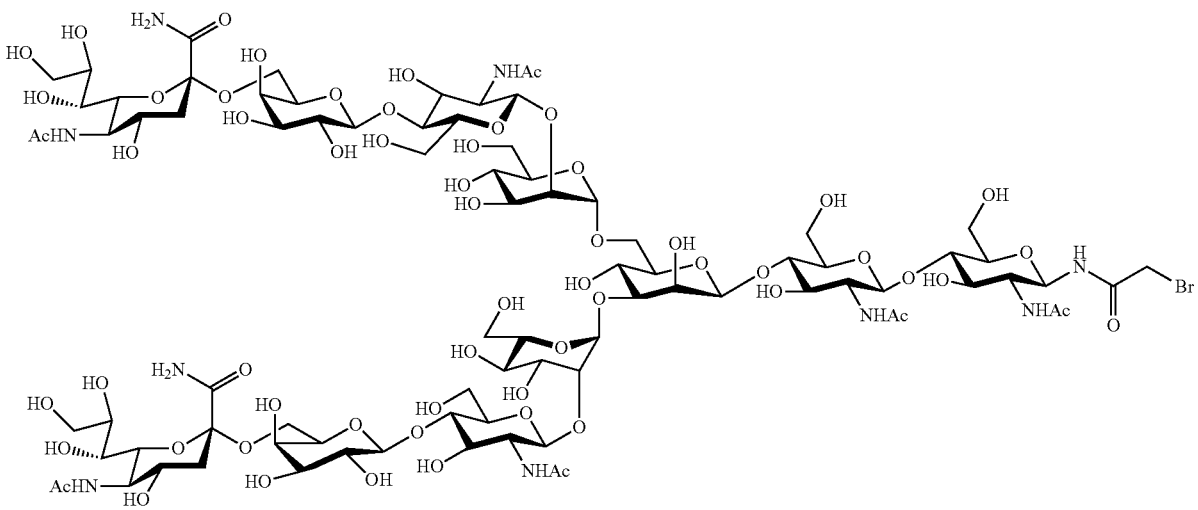

[Chemical Formula 171]

(139)

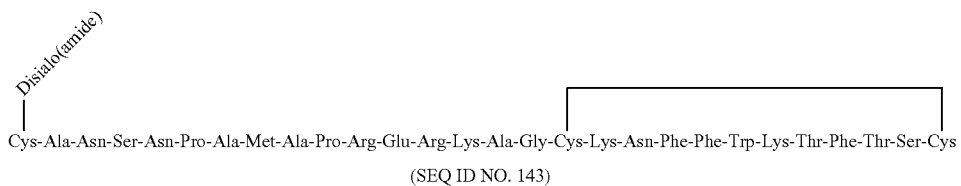

Cys-Ala-Asn-Ser-Asn-Pro-Ala-Met-Ala-Pro-Arg-Glu-Arg-Lys-Ala-Gly-Cys-Lys-Asn-Phe-Phe-Trp-Lys-Thr-Phe-Thr-Ser-Cys (SEQ ID NO. 143)

Example 61 Synthesis of S1C(Disialo(Bn))-SRIF28

A compound represented by the following formula (140) (S1C(disialo(Bn))-SRIF28) (SEQ ID NO. 144) was synthesized similarly to Example 1, except that compound g was employed instead of compound a.

[Chemical Formula 172]

(140)

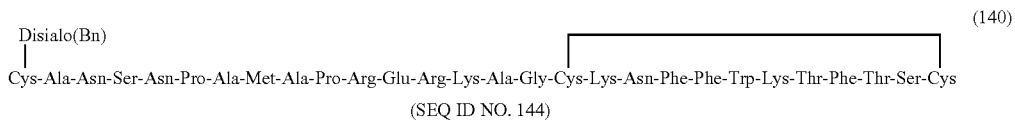

Disialo(Bn)
|
Cys-Ala-Asn-Ser-Asn-Pro-Ala-Met-Ala-Pro-Arg-Glu-Arg-Lys-Ala-Gly-Cys-Lys-Asn-Phe-Phe-Trp-Lys-Thr-Phe-Thr-Ser-Cys (SEQ ID NO. 144)

Example 62 Synthesis of S1C(Disialo (Hexadecylamide))-SRIF28

62-1 Synthesis of Bromoacetamidated Disialo Sugar Chain Derivative

To compound k (from Otsuka Chemical Co., Ltd.) (140 mg, 63.0 μmol) were added water (1.5 mL), methanol (1.5 mL), and hexadecylamine (300 mg, 126 μmol), and this was stirred at room temperature for 1 hour. After lyophilization, to the lyophilizate obtained were added DMF (5 mL), HATU (239 mg, 630 μmol), and DIPEA (110 μL, 630 μmol), and reacted at 37° C. After 18 hours, diethyl ether (100 mL) was added to the solution, and the deposited precipitate was collected by filtration. This precipitate was dissolved in DMF (5 mL) and purified with HPLC [column: SHISEIDO CAPCELL PAK C18 UG-120 (5 μm), φ20×250 mm, flow rate: 8.0 mL/min, eluent: water:acetonitrile=40:60→10:90, 30 minutes, linear gradient elution] to obtain compound p represented by the following formula (p) (71.1 mg, 26.6 μmol, yield 42%).

[Chemical Formula 173]

(p)

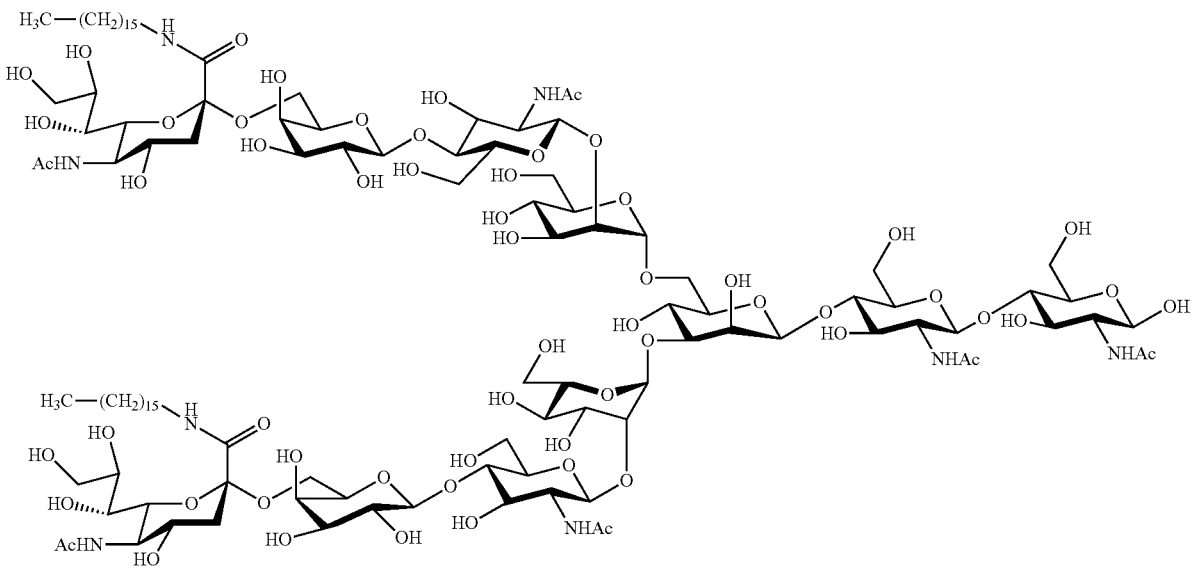

MALDI-MS: (m/z) calcd for $C_{116}H_{204}N_8O_{60}$: $[M+Na]^+$ 2692.3. found 2691.9.

The obtained compound p (71.7 mg, 26.6 μmol) and ammonium hydrogen carbonate (21.8 mg, 266 μmol) were dissolved in water (0.7 mL) and methanol (0.7 mL), and reacted at room temperature. After 7 days, to the lyophilizate obtained by lyophilization were sequentially added water (0.7 mL), methanol (0.7 mL), DCC (27.4 mg, 133 μmol), and bromoacetic acid (18.5 mg, 133 μmol) dissolved in DMF (0.7 mL). After 1 hour of reaction under ice cooling, the solution was purified with HPLC [column: SHISEIDO CAPCELL PAK C18 UG-120 (5 μm), φ20×250 mm, flow rate: 8.0 mL/min, eluent: water:acetonitrile 40:60→10:90, 30 minutes, linear gradient elution] to obtain compound q represented by the following formula (q) (bromoacetamidated disialo sugar chain: 24.9 mg, 8.9 μmol, yield 33%).

[Chemical Formula 174]

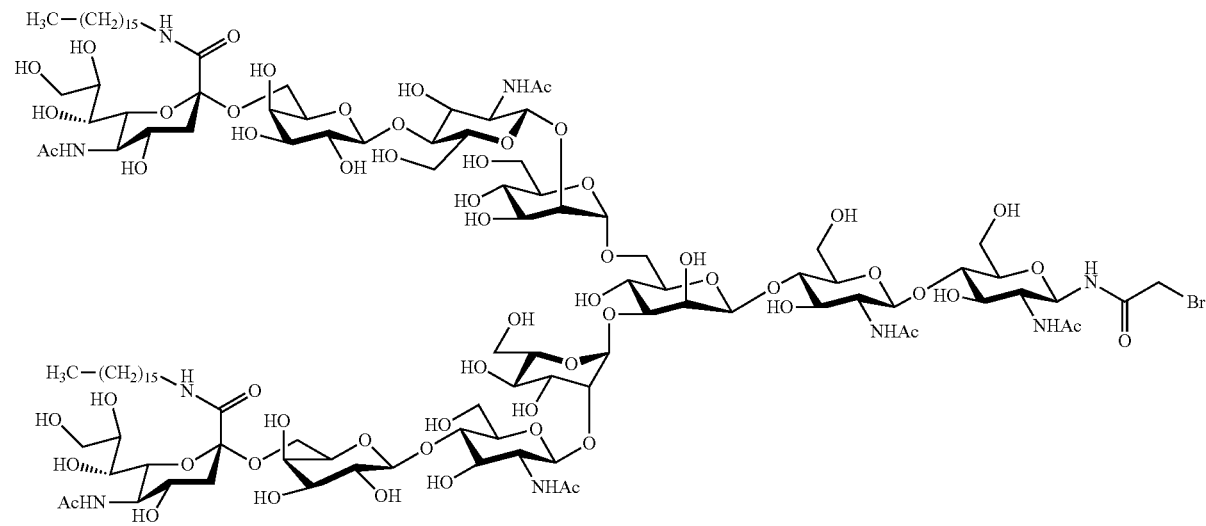

(q)

MALDI-MS: (m/z) calcd for $C_{118}H_{206}BrN_9O_{60}$: $[M+Na]^+$ 2811.2. found 2811.0.

62-2 Glycosylation Reaction of Thiol

Peptide 1 (10.4 mg, 3.14 μmol) was dissolved in 0.5 M phosphate buffer (pH 7.4, 62 μL) containing 30 μM TCEP. To this solution was added a solution of compound q obtained in the method described in the above 62-1 (79.4 mg, 28.5 μmol) in DMSO (3.7 mL), and reacted at room temperature for 20 minutes. The reaction solution was purified with HPLC [column: SHISEIDO Proteonavi (5 μm), φ20×250 mm, flow rate: 7.0 mL/min, eluent A: 0.1% aqueous TFA, B: 0.09% TFA/10% water/90% acetonitrile, gradient A:B=50:50→22:78, 14 minutes, linear gradient elution] to obtain glycopeptide 141 (SEQ ID NO. 145) represented by the following formula (141) (6.4 mg, 1.1 μmol, yield 35%).

[Chemical Formula 175]

(141)

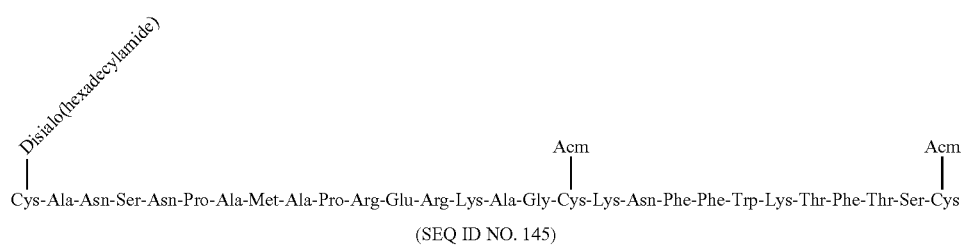

(SEQ ID NO. 145)

ESI-MS: (m/z) calcd for $C_{261}H_{424}N_{52}O_{100}S_4$: $[M+3H]^{3+}$ 2007.2, $[M+4H]^{4+}$ 1505.7, $[M+5H]^{5+}$ 1204.7, $[M+6H]^{6+}$ 1004.1. found 2007.4, 1505.5, 1204.8, 1004.0.

62-3 Deprotection of Acm Group

To glycopeptide 141 obtained in the method described in the above 62-2 (6.4 mg, 1.1 µmol) was added an aqueous solution (0.8 mL) of silver(I) acetate (3.8 mg, 23 µmol), and reacted at room temperature for 40 minutes. Then, DTT (8.8 mg, 57 µmol) dissolved in 200 mM phosphate buffer (pH 7.4, 377 µL) and 100 mM ascorbic acid aqueous solution (106 µL) were added, and this was promptly filtered with a filter. The filtrate was purified with HPLC [column: SHISEIDO Proteonavi (5 µm), φ20×250 mm, flow rate: 7.0 mL/min, eluent A: 0.1% aqueous TFA, B: 0.09% TFA/10% water/90% acetonitrile, gradient A:B=48:52→38:62, 3 minutes, then 38:62→30:70, 8 minutes, linear gradient elution] to obtain glycopeptide 142 (SEQ ID NO. 146) represented by the following formula (142) (3.2 mg, 0.54 µmol, yield 49%).

[Chemical Formula 176]

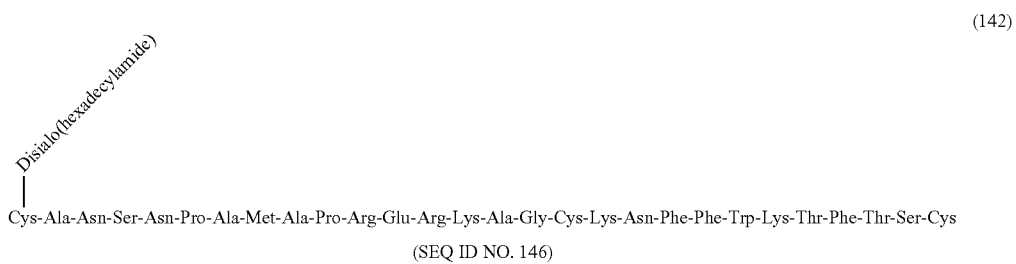

(142)

(SEQ ID NO. 146)

ESI-MS: (m/z) calcd for $C_{255}H_{414}N_{50}O_{98}S_4$: $[M+3H]^{3+}$ 1959.9, $[M+4H]^{4+}$ 1470.1, $[M+5H]^{5+}$ 1176.3, $[M+6H]^{6+}$ 980.4. found 1959.6, 1469.9, 1176.1, 980.5.

62-3 Formation of Disulfide Bond

Glycopeptide 142 obtained in the method described in the above 62-2 (3.2 mg, 0.54 µmol) was dissolved in 100 mM Tris-HCl buffer (pH 8.0)-DMSO (1/1, v/v, 1.1 mL), and reacted at room temperature for 2 days. The reaction solution was purified with HPLC [column: SHISEIDO Proteonavi (5 µm), φ20×250 mm, flow rate: 7.0 mL/min, eluent A: 0.1% aqueous TFA, B: 0.09% TFA/10% water/90% acetonitrile, gradient A:B=48:52→38:62, 3 minutes, then 38:62→30:70, 8 minutes, linear gradient elution] to obtain a compound represented by the following formula (143) (S1C (disialo (hexadecylamide))-SRIF28) (SEQ ID NO. 147) (2.8 mg, 0.48 µmol, yield 89%).

[Chemical Formula 177]

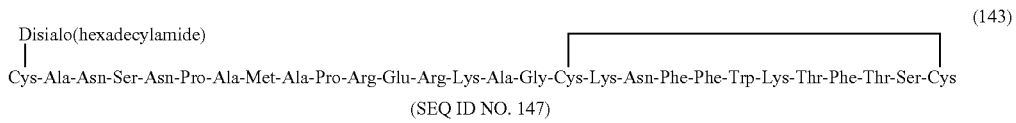

(143)

(SEQ ID NO. 147)

ESI-MS: (m/z) calcd for $C_{255}H_{412}N_{50}O_{98}S_4$: $[M+3H]^{3+}$ 1959.2, $[M+4H]^{4+}$ 1469.6, $[M+5H]^{5+}$ 1175.9, $[M+6H]^{6+}$ 980.1. found 1958.9, 1469.4, 1175.7, 979.9.

Example 63 Synthesis of S1-2C(Disialo(Amide))-SRIF28

A compound represented by the following formula (144) (S1-2C(disialo(amide))-SRIF28) (SEQ ID NO. 148) was synthesized similarly to Example 28, except that compound o was employed instead of compound c.

[Chemical Formula 178]

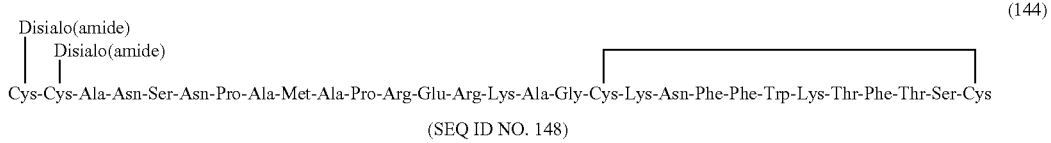

(144)

(SEQ ID NO. 148)

Example 64 Synthesis of S1-2C(Disialo(Bn))-SRIF28

A compound represented by the following formula (145) (S1-2C(disialo(Bn))-SRIF28) (SEQ ID NO. 149) was synthesized similarly to Example 28, except that compound g was employed instead of compound c.

[Chemical Formula 179]

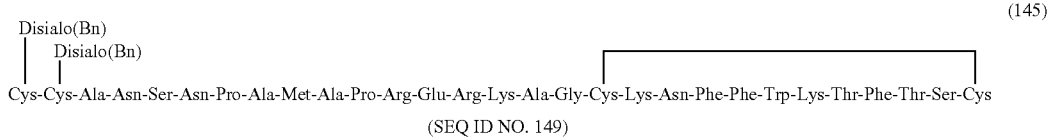

(145)

(SEQ ID NO. 149)

Example 65 Synthesis of S1C(Asn(Disialo))-SRIF28

A compound represented by the following formula (146) (S1C(Asn(disialo))-SRIF28) (SEQ ID NO. 150) was synthesized similarly to Example 1, except that compound r represented by the following formula (r) (bromoacetylated glycosylated Asn: from Otsuka Chemical Co., Ltd.) was employed instead of compound a.

[Chemical Formula 180]

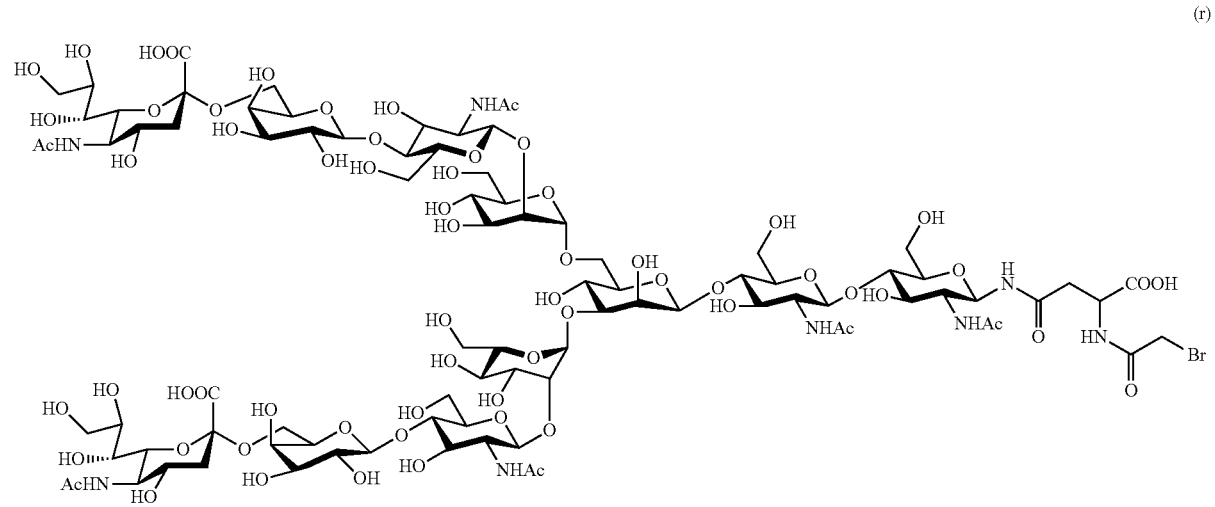

(r)

[Chemical Formula 181]

(146)

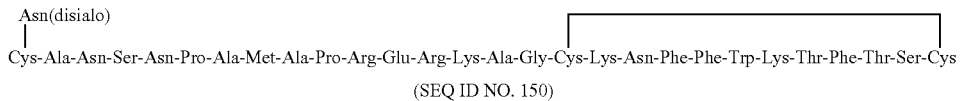

(SEQ ID NO. 150)

Example 66 Synthesis of S1N(Disialo)•N19C(diMan)-SRIF28

66-1 Solid Phase Synthesis of Glycopeptide 2-chlorotrityl chloride resin (100 μmol) was taken in a column for solid phase synthesis, and after washing with DMF and dichloromethane, a solution of Fmoc-Cys(Trt)-OH (72.5 mg, 120 μmol) and DIPEA (104.6 μL, 600 μmol) in dichloromethane (3.0 mL) was added, and this was shaken for 1 hour. After washing with dichloromethane and DMF, the Fmoc protecting group was removed by treating with 20% piperidine in DMF. After washing with DMF, in a peptide solid phase synthesis method with Fmoc strategy employing a Prelude™ peptide synthesizer, a protected peptide 147 (SEQ ID NO. 151) represented by the following formula (147) was synthesized in a state bound to the resin. The condensation reaction was performed in DMF using HCTU as the condensation agent.

[Chemical Formula 182]

(147)

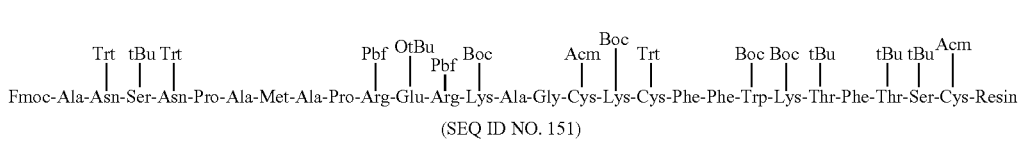

(SEQ ID NO. 151)

Next, the Fmoc protecting group was removed by treating with 20% piperidine in DMF. After washing with DMF, compound d (141.0 mg, 51.5 μmol), DMSO-DMF (1/1, v/v, 1.1 mL) solution, TBTU (21.2 mg, 66.0 μmol), and DIPEA (17.2 μL, 98.7 μmol) were sequentially added to the resin, and this was shaken at room temperature for 4 hours to allow condensation. After washing with DMF, this condensation operation was repeated once. After washing the resin with DMF and dichloromethane, this was shaken with 20% piperidine in DMF for 20 minutes to deprotect the Fmoc group, and the resin was washed with DMF to synthesize a protected peptide 148 (SEQ ID NO. 152) represented by the following formula (148) in a state bound to the resin.

[Chemical Formula 183]

(148)

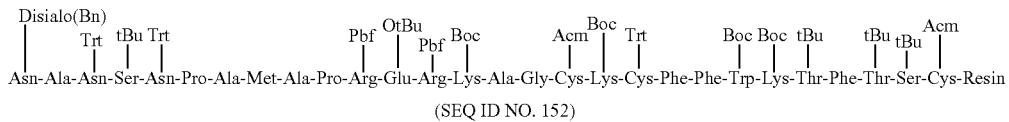

(SEQ ID NO. 152)

After washing with DMF and dichloromethane, TFA:water:triisopropylsilane:ethanedithiol (=90:2.5:5:2.5) was added, and this was shaken at room temperature for 3 hours. The resin was filtered off, cold diethyl ether was added to the filtrate, and crude peptide was obtained as precipitate. This crude peptide was purified with HPLC [column: SHISEIDO CAPCELL PAK C18 UG-120 (5 μm), φ20×250 mm, flow rate: 7.0 mL/min, eluent A: 0.1% aqueous TFA, B: 0.09% TFA/10% water/90% acetonitrile, A:B=70:30] to obtain glycopeptide 149 (SEQ ID NO. 153) represented by the following formula (149) (5.8 mg, 1.1 μmol).

[Chemical Formula 184]

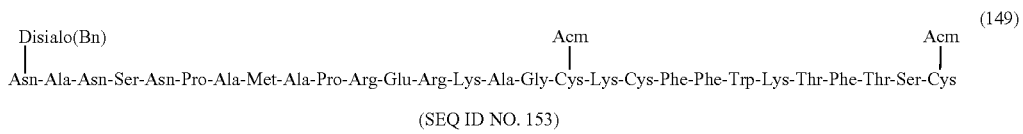

(SEQ ID NO. 153)

ESI-MS: (m/z) calcd for $C_{241}H_{367}N_{49}O_{101}S_4$: $[M+4H]^{4+}$ 1424.8, $[M+5H]^{5+}$ 1140.0. found 1424.6, 1139.9.

66-2 Glycosylation Reaction of Thiol

Glycopeptide 149 obtained in the method described in the above 66-1 (10.8 mg, 1.90 μmol) and compound f (5.3 mg, 5.1 μmol) were dissolved in 100 mM phosphate buffer (pH 7.4, 0.8 mL) containing 141 μM TCEP, and reacted at room temperature for 24 hours. The reaction solution was purified with HPLC [column: SHISEIDO CAPCELL PAK C18 UG-120 (5 μm), φ20×250 mm, flow rate: 7.0 mL/min, eluent A: 0.1% aqueous TFA, B: 0.09% TFA/10% water/90% acetonitrile, A:B=75:25→60:40, 30 minutes, linear gradient elution] to obtain glycopeptide 150 (SEQ ID NO. 154) represented by the following formula (150) (4.9 mg, 0.74 μmol, yield 39%).

[Chemical Formula 185]

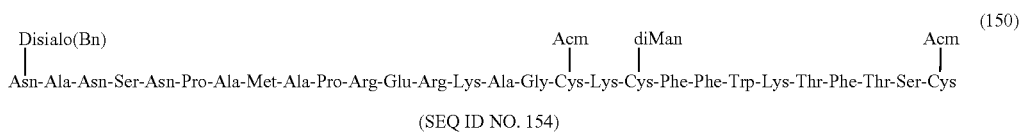

(SEQ ID NO. 154)

ESI-MS: (m/z) calcd for $C_{277}H_{426}N_{52}O_{127}S_4$: $[M+3H]^{3+}$ 2216.0, $[M+4H]^{4+}$ 1662.2, $[M+5H]^{5+}$ 1330.0. found 2215.6, 1661.9, 1330.1.

66-3 Deprotection of Acm Group

To glycopeptide 150 obtained in the method described in the above 66-2 (4.9 mg, 0.74 μmol) was added an aqueous solution (148 μL) of silver(I) acetate (1.5 mg, 9.0 μmol), and reacted at room temperature for 1.5 hours reaction. DTT (3.5 mg, 23 μmol) dissolved in 200 mM phosphate buffer (pH 7.4, 145 μL) and 100 mM ascorbic acid aqueous solution (37 μL) were added, and this was promptly filtered with a filter. The filtrate was purified with HPLC [column: SHISEIDO CAPCELL PAK C18 UG-120 (5 μm), φ20×250 mm, flow rate: 7.0 mL/min, eluent A: 0.1% aqueous TFA, B: 0.09% TFA/10% water/90% acetonitrile, gradient A:B=74:26→64:36, 30 minutes, linear gradient elution] to obtain glycopeptide 151 (SEQ ID NO. 155) represented by the following formula (151) (3.7 mg, 0.57 μmol, yield 77%).

[Chemical Formula 186]

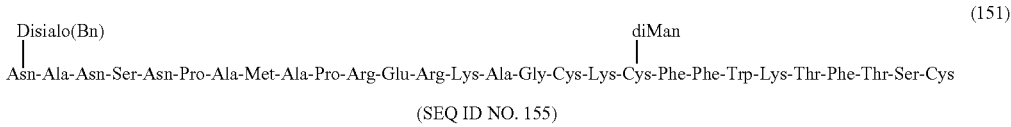

(151)

(SEQ ID NO. 155)

ESI-MS: (m/z) calcd for $C_{271}H_{416}N_{50}O_{125}S_4$: $[M+3H]^{3+}$ 2168.6, $[M+4H]^{4+}$ 1626.7, $[M+5H]^{5+}$ 1301.5. found 2168.6, 1626.4, 1301.3.

66-4 Formation of Disulfide Bond

Glycopeptide 151 obtained in the method described in the above 66-3 (3.7 mg, 0.54 μmol) was dissolved in 100 mM Tris-HCl buffer (pH 8.0)-DMSO (1/1, v/v, 1.4 mL), and reacted at room temperature for 31 hours. The reaction solution was purified with HPLC [column: SHISEIDO CAPCELL PAK C18 UG-120 (5 μm), φ20×250 mm, flow rate: 7.0 mL/min, eluent A: 0.1% aqueous TFA, B: 0.09% TFA/10% water/90% acetonitrile, gradient A:B=75:25→60:40, 30 minutes, linear gradient elution] to obtain glycopeptide 152 (SEQ ID NO. 156) represented by the following formula (152) (2.9 mg, 0.45 μmol, yield 78%).

[Chemical Formula 187]

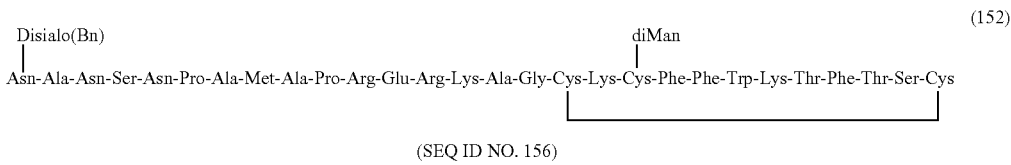

(152)

(SEQ ID NO. 156)

ESI-MS: (m/z) calcd for $C_{271}H_{414}N_{50}O_{125}S_4$: $[M+3H]^{3+}$ 2167.9, $[M+4H]^{4+}$ 1626.2, $[M+5H]^{5+}$ 1301.1. found 2167.9, 1626.0, 1301.2.

66-5 Deprotection of Benzyl Group

Glycopeptide 152 obtained in the method described in the above 66-4 (2.9 mg, 0.45 μmol) was dissolved in 50 mM sodium hydroxide aqueous solution (13.6 mL), and reacted at 0° C. for 1 hour. 200 mM acetic acid aqueous solution (3.4 mL) was added, and the mixed solution was purified with HPLC [column: SHISEIDO CAPCELL PAK C18 UG-120 (5 μm), φ20×250 mm, flow rate: 7.0 mL/min, eluent A: 0.1% aqueous TFA, B: 0.09% TFA/10% water/90% acetonitrile, gradient A:B=75:25→60:40, 20 minutes, linear gradient elution] to obtain a fraction containing compound (S1N(disialo)•N19C(diMan)-SRIF28) represented by the following formula 153 (SEQ ID NO. 157).

[Chemical Formula 188]

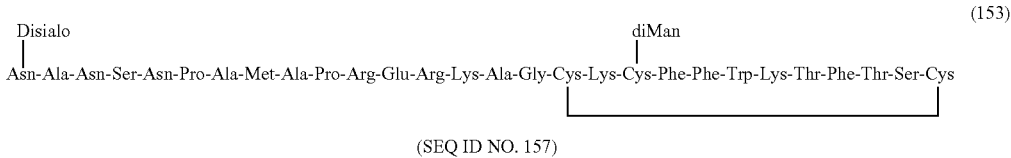

(153)

(SEQ ID NO. 157)

This fraction was further purified with HPLC [column: SHISEIDO CAPCELL PAK C18 UG-120 (5 μm), φ4.6×250 mm, flow rate: 0.7 mL/min, eluent A: 0.1% aqueous AcOH, B: 0.09% AcOH/10% water/90% acetonitrile, gradient A:B=95:5→85:15, 2 minutes, then 85:15→65:35, 20 minutes, linear gradient elution] to obtain S1N(disialo)•N19C(diMan)-SRIF28 (1.6 mg, 0.25 μmol, yield 57%).

ESI-MS: calcd for $C_{257}H_{402}N_{50}O_{125}S_4$: $[M+3H]^{3+}$ 2107.8, $[M+4H]^{4+}$ 1581.1, $[M+5H]^{5+}$ 1265.1. found 2107.9, 1580.9, 1265.1.

Example 67 Synthesis of C(Disialo(Aminoethylamide))•S1C(Disialo)-SRIF28

67-1 Synthesis of Peptide 2-chlorotrityl chloride resin (100 μmol) was taken in a column for solid phase synthesis, and after washing with DMF and dichloromethane, a solution of Fmoc-Cys(Acm)-OH (49.7 mg, 120 μmol) and DIPEA (104.5 μL, 600 μmol) in dichloromethane (3.0 mL) was added, and this was shaken for 1 hour. After washing with dichloromethane and DMF, the Fmoc protecting group was removed by treating with 20% piperidine in DMF. After washing with DMF, in a peptide solid phase synthesis method with Fmoc strategy employing a Prelude™ peptide synthesizer, a protected peptide 154 (SEQ ID NO. 158) represented by the following formula (154) was synthesized in a state bound to the resin. The condensation reaction was performed in DMF using HCTU as the condensation agent.

[Chemical Formula 189]

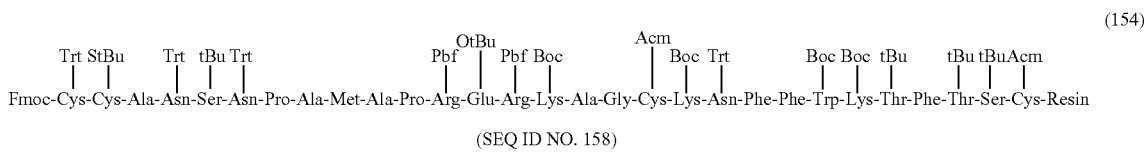

(154)

(SEQ ID NO. 158)

A part of the resin (50 μmol) was taken, and the Fmoc protecting group was removed by treating with 20% piperidine in DMF. After washing with DMF and dichloromethane, TFA:water:triisopropylsilane:ethanedithiol (=90:2.5:5:2.5) was added, and this was shaken at room temperature for 3 hours. The resin was filtered off, cold diethyl ether was added to the filtrate, and crude peptide was obtained as precipitate. The crude peptide was purified with HPLC [column: SHISEIDO CAPCELL PAK C18 UG-120 (5 μm), φ20×250 mm, flow rate: 7.0 mL/min, eluent A: 0.1% aqueous TFA, B: 0.09% TFA/10% water/90% acetonitrile, gradient A:B=73:27→63:37, 30 minutes, linear gradient elution] to obtain peptide 155 (SEQ ID NO. 159) represented by the following formula (155) (30.4 mg).

[Chemical Formula 190]

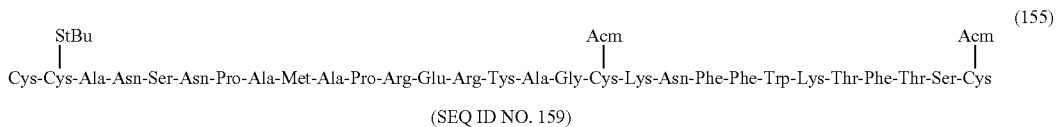

(155)

(SEQ ID NO. 159)

ESI-MS: (m/z) (m/z) calcd for $C_{150}H_{232}N_{44}O_{41}S_6$: $[M+3H]^{3+}$ 1167.7, $[M+4H]^{4+}$ 876.0. found 1167.5, 875.9.

67-2 Deprotection of Boc Group in Sugar Chain Derivative

Compound m (50.0 mg, 19.0 μmol) was dissolved in a TFA-$H_2O$ (95/5, v/v, 2.5 mL) solution, and this was shaken at room temperature. After 10 minutes, diethyl ether (15 mL) was added, and the deposited precipitate was centrifuged (10,000×g 10 minutes). The precipitate was dissolved in water and lyophilized to obtain compound s represented by the following formula (s) (bromoacetamidated disialo sugar chain: 46.0 mg, 18.9 μmol, yield 99%).

[Chemical Formula 191]

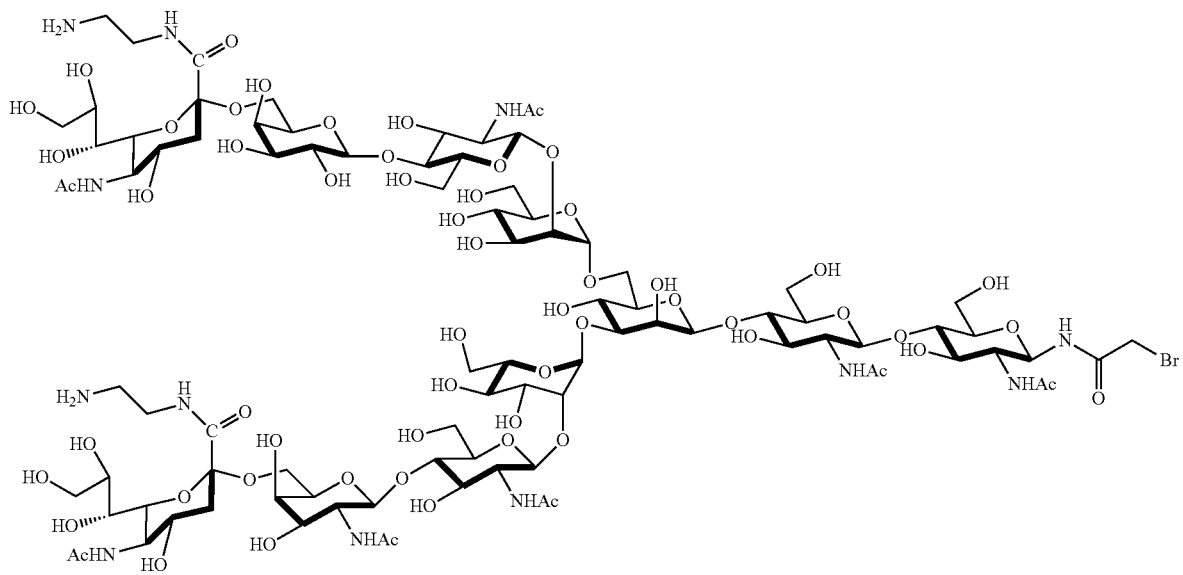

(S)

ESI-MS: (m/z) calcd for $C_{90}H_{152}BrN_{11}O_{60}$: $[M+2H]^{2+}$ 1215.1, $[M+3H]^{3+}$ 810.4. found 1214.9, 810.3.

67-3 Glycosylation of Thiol

Peptide 155 obtained in the method described in the above 67-1 (20.6 mg, 5.89 μmol) and compound s obtained in the method described in the above 67-2 (28.6 mg, 11.8 μmol) were dissolved in 33 mM phosphate buffer (pH 7.4, 1.8 mL), and reacted at room temperature for 30 minutes. The reaction solution was purified with HPLC [column: SHISEIDO CAPCELL PAK C18 UG-120 (5 μm), φ20×250 mm, flow rate: 7.0 mL/min, eluent A: 0.1% aqueous TFA, B: 0.09% TFA/10% water/90% acetonitrile, gradient A:B=74:26→64:36, 20 minutes, linear gradient elution] to obtain glycopeptide 156 (SEQ ID NO. 160) represented by the following formula (156) (17.1 mg, 2.93 μmol, yield 50%).

[Chemical Formula 192]

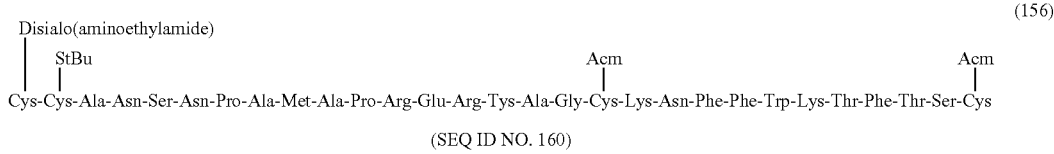

(156)

(SEQ ID NO. 160)

ESI-MS: (m/z) calcd for $C_{240}H_{383}N_{55}O_{101}S_6$: $[M+3H]^{3+}$ 1950.1, $[M+4H]^{4+}$ 1462.8, $[M+5H]^{5+}$ 1170.5, $[M+6H]^{6+}$ 975.6. found 1949.9, 1462.6, 1170.3, 975.4.

67-4 Deprotection of StBu Group

To glycopeptide 156 obtained in the method described in the above 67-3 (17.1 mg, 2.93 μmol) was added DTT (52.9 mg, 343 μmol) dissolved in 0.1 M phosphate buffer (pH 7.4, 3.4 mL), and reacted at room temperature for 3 hours. The reaction solution was purified with HPLC [column: SHISEIDO CAPCELL PAK C18 UG-120 (5 μm), φ20×250 mm, flow rate: 7.0 mL/min, eluent A: 0.1% aqueous TFA, B: 0.09% TFA/10% water/90% acetonitrile, gradient A:B=95:5→75:25, 20 minutes, linear gradient elution] to obtain glycopeptide 157 (SEQ ID NO. 161) represented by the following formula (157) (8.6 mg, 1.5 μmol, yield 51%).

[Chemical Formula 193]

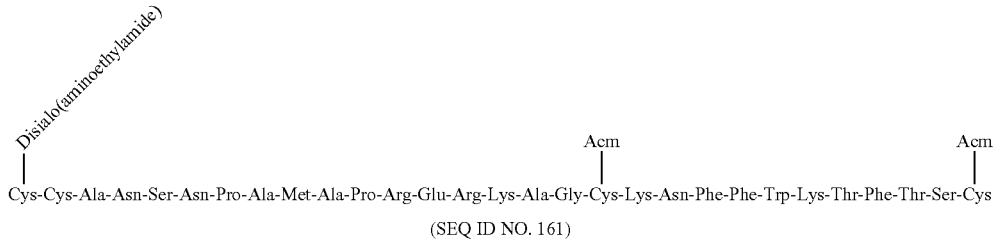

(157)

(SEQ ID NO. 161)

ESI-MS: (m/z) calcd for $C_{236}H_{375}N_{55}O_{111}S_5$: $[M+3H]^{3+}$ 1920.7, $[M+4H]^{4+}$ 1440.8, $[M+5H]^{5+}$ 1152.8, $[M+6H]^{6+}$ 960.9, $[M+7H]^{7+}$ 823.7. found 1920.5, 1440.6, 1152.7, 960.6, 823.6.

67-5 Glycosylation Reaction of Thiol

Peptide 157 obtained in the method described in the above 67-4 (6.2 mg, 1.1 μmol) and compound a (3.8 mg, 1.6 μmol) were dissolved in 0.36 M phosphate buffer (pH 7.4, 339 mL) containing 1.6 mM DTT, and reacted at room temperature for 2.5 hours The reaction solution was purified with HPLC [column: SHISEIDO CAPCELL PAK C18 UG-120 (5 μm), φ20×250 mm, flow rate: 7.0 mL/min, eluent A: 0.1% aqueous AcOH, B: 0.09% AcOH/10% water/90% acetonitrile, gradient A:B=90:10→75:25, 30 minutes, linear gradient elution] to obtain glycopeptide 158 (SEQ ID NO. 162) represented by the following formula (158) (6.4 mg, 0.80 μmol, yield 73%).

[Chemical Formula 194]

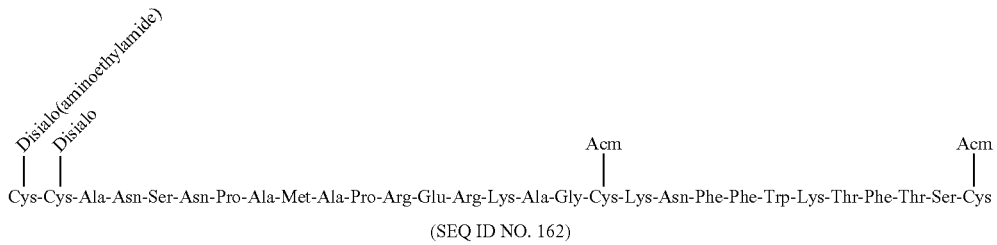

(158)

(SEQ ID NO. 162)

ESI-MS: (m/z) calcd for $C_{322}H_{514}N_{62}O_{163}S_5$: $[M+4H]^{4+}$ 2006.5, $[M+5H]^{5+}$ 1605.4, $[M+6H]^{6+}$ 1338.0. found 2006.6, 1605.3, 1338.0.

67-6 Deprotection of Acm Group

To glycopeptide 158 obtained in the method described in the above 67-5 (8.2 mg, 1.0 μmol) was added an aqueous solution (225 μL) of silver(I) acetate (2.1 mg, 13 μmol), and reacted at room temperature for 1 hour. DTT (4.8 mg, 31 μmol) dissolved in 100 mM phosphate buffer (pH 7.4, 204 μL) and 100 mM ascorbic acid aqueous solution (51 μL) were added, and this was promptly filtered with a filter. The filtrate was purified with HPLC [column: SHISEIDO CAPCELL PAK C18 UG-120 (5 μm), φ20×250 mm, flow rate: 7.0 mL/min, eluent A: 0.1% aqueous AcOH, B: 0.09% AcOH/10% water/90% acetonitrile, gradient A:B=90:10→75:25, 30 minutes, linear gradient elution] to obtain glycopeptide 159 (SEQ ID NO. 163) represented by the following formula (159) (5.5 mg, 0.70 μmol, yield 70%).

[Chemical Formula 195]

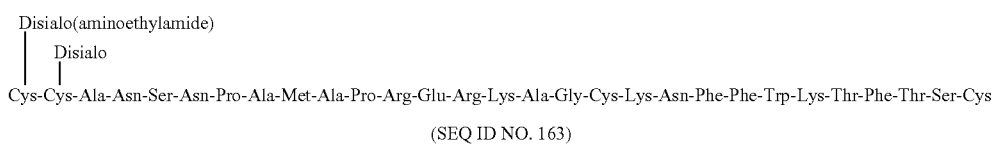

(SEQ ID NO. 163)

ESI-MS: (m/z) calcd for $C_{316}H_{504}N_{60}O_{161}S_5$: $[M+4H]^{4+}$ 1971.0, $[M+5H]^{5+}$ 1577.0, $[M+6H]^{6+}$ 1314.3. found 1970.6, 1576.8, 1314.2.

67-7 Formation of Disulfide Bond

Glycopeptide 159 obtained in the method described in the above 67-6 (5.4 mg, 0.69 μmol) was dissolved in 100 mM Tris-HCl buffer (pH 8.0)-DMSO (1/1, v/v, 1.7 mL), and reacted overnight at room temperature. The reaction solution was purified with HPLC [column: SHISEIDO CAPCELL PAK C18 UG-120 (5 μm), φ20×250 mm, flow rate: 7.0 mL/min, eluent A: 0.1% aqueous TFA, B: 0.09% TFA/10% water/90% acetonitrile, gradient A:B=75:25→65:35, 30 minutes, linear gradient elution] to obtain a fraction containing compound (C(disialo(aminoethylamide))/S1C(disialo)-SRIF28) represented by the following formula 160 (SEQ ID NO. 164).

This fraction was further purified with HPLC [column: SHISEIDO CAPCELL PAK C18 UG-120 (5 μm), φ20×250 mm, flow rate: 7.0 mL/min, eluent A: 0.1% aqueous AcOH, B: 0.09% AcOH/10% water/90% acetonitrile, gradient A:B=90:10→75:25, minutes, linear gradient elution] to obtain C(disialo(aminoethylamide))/S1C(disialo)-SRIF28 (3.1 mg, 0.40 μmol, yield 58%).

ESI-MS: calcd for $C_{316}H_{502}N_{60}O_{161}S_5$: $[M+4H]^{4+}$ 1970.5, $[M+5H]^{5+}$ 1576.6, $[M+6H]^{6+}$ 1314.0, $[M+7H]^{7+}$ 1126.4, $[M+8H]^{8+}$ 985.8, $[M+9H]^{9+}$ 876.3. found 1970.3, 1576.4, 1313.9, 1126.4, 985.5, 876.1.

Example 68 Synthesis of S1-4C(Disialo)-SRIF28

68-1 Synthesis of Peptide 2-chlorotrityl chloride resin (100 μmol) was taken in a column for solid phase synthesis, and after washing with DMF and dichloromethane, a solution of Fmoc-Cys(Acm)-OH (49.7 mg, 120 μmol) and DIPEA (104.5 μL, 600 μmol) in dichloromethane (3.0 mL) was added, and this was shaken for 1 hour. After washing with dichloromethane and DMF, the Fmoc protecting group was removed by treating with 20% piperidine in DMF. After washing with DMF, in a peptide solid phase synthesis method with Fmoc strategy employing a Prelude™ peptide synthesizer, a protected peptide 161 (SEQ ID NO. 165) represented by the following

[Chemical Formula 196]

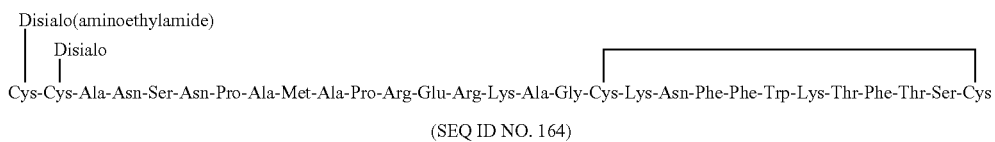

(SEQ ID NO. 164)

formula (161) was synthesized in a state bound to the resin. The condensation reaction was performed in DMF using HCTU as the condensation agent.

[Chemical Formula 197]

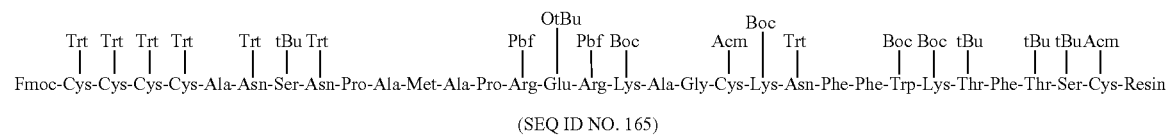

(SEQ ID NO. 165)

The Fmoc protecting group was removed by treating with 20% piperidine in DMF. After washing with DMF and dichloromethane, TFA:water:triisopropylsilane:ethanedithiol (=90:2.5:5:2.5) was added, and this was shaken at room temperature for 3 hours. The resin was filtered off, cold diethyl ether was added to the filtrate, and crude peptide was obtained as precipitate. The crude peptide was purified with HPLC [column: SHISEIDO CAPCELL PAK C18 UG-120 (5 μm), φ50×250 mm, flow rate: 43.7 mL/min, eluent A: 0.1% aqueous TFA, B: 0.09% TFA/10% water/90% acetonitrile, gradient A:B=75:25→65:35, 20 minutes, linear gradient elution] to obtain peptide 162 (SEQ ID NO. 166) represented by the following formula (162) (127.2 mg).

[Chemical Formula 198]

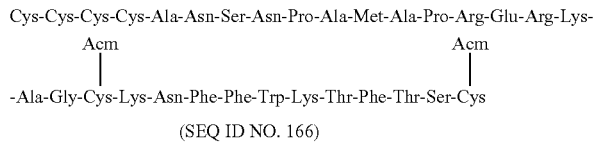

(SEQ ID NO. 166)

ESI-MS: (m/z) calcd for $C_{152}H_{234}N_{46}O_{43}S_7$: $[M+3H]^3$ 1207.1, $[M+4H]^{4+}$ 905.6, $[M+5H]^{5+}$ 724.6. found 1206.9, 905.1, 724.5.

68-2 Glycosylation Reaction of Thiol

Peptide 162 obtained in the method described in the above 68-1 (30.4 mg, 8.40 μmol) and compound a (128 mg, 54.7 μmol) were dissolved in 33 mM phosphate buffer (pH 7.4, 2.5 mL), and reacted overnight at room temperature. The reaction solution was purified with HPLC [column: SHISEIDO Proteonavi (5 μm), φ20×250 mm, flow rate: 7.0 mL/min, eluent A: 0.1% aqueous AcOH, B: 0.09% AcOH/10% water/90% acetonitrile, gradient A:B=82:18→71:29, 20 minutes, linear gradient elution] to obtain glycopeptide 163 (SEQ ID NO. 167) represented by the following formula (163) (30.9 mg, 2.44 μmol, yield 29%).

ESI-MS: (m/z) calcd for $C_{496}H_{790}N_{74}O_{291}S_7$: $[M+6H]^{6+}$ 2112.7, $[M+7H]^{7+}$ 1811.1. found 2112.8, 1811.0.

[Chemical Formula 199]

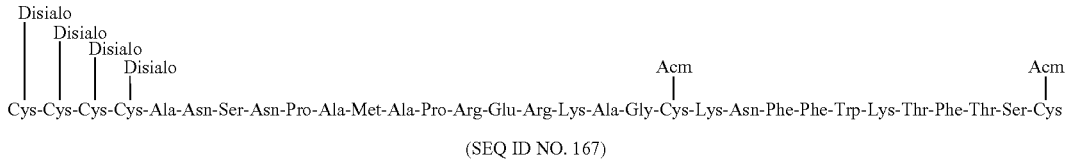

(SEQ ID NO. 167)

68-3 Deprotection of Acm Group

To glycopeptide 163 obtained in the method described in the above 68-2 (30.9 mg, 2.44 μmol) was added an aqueous solution (0.98 mL) of silver(I) acetate (5.0 mg, 30 μmol), and reacted at room temperature for 20 minutes. Then, DTT (11.8 mg, 76.5 μmol) dissolved in 200 mM Tris-HCl buffer (pH 7.4, 0.98 mL) and 100 mM ascorbic acid aqueous solution (244 μL) were added, and this was promptly filtered with a filter. The filtrate was purified with HPLC [column: SHISEIDO Proteonavi (5 μm), φ20×250 mm, flow rate: 7.0 mL/min, eluent A: 0.1% aqueous AcOH, B: 0.09% AcOH/10% water/90% acetonitrile, gradient A:B=82:18→70:30, 20 minutes, linear gradient elution] to obtain glycopeptide 164 (SEQ ID NO. 168) represented by the following formula (164) (20.6 mg, 1.64 μmol, yield 67%).

[Chemical Formula 200]

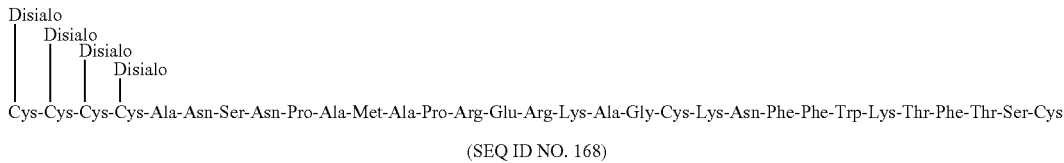

(SEQ ID NO. 168)

ESI-MS: (m/z) calcd for $C_{490}H_{780}N_{72}O_{289}S_7$: $[M+5H]^{5+}$ 2506.6, $[M+6H]^{6+}$ 2089.0, $[M+7H]^{7+}$ 1790.7. found 2506.5, 2088.8, 1790.4.

68-4 Formation of Disulfide Bond

Glycopeptide 164 obtained in the method described in the above 68-3 (20.6 mg, 1.64 μmol) was dissolved in 100 mM Tris-HCl buffer (pH 8.0)-DMSO (1/1, v/v, 2.1 mL), and reacted at room temperature for 2 days. Then, the reaction solution was purified with HPLC [column: SHISEIDO Proteonavi (5 μm), ϕ20×250 mm, flow rate: 7.0 mL/min, eluent A: 10 mM ammonium acetate aqueous solution, B: 10 mM ammonium acetate-acetonitrile (1/9, v/v), gradient A:B=75:25→72:28, 15 minutes, linear gradient elution] to obtain S1-4C(disialo)-SRIF28 (SEQ ID NO. 169) represented by the following formula (165) (11.6 mg, 0.93 μmol, yield 57%).

[Chemical Formula 201]

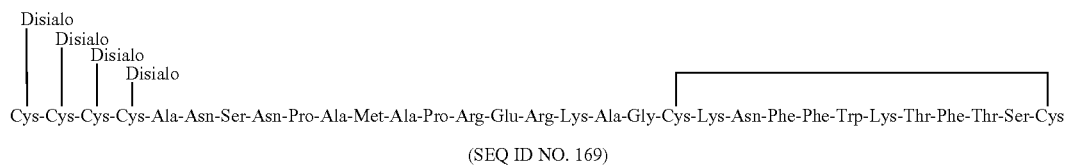

(165)

(SEQ ID NO. 169)

ESI-MS: (m/z) calcd for $C_{490}H_{778}N_{72}O_{289}S_7$: $[M+5H]^{5+}$ 2506.2, $[M+6H]^{6+}$ 2088.7, $[M+7H]^{7+}$ 1790.5. found 2506.1, 2088.6, 1790.4.

Tables 1-1 to 1-7 show the MS spectrum data (ESI-MS) of the glycosylated SRIF peptides obtained in the methods described in Examples 1-68. The molecular mass was obtained by performing deconvolution of polyvalent protein mass spectrometry with MassLynx version 4.1 (from Waters).

TABLE 1-1

| Example | Compound | Calculated molecular weight | Observed ions (m/z) | | Observed molecular weight |
|---|---|---|---|---|---|
| 1 | S1C(disialo)-SRIF28 | 5427.7 | $[M+3H]^{3+}$ | 1810.0 | 5427.0 |
| | | | $[M+4H]^{4+}$ | 1357.5 | |
| | | | $[M+5H]^{5+}$ | 1086.4 | |
| 2 | N5C(disialo)-SRIF28 | 5400.6 | $[M+3H]^{3+}$ | 1801.0 | 5400.1 |
| | | | $[M+4H]^{4+}$ | 1350.8 | |
| | | | $[M+5H]^{5+}$ | 1081.2 | |
| 3 | A9C(disialo)-SRIF28 | 5443.7 | $[M+3H]^{3+}$ | 1815.4 | 5443.1 |
| | | | $[M+4H]^{4+}$ | 1361.8 | |
| | | | $[M+5H]^{5+}$ | 1089.6 | |
| 4 | E12C(disialo)-SRIF28 | 5385.6 | $[M+3H]^{3+}$ | 1796.0 | 5384.0 |
| | | | $[M+4H]^{4+}$ | 1347.0 | |
| | | | $[M+5H]^{5+}$ | 1078.0 | |
| 5 | R13C(disialo)-SRIF28 | 5358.6 | $[M+3H]^{3+}$ | 1787.0 | 5358.0 |
| | | | $[M+4H]^{4+}$ | 1340.5 | |
| | | | $[M+5H]^{5+}$ | 1072.6 | |
| 6 | K14C(disialo)-SRIF28 | 6386.6 | $[M+3H]^{3+}$ | 1796.4 | 5386.0 |
| | | | $[M+4H]^{4+}$ | 1347.5 | |
| | | | $[M+5H]^{5+}$ | 1078.2 | |
| 7 | A15C(disialo)-SRIF28 | 5443.7 | $[M+3H]^{3+}$ | 1815.4 | 5443.1 |
| | | | $[M+4H]^{4+}$ | 1361.8 | |
| | | | $[M+5H]^{5+}$ | 1089.6 | |
| 8 | G16C(disialo)-SRIF28 | 5457.7 | $[M+3H]^{3+}$ | 1820.0 | 5457.1 |
| | | | $[M+4H]^{4+}$ | 1365.3 | |
| | | | $[M+5H]^{5+}$ | 1092.2 | |
| 9 | K18C(disialo)-SRIF28 | 5386.6 | $[M+3H]^{3+}$ | 1796.4 | 5386.1 |
| | | | $[M+4H]^{4+}$ | 1347.5 | |
| | | | $[M+5H]^{5+}$ | 1078.2 | |

TABLE 1-1-continued

| Example | Compound | Calculated molecular weight | Observed ions (m/z) | | Observed molecular weight |
|---|---|---|---|---|---|
| | | | $[M+6H]^{6+}$ | 898.7 | |
| | | | $[M+7H]^{7+}$ | 770.5 | |

TABLE 1-2

| Example | Compound | Calculated molecular weight | Observed ions (m/z) | | Observed molecular weight |
|---|---|---|---|---|---|
| 10 | N19C(disialo)-SRIF28 | 5400.6 | $[M+3H]^{3+}$ | 1801.0 | 5400.1 |
| | | | $[M+4H]^{4+}$ | 1351.0 | |
| | | | $[M+5H]^{5+}$ | 1080.8 | |

TABLE 1-2-continued

| Example | Compound | Calculated molecular weight | Observed ions (m/z) | | Observed molecular weight |
|---|---|---|---|---|---|
| 11 | F21C(disialo)-SRIF28 | 5367.6 | $[M+3H]^{3+}$ | 1790.0 | 5366.9 |
| | | | $[M+4H]^{4+}$ | 1342.7 | |
| | | | $[M+5H]^{5+}$ | 1074.4 | |
| 12 | T26C(disialo)-SRIF28 | 5413.6 | $[M+3H]^{3+}$ | 1354.3 | 5412.1 |
| | | | $[M+4H]^{4+}$ | 1083.4 | |
| | | | $[M+5H]^{5+}$ | 903.0 | |
| | | | $[M+6H]^{6+}$ | 774.3 | |
| 13 | 29C(disialo)-SRIF28 | 5514.7 | $[M+3H]^{3+}$ | 1839.1 | 5514.1 |
| | | | $[M+4H]^{4+}$ | 1379.5 | |
| | | | $[M+5H]^{5+}$ | 1103.8 | |
| 14 | 30C(disialo)-SRIF28 | 5615.8 | $[M+3H]^{3+}$ | 1872.7 | 5615.1 |
| | | | $[M+4H]^{4+}$ | 1404.8 | |
| | | | $[M+5H]^{5+}$ | 1124.0 | |
| 15 | S1C(disialo)-D-Trp22-SRIF28 | 5427.7 | $[M+3H]^{3+}$ | 1810.1 | 5427.2 |
| | | | $[M+4H]^{4+}$ | 1357.8 | |
| | | | $[M+5H]^{5+}$ | 1086.4 | |
| | | | $[M+6H]^{6+}$ | 905.5 | |
| 16 | A9C(disialo)-D-Trp22-SRIF28 | 5443.7 | $[M+3H]^{3+}$ | 1815.4 | 5442.9 |
| | | | $[M+4H]^{4+}$ | 1361.8 | |
| | | | $[M+5H]^{5+}$ | 1089.6 | |
| 17 | C(disialo)-SRIF14 | 4004.1 | $[M+2H]^{2+}$ | 2002.9 | 4003.3 |
| | | | $[M+3H]^{3+}$ | 1335.4 | |
| | | | $[M+4H]^{4+}$ | 1001.8 | |
| 18 | C(disialo)-R-K-SRIF14 | 4288.4 | $[M+3H]^{3+}$ | 1430.2 | 4287.5 |
| | | | $[M+4H]^{4+}$ | 1072.9 | |
| 19 | C(disialo)-C12linker-SRIF14 | 4201.4 | $[M+3H]^{3+}$ | 1401.2 | 4200.5 |
| | | | $[M+4H]^{4+}$ | 1051.2 | |
| | | | $[M+5H]^{5+}$ | 841.1 | |

TABLE 1-3

| Example | Compound | Calculated molecular weight | Observed ions (m/z) | | Observed molecular weight |
|---|---|---|---|---|---|
| 20 | S1-2C(disialo)-SRIF28 | 7793.8 | [M + 4H]$^{4+}$ | 1949.4 | 7793.4 |
|  |  |  | [M + 5H]$^{5+}$ | 1559.7 |  |
|  |  |  | [M + 6H]$^{6+}$ | 1299.9 |  |
| 21 | S1C(disialo)-N5C(disialo)-SRIF28 | 7679.7 | [M + 3H]$^{3+}$ | 1920.4 | 7678.7 |
|  |  |  | [M + 4H]$^{4+}$ | 1536.8 |  |
|  |  |  | [M + 5H]$^{5+}$ | 1280.9 |  |
| 22 | S1C(disialo)-R13C(disialo)-SRIF28 | 7637.7 | [M + 3H]$^{3+}$ | 1910.2 | 7636.6 |
|  |  |  | [M + 4H]$^{4+}$ | 1528.3 |  |
|  |  |  | [M + 5H]$^{5+}$ | 1273.8 |  |
| 23 | N5C(disialo)-A9C(disialo)-SRIF28 | 7695.7 | [M + 5H]$^{5+}$ | 1540.1 | 7695.2 |
|  |  |  | [M + 6H]$^{6+}$ | 1283.6 |  |
|  |  |  | [M + 7H]$^{7+}$ | 1100.3 |  |
|  |  |  | [M + 8H]$^{8+}$ | 962.9 |  |
| 24 | S1-3C(disialo)-SRIF28 | 10160.0 | [M + 3H]$^{3+}$ | 3387.6 | 10158.2 |
|  |  |  | [M + 4H]$^{4+}$ | 2540.9 |  |
|  |  |  | [M + 5H]$^{5+}$ | 2032.7 |  |
|  |  |  | [M + 6H]$^{6+}$ | 1694.2 |  |
|  |  |  | [M + 7H]$^{7+}$ | 1452.3 |  |
| 25 | S1C(disialo)-N5C(disialo)-A9C(disialo)-SRIF28 | 9974.8 | [M + 5H]$^{5+}$ | 1995.9 | 9974.3 |
|  |  |  | [M + 6H]$^{6+}$ | 1663.2 |  |
| 26 | S1C(monosialo)-SRIF28 | 5136.4 | [M + 3H]$^{3+}$ | 1713.0 | 5134.9 |
|  |  |  | [M + 4H]$^{4+}$ | 1284.7 |  |
|  |  |  | [M + 5H]$^{5+}$ | 1028.2 |  |
|  |  |  | [M + 6H]$^{6+}$ | 856.8 |  |

TABLE 1-4

| Example | Compound | Calculated molecular weight | Observed ions (m/z) | | Observed molecular weight |
|---|---|---|---|---|---|
| 27 | S1C(asialo)-SRIF28 | 4845.1 | [M + 3H]$^{3+}$ | 2615.7 | 4843.9 |
|  |  |  | [M + 4H]$^{4+}$ | 1212.0 |  |
|  |  |  | [M + 5H]$^{5+}$ | 969.8 |  |
| 28 | S1-2C(asialo)-SRIF28 | 6628.8 | [M + 4H]$^{4+}$ | 1658.1 | 6627.2 |
|  |  |  | [M + 5H]$^{5+}$ | 1326.7 |  |
|  |  |  | [M + 6H]$^{6+}$ | 1105.6 |  |
|  |  |  | [M + 7H]$^{7+}$ | 947.8 |  |
|  |  |  | [M + 8H]$^{8+}$ | 829.4 |  |
| 29 | S1-3C(asialo)-SRIF28 | 8412.5 | [M + 4H]$^{4+}$ | 2103.7 | 8411.7 |
|  |  |  | [M + 5H]$^{5+}$ | 1683.3 |  |
|  |  |  | [M + 6H]$^{6+}$ | 1403.0 |  |
| 30 | N5N(disialo)-SRIF28 | 5354.5 | [M + 3H]$^{3+}$ | 1785.9 | 5354.0 |
|  |  |  | [M + 4H]$^{4+}$ | 1339.5 |  |
|  |  |  | [M + 5H]$^{5+}$ | 1071.8 |  |
| 31 | S1N(disialo)-SRIF28 | 5381.6 | [M + 3H]$^{3+}$ | 1794.7 | 5380.9 |
|  |  |  | [M + 4H]$^{4+}$ | 1346.2 |  |
|  |  |  | [M + 5H]$^{5+}$ | 1077.2 |  |
| 32 | S1C(disialo)-N19C(GlcNAc)-SRIF28 | 5676.9 | [M + 3H]$^{3+}$ | 1893.5 | 5676.4 |
|  |  |  | [M + 4H]$^{4+}$ | 1420.1 |  |
|  |  |  | [M + 5H]$^{5+}$ | 1136.3 |  |
| 33 | S1C(disialo)-N19C(diMan)-SRIF28 | 6366.6 | [M + 3H]$^{3+}$ | 2122.9 | 6366.7 |
|  |  |  | [M + 4H]$^{4+}$ | 1592.5 |  |
|  |  |  | [M + 5H]$^{5+}$ | 1274.4 |  |
| 34 | S1-5C(disialo)-SRIF28 | 14892.4 | [M + 4H]$^{4+}$ | 3723.7 | 14891.3 |
|  |  |  | [M + 5H]$^{5+}$ | 2979.1 |  |
|  |  |  | [M + 6H]$^{6+}$ | 2482.9 |  |
|  |  |  | [M + 7H]$^{7+}$ | 2128.2 |  |
|  |  |  | [M + 8H]$^{8+}$ | 1862.4 |  |
| 35 | S1-10C(disialo)-SRIF28 | 26723.2 | [M + 7H]$^{7+}$ | 3818.3 | 26721.8 |
|  |  |  | [M + 8H]$^{8+}$ | 3341.0 |  |
|  |  |  | [M + 9H]$^{9+}$ | 2970.1 |  |
|  |  |  | [M + 10H]$^{10+}$ | 2673.1 |  |

TABLE 1-5

| Example | Compound | Calculated molecular weight | Observed ions (m/z) | | Observed molecular weight |
|---|---|---|---|---|---|
| 36 | C(disialo)-SRIF28 | 5514.7 | $[M + 4H]^{4+}$ | 1379.7 | 5514.6 |
| | | | $[M + 5H]^{5+}$ | 1103.9 | |
| | | | $[M + 6H]^{6+}$ | 920.1 | |
| | | | $[M + 7H]^{7+}$ | 788.8 | |
| 37 | R11C(disialo)-SRIF28 | 5358.5 | $[M + 3H]^{3+}$ | 1787.4 | 5358.6 |
| | | | $[M + 4H]^{4+}$ | 1340.7 | |
| | | | $[M + 5H]^{5+}$ | 1072.7 | |
| 38 | F20C(disialo)-SRIF28 | 5367.6 | $[M + 3H]^{3+}$ | 1790.1 | 5367.1 |
| | | | $[M + 4H]^{4+}$ | 1342.8 | |
| | | | $[M + 5H]^{5+}$ | 1074.4 | |
| 39 | T24C(disialo)-SRIF28 | 5413.6 | $[M + 3H]^{3+}$ | 1805.7 | 5412.6 |
| | | | $[M + 4H]^{4+}$ | 1354.2 | |
| | | | $[M + 5H]^{5+}$ | 1083.7 | |
| 40 | F25C(disialo)-SRIF28 | 5367.6 | $[M + 3H]^{3+}$ | 1790.1 | 5367.1 |
| | | | $[M + 4H]^{4+}$ | 1342.8 | |
| | | | $[M + 5H]^{5+}$ | 1074.4 | |
| | | | $[M + 6H]^{6+}$ | 895.4 | |
| 41 | S27C(disialo)-SRIF28 | 5427.7 | $[M + 3H]^{3+}$ | 1810.1 | 5427.4 |
| | | | $[M + 4H]^{4+}$ | 1357.8 | |
| 42 | C(disialo)-K-SRIF14 | 4131.2 | $[M + 2H]^{2+}$ | 2066.9 | 4131.7 |
| | | | $[M + 3H]^{3+}$ | 1378.2 | |
| | | | $[M + 4H]^{4+}$ | 1033.9 | |
| 43 | S1C(disialo)-F25Y-SRIF28 | 5443.7 | $[M + 3H]^{3+}$ | 1815.4 | 5443.1 |
| | | | $[M + 4H]^{4+}$ | 1361.6 | |
| | | | $[M + 5H]^{5+}$ | 1089.6 | |
| 44 | S1C(disialo)-SRIF28-amide | 5426.7 | $[M + 3H]^{3+}$ | 1809.8 | 5426.2 |
| | | | $[M + 4H]^{4+}$ | 1357.6 | |
| | | | $[M + 5H]^{5+}$ | 1086.2 | |
| | | | $[M + 6H]^{6+}$ | 905.2 | |
| 45 | C(disialo)-PEGlinker-SRIF14 | 4207.3 | $[M + 3H]^{3+}$ | 1403.2 | 4206.6 |
| | | | $[M + 4H]^{4+}$ | 1052.7 | |
| | | | $[M + 5H]^{5+}$ | 842.3 | |
| 46 | Biotin-S1C(disialo)-SRIF28 | 5654.0 | $[M + 3H]^{3+}$ | 1885.4 | 5653.2 |
| | | | $[M + 4H]^{4+}$ | 1414.3 | |
| | | | $[M + 5H]^{5+}$ | 1131.7 | |
| | | | $[M + 6H]^{6+}$ | 943.2 | |
| 47 | Biotin-PEGlinker-S1C(disialo)-SRIF28 | 5857.2 | $[M + 3H]^{3+}$ | 1953.2 | 5856.4 |
| | | | $[M + 4H]^{4+}$ | 1465.1 | |
| | | | $[M + 5H]^{5+}$ | 1172.1 | |
| | | | $[M + 6H]^{6+}$ | 977.1 | |
| | | | $[M + 7H]^{7+}$ | 837.6 | |

TABLE 1-6

| Example | Compound | Calculated molecular weight | Observed ions (m/z) | | Observed molecular weight |
|---|---|---|---|---|---|
| 48 | Azido-S1C(disialo)-SRIF28 | 5552.8 | $[M + 3H]^{3+}$ | 1851.8 | 5552.3 |
| | | | $[M + 4H]^{4+}$ | 1389.1 | |
| | | | $[M + 5H]^{5+}$ | 1111.7 | |
| 49 | S1C(disialo)-E12C(disialo)-SRIF28 | 7664.7 | $[M + 4H]^{4+}$ | 1917.1 | 7664.1 |
| | | | $[M + 5H]^{5+}$ | 1533.8 | |
| | | | $[M + 6H]^{6+}$ | 1278.4 | |
| 50 | 2C(disialo)-R-K-SRIF14 | 6654.6 | $[M + 3H]^{3+}$ | 2219.2 | 6653.4 |
| | | | $[M + 4H]^{4+}$ | 1664.4 | |
| | | | $[M + 5H]^{5+}$ | 1331.9 | |
| | | | $[M + 6H]^{6+}$ | 1109.9 | |
| 51 | 3C(disialo)-R-K-SRIF14 | 9020.8 | $[M + 4H]^{4+}$ | 2256.1 | 9020.2 |
| | | | $[M + 5H]^{5+}$ | 1805.1 | |
| | | | $[M + 6H]^{6+}$ | 1504.4 | |
| 52 | S1C(diGlcNAc)-SRIF28 | 4520.9 | $[M + 3H]^{3+}$ | 1507.7 | 4519.9 |
| | | | $[M + 4H]^{4+}$ | 1131.0 | |
| | | | $[M + 5H]^{5+}$ | 905.0 | |
| 53 | S1C(diMan)-SRIF28 | 4114.5 | $[M + 3H]^{3+}$ | 1372.3 | 4113.8 |
| | | | $[M + 4H]^{4+}$ | 1029.5 | |
| | | | $[M + 5H]^{5+}$ | 823.8 | |
| 54 | N19C(diMan)-SRIF28 | 4087.5 | $[M + 3H]^{3+}$ | 1363.3 | 4086.8 |
| | | | $[M + 4H]^{4+}$ | 1023.0 | |
| 55 | S1C(GlcNAc)-SRIF28 | 3424.9 | $[M + 2H]^{2+}$ | 1713.3 | 3424.5 |
| | | | $[M + 3H]^{3+}$ | 1142.5 | |
| | | | $[M + 4H]^{4+}$ | 856.9 | |
| | | | $[M + 5H]^{5+}$ | 686.1 | |
| 56 | N19C(GlcNAc)-SRIF28 | 3397.8 | $[M + 2H]^{2+}$ | 1699.8 | 3397.5 |
| | | | $[M + 3H]^{3+}$ | 1133.5 | |
| | | | $[M + 4H]^{4+}$ | 850.4 | |
| 57 | S1C(trisialo)-SRIF28 | 6084.2 | $[M + 3H]^{3+}$ | 2028.8 | 6083.4 |
| | | | $[M + 4H]^{4+}$ | 1521.9 | |
| | | | $[M + 5H]^{5+}$ | 1217.7 | |
| | | | $[M + 6H]^{6+}$ | 1014.9 | |
| 58 | S1C(tetrasialo)-SRIF28 | 6740.8 | $[M + 3H]^{3+}$ | 2247.7 | 6739.6 |
| | | | $[M + 4H]^{4+}$ | 1685.9 | |
| | | | $[M + 5H]^{5+}$ | 1349.1 | |
| | | | $[M + 6H]^{6+}$ | 1124.3 | |
| | | | $[M + 7H]^{7+}$ | 963.8 | |
| 59 | S1C(disialo(aminoethylamide))-SRIF28 | 5511.8 | $[M + 3H]^{3+}$ | 1838.0 | 5511.1 |
| | | | $[M + 4H]^{4+}$ | 1378.5 | |
| | | | $[M + 5H]^{5+}$ | 1103.2 | |
| | | | $[M + 6H]^{6+}$ | 919.5 | |
| | | | $[M + 7H]^{7+}$ | 788.2 | |

TABLE 1-7

| Example | Compound | Calculated molecular weight | Observed ions (m/z) | | Observed molecular weight |
|---|---|---|---|---|---|
| 60 | S1C(disialo(amide))-SRIF28 | 5425.7 | $[M + 3H]^{3+}$ | 1809.3 | 5423.9 |
| | | | $[M + 4H]^{4+}$ | 1357.0 | |
| | | | $[M + 5H]^{5+}$ | 1085.8 | |
| | | | $[M + 6H]^{6+}$ | 905.2 | |
| 61 | S1C(disialo(Bn))-SRIF28 | 5607.9 | $[M + 3H]^{3+}$ | 1870.0 | 5605.9 |
| | | | $[M + 4H]^{4+}$ | 1402.5 | |
| | | | $[M + 5H]^{5+}$ | 1122.2 | |
| | | | $[M + 6H]^{6+}$ | 935.5 | |
| 62 | S1C(disialo(hexadecylamide))-SRIF28 | 5874.5 | $[M + 3H]^{3+}$ | 1958.9 | 5873.6 |
| | | | $[M + 4H]^{4+}$ | 1469.4 | |
| | | | $[M + 5H]^{5+}$ | 1175.7 | |
| | | | $[M + 6H]^{6+}$ | 979.9 | |
| 63 | S1-2C(disialo(amide))-SRIF28 | 7789.9 | $[M + 4H]^{4+}$ | 1948.2 | 7789.9 |
| | | | $[M + 5H]^{5+}$ | 1559.0 | |
| | | | $[M + 6H]^{6+}$ | 1299.2 | |
| 64 | S1-2C(disialo(Bn))-SRIF28 | 8154.3 | $[M + 4H]^{4+}$ | 2039.3 | 8153.0 |
| | | | $[M + 5H]^{5+}$ | 1631.6 | |
| | | | $[M + 6H]^{6+}$ | 1360.2 | |
| 65 | S1C(Asn(disialo))-SRIF28 | 5542.7 | $[M + 3H]^{3+}$ | 1848.4 | 5542.2 |
| | | | $[M + 4H]^{4+}$ | 1386.6 | |
| | | | $[M + 5H]^{5+}$ | 1109.4 | |
| | | | $[M + 6H]^{6+}$ | 924.9 | |
| 66 | S1N(disialo)-N19C(diMan)-SRIF28 | 6320.5 | $[M + 3H]^{3+}$ | 2107.9 | 6319.5 |
| | | | $[M + 4H]^{4+}$ | 1580.9 | |
| | | | $[M + 5H]^{5+}$ | 1265.1 | |
| 67 | C(disialo(aminoethylamide))-S1C(disialo)-SRIF28 | 7878.0 | $[M + 4H]^{4+}$ | 1970.3 | 7878.1 |
| | | | $[M + 5H]^{5+}$ | 1576.4 | |
| | | | $[M + 6H]^{6+}$ | 1313.9 | |
| | | | $[M + 7H]^{7+}$ | 1126.4 | |
| | | | $[M + 8H]^{8+}$ | 985.5 | |
| | | | $[M + 9H]^{9+}$ | 876.1 | |
| 68 | S1-4C(disialo)-SRIF28 | 12526.2 | $[M + 5H]^{5+}$ | 2506.1 | 12525.5 |
| | | | $[M + 6H]^{6+}$ | 2088.6 | |
| | | | $[M + 7H]^{7+}$ | 1790.4 | |

Example 69-1 Calculation of Receptor Binding Affinity

Competitive binding assay was performed with the method below to calculate receptor binding affinity.

Reagents employed in the competitive binding assay and their proper chemical names are as follows: HEPES (4-(2-hydroxyethyl)-1-piperazineethanesulfonic acid) and BSA (bovine serum albumin).

Competitive binding assay was consigned to Ricerca Biosciences, and experiment and data analysis was performed. The receptor subtypes and receptor membrane samples employed are shown in Table 2. Common in each binding assay, [$^{125}$I] Tyr$^{11}$-Somatostatin 14 (Tyr11-SRIF14) was used as the labeled ligand, Somatostatin-14 (SRIF14) was used as the unlabeled ligand, and 25 mM HEPES containing 5 mM MgCl$_2$, 1 mM CaCl$_2$, and 0.1% BSA, pH 7.4 was used as the buffer. The test substance was used at a concentration of 0.01 nM, 0.1 nM, 1 nM, 10 nM, 100 nM, or 1000 nM, and mixed with the membrane sample into a reaction solution. Moreover, the concentrations of the labeled and unlabeled ligands added to the reaction solution are shown in Table 2. The incubation condition of the reaction solution was at 25° C. for 4 hours for SSTR2 and at 25° C. for 2 hours for SSTR1, SSTR3, SSTR4, and SSTR5. For each experiment run, SRIF14 was used as the positive control. For data analysis, 50% inhibitory concentration (IC$_{50}$ value) was determined using MathIQ™ (ID Business Solutions, UK) in a nonlinear least squares method based on the numerical data of the binding inhibition rate. The binding inhibition constant (Ki value) was calculated by the method of Cheng, Y et al. (Biochem Pharmacol, 22, 3099-3108, 1973).

TABLE 2

| | SSTR1 | SSTR2 | SSTR3 | SSTR4 | SSTR5 |
|---|---|---|---|---|---|
| Labeled ligand | 0.1 nM | 0.03 nM | 0.1 nM | 0.1 nM | 0.1 nM |
| Unlabeled ligand | 1 μM | 1 μM | 1 μM | 1 μM | 1 μM |
| Source | Human recombinant CHO-K1 cells | Human recombinant CHO-K1 cells | Human recombinant CHO-K1 cells | Human recombinant Chem-1 cells | Human recombinant Chem-1 cells |

Compounds subjected to binding assay and the results of the binding experiment are shown in Table 3A. Moreover, octreotide, SRIF14 and SRIF28 were similarly evaluated as control compounds. Note that for octreotide, IC$_{50}$ values could not be calculated for SSTR1 and SSTR4 since the maximum concentration was 100 nM, and is thus shown as >100 nM.

FIGS. 1A and 1B show examples of the structures of glycosylated peptides (glycosylated forms) corresponding to the compound names in Table 3A.

all showing sufficient receptor binding affinity. Moreover, where the binding affinity of SRIF14 against SSTR5, was 0.326 nM, the compounds of the present invention having

TABLE 3A

| Example | | SSTR1 | | SSTR2 | | SSTR3 | | SSTR4 | | SSTR5 | |
|---|---|---|---|---|---|---|---|---|---|---|---|
| | | $IC_{50}$ (nM) | Ki (nM) | $IC_{50}$ (nM) | Ki (nM) | $IC_{50}$ (nM) | Ki (nM) | $IC_{50}$ (nM) | Ki (nM) | $IC_{50}$ (nM) | Ki (nM) |
| 1 | S1C(disialo)-SRIF28 | 2.19 | 1.81 | 0.109 | 0.0576 | 0.480 | 0.164 | 2.30 | 2.07 | 0.442 | 0.250 |
| 2 | N5C(disialo)-SRIF28 | 1.10 | 0.912 | 0.0945 | 0.0502 | 0.278 | 0.0950 | 1.30 | 1.17 | 0.458 | 0.259 |
| 3 | A9C(disialo)-SRIF28 | 2.08 | 1.72 | 0.0741 | 0.0394 | 0.593 | 0.203 | 1.72 | 1.54 | 0.473 | 0.265 |
| 4 | E12C(disialo)-SRIF28 | 1.70 | 1.40 | 0.112 | 0.0598 | 0.362 | 0.124 | 2.04 | 1.84 | 0.376 | 0.212 |
| 5 | R13C(disialo)-SRIF28 | 15.4 | 13.6 | 0.310 | 0.165 | 2.87 | 0.981 | 6.43 | 5.79 | 3.28 | 1.85 |
| 6 | K14C(disialo)-SRIF28 | 13.8 | 11.4 | 0.481 | 0.256 | 2.59 | 0.887 | 8.02 | 7.22 | 4.01 | 2.27 |
| 10 | N19C(disialo)-SRIF28 | 15.1 | 13.3 | 1.21 | 0.645 | 1.17 | 0.503 | 12.2 | 15.0 | 3.69 | 2.09 |
| 13 | 29C(disialo)-SRIF28 | 4.43 | 3.67 | 0.738 | 0.392 | 7.00 | 2.39 | 6.11 | 5.50 | 3.73 | 2.11 |
| 14 | 30C(disialo)-SRIF28 | 4.21 | 3.48 | 0.5128 | 0.275 | 6.91 | 2.36 | 2.53 | 2.28 | 1.36 | 1.05 |
| 15 | S1C(disialo)-D-Trp22-SRIF28 | 2.23 | 1.85 | 0.0324 | 0.0172 | 0.834 | 0.285 | 5.85 | 5.26 | 0.565 | 0.319 |
| 16 | A9C(disialo)-D-Trp22-SRIF28 | 6.92 | 6.73 | 0.0396 | 0.0210 | 0.256 | 0.0876 | 4.87 | 4.38 | 0.194 | 0.110 |
| 17 | C(disialo)-SRIF14 | 32.3 | 26.7 | 0.336 | 0.179 | 4.62 | 1.58 | 8.24 | 7.41 | 5.70 | 3.22 |
| 18 | C(disialo)-R-K-SRIF14 | 3.09 | 2.56 | 0.104 | 0.0551 | 0.231 | 0.0791 | 1.06 | 0.951 | 0.187 | 0.106 |
| 19 | C(disialo)-C12linker-SRIF14 | 15.5 | 12.8 | 0.502 | 0.267 | 3.12 | 1.07 | 2.92 | 7.62 | 2.29 | 1.29 |
| 20 | S1-2C(disialo)-SRIF28 | 18.8 | 15.5 | 0.338 | 0.179 | 1.28 | 0.439 | 5.61 | 5.05 | 0.607 | 0.343 |
| 21 | S1C(disialo)•N5C(disialo)-SRIF28 | 6.89 | 5.70 | 0.224 | 0.119 | 1.58 | 0.539 | 4.09 | 3.60 | 0.728 | 0.411 |
| 22 | S1C(disialo)•R13C(disialo)-SRIF28 | 177 | 147 | 6.28 | 3.33 | 11.0 | 3.77 | 45.0 | 40.5 | 14.7 | 8.33 |
| 23 | N5C(disialo)•A9C(disialo)-SRIF28 | 30.0 | 24.9 | 0.793 | 0.424 | 4.09 | 1.49 | 14.2 | 12.8 | 1.81 | 1.02 |
| 24 | S1-3C(disialo)-SRIF28 | 20.4 | 16.9 | 0.421 | 0.224 | 3.30 | 1.13 | 7.69 | 6.92 | 0.927 | 0.524 |
| 25 | S1C(disialo)•N5C(disialo)•A9C(disialo)-SRIF28 | 69.2 | 57.3 | 0.985 | 0.523 | 7.93 | 2.71 | 26.2 | 22.7 | 4.14 | 2.34 |
| 26 | S1C(monosialo)-SRIF28 | 1.43 | 1.19 | 0.0465 | 0.0247 | 0.322 | 0.110 | 1.14 | 1.03 | 0.372 | 0.210 |
| 27 | S1C(asialo)-SRIF28 | 0.851 | 0.704 | 0.0224 | 0.0119 | 0.155 | 0.0531 | 0.627 | 0.564 | 0.460 | 0.260 |
| 28 | S1-2C(asialo)-SRIF28 | 0.860 | 0.712 | 0.0632 | 0.0336 | 0.177 | 0.0604 | 0.780 | 0.702 | 0.190 | 0.107 |
| 29 | S1-3C(asialo)-SRIF28 | 4.21 | 3.49 | 0.0978 | 0.0519 | 0.581 | 0.199 | 1.44 | 1.29 | 0.369 | 0.209 |
| 30 | N5N(disialo)-SRIF28 | 3.62 | 2.50 | 0.0685 | 0.0364 | 0.579 | 0.198 | 2.86 | 2.57 | 0.465 | 0.263 |
| 31 | S1N(disialo)-SRIF28 | 2.68 | 2.21 | 0.0764 | 0.0401 | 0.314 | 0.107 | 1.07 | 0.956 | 0.272 | 0.154 |
| — | SRIF14 | 0.433 | 0.362 | 0.0142 | 0.00755 | 0.131 | 0.0450 | 0.303 | 0.273 | 0.578 | 0.326 |
| — | Octreotide | >100 | — | 0.0628 | 0.0334 | 6.41 | 2.19 | >100 | — | 9.39 | 5.31 |
| — | SRIF28 | 0.353 | 0.292 | 0.0271 | 0.0144 | 0.0368 | 0.0297 | 0.294 | 0.265 | 0.423 | 0.239 |

The control octreotide bound to each of receptors SSTR2, SSTR3, and SSTR5, and SRIF14 and SRIF28 bound to all SSTRs. As shown in Table 3A, the compounds according to the present invention potently bound to all SSTRs. The binding affinity of the positive control SRIF14 against SSTR1 in terms of Ki value was 0.362 nM, and where compounds having one sugar chain was 0.704-26.7 nM, the compounds of the present invention having two sugar chains (the compounds of Examples 20-23 and 28) were 0.712-147 nM, showing similarly sufficient receptor binding affinity. Moreover, the compounds of the present invention having three sugar chains (the compounds of Examples 24, 25, and 29) also had sufficient receptor binding affinity, showing 3.49 nM, 16.9 nM, and 57.3 nM. Since bioavailability (BA) will be considerably increased due to the extension of its half-life in blood, they can work effectively on receptors in vivo even if the Ki value of the binding affinity is somewhat high. Similarly, where the binding affinity of SRIF14 against SSTR2, SSTR3, and SSTR4 in terms of Ki value were each 0.00755 nM, 0.0450 nM, and 0.273 nM, the compounds of the present invention having two or more sugar chains were each 0.0336-3.33 nM, 0.0604-3.77 nM, and 0.702-40.5 nM, two or more sugar chains showed a sufficient receptor binding affinity of up to 8.33 nM.

In this way, it was found that Examples 20-23 and 28 are diglycosylated modified forms having affinity towards all receptors SSTR1-SSTR5, and Examples 24, 25, and 29 are triglycosylated modified forms having affinity towards all receptors SSTR1-SSTR5.

Example 69-2 Calculation of Receptor Binding Affinity—2

Competitive binding assay was performed with each compound shown in Table 3B with the method described in Example 69-1, and receptor binding affinity was calculated. Moreover, SRIF14 and SRIF28 were similarly evaluated as control compounds. The results of the binding assay are shown in Table 3B.

FIGS. 1C and 1D show examples of the structures of glycosylated peptides corresponding to the compound names in Table 3B.

TABLE 3B

| Example | | SSTR1 | | SSTR2 | | SSTR3 | |
|---|---|---|---|---|---|---|---|
| | | $IC_{50}$ (nM) | $K_i$ (nM) | $IC_{50}$ (nM) | $K_i$ (nM) | $IC_{50}$ (nM) | $K_i$ (nM) |
| 1 | S1C(disialo)-SRIF28 | 7.71 | 6.45 | 0.543 | 0.289 | 1.98 | 0.676 |
| 7 | A15C(disialo)-SRIF28 | 11.4 | 9.43 | 0.938 | 0.498 | 3.49 | 1.19 |
| 8 | G16C(disialo)-SRIF28 | 17.4 | 14.4 | 1.22 | 0.646 | 3.12 | 1.07 |
| 9 | K18C(disialo)-SRIF28 | 45.4 | 37.6 | 12.2 | 6.51 | 14.7 | 5.03 |
| 12 | T26C(disialo)-SRIF28 | 21.6 | 17.9 | 310 | 160 | 21.7 | 7.44 |
| 26 | S1C(monosialo)-SRIF28 | 5.38 | 4.46 | 0.213 | 0.112 | 1.18 | 0.405 |
| 27 | S1C(asialo)-SRIF28 | 3.97 | 3.29 | 0.200 | 0.105 | 1.02 | 0.349 |
| 32 | S1C(disialo)•N19C(GlcNAc)-SRIF28 | <10 | <8.27 | 2.20 | 1.17 | 3.05 | 1.04 |
| 33 | S1C(disialo)•N19C(diMan)-SRIF28 | 44 | 37.0 | 3.73 | 1.98 | 3.63 | 1.24 |
| 34 | S1-5C(disialo)-SRIF28 | 110 | 91.9 | 12.7 | 6.58 | 21.3 | 7.29 |
| 35 | S1-10C(disialo)-SRIF28 | 117 | 95.5 | 10.1 | 5.35 | 40.4 | 13.8 |
| 36 | C(disialo)-SRIF28 | 5.57 | 4.61 | 0.478 | 0.255 | 2.55 | 0.870 |
| 37 | R11C(disialo)-SRIF28 | 22.0 | 18.2 | 1.38 | 0.735 | 6.34 | 2.17 |
| 40 | F25C(disialo)-SRIF28 | >1000 | >828 | >1000 | >531 | >1000 | >342 |
| 41 | S27C(disialo)-SRIF28 | 28.4 | 23.5 | 0.326 | 0.170 | 6.77 | 2.31 |
| 42 | C(disialo)-K-SRIF14 | 20.7 | 17.2 | 1.97 | 1.05 | 3.55 | 1.21 |
| 43 | S1C(disialo)-F25Y-SRIF28 | 1.77 | 1.46 | 0.310 | 0.160 | 0.480 | 0.160 |
| 44 | S1C(disialo)-SRIF28-amide | 4.87 | 4.03 | 1.32 | 0.700 | 5.91 | 2.02 |
| 45 | C(disialo)-PEGlinker-SRIF14 | 36.0 | 30.0 | 4.67 | 2.48 | 8.71 | 2.98 |
| 46 | Biotin-S1C(disialo)-SRIF28 | 11.0 | 9.05 | 1.68 | 0.890 | 2.92 | 1.00 |
| 47 | Biotin-PEGlinker-S1C(disialo)-SRIF28 | 9.41 | 7.79 | 1.96 | 1.04 | 3.41 | 1.17 |
| 48 | azido-S1C(disialo)-SRIF28 | 8.82 | 7.30 | 1.29 | 0.690 | 3.17 | 1.09 |
| 49 | S1C(disialo)•E12C(disialo)-SRIF28 | 22.0 | 19.0 | 2.70 | 1.44 | 4.62 | 1.58 |
| 50 | 2C(disialo)-RK-SRIF14 | 48.0 | 40.0 | 5.35 | 2.84 | 9.74 | 3.33 |
| 51 | 3C(disialo)-RK-SRIF14 | 270 | 230 | 32.0 | 17.0 | 40.0 | 14.0 |
| 52 | S1C(diGlcNAc)-SRIF28 | 5.04 | 4.17 | 0.190 | 0.100 | 2.02 | 0.690 |
| 53 | S1C(diMan)-SRIF28 | 5.06 | 4.18 | 0.140 | 0.0750 | 1.32 | 0.450 |
| 54 | N19C(diMan)-SRIF28 | 6.58 | 5.44 | 1.17 | 0.620 | 1.55 | 0.530 |
| 55 | S1C(GlcNAc)-SRIF28 | 5.91 | 4.89 | 0.225 | 0.120 | 1.65 | 0.585 |
| 56 | N19C(GlcNAc)-SRIF28 | 2.60 | 2.15 | 0.940 | 0.500 | <1 | <0.342 |
| 57 | S1C(trisialo)-SRIF28 | 17.0 | 14.0 | 0.780 | 0.410 | 5.59 | 1.91 |
| 58 | S1C(tetrasialo)-SRIF28 | 17.3 | 14.2 | 1.12 | 0.597 | 5.63 | 1.93 |
| 59 | S1C(disialo(aminoethylamide))-SRIF28 | 2.35 | 1.94 | 0.101 | 0.0536 | 0.766 | 0.264 |
| 60 | S1C(disialo(amide))-SRIF28 | 5.09 | 4.21 | 0.207 | 0.110 | 1.53 | 0.522 |
| 61 | S1C(disialo(Bn))-SRIF28 | 6.20 | 5.12 | 0.247 | 0.130 | 2.15 | 0.733 |
| 62 | S1C(disialo(hexadexylamide))-SRIF28 | 5.53 | 4.57 | 1.04 | 0.550 | 11.0 | 3.75 |
| 63 | S1-2C(disialo(amide))-SRIF28 | 6.92 | 5.73 | 0.830 | 0.440 | 2.06 | 0.710 |
| 64 | S1-2C(disialo(Bn))-SRIF28 | 6.01 | 4.97 | 0.830 | 0.440 | 2.58 | 0.880 |
| 65 | S1C(Asn(disialo))-SRIF28 | 15.0 | 13.0 | 0.610 | 0.330 | 5.57 | 1.91 |
| 66 | S1N(disialo)•N19C(diMan)-SRIF28 | 35.0 | 29.0 | 5.65 | 3.00 | 3.90 | 1.33 |
| 67 | C(disialo(aminoethylamide))•S1C(disialo)-SRIF28 | 6.20 | 5.13 | 0.960 | 0.51 | 1.89 | 0.650 |
| 68 | S1-4C(disialo)-SRIF28 | 130 | 100 | 3.76 | 2.00 | 10.0 | 3.43 |
| — | SRIF28 | 0.533 | 1.80 | 0.0680 | 0.0565 | 0.206 | 0.116 |
| — | SRIF14 | 1.25 | 2.69 | 0.0329 | 0.0993 | 0.0697 | 0.403 |

| Example | | SSTR4 | | SSTR5 | |
|---|---|---|---|---|---|
| | | $IC_{50}$(nM) | $K_i$ (nM) | $IC_{50}$ (nM) | $K_i$ (nM) |
| 1 | S1C(disialo)-SRIF28 | 7.10 | 6.39 | 1.61 | 0.011 |
| 7 | A15C(disialo)-SRIF28 | 8.18 | 7.30 | 3.84 | 2.17 |
| 8 | G16C(disialo)-SRIF28 | 12.2 | 11.0 | 5.67 | 3.21 |
| 9 | K18C(disialo)-SRIF28 | 62.7 | 56.5 | 160 | 95.0 |
| 12 | T26C(disialo)-SRIF28 | 26.8 | 24.1 | 480 | 230 |
| 26 | S1C(monosialo)-SRIF28 | 2.35 | 2.12 | 0.816 | 0.460 |
| 27 | S1C(asialo)-SRIF28 | 2.98 | 2.68 | 1.04 | 0.588 |
| 32 | S1C(disialo)•N19C(GlcNAc)-SRIF28 | 8.55 | 7.69 | 2.37 | 1.34 |
| 33 | S1C(disialo)•N19C(diMan)-SRIF28 | 25.0 | 23.0 | 5.69 | 3.22 |
| 34 | S1-5C(disialo)-SRIF28 | 62.3 | 58.4 | 7.23 | 4.08 |
| 35 | S1-10C(disialo)-SRIF28 | 191 | 172 | 34.6 | 19.7 |
| 36 | C(disialo)-SRIF28 | 8.65 | 7.79 | 2.62 | 1.48 |
| 37 | R11C(disialo)-SRIF28 | 20.2 | 18.1 | 3.65 | 2.07 |
| 40 | F25C(disialo)-SRIF28 | 130 | 110 | 58.0 | 33.0 |
| 41 | S27C(disialo)-SRIF28 | 33.4 | 30.1 | 4.94 | 2.80 |
| 42 | C(disialo)-K-SRIF14 | 11.0 | 9.77 | 3.52 | 1.99 |
| 43 | S1C(disialo)-F25Y-SRIF28 | 1.55 | 1.39 | 1.09 | 0.620 |
| 44 | S1C(disialo)-SRIF28-amide | 6.88 | 6.19 | 3.75 | 2.12 |
| 45 | C(disialo)-PEGlinker-SRIF14 | 21.0 | 19.0 | >10 | >5.65 |
| 46 | Biotin-S1C(disialo)-SRIF28 | 9.28 | 8.35 | 2.42 | 1.37 |
| 47 | Biotin-PEGlinker-S1C(disialo)-SRIF28 | 9.31 | 8.38 | 2.00 | 1.13 |
| 48 | azido-S1C(disialo)-SRIF28 | 5.34 | 4.81 | 0.840 | 0.470 |
| 49 | S1C(disialo)•E12C(disialo)-SRIF28 | 20.0 | 18.0 | 2.11 | 1.19 |
| 50 | 2C(disialo)-RK-SRIF14 | 49.0 | 44.0 | 6.16 | 3.48 |
| 51 | 3C(disialo)-RK-SRIF14 | >100 | >90.0 | 41.0 | 23.0 |
| 52 | S1C(diGlcNAc)-SRIF28 | 3.91 | 3.52 | 1.45 | 0.820 |
| 53 | S1C(diMan)-SRIF28 | 3.01 | 2.70 | 0.550 | 0.310 |

TABLE 3B-continued

| | | | | | |
|---|---|---|---|---|---|
| 54 | N19C(diMan)-SRIF28 | 6.02 | 7.22 | 2.94 | 1.66 |
| 55 | S1C(GlcNAc)-SRIF28 | 2.89 | 2.60 | 1.15 | 0.650 |
| 56 | N19C(GlcNAc)-SRIF28 | 2.38 | 2.15 | 1.89 | 1.07 |
| 57 | S1C(trisialo)-SRIF28 | 15.0 | 14.0 | 1.95 | 1.10 |
| 58 | S1C(tetrasialo)-SRIF28 | 14.3 | 12.6 | 2.12 | 1.20 |
| 59 | S1C(disialo(aminoethylamide))-SRIF28 | 2.24 | 2.01 | 2.08 | 1.18 |
| 60 | S1C(disialo(amide))-SRIF28 | 6.12 | 5.50 | 2.60 | 1.47 |
| 61 | S1C(disialo(Bn))-SRIF28 | 6.01 | 5.41 | 3.25 | 1.83 |
| 62 | S1C(disialo(hexadexylamide))-SRIF28 | 26.0 | 24.0 | 37.0 | 21.0 |
| 63 | S1-2C(disialo(amide))-SRIF28 | 4.76 | 4.28 | 2.67 | 1.51 |
| 64 | S1-2C(disialo(Bn))-SRIF28 | 8.20 | 7.38 | 2.60 | 1.47 |
| 65 | S1C(Asn(disialo))-SRIF28 | 15.0 | 14.0 | 1.61 | 0.910 |
| 66 | S1N(disialo)•N19C(diMan)-SRIF28 | 25.0 | 22.0 | 8.53 | 4.82 |
| 67 | C(disialo(aminoethylamide))•S1C(disialo)-SRIF28 | 6.12 | 5.51 | 1.81 | 1.02 |
| 68 | S1-4C(disialo)-SRIF28 | 66.0 | 59.0 | 10.0 | 5.82 |
| — | SRIF28 | 0.776 | 1.23 | 0.189 | 0.666 |
| — | SRIF14 | 0.823 | 1.95 | 0.416 | 0.813 |

As shown in Table 3B, the controls SRIF14 and SRIF28 bound to all receptors SSTR1-SSTR5. Since the number of test runs etc. was different from Example 69-1, the Ki value of SRIF14 against each receptor was different at a high value of 2.5 to 13.2. The Ki values of the compounds of Examples 1, 7, 8, 9, 26, 27, 32, 33, 34, 35, 36, 37, 41, 42, 43, 44, 45, 46, 47, 48, 49, 50, 52, 53, 54, 55, 56, 57, 58, 59, 60, 61, 62, 63, 64, 65, 66, 67, and 68 against SSTR1 were 1.46-100 nM, and similarly 0.0536-6.58 nM for SSTR2, 0.160-13.8 nM for SSTR3, 1.39-172 nM for SSTR4, and 0.310-95.0 nM for SSTR5, showing high binding affinity towards all the receptors. The Ki values of the compound of Example 12 against SSTR2 and SSTR5 were 280-1600-folds that of SRIF14 but the Ki values against SSTR1, SSTR3, and SSTR4 were 17.9, 7.44, and 24.1 nM, and it was thought that binding affinity was retained. The affinity of the compound of Example 40 against SSTR1, SSTR2, and SSTR3 was significantly reduced with Ki values of 310-5300-folds that of SRIF14 but the Ki values against SSTR4 and SSTR5 were 110 and 33.0 nM, and it was thought that binding affinity was retained. The Ki values of the compound of Example 51 against SSTR2 and SSTR4 were 170-folds and 46-folds or more that of SRIF14 but the Ki values against SSTR1, SSTR3, and SSTR5 were each 270 nM, 14.0 nM, and 23.0 nM, and it was thought that binding affinity was retained.

Example 69-3 Agonist Activity Evaluation Employing Receptor Expression Cells—1

Somatostatin receptor is a G-protein-coupled receptor (GPCR). SSTR1-SSTR5 all suppress adenyl cyclase activity via G-protein subfamily Gi/Go and reduces intracellular cAMP concentration. In this experimental line, each somatostatin receptor expression cells was employed to calculate the $IC_{50}$ value of the cAMP production suppressing action of the test substance to evaluate agonist activity. Moreover, SRIF14, SRIF28 were similarly evaluated as control compounds.

Reagents employed in the present experiment and their proper chemical names are as follows: DMEM (Dulbecco's Modified Eagle's Medium), IBMX (3-isobutyl-1-methylxanthine), and HBSS (Hank's Buffered Salt Solution).

For evaluations of SSTR2-SSTR5, experiments were performed under the following conditions. DMEM containing 0.3% BSA and 0.5 mM IBMX was employed as the buffer, and receptor expression cells shown in Table 3C were seeded at $10^4$ cells/well. The test compounds was treated by mixing at a concentration of 0.00001 nM, 0.0001 nM, 0.001 nM, 0.01 nM, 0.1 nM, 1 nM, 10 nM, 100 nM, or 1000 nM with 10 μM forskolin, and allowed to react at room temperature for 30 minutes. After the reaction, the cells were dissolved with 0.2 N HCl, and the amount of cAMP accumulated in the cell was measured with Cayman cyclic AMP EIA kit (Cayman, 582002).

Evaluation of SSTR1 was consigned to Cerep, and the experiment was performed. HBSS containing 20 mM HEPES (pH 7.4) and 500 μM IBMX was used as the buffer, and SSTR1 receptor expression cells were seeded at $10^4$ cells/well. The test substance was treated by mixing at a concentration of 0.001 nM, 0.01 nM, 0.1 nM, 1 nM, 10 nM, or 100 nM with 1 μM NKH477, and allowed to react at 37° C. for 20 minutes. After the reaction, the amount of cAMP accumulated in the cell was measured with Cisbio cAMP dynamic2 kit (Cisbio, 62AM4PE).

TABLE 3C

| | SSTR2 | SSTR3 | SSTR4 | SSTR5 |
|---|---|---|---|---|
| Distributer | | Perkin Elmer | | |
| Serial Number | ES-521-CF | ES-523-CF | ES-524-CF | ES-522-CF |
| Derived cell | | CHO-K1 cells | | |

The experimental results ($IC_{50}$ (nM)) of the agonist activity evaluation test when employing the compounds of Examples 1, 18, 27, 28, 59, and 60 as the glycosylated form are shown in Table 3D and FIG. 1E. $IC_{50}$ of the control compounds SRIF14 and SRIF28 was 0.83-0.89 nM against SSTR1, and 0.0076-0.073 nM, 0.029-0.21 nM, 0.015-0.074 nM, and 0.066-0.12 nM against SSTR2, SSTR3, SSTR4, and SSTR5, respectively. $IC_{50}$ of the agonist activity of the glycosylated compounds against SSTR1, SSTR2, SSTR3, SSTR4, and SSTR5 were 1.0-2.4 nM, 0.041-0.10 nM, 0.12-0.30 nM, 0.039-0.085 nM, and 0.043-0.081 nM, respectively, and potent agonist activity was shown against all receptors SSTR1-SSTR5. From the results shown in Examples 69-1 and 69-2, it is apparent that these compounds have receptor binding affinity, and it became clear that these compounds exert proper agonistic action by binding to a receptor.

TABLE 3D

| Example | | SSTR1 | SSTR2 | SSTR3 | SSTR4 | SSTR5 |
|---|---|---|---|---|---|---|
| — | SRIF14 | 0.83 ± 0.52 | 0.0076 ± 0.0012 | 0.029 ± 0.017 | 0.015 ± 0.006 | 0.12 ± 0.03 |
| — | SRIF28 | 0.89 ± 0.41 | 0.073 ± 0.014 | 0.21 ± 0.08 | 0.074 ± 0.058 | 0.066 ± 0.033 |
| 1 | S1C(disialo)-SRIF28 | 2.2 ± 1.1 | 0.075 ± 0.030 | 0.13 ± 0.06 | 0.065 ± 0.042 | 0.056 ± 0.028 |
| 18 | Cys(disialo)-R-K-SRIF14 | 1.2 ± 0.6 | 0.055 ± 0.015 | 0.18 ± 0.10 | 0.050 ± 0.025 | 0.052 ± 0.032 |
| 27 | S1C(asialo)-SRIF28 | 1.6 ± 0.6 | 0.041 ± 0.006 | 0.12 ± 0.05 | 0.039 ± 0.021 | 0.055 ± 0.031 |
| 28 | S1-2C(asialo)-SRIF28 | 1.5 ± 0.6 | 0.079 ± 0.033 | 0.15 ± 0.08 | 0.051 ± 0.046 | 0.064 ± 0.029 |
| 59 | S1C(disialo(aminoethylamide))-SRIF28 | 1.0 ± 0.9 | 0.10 ± 0.02 | 0.30 ± 0.15 | 0.085 ± 0.011 | 0.081 ± 0.019 |
| 60 | S1C(disialo(amide))-SRIF28 | 2.4 ± 1.7 | 0.055 ± 0.013 | 0.14 ± 0.06 | 0.043 ± 0.023 | 0.043 ± 0.015 |

Example 69-4 Agonist Activity Evaluation Employing Receptor Expression Cells—2

Agonist activity evaluation test was carried out similarly to Example 69-3 employing each of the compounds described in Table 3E as the glycosylated form. The experimental results are shown in Table 3E. In Table 3E, fields with "- (hyphen)" shown indicates that the test was not performed.

TABLE 3E

| Experiment | | SSTR1 | SSTR2 | SSTR3 | SSTR4 | SSTR5 |
|---|---|---|---|---|---|---|
| — | SRIF14 | 0.83 | 0.0076 | 0.029 | 0.015 | 0.12 |
| — | SRIF28 | 0.89 | 0.073 | 0.21 | 0.074 | 0.056 |
| 4 | E12C(disialo)-SRIF28 | 2.3 | — | — | — | — |
| 10 | N19C(disialo)-SRIF28 | 22 | — | — | — | — |
| 15 | S1C(disialo)-D-Trp22-SRIF28 | 3.5 | — | — | — | — |
| 17 | C(disialo)-SRIF14 | — | 0.029 | 0.18 | 0.10 | 0.23 |
| 19 | C(disialo)-C12linker-SRIF14 | — | — | — | 0.11 | — |
| 20 | S1-2C(disialo)-SRIF28 | — | — | 0.55 | 0.14 | 0.22 |
| 21 | S1C(disialo)•N5C(disialo)-SRIF28 | — | 0.072 | 0.37 | 0.041 | 0.090 |
| 23 | N5C(disialo)•A9C(disialo)-SRIF28 | — | 0.096 | 0.29 | 0.091 | 0.13 |
| 24 | S1-3C(disialo)-SRIF28 | 7.5 | 0.19 | 0.79 | 0.36 | 0.97 |
| 25 | S1C(disialo)•N5C(disialo)•A9C(disialo)-SRIF28 | — | 1.4 | 2.4 | 0.16 | 1.1 |
| 26 | S1C(monosialo)-SRIF28 | 1.5 | 0.059 | 0.15 | 0.046 | 0.062 |
| 29 | S1-3C(asialo)-SRIF28 | — | 0.19 | — | 0.10 | — |
| 31 | S1N(disialo)-SRIF28 | 2.3 | — | — | — | — |
| 32 | S1C(disialo)•N19C(GlcNac)-SRIF28 | — | 0.080 | 0.039 | 0.033 | 0.088 |
| 34 | S1-5C(disialo)-SRIF28 | 18 | 0.81 | 2.0 | 0.27 | — |
| 42 | C(disialo)-K-SRIF14 | — | 0.019 | 0.10 | 0.059 | — |
| 44 | S1C(disialo)-SRIF28-amide | 1.7 | — | — | — | — |
| 47 | C(disialo)-PEG2linker-SRIF14 | — | 0.034 | 0.15 | 0.066 | 0.18 |
| 50 | 2C(disialo)-R-K-SRIF14 | — | 0.15 | 0.55 | 1.1 | — |
| 51 | 3C(disialo)-R-K-SRIF14 | — | 1.4 | 3.8 | 1.6 | — |
| 52 | S1C(diGlcNAc)-SRIF28 | 1.2 | 0.045 | 0.14 | 0.050 | 0.033 |
| 53 | S1C(diMan)-SRIF28 | 1.2 | 0.035 | 0.11 | 0.043 | 0.037 |
| 54 | N19C(diMan)-SRIF28 | — | — | — | 0.11 | — |
| 55 | S1C(GlcNAc)-SRIF28 | 1.4 | 0.040 | 0.14 | 0.049 | 0.031 |
| 56 | N19C(GlcNAc)-SRIF28 | — | — | — | 0.092 | — |
| 57 | S1C(trisialo)-SRIF28 | 4.9 | 0.11 | 0.38 | 0.092 | 0.095 |
| 58 | S1C(tetrasialo)-SRIF28 | 2.8 | 0.13 | 0.25 | 0.081 | 0.11 |
| 61 | S1C(disialo(Bn))-SRIF28 | 1.4 | — | — | — | — |
| 62 | S1C(disialo(hexadecylamide))-SRIF28 | 1.3 | — | — | — | — |
| 65 | S1C(Asn(disialo))-SRIF28 | 2.6 | — | — | 0.13 | — |
| 67 | C(disialo(aminoethylamide))•S1C(disialo)-SRIF28 | — | 0.039 | 0.17 | 0.047 | 0.034 |

(—: Not performed)

In Table 3E, $IC_{50}$ of the agonist activity of the glycosylated compounds against SSTR1, SSTR2, SSTR3, SSTR4, and SSTR5 were 1.2-22 nM, 0.019-1.4 nM, 0.039-3.8 nM, 0.033-1.6 nM, and 0.031-1.1 nM, respectively, and agonist activity was shown against receptors SSTR1-SSTR5. From the results shown in Examples 69-1 and 69-2, it became clear that these compounds have receptor binding affinity, and these compounds exert agonist activity by binding to a receptor.

Example 70 Pharmacokinetics Test with Rats 1

In order to confirm that the glycosylated polypeptide of the present invention (glycosylated form) had improved pharmacokinetics profiles such as drug plasma concentration-area under the time curve (AUC), half-life in blood ($t_{1/2}$), mean retention time (MRT), and bioavailability compared to a non-glycosylated SRIF28, pharmacokinetics analysis by intravenous and subcutaneous administrations was performed with rats.

70-1 Preparation of Administration Solution and Reagent

The glycosylated form (S1C(disialo)-SRIF28) was dissolved in Japanese Pharmacopeia saline (from Otsuka Pharmaceutical factory, Inc.) to prepare a 40 µM solution to make an administration solution. PBS solution was prepared by dissolving 1 tablet of Phosphate buffered saline (P4417 from Sigma) in 200 mL of ultrapure water. EDTA-PBS was prepared by dissolving EDTA-2Na (from Wako Pure Chemical Industries, Ltd.) in PBS to 2 mg/mL. Aprotinin-containing EDTA-PBS solution was prepared by dissolving aprotinin (010-11834 from Wako Pure Chemical Industries, Ltd.) in EDTA-PBS to 0.142 mg/mL, and was employed as an anticoagulant for collected blood.

70-2 Preparation of Plasma Sample

To the tail vain or dorsal subcutaneous of male SD rats (Crl: CD (SD), Charles River Japan, 6 weeks-old, n=3, body weight 161.3-239.3 g), the administration solution prepared in the above 70-1 was administered under nonfasting condition at a dosage of 1 mL/kg with a glass syringe and a 26 G injection needle (all from Terumo Corporation) (40 nmol/kg as S1C(disialo)-SRIF28). Blood was collected from the rat cervical vein before administration, as well as at 2 minutes, 5 minutes, 15 minutes, 30 minutes, 1 hour, 2 hours, 4 hours, and 8 hours after administration. 0.2 mL of the collected blood was promptly mixed with 0.2 mL of the aprotinin-containing EDTA-PBS solution prepared in the above 70-1, and left on ice for 30 minutes or more. After centrifugal separation (1,870×g, 4° C., 10 minutes), 250 μL of the supernatant was taken as the plasma sample. As blank plasma, plasma obtained by similarly treating the blood collected from untreated rat cervical vein was employed. Plasma samples were frozen in storage until employed for measurement. Tips and tubes used were low absorbent products from BM Equipment Co., Ltd.

70-3 Measurement of Concentration in Plasma

Figure 2:
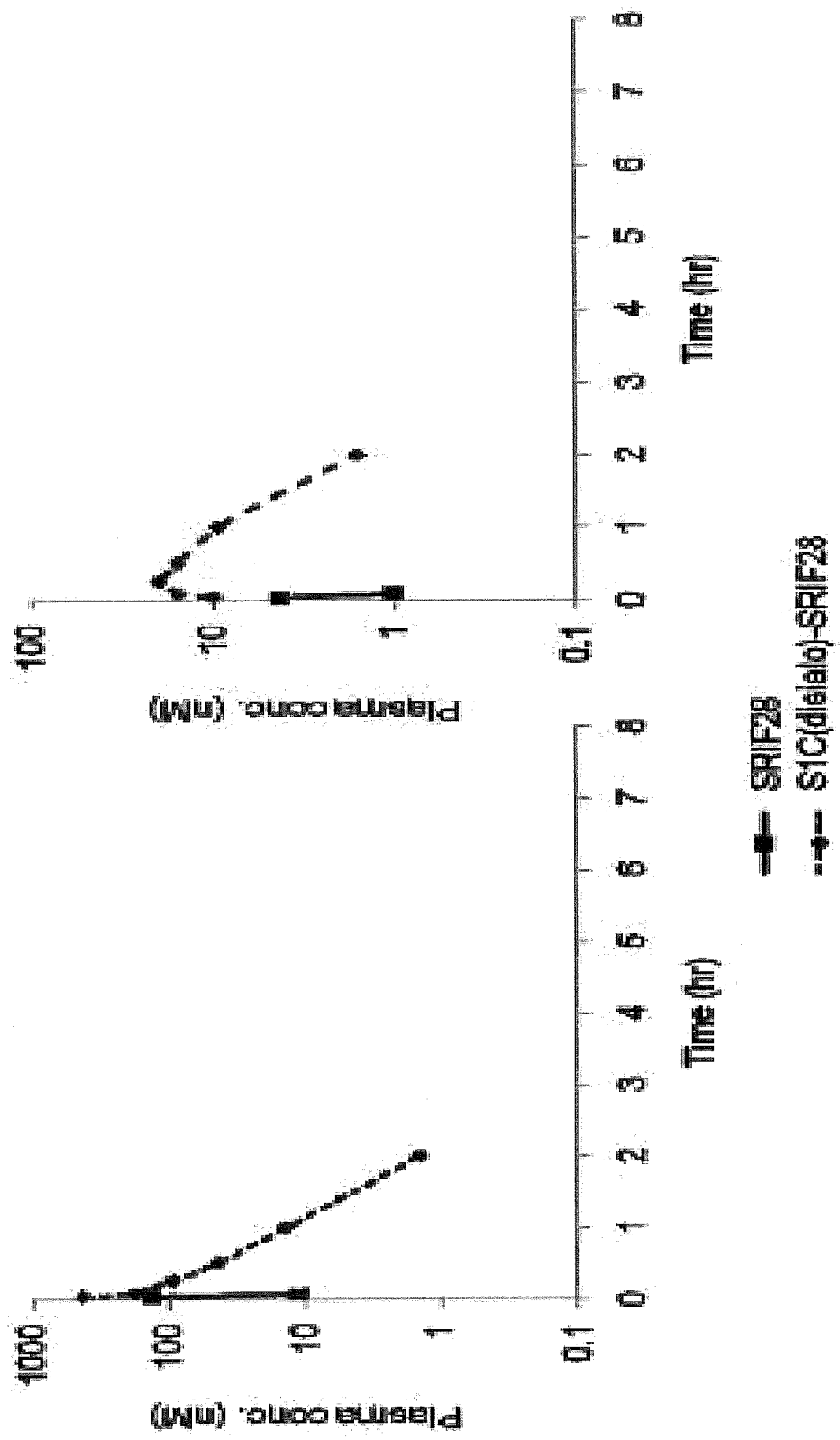
FIG. 2 is graphs showing the plasma concentration transition of each polypeptide when SRIF28 and S1C(disialo)-SRIF28 were administered intravenously or subcutaneously to rats.

Measurement of plasma concentration of S1C(disialo)-SRIF28 in the plasma sample obtained in the above 70-2 was performed with Phoenix Pharmaceuticals somatostatin EIA kit (Phoenix Pharmaceuticals Inc, EK-060-03). The plasma sample was diluted with the assay buffer supplied in the EIA kit to 5, 20, 100, 400, and 1600-folds as measurement samples. The standard solution for creating a standard curve was prepared as follows. First, the blank plasma obtained in the above 70-2 was diluted with the assay buffer supplied in the EIA kit similarly to the plasma sample, and this was used as the assay buffer for standard solution preparation (for example, when diluting the plasma sample to 100-fold, 1/100 amount of blank plasma was added to the assay buffer supplied in the EIA kit, and this was used as the assay buffer for standard solution preparation). S1C(disialo)-SRIF28 was diluted with PBS solution to prepare a 100 μM solution, and a 2 μM solution was prepared from the 100 μM solution. The 2 μM S1C(disialo)-SRIF28 solution obtained was serially diluted with the assay buffer for standard solution preparation to prepare standard solutions of 20 nM, 10 nM, 2 nM, 0.4 nM, 0.08 nM, and 0.04 nM. By multiplying the results obtained and the dilution ratio, and further multiplying the dilution ratio 2 in the aprotinin-containing EDTA-PBS solution used as anticoagulant treatment, the plasma concentration was calculated. As a control, a similar operation was carried out employing non-glycosylated SRIF28 instead of the glycosylated form. The transition of plasma S1C(disialo)-SRIF28 concentration obtained is shown in FIG. 2.

70-4 Estimation of Pharmacokinetics Parameter

From the transition of S1C(disialo)-SRIF28 concentration obtained, AUC was calculated by the moment analysis method and the trapezoidal rule. Moreover, the predicted initial concentration ($C_0$) was determined by the extrapolation method for intravenous administration, $t_{1/2}$ and MRT were calculated, and the maximum plasma concentration ($C_{max}$) was determined from the actual value for subcutaneous administration. The pharmacokinetics parameters obtained are shown in Table 4.

TABLE 4

| | Intravenous administration | | | | Subcutaneous administration | | | |
|---|---|---|---|---|---|---|---|---|
| | $t_{1/2}$ | AUC | MRT | $C_0$ | $t_{1/2}$ | AUC | MRT | $C_{max}$ |
| S1C(disialo)-SRIF28 | 18.1 | 5086 | 20.4 | 780 | 26.0 | 1273 | 43.8 | 19.9 |
| SRIF28 | 0.8 | 358 | 2.3 | 678 | 1.5 | 15 | 3.2 | 4.4 |

($t_{1/2}$: min, AUC: min · nM, MRT: min, $C_0$: nM, $C_{max}$: nM)

As is clear from the results shown in FIG. 2 and Table 4, S1C(disialo)-SRIF28 has significantly extended $t_{1/2}$ and MRT compared to the non-glycosylated SRIF28, and an increase in AUC and $C_{max}$ was recognized. These are thought to be due to the increase in resistance to degradation activity in blood by glycosylation. It is clear that the glycosylated form has improved stability in vivo compared to the non-glycosylated form. Moreover, as factors for the increase in AUC and $C_{max}$, the improvement of bioavailability according to the present invention, as well as improvement of stability thereof in vivo are thought to be factors.

Example 71 Pharmacokinetics Test with Rats 2

Figure 3:
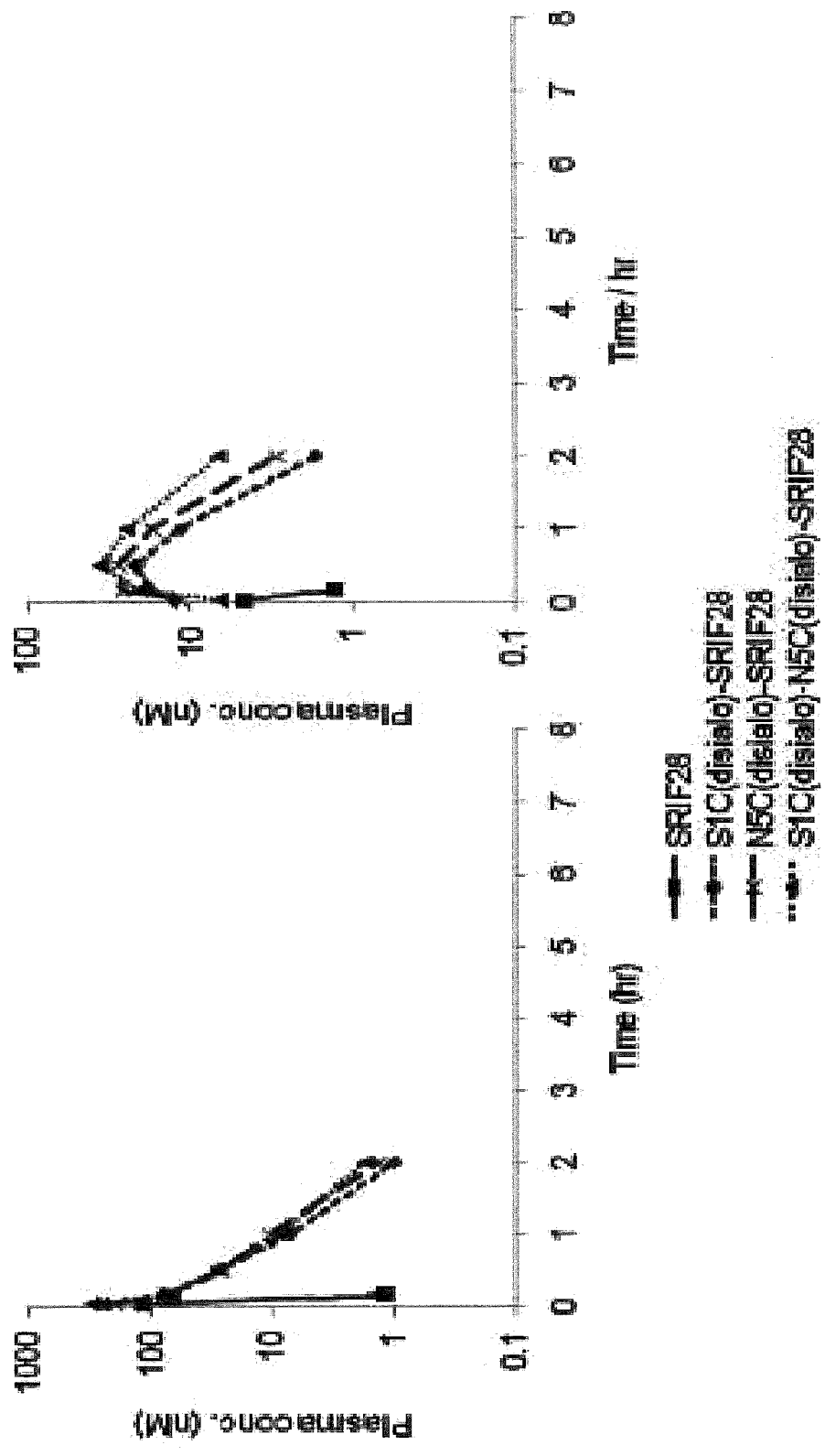
FIG. 3 is graphs showing the plasma concentration transition when SRIF28, S1C(disialo)-SRIF28, N5C(disialo)-SRIF28, and S1C(disialo)•N5C(disialo)-SRIF28 were administered intravenously and subcutaneously to rats.

A pharmacokinetics test was carried out similarly to Example 70, except that S1C(disialo)-SRIF28, N5C(disialo)-SRIF28, and S1C(disialo)•N5C(disialo)-SRIF28 were employed as the glycosylated forms. As a control, non-glycosylated SRIF28 was employed instead of the glycosylated form. The compound plasma concentration transition obtained is shown in FIG. 3.

Example 72 Pharmacokinetics Test with Rats 3

Figure 4:
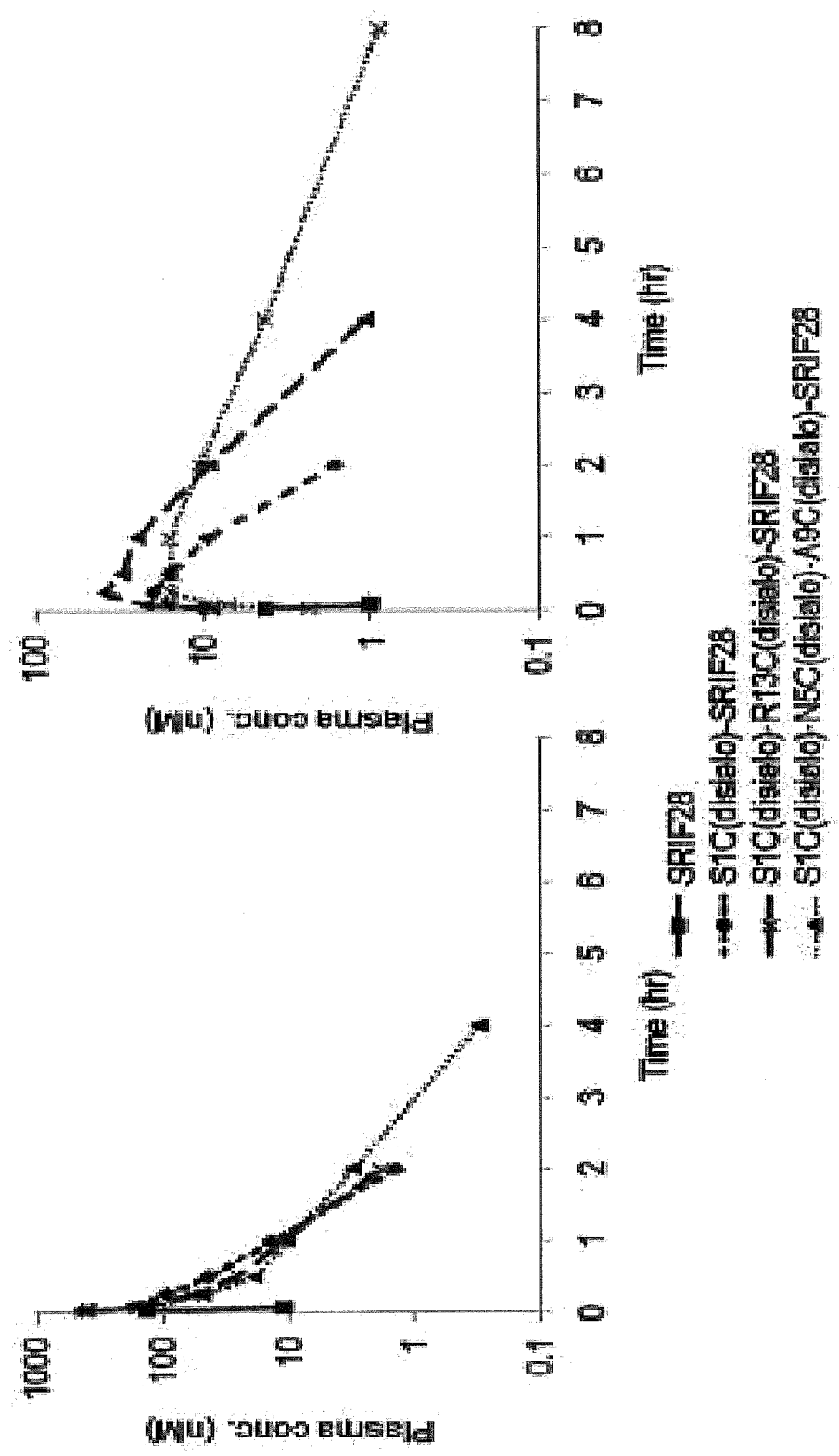
FIG. 4 is graphs showing the plasma concentration transition when SRIF28, S1C(disialo)-SRIF28, S1C(disialo)•R13C(disialo)-SRIF28, and S1C(disialo)•N5C(disialo)•A9C(disialo)-SRIF28 were administered intravenously and subcutaneously to rats.

A pharmacokinetics test was carried out similarly to Example 70, except that S1C(disialo)-SRIF28, S1C(disialo)•R13C(disialo)-SRIF28, and S1C(disialo)•N5C(disialo)•A9C(disialo)-SRIF28 were employed as the glycosylated forms. As a control, non-glycosylated SRIF28 was employed instead of the glycosylated form. The compound plasma concentration transition obtained is shown in FIG. 4.

Example 73 Pharmacokinetics Test with Rats 4

Figure 5:
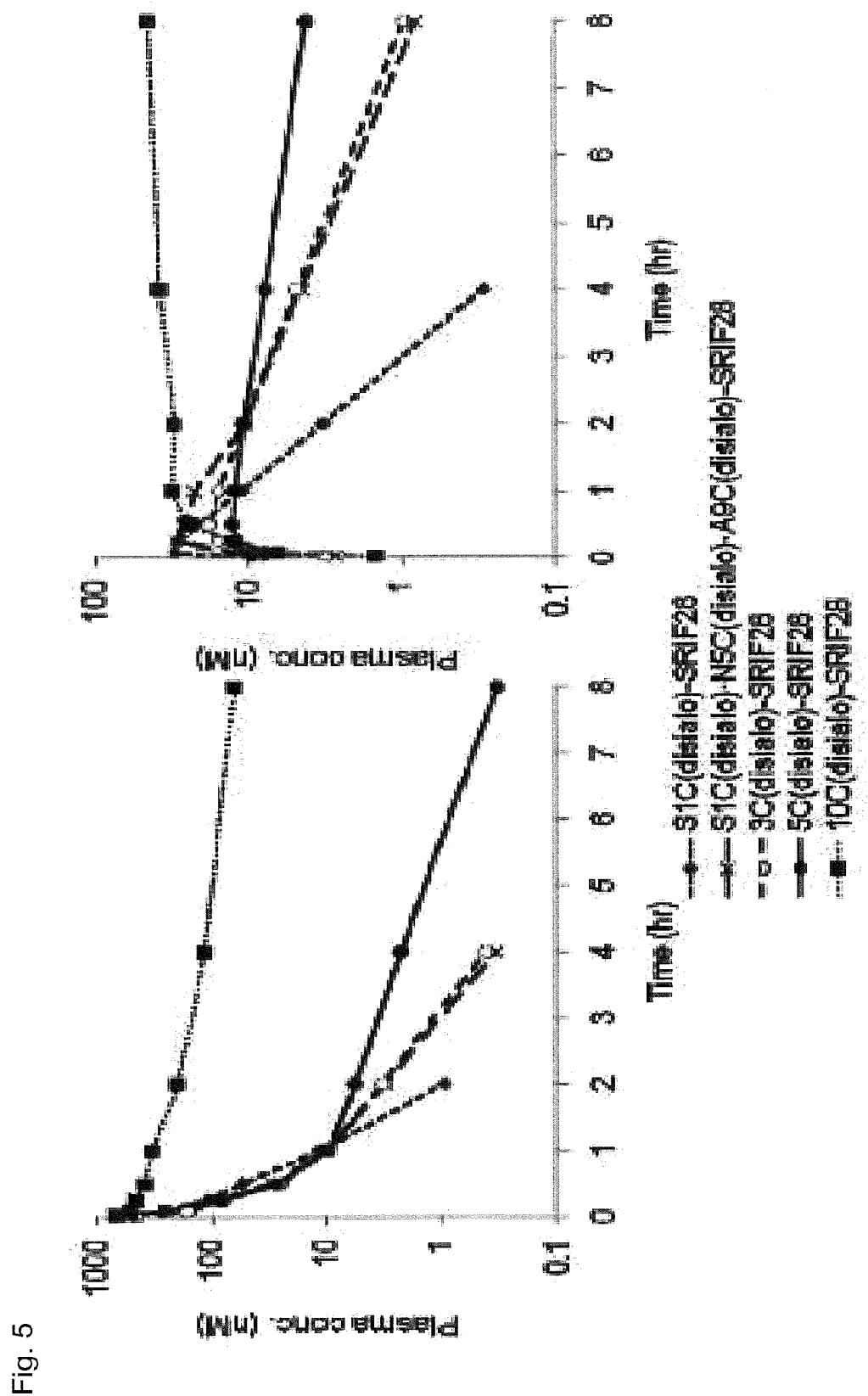
FIG. 5 is graphs showing the plasma concentration transition when S1C(disialo)-SRIF28, S1C(disialo)•N5C(disialo)•A9C(disialo)-SRIF28, 3C(disialo)-SRIF28, 5C(disialo)-SRIF28, and 10C(disialo)-SRIF28 were administered intravenously and subcutaneously to rats.

A pharmacokinetics test was carried out similarly to Example 70, except that S1C(disialo)-SRIF28, S1C(disialo)•N5C(disialo)•A9C(disialo)-SRIF28, S1-3C(disialo)-SRIF28, S1-5C(disialo)-SRIF28, and S1-10C(disialo)-SRIF28 were employed as the glycosylated forms. The compound plasma concentration transition obtained is shown in FIG. 5.

Example 74 Pharmacokinetics Test with Rats 5

Figure 6:
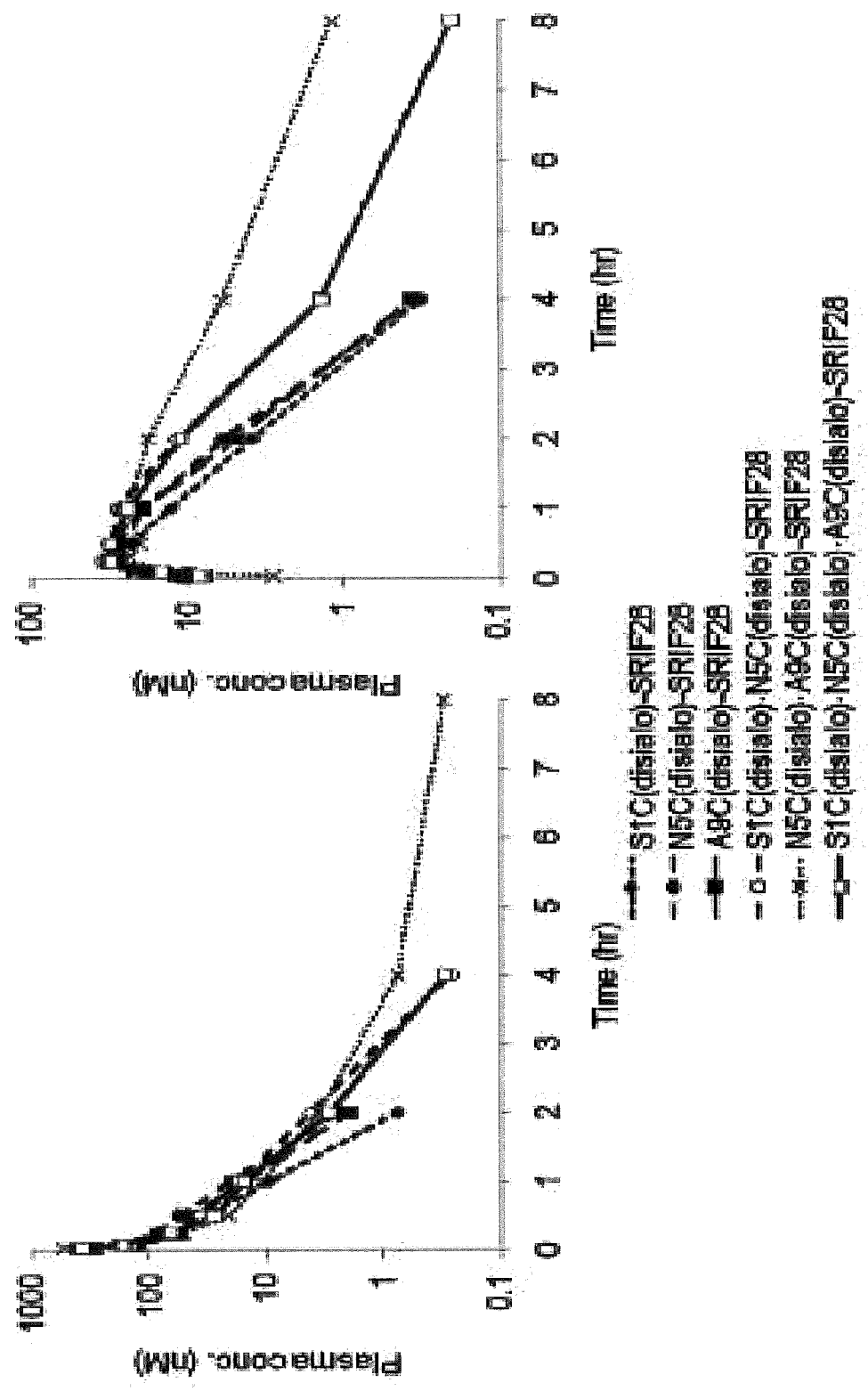
FIG. 6 is graphs showing the plasma concentration transition when S1C(disialo)-SRIF28, N5C(disialo)-SRIF28, A9C(disialo)-SRIF28, S1C(disialo)•N5C(disialo)-SRIF28, N5C(disialo)•A9C(disialo)-SRIF28, and S1C(disialo)•N5C(disialo)•A9C(disialo)-SRIF28 were administered intravenously and subcutaneously to rats.

A pharmacokinetics test was carried out similarly to Example 70, except that S1C(disialo)-SRIF28, N5C(disialo)-SRIF28, A9C(disialo)-SRIF28, S1C(disialo)•N5C(disialo)-SRIF28, N5C(disialo)•A9C(disialo)-SRIF28, and S1C(disialo)•N5C(disialo)•A9C(disialo)-SRIF28 were employed as the glycosylated forms. The compound plasma concentration transition obtained is shown in FIG. 6.

Example 75 Pharmacokinetics Test with Rats 6

Figure 7:
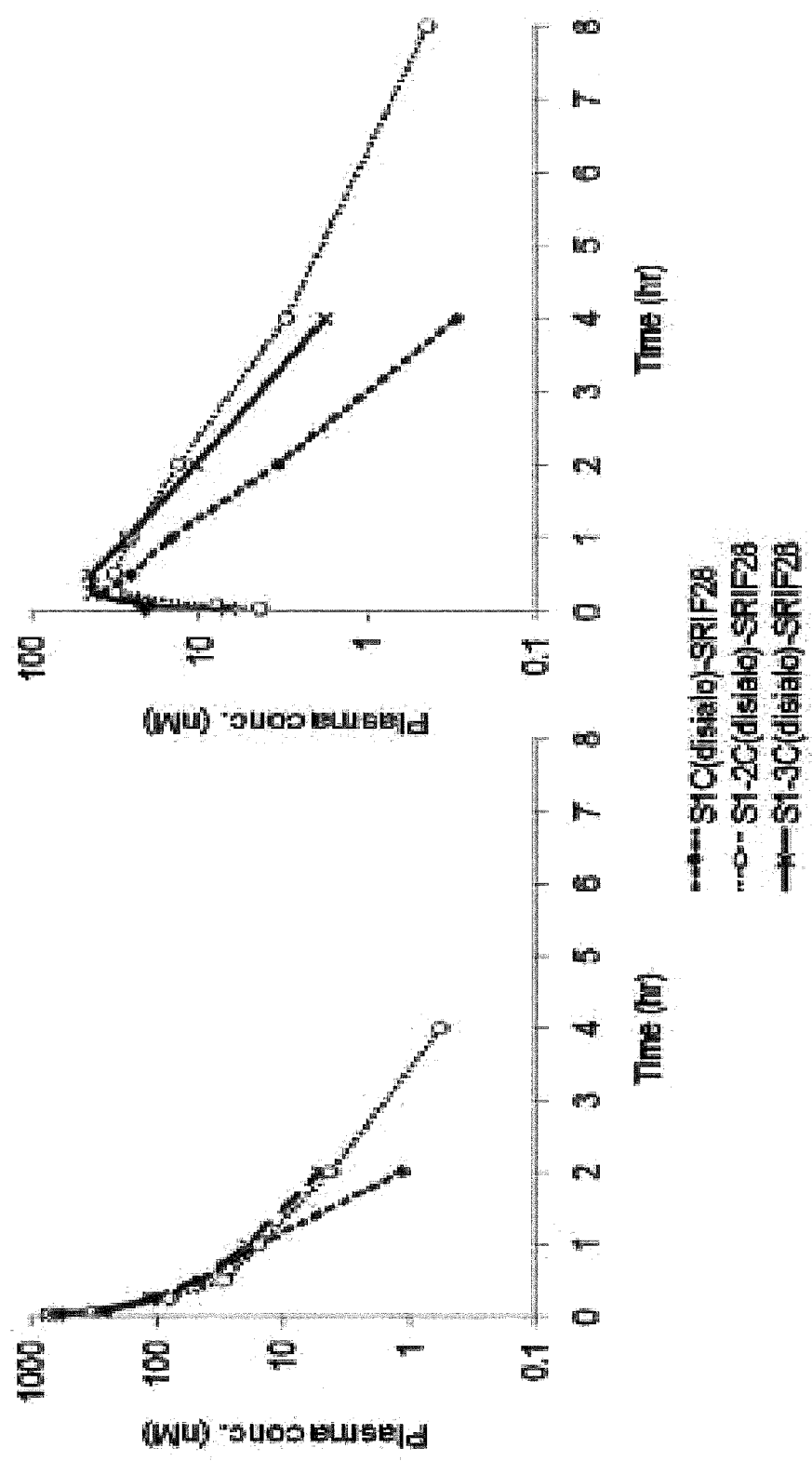
FIG. 7 is graphs showing the plasma concentration transition when S1C(disialo)-SRIF28, S1-2C(disialo)-SRIF28, and S1-3C(disialo)-SRIF28 were administered intravenously and subcutaneously to rats.

A pharmacokinetics test was carried out similarly to Example 70, except that S1C(disialo)-SRIF28, S1-2C(disialo)-SRIF28, and S1-3C(disialo)-SRIF28 were employed as the glycosylated forms. The compound plasma concentration transition obtained is shown in FIG. 7.

From the compound plasma concentration transition obtained in the pharmacokinetics tests of Examples 71-75, the pharmacokinetics parameters of each compound were calculated similarly to Example 70. Moreover, the parameters obtained were employed to calculate bioavailability from the following mathematical formula. The results are shown in Table 5A.

BA (%)=(AUC$_{(sc)}$/Dose$_{(sc)}$)/(AUC$_{(iv)}$/Dose$_{(iv)}$)

AUC$_{(sc)}$: AUC for subcutaneous administration (min·nM)
Dose$_{(sc)}$: Administration dose for subcutaneous administration (nmol/kg)
AUC$_{(iv)}$: AUC for intravenous administration (min·nM)
Dose$_{(iv)}$: Administration dose for intravenous administration (nmol/kg)

sylated form was 37-60% in the glycosylated polypeptide having one sugar chain added, an increase of 50% on average. On the other hand, it was found that this was increased to 77-85%, 81% on average in those having two sugar chains added with intervals, and to 91% in those having three sugar chains added with intervals. Moreover, comparing those with dense glycosylation intervals, it was found that there was a 37% increase in those having one added, 55% in those having two added, 69% in those having three added, and 92% in those having five added (the compounds of Examples 1, 20, 24, and 34). For those having ten sugar chains added, as shown in FIG. 5, AUC could not be measured because the rise in plasma concentration was maintained throughout the measurement time, and as a result bioavailability could not be calculated. From these results, it was proven that bioavailability is significantly improved by glycosylation according to the present invention compared

TABLE 5A

| | Compound | The number of sugar chains | Value of n | Intravenous administration | | | |
|---|---|---|---|---|---|---|---|
| | | | | $t_{1/2}$ | AUC | MRT | $C_0$ |
| — | SRIF28 | None | 6 | 1.00 ± 0.20 | 472 ± 166 | 2.20 ± 0.11 | 554 ± 221 |
| 1 | S1C(disialo)-SRIF28 | 1 | 15 | 16.9 ± 1.02 | 4855 ± 1030 | 18.6 ± 1.72 | 686 ± 363 |
| 2 | N5C(disialo)-SRIF28 | 1 | 6 | 20.1 ± 1.49 | 4421 ± 1366 | 22.9 ± 2.16 | 496 ± 312 |
| 3 | A9C(disialo)-SRIF28 | 1 | 3 | 19.9 ± 0.33 | 4083 ± 515 | 25.2 ± 0.38 | 547 ± 211 |
| | Average value | | | 19.0 | 4453 | 22.2 | 576.3 |
| 20 | S1-2C(disialo)-SRIF28 | 2 (dense) | 3 | 28.8 ± 3.11 | 7306 ± 625 | 23.3 ± 2.63 | 1382 ± 321 |
| 21 | S1C(disialo)•N5C(disialo)-SRIF28 | 2 (with intervals) | 6 | 25.8 ± 3.41 | 4099 ± 634 | 24.6 ± 5.97 | 558 ± 248 |
| 22 | S1C(disialo)•R13C(disialo)-SRIF28 | 2 (with intervals) | 3 | 23.4 ± 0.66 | 4029 ± 184 | 20.6 ± 1.32 | 822 ± 106 |
| 23 | N5C(disialo)•A9C(disialo)-SRIF28 | 2 (with intervals) | 3 | 32.4 ± 1.66 | 4465 ± 833 | 26.6 ± 0.27 | 664 ± 104 |
| | | | | 27.2 | 4198 | 23.9 | 681.3 |
| 24 | S1-3C(disialo)-SRIF28 | 3 (dense) | 6 | 38.5 ± 2.83 | 5660 ± 1354 | 24.0 ± 3.92 | 1061 ± 209 |
| 25 | S1C(disialo)•N5C(disialo)•A9C(disialo)-SRIF28 | 3 (with intervals) | 9 | 39.8 ± 1.87 | 4402 ± 999 | 25.8 ± 2.87 | 938 ± 145 |
| 34 | S1-5C(disialo)-SRIF28 | 5 (dense) | 3 | 99.5 ± 14.0 | 6016 ± 873 | 49.0 ± 6.06 | 752 ± 81.4 |
| 35 | S1-10C(disialo)-SRIF28 | 1.0 (dense) | 3 | 219 ± 6.27 | 100259 ± 10463 | 272 ± 14.3 | 821 ± 264 |

| | Compound | Subcutaneous administration | | | | |
|---|---|---|---|---|---|---|
| | | $t_{1/2}$ | AUC | MRT | $C_{max}$ | BA |
| — | SRIF28 | 2.94 ± 1.59 | 25.5 ± 13.8 | 4.76 ± 1.80 | 4.47 ± 1.21 | 5 |
| 1 | S1C(disialo)-SRIF28 | 29.8 ± 2.68 | 1773 ± 281 | 47.9 ± 2.68 | 28.9 ± 3.23 | 37 |
| 2 | N5C(disialo)-SRIF28 | 28.1 ± 3.72 | 2392 ± 443 | 51.9 ± 5.92 | 32.4 ± 4.87 | 54 |
| 3 | A9C(disialo)-SRIF28 | 30.3 ± 2.45 | 2462 ± 64.0 | 55.6 ± 5.81 | 30.2 ± 5.05 | 60 |
| | Average value | 29.4 | 2209 | 51.8 | 30.5 | 50 |
| 20 | S1-2C(disialo)-SRIF28 | 40.9 ± 12.2 | 4046 ± 248 | 67.9 ± 15.0 | 46.3 ± 9.75 | 55 |
| 21 | S1C(disialo)•N5C(disialo)-SRIF28 | 38.4 ± 4.93 | 3344 ± 663 | 67.9 ± 8.39 | 35.5 ± 6.38 | 82 |
| 22 | S1C(disialo)•R13C(disialo)-SRIF28 | 39.6 ± 2.50 | 3407 ± 436 | 67.7 ± 5.39 | 38.7 ± 8.73 | 85 |
| 23 | N5C(disialo)•A9C(disialo)-SRIF28 | 42.7 ± 9.76 | 3450 ± 784 | 75.0 ± 12.4 | 32.5 ± 7.06 | 77 |
| | | 40.2 | 3400 | 70.2 | 35.6 | 81 |
| 24 | S1-3C(disialo)-SRIF28 | 87.7 ± 21.4 | 3884 ± 543 | 126 ± 31.7 | 27.5 ± 10.8 | 69 |
| 25 | S1C(disialo)•N5C(disialo)•A9C(disialo)-SRIF28 | 87.4 ± 17.1 | 4015 ± 944 | 132 ± 19.8 | 24.8 ± 9.03 | 91 |
| 34 | S1-5C(disialo)-SRIF28 | 271 ± 38.7 | 5524 ± 633 | 389 ± 50.0 | 13.5 ± 2.85 | 92 |
| 35 | S1-10C(disialo)-SRIF28 | >480 | — | — | 45.9 ± 2.32 | — |

($t_{1/2}$: min, AUC: min · nM, MRT: min, $C_0$: nM, $C_{max}$: nM, BA: %)

As is clear from the results shown in Table 5A, the bioavailability of the glycosylated form of the present invention increased as the number of modifying sugar chains increased. In other words, what was 5% in the non-glyco- to somatostatin without any glycosylation, and a further improved bioavailability could be obtained by adding two or more sugar chains compared to those having one sugar chain added.

As factors for the increase in bio-availability for subcutaneous administration, various pharmacokinetic factors exist. Among these factors, some are thought to be the stability of the compound in blood, or transitivity into the blood (from the administration site). As shown in Table 5A, it is recognized that the AUC for subcutaneous administration which will be an indicator for speculating the transit to blood for subcutaneous administration will increase with the increase in the number of modifying sugar chains (1: 2209 min·nM, 2 (with intervals): 3400 min·nM, and 3 (with intervals): 4015 min·nM), and it was speculated to contribute to improvement bioavailability.

Moreover, it was recognized that as the number of modifying sugar chains increased, $t_{1/2}$ and MRT extension effect for intravenous and subcutaneous administrations (for example, $t_{1/2}$ for intravenous administration was 1: 19.0 min, 2 (with intervals): 27.2 min, and 3 (with intervals): 39.8 min), and it was speculated that stability in blood was improved. On the other hand, AUC for intravenous administration was not an increase in proportion to the number of modifying sugar chains (1: 4453 min·nM, 2 (with intervals): 4198 min·nM, and 3 (with intervals): 4402 min·nM), and it is thought that the increase in the stability in blood of the compound by the increase in the number of modifying sugar chains is not the only factor contributing to the increase in bioavailability.

$C_{max}$ for subcutaneous administration increased compared to the non-glycosylated form up until the number of modifying sugar chains was two (0: 4.47 nM, 1: 30.5 nM, and 2 (with intervals): 35.6 nM), and three (with intervals) (24.8 nM) resulted in an adverse decrease. When considering blood transit from the administration site (subcutaneous administration in the present Example), speculated factors for the increase in AUC are two formats of rapid transit to blood, or mild but continuous transit to blood. The former has the advantage of avoiding degradation at the administration site, but if there is no problem in stability, it is speculated that the latter format has a higher transit in blood. The fact that $C_{max}$ had decreased in those having three modifying sugar chains with high bioavailability is thought to be the result showing not a sudden but a mild and continuous migration in blood. From this, it is thought that the increase in the number of modifying sugar chains related to the present invention shows a continuous migration in blood without a rapid rise in plasma concentration (may generally be referred to as absorption delaying effect).

As is clear from the results shown in Table 5A, there was no significant difference in $t_{1/2}$ and MRT when the modifying positions had intervals and when they were dense (for example, $t_{1/2}$ for intravenous administration was 2 (dense): 28.8 min, 2 (with intervals): 27.2 min, 3 (dense): 38.5 min, and 3 (with intervals): 39.8 min).

Moreover, with respect to AUC, for intravenous administration, AUC was increased when glycosylation was dense. In other words, for two sugar chains, this was 4029-4465 min·nM for compounds 21, 22, and 23 with intervals as opposed to 7306 min·nM for a dense compound 20, and for three sugar chains, compound 25 with intervals was 4402 min·nM whereas a dense compound 24 was 5660 min·nM.

On the other hand, bioavailability increased when there were intervals in the glycosylation positions compared to when they were dense. In other words, for two sugar chains, a dense compound 20 was 55% whereas compounds 21, 22, and 23 with intervals were 77-85% (81% on average), and for three sugar chains, a dense compound 24 was 69% whereas compound 25 with intervals was 91%. From this, it is thought that for glycosylation positions related to the present invention, multiple modifications with intervals contribute more to the improvement of bioavailability than dense multiple modifications.

Example 76 Pharmacokinetics Test with Rats 7

Figure 8:
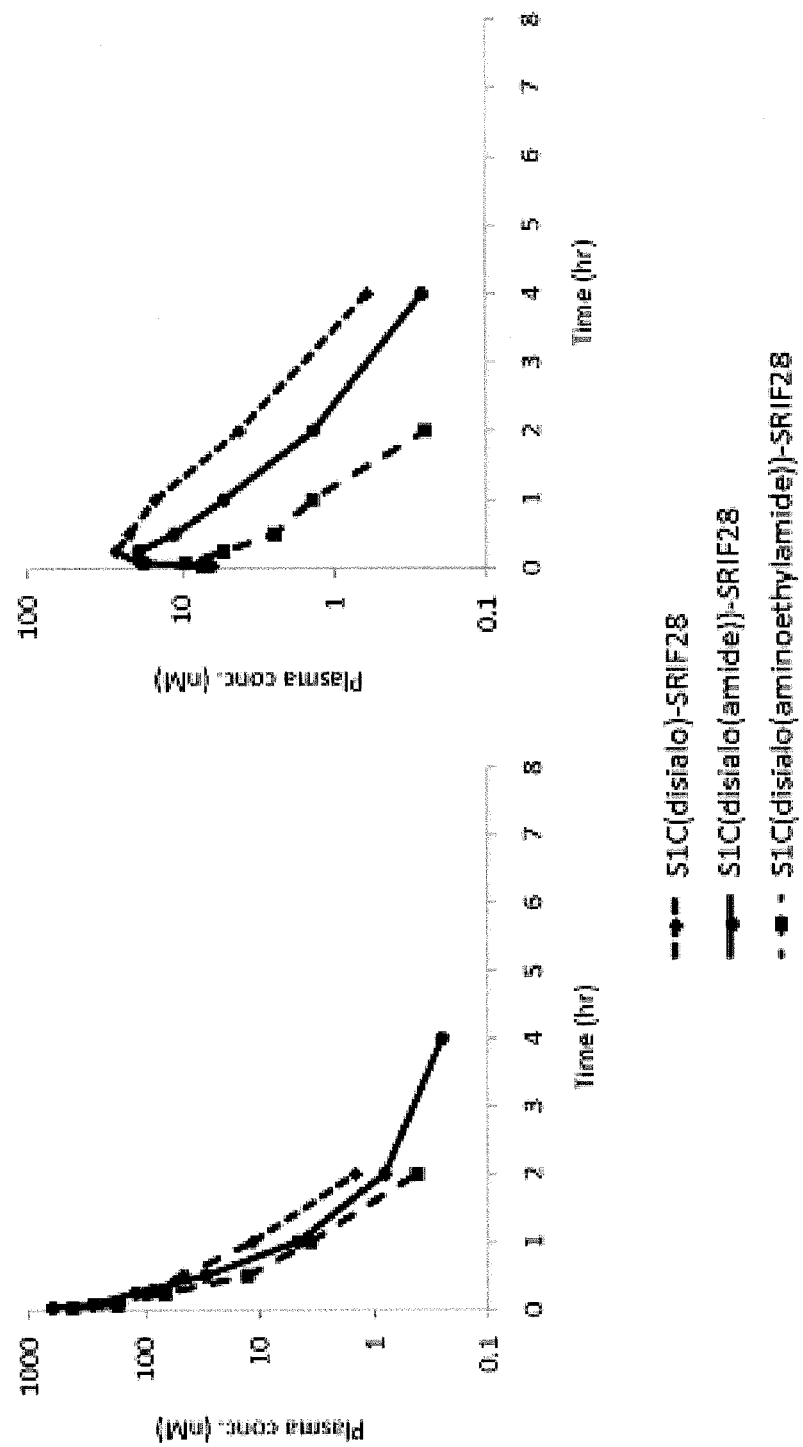
FIG. 8 is graphs showing the plasma concentration transition when S1C(disialo)-SRIF28, S1C(disialo(amide))-SRIF28, and S1C(disialo(aminoethylamide))-SRIF28 were administered intravenously and subcutaneously to rats.

A pharmacokinetics test was carried out similarly to Example 70, except that S1C(disialo)-SRIF28, S1C(disialo (amide))-SRIF28, and S1C(disialo(aminoethylamide))-SRIF28 were employed as the glycosylated forms. The compound plasma concentration transition obtained is shown in FIG. 8.

Example 77 Pharmacokinetics Test with Rats 8

Figure 9:
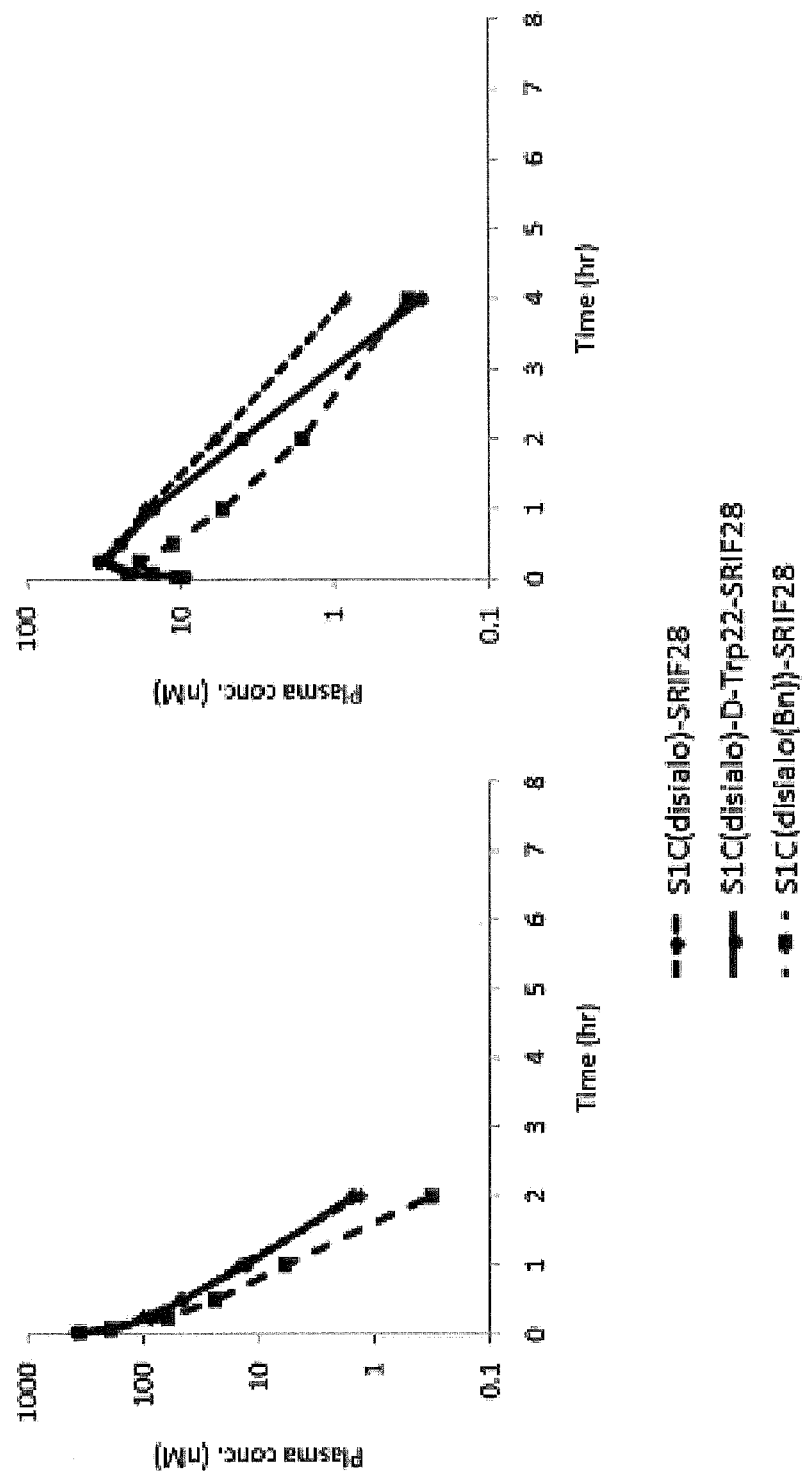
FIG. 9 is graphs showing the plasma concentration transition when S1C(disialo)-SRIF28, S1C(disialo)-D-Trp22-SRIF28, and S1C(disialo(Bn))-SRIF28 were administered intravenously and subcutaneously to rats.

A pharmacokinetics test was carried out similarly to Example 70, except that S1C(disialo)-SRIF28, S1C(disialo (Bn))-SRIF28, and S1C(disialo)-D-Trp22-SRIF28 were employed as the glycosylated forms. The compound plasma concentration transition obtained is shown in FIG. 9.

Example 78 Pharmacokinetics Test with Rats 9

Figure 10:
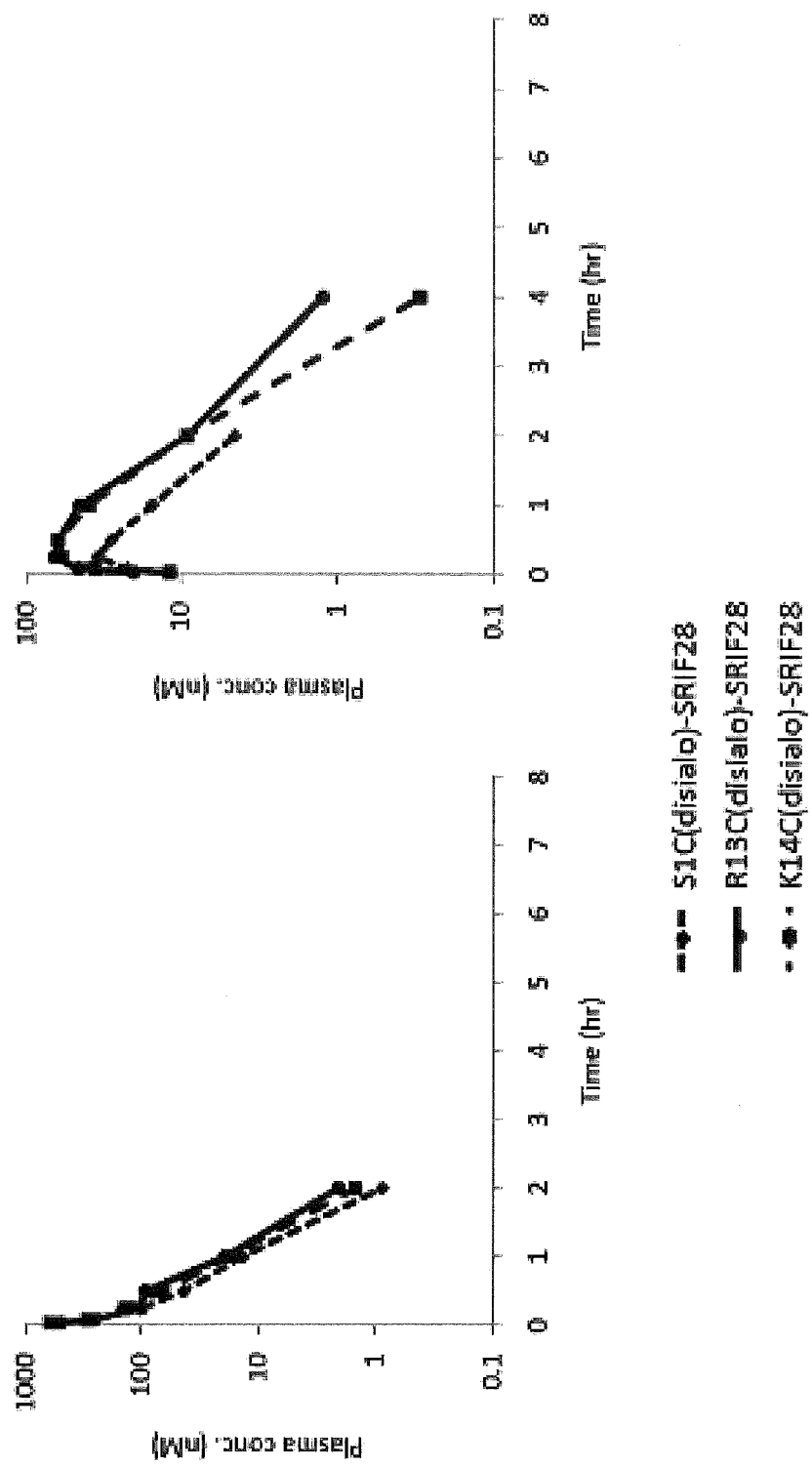
FIG. 10 is graphs showing the plasma concentration transition when S1C(disialo)-SRIF28, R13C(disialo)-SRIF28, and K14C(disialo)-SRIF28 were administered intravenously and subcutaneously to rats.

A pharmacokinetics test was carried out similarly to Example 70, except that S1C(disialo)-SRIF28, R13C(disialo)-SRIF28, and K14C(disialo)-SRIF28 were employed as the glycosylated forms. The compound plasma concentration transition obtained is shown in FIG. 10.

Example 79 Pharmacokinetics Test with Rats 10

Figure 11:
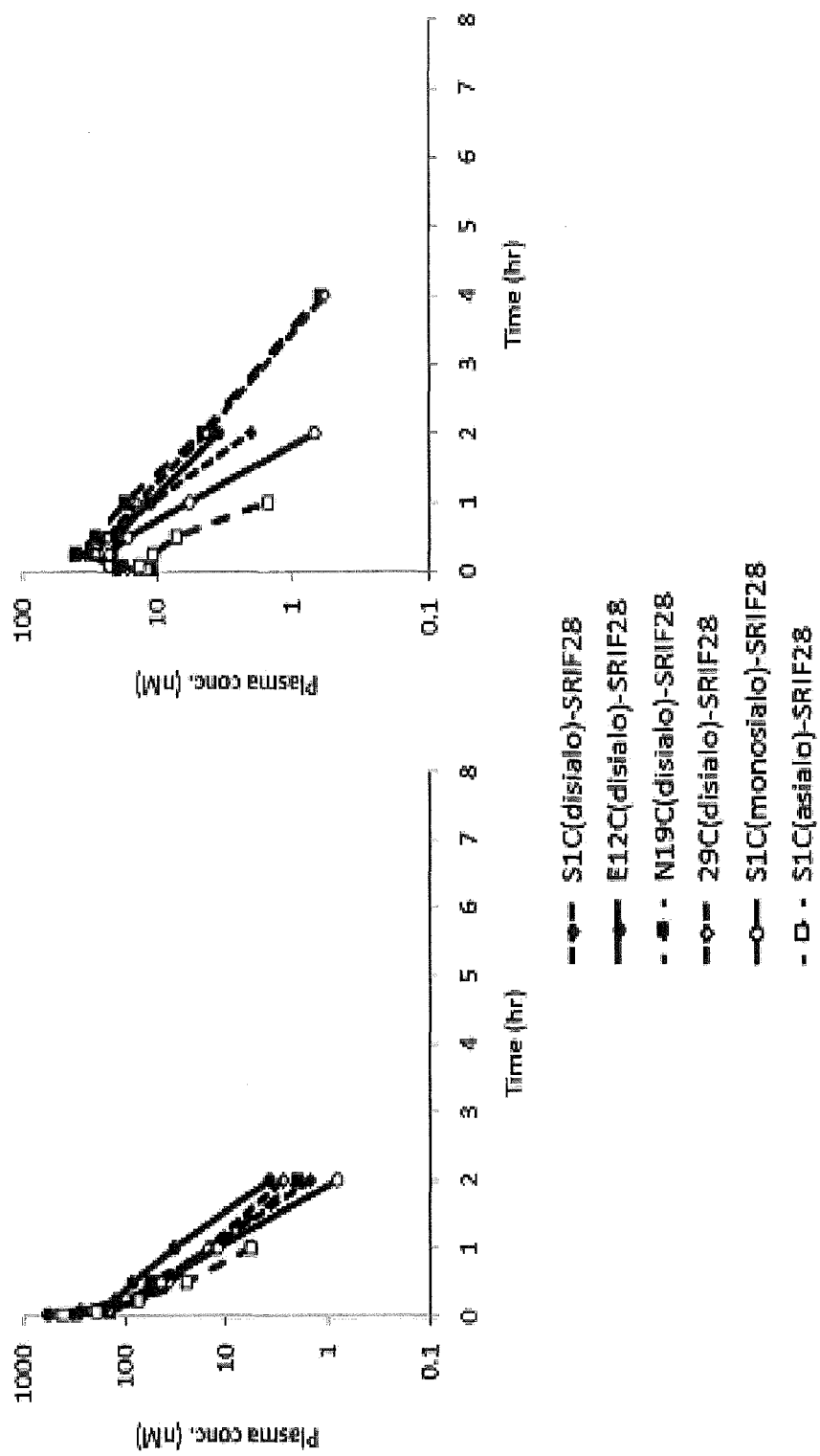
FIG. 11 is graphs showing the plasma concentration transition when S1C(disialo)-SRIF28, E12C(disialo)-SRIF28, N19C(disialo)-SRIF28, 29C(disialo)-SRIF28, S1C(monosialo)-SRIF28, and S1C(asialo)-SRIF28 were administered intravenously and subcutaneously to rats.

A pharmacokinetics test was carried out similarly to Example 70, except that S1C(disialo)-SRIF28, E12C(disialo)-SRIF28, N19C(disialo)-SRIF28, 29C(disialo)-SRIF28, S1C(monosialo)-SRIF28, and S1C(asialo)-SRIF28 were employed as the glycosylated forms. The compound plasma concentration transition obtained is shown in FIG. 11.

Example 80 Pharmacokinetics Test with Rats 11

Figure 12:
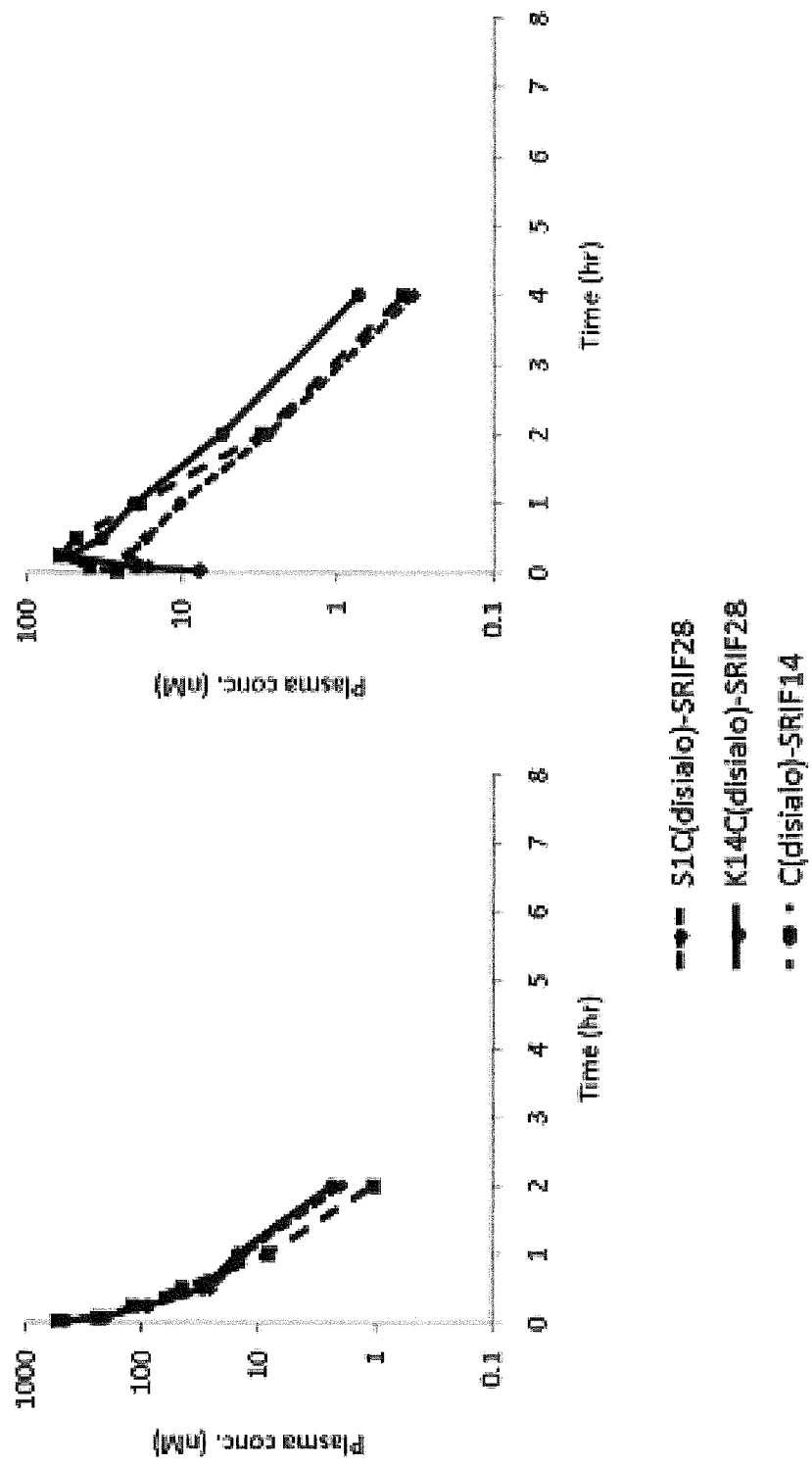
FIG. 12 is graphs showing the plasma concentration transition when S1C(disialo)-SRIF28, K14C(disialo)-SRIF28, and C(disialo)-SRIF14 were administered intravenously and subcutaneously to rats.

A pharmacokinetics test was carried out similarly to Example 70, except that S1C(disialo)-SRIF28, K14C(disialo)-SRIF28, and C(disialo)-SRIF14 were employed as the glycosylated forms. The compound plasma concentration transition obtained is shown in FIG. 12.

Example 81 Pharmacokinetics Test with Rats 12

Figure 13:
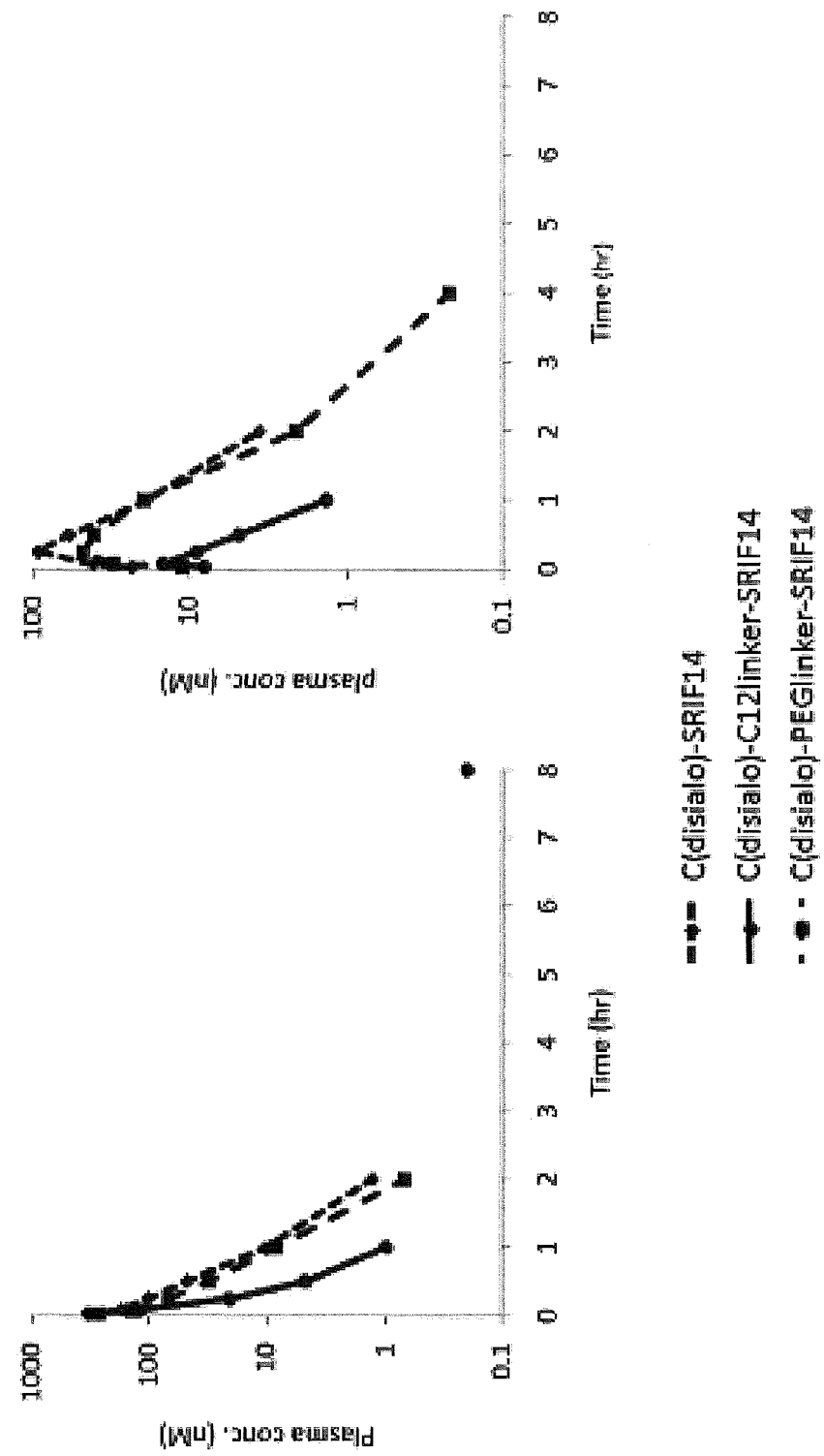
FIG. 13 is graphs showing the plasma concentration transition when C(disialo)-SRIF14, C(disialo)-C12 linker-SRIF14, and C(disialo)-PEG linker-SRIF14 were administered intravenously and subcutaneously to rats.

A pharmacokinetics test was carried out similarly to Example 70, except that C(disialo)-SRIF14, C(disialo)-C12 linker-SRIF14, and C(disialo)-PEG linker-SRIF14 were employed as the glycosylated forms. The compound plasma concentration transition obtained is shown in FIG. 13.

Example 82 Pharmacokinetics Test with Rats 13

Figure 14:
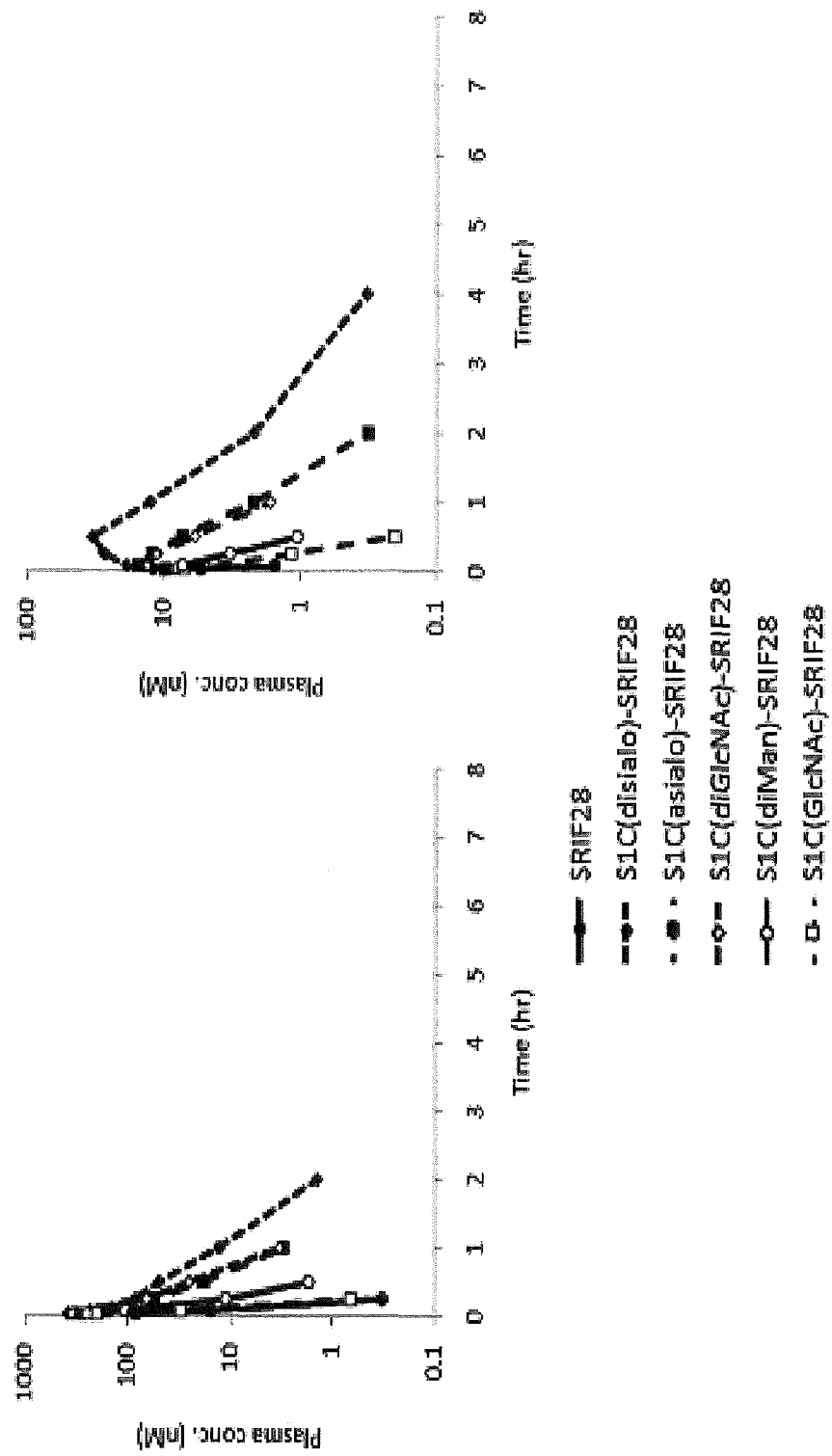
FIG. 14 is graphs showing the plasma concentration transition when SRIF28, S1C(disialo)-SRIF28, S1C(asialo)-SRIF28, S1C(diGlcNAc)-SRIF28, S1C(diMan)-SRIF28, and S1C(GlcNAc)-SRIF28 were administered intravenously and subcutaneously to rats.

A pharmacokinetics test was carried out similarly to Example 70, except that SRIF28, S1C(disialo)-SRIF28, S1C(asialo)-SRIF28, S1C(diGlcNAc)-SRIF28, S1C(diMan)-SRIF28, and S1C(GlcNAc)-SRIF28 were employed as the glycosylated forms. The compound plasma concentration transition obtained is shown in FIG. 14.

Example 83 Pharmacokinetics Test with Rats 14

Figure 15:
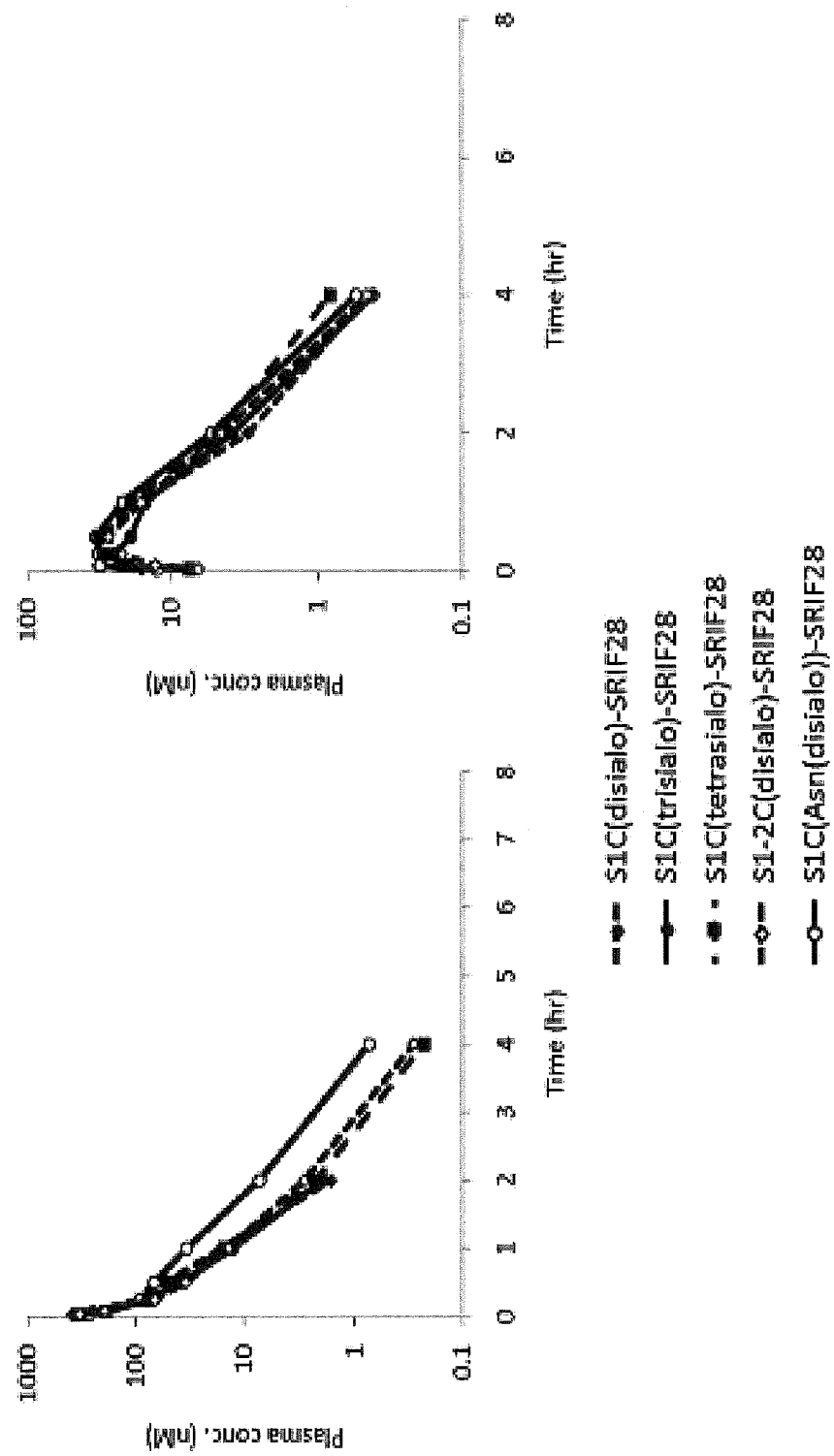
FIG. 15 is graphs showing the plasma concentration transition when S1C(disialo)-SRIF28, S1C(trisialo)-SRIF28, S1C(tetrasialo)-SRIF28, S1-2C(disialo)-SRIF28, and S1C(Asn(disialo))-SRIF28 were administered intravenously and subcutaneously to rats.

A pharmacokinetics test was carried out similarly to Example 70, except that S1C(disialo)-SRIF28, S1C(tetrasialo)-SRIF28, S1C(trisialo)-SRIF28, S1C(Asn(disialo))-SRIF28, and S1-2C(disialo)-SRIF28 were employed as the glycosylated forms. The compound plasma concentration transition obtained is shown in FIG. 15.

Example 84 Pharmacokinetics Test with Rats 15

Figure 16:
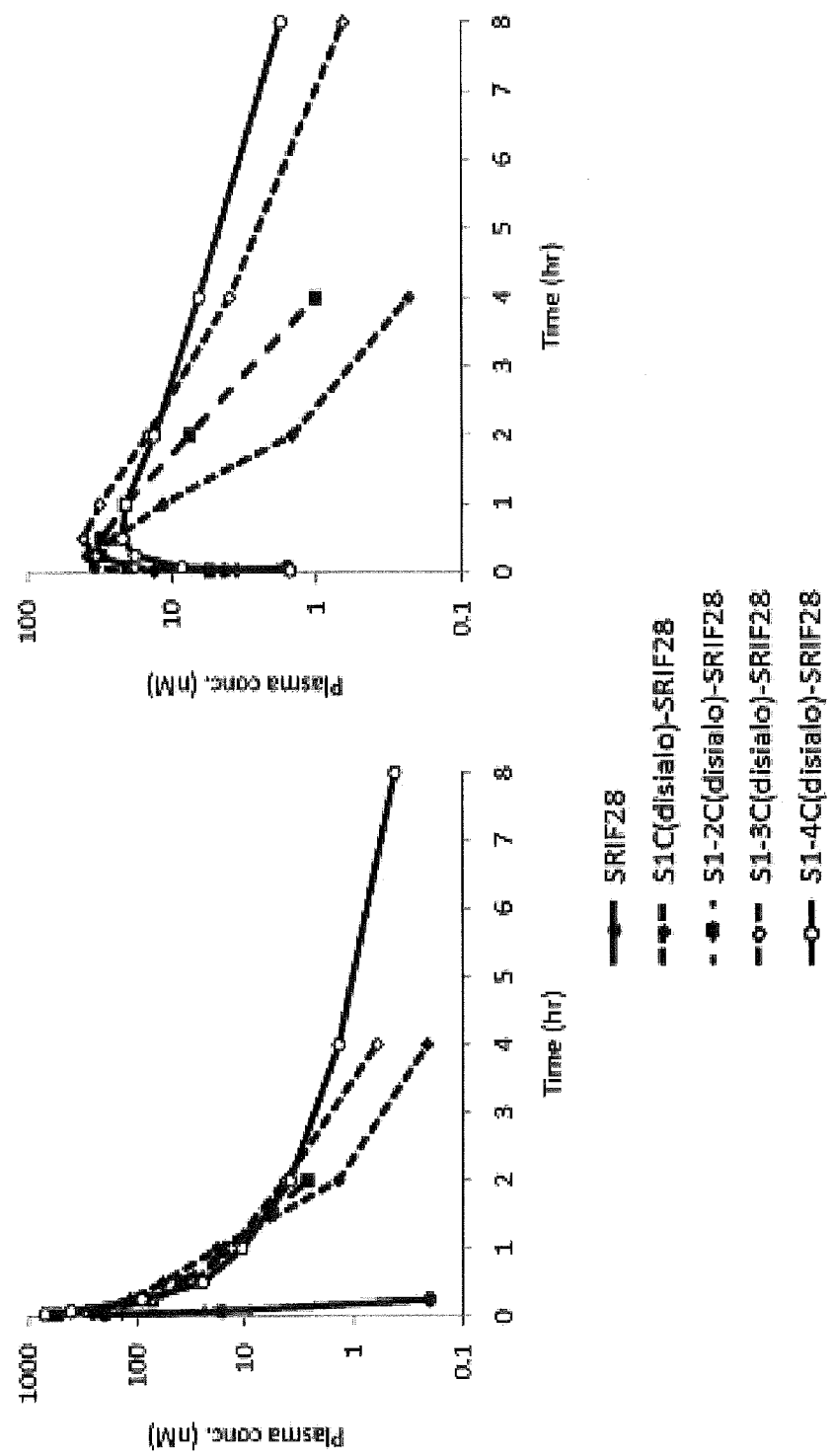
FIG. 16 is graphs showing the plasma concentration transition when SRIF28, S1C(disialo)-SRIF28, S1-2C(disialo)-SRIF28, S1-3C(disialo)-SRIF28, and S1-4C(disialo)-SRIF28 were administered intravenously and subcutaneously to rats.

A pharmacokinetics test was carried out similarly to Example 70, except that SRIF28, S1C(disialo)-SRIF28, S1-2C(disialo)-SRIF28, S1-3C(disialo)-SRIF28, and S1-4C(disialo)-SRIF28 were employed as the glycosylated forms. The compound plasma concentration transition obtained is shown in FIG. 16.

Example 85 Pharmacokinetics Test with Rats 16

Figure 17:
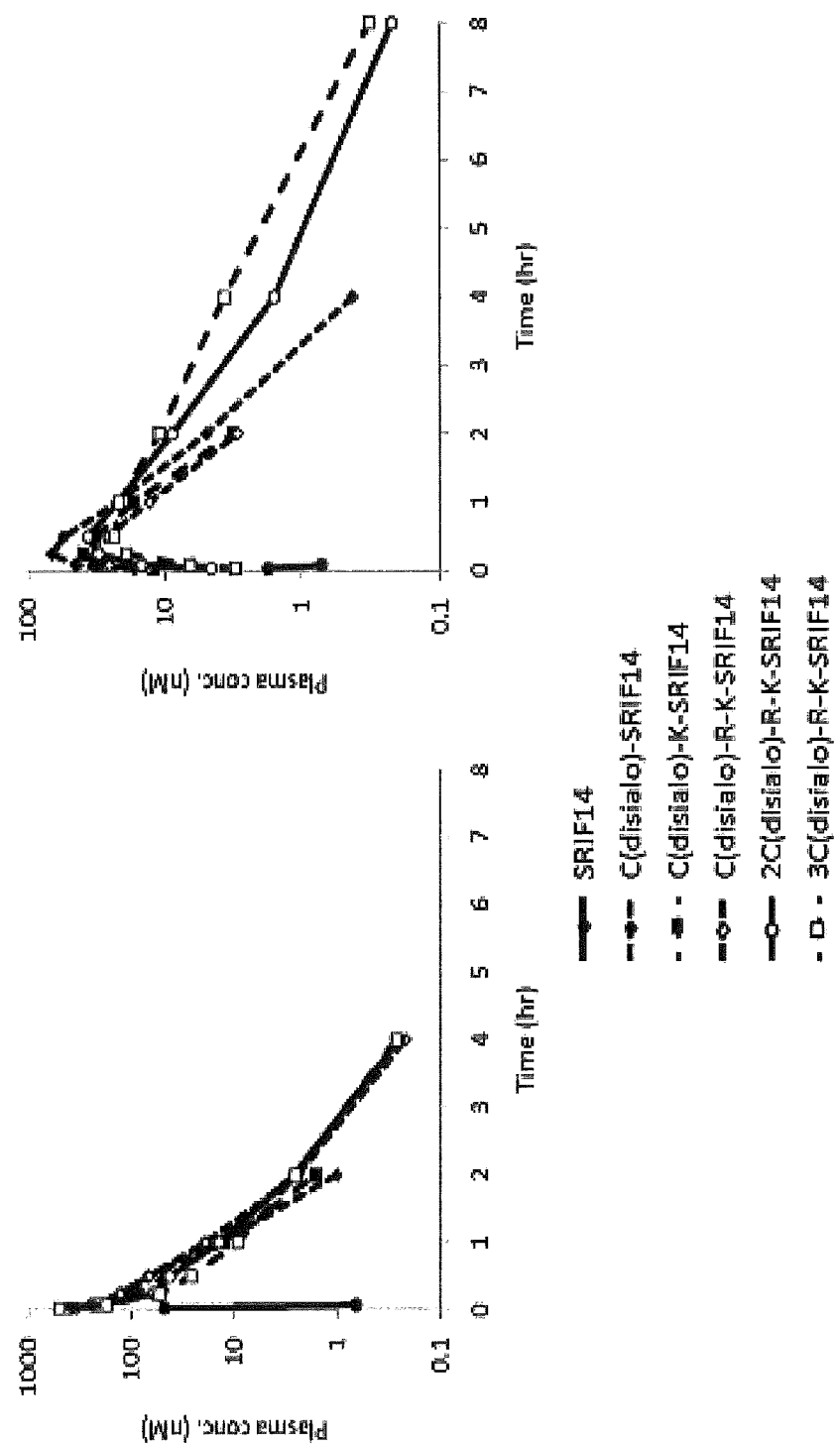
FIG. 17 is graphs showing the plasma concentration transition when SRIF14, C(disialo)-SRIF14, C(disialo)-K-SRIF14, C(disialo)-R-K-SRIF14, 2C(disialo)-R-K-SRIF14, and 3C(disialo)-R-K-SRIF14 were administered intravenously and subcutaneously to rats.

A pharmacokinetics test was carried out similarly to Example 70, except that SRIF14, C(disialo)-SRIF14, C(disialo)-K-SRIF14, C(disialo)-R-K-SRIF14, 2C(disialo)-R-K-SRIF14, and 3C(disialo)-R-K-SRIF14 were employed as the glycosylated forms. The compound plasma concentration transition obtained is shown in FIG. 17.

Example 86 Pharmacokinetics Test with Rats 17

Figure 18:
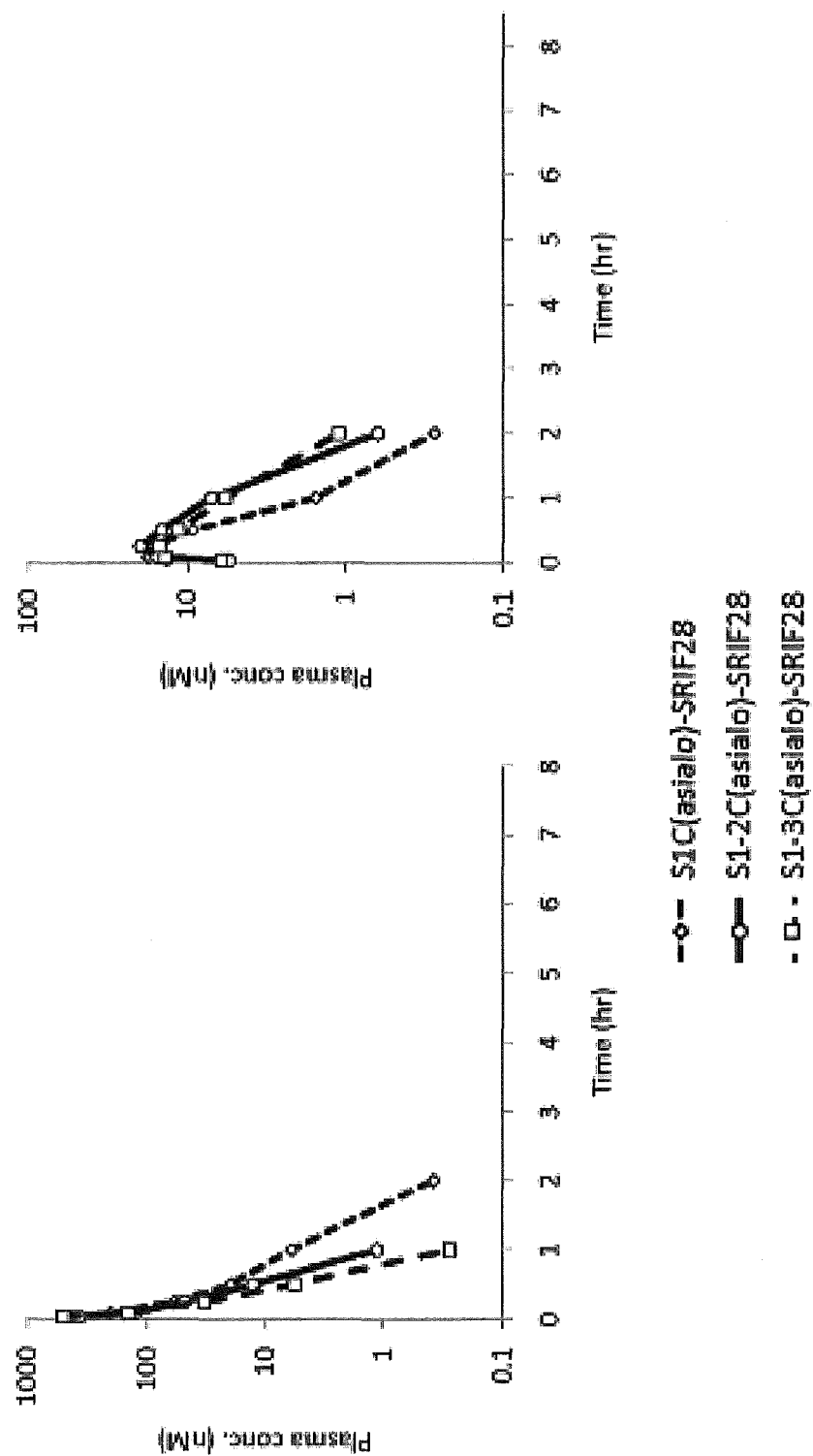
FIG. 18 is graphs showing the plasma concentration transition when S1C(asialo)-SRIF28, S1-2C(asialo)-SRIF28, and S1-3C(asialo)-SRIF28 were administered intravenously and subcutaneously to rats.

A pharmacokinetics test was carried out similarly to Example 70, except that S1C(asialo)-SRIF28, S1-2C(asialo)-SRIF28, and S1-3C(asialo)-SRIF28 were employed as the glycosylated forms. The compound plasma concentration transition obtained is shown in FIG. 18.

Example 87 Pharmacokinetics Test with Rats 18

Figure 19:
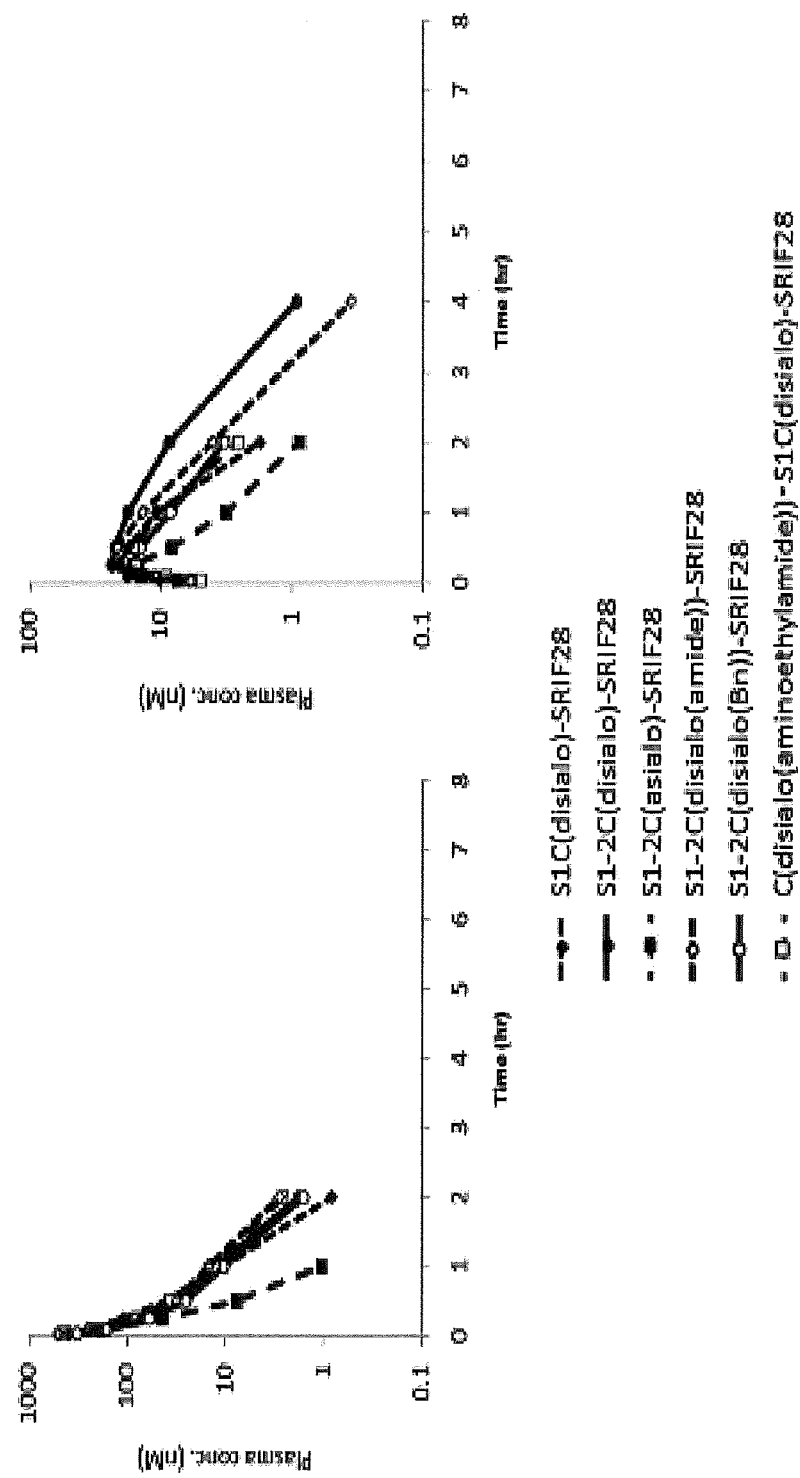
FIG. 19 is graphs showing the plasma concentration transition when S1C(disialo)-SRIF28, S1-2C(disialo)-SRIF28, S1-2C(asialo)-SRIF28, S1-2C(disialo(amide))-SRIF28, S1-2C(disialo(Bn))-SRIF28, and C(disialo(aminoethylamide))-S1C(disialo)-SRIF28 were administered intravenously and subcutaneously to rats.

A pharmacokinetics test was carried out similarly to Example 70, except that S1C(disialo)-SRIF28, S1-2C(disialo)-SRIF28, S1-2C(asialo)-SRIF28, C(disialo(aminoethylamide)/S1C(disialo)-SRIF28, S1-2C(disialo(Bn))-SRIF28, and S1-2C(disialo(amide))-SRIF28 were employed as the glycosylated forms. The compound plasma concentration transition obtained is shown in FIG. 19.

From the compound plasma concentration transition obtained in pharmacokinetics tests 7-18 of Examples 76-87, the pharmacokinetics parameters of each compound were calculated similarly to Example 70. The pharmacokinetics parameters obtained are shown in Tables 5B-5F.

TABLE 5B

| Example | | Intravenous administration | | | | Subcutaneous administration | | | | |
|---|---|---|---|---|---|---|---|---|---|---|
| | | $T_{1/2}$ | AUC | MRT | $C_0$ | $T_{1/2}$ | AUC | MRT | Cmax | BA |
| — | SRIF14 | 0.500 | 119 | 2.00 | 819 | 2.30 | 8 | 4.30 | 1.80 | 7 |
| — | SRIF28 | 1.32 | 467 | 2.46 | 518 | 2.38 | 22 | 4.18 | 4.65 | 5 |
| 1 | S1C(disialo)-SRIF28 | 17.7 | 5190 | 19.1 | 633 | 31.2 | 1946 | 49.2 | 30.1 | 38 |
| 4 | E12C(disialo)-SRIF28 | 19.5 | 10521 | 27.5 | 1086 | 38.2 | 2891 | 57.5 | 34.7 | 27 |
| 5 | R13C(disialo)-SRIF28 | 20.3 | 4926 | 22.8 | 481 | 35.4 | 5528 | 55.9 | 65.9 | 78 |
| 6 | K14C(disialo)-SRIF28 | 20.4 | 6278 | 20.0 | 884 | 35.1 | 3945 | 55.1 | 57.5 | 62 |
| 10 | N19C(disialo)-SRIF28 | 18.8 | 3854 | 21.5 | 407 | 37.9 | 2624 | 55.3 | 41.7 | 56 |
| 13 | 29C(disialo)-SRIF28 | 23.7 | 3736 | 25.3 | 359 | 39.3 | 2176 | 57.6 | 29.4 | 51 |
| 15 | S1C(disialo)-D-Trp-SRIF28 | 18.3 | 4924 | 20.6 | 588 | 31.0 | 2220 | 51.9 | 34.0 | 45 |
| 18 | C(disialo)-R-K-SRIF14 | 18.9 | 6571 | 22.5 | 429 | 28.4 | 1996 | 45.2 | 32.5 | 30 |
| 42 | C(disialo)-K-SRIF14 | 18.8 | 5277 | 19.4 | 646 | 26.4 | 2446 | 43.7 | 40.5 | 46 |
| 17 | C(disialo)-SRIF14 | 16.5 | 5614 | 18.3 | 725 | 27.2 | 3641 | 40.0 | 73.6 | 66 |
| 19 | C(disialo)-C12linker-SRIF14 | 11.0 | 1686 | 7.60 | 500 | 14.4 | 345 | 22.0 | 13.4 | 21 |
| 43 | C(disialo)-PEGlinker-SRIF14 | 16.4 | 3538 | 18.8 | 412 | 20.7 | 2725 | 39.2 | 47.8 | 77 |

As is clear from the results shown in Table 5B, S1C(disialo)-SRIF28, E12C(disialo)-SRIF28, R13C(disialo)-SRIF28, K14C(disialo)-SRIF28, N19C(disialo)-SRIF28, and 29C(disialo)-SRIF28, S1C(disialo)-D-Trp22-SRIF28 extended $t_{1/2}$ by 13-18-folds and increased AUC by 8-23-folds compared to the non-glycosylated form SRIF28 when administered intravenously. Moreover, C(disialo)-SRIF14, C(disialo)-K-SRIF14, and C(disialo)-R-K-SRIF14 extended $t_{1/2}$ by 33-38-folds and increased AUC by 44-55-folds compared to the non-glycosylated form SRIF14 when administered intravenously. Moreover, C(disialo)-C12 linker-SRIF14 and C(disialo)-PEG linker-SRIF14 extended $t_{1/2}$ by 22-33-folds and increased AUC by 14-30-folds compared to the non-glycosylated form SRIF14. In other words, similarly to Example 70, this was thought to be the result of improved stability in blood by glycosylation.

TABLE 5C

| Example | | Intravenous administration | | | | Subcutaneous administration | | | | |
|---|---|---|---|---|---|---|---|---|---|---|
| | | $T_{1/2}$ | AUC | MRT | $C_0$ | $T_{1/2}$ | AUC | MRT | Cmax | BA |
| — | SRIF28 | 1.32 | 467 | 2.46 | 518 | 2.38 | 22 | 4.18 | 4.65 | 5 |
| 55 | S1C(GlcNAc)-SRIF28 | 1.80 | 690 | 3.00 | 666 | 5.90 | 63 | 7.90 | 7.10 | 9 |

TABLE 5C-continued

| Example | | Intravenous administration | | | | Subcutaneous administration | | | | |
|---|---|---|---|---|---|---|---|---|---|---|
| | | $T_{1/2}$ | AUC | MRT | $C_0$ | $T_{1/2}$ | AUC | MRT | Cmax | BA |
| 53 | S1C(diMan)-SRIF28 | 5.50 | 1445 | 5.20 | 423 | 9.10 | 124 | 13.9 | 7.30 | 9 |
| 52 | S1C(diGlcNAc)-SRIF28 | 10.5 | 3588 | 12.3 | 495 | 16.5 | 445 | 25.7 | 13.2 | 12 |
| 27 | S1C(asialo)-SRIF28 | 13.4 | 4602 | 12.5 | 749 | 19.7 | 710 | 29.0 | 17.2 | 16 |
| 26 | S1C(monosialo)-SRIF28 | 15.9 | 6618 | 15.3 | 1061 | 24.5 | 995 | 37.8 | 19.4 | 17 |
| 1 | S1C(disialo)-SRIF28 | 17.7 | 5190 | 19.1 | 633 | 31.2 | 1946 | 49.2 | 30.1 | 38 |
| 57 | S1C(trisialo)-SRIF28 | 21.1 | 4428 | 22.0 | 423 | 36.6 | 1979 | 56.9 | 24.9 | 45 |
| 58 | S1C(tetrasialo)-SRIF28 | 20.9 | 4851 | 23.0 | 471 | 40.5 | 2624 | 59.4 | 32.2 | 54 |
| 65 | S1C(Asn(disialo))-SRIF28 | 27.9 | 6488 | 35.9 | 365 | 34.0 | 2935 | 55.3 | 33.9 | 45 |
| 59 | S1C(disialo(aminoethylamide))-SRIF28 | 18.6 | 3473 | 12.1 | 746 | 27.1 | 284 | 33.2 | 9.60 | 8 |
| 60 | S1C(disialo(amide))-SRIF28 | 18.0 | 5814 | 12.6 | 1048 | 30.0 | 961 | 42.5 | 19.1 | 17 |
| 61 | S1C(disialo(Bn))-SRIF28 | 14.4 | 3708 | 14.5 | 526 | 45.5 | 1047 | 52.6 | 18.7 | 28 |

As is clear from the results shown in Table 5C, when the size of the modifying sugar chain is altered to GlcNAc (monosaccharide), diMan (5 sugars), diGlcNAc (7 sugars), asialo (9 sugars), monosialo (10 sugars), disialo (11 sugars), trisialo (14 sugars), and tetrasialo (17 sugars), the $t_{1/2}$, AUC, and bioavailability when administered subcutaneously increased to 2-17-folds, 3-120-folds, and 2-11-folds, respectively, according to the size of the modifying sugar chain. From this, it became clear that altering the size of the modifying sugar chain not only improved the stability in blood, but allowed change in its increase rate. Moreover, since it is known that dimannose or asialo sugar chains etc. among these sugar chains interact with particular proteins, they are thought to be utilizable for targeting a particular protein or organs and cells having the particular protein.

Moreover, as modification of the sialic acid at the non-reducing terminal, S1C(disialo(aminoethylamide))-SRIF28, S1C(disialo(amide))-SRIF28, and S1C(disialo(Bn))-SRIF28 having added a sugar chain with altered charge by e.g. the introduction of an aminoethylamide, amide, and Bn to the carboxy group extended $t_{1/2}$ by 11-14-folds and increased AUC by 7-12-folds, and improved stability in blood compared to the non-glycosylated form when administered intravenously. This shows that the carboxy group of the sialic acid has a large influence on retentivity in blood, and shows the possibility for (usage in) blood clearance or body distribution control by abstraction of the negative charge of the carboxy group (disialo(Bn) and disialo(amide)) or conversion into a positive charge (disialo(aminoethylamide)).

TABLE 5D

| Example | | Intravenous administration | | | | Subcutaneous administration | | | | |
|---|---|---|---|---|---|---|---|---|---|---|
| | | $T_{1/2}$ | AUC | MRT | $C_0$ | $T_{1/2}$ | AUC | MRT | Cmax | BA |
| — | SRIF14 | 0.500 | 119 | 2.00 | 819 | 2.30 | 8 | 4.30 | 1.80 | 7 |
| — | SRIF28 | 1.32 | 467 | 2.46 | 518 | 2.38 | 22 | 4.18 | 4.65 | 5 |
| 18 | C(disialo)-R-K-SRIF14 | 18.9 | 6571 | 22.5 | 429 | 28.4 | 1996 | 45.2 | 32.5 | 30 |
| 50 | 2C(disialo)R-K-SRIF14 | 31.7 | 5041 | 24.1 | 704 | 47.7 | 3310 | 73.4 | 36.7 | 66 |
| 51 | 3C(disialo)R-K-SRIF14 | 35.7 | 4288 | 22.2 | 1013 | 70.6 | 3515 | 112 | 23.5 | 82 |
| 1 | S1C(disialo)-SRIF28 | 17.7 | 5190 | 19.1 | 633 | 31.2 | 1946 | 49.2 | 30.1 | 38 |
| 20 | S1-2C(disialo)-SRIF28 | 28.2 | 5804 | 23.0 | 950 | 40.8 | 3091 | 65.3 | 34.6 | 53 |
| 24 | S1-3C(disialo)-SRIF28 | 39.5 | 5834 | 23.8 | 1083 | 79.3 | 4174 | 115 | 30.7 | 72 |
| 68 | S1-4C(disialo)-SRIF28 | 63.5 | 7070 | 25.2 | 1007 | 119 | 4554 | 172 | 22.0 | 64 |

As is clear from the results shown in Table 5D, C(disialo)-R-K-SRIF14 modified with one disialosugar chain, 2C(disialo)-R-K-SRIF14 modified with two disialosugar chains, and 3C(disialo)-R-K-SRIF14 modified with three disialosugar chains on SRIF14 each extended $t_{1/2}$ by 38, 63, and 71-folds and increased AUC by 55, 42, and 36-folds compared to the non-glycosylated form when administered intravenously. Similarly, S1C(disialo)-SRIF28 modified with one disialosugar chain, S1-2C(disialo)-SRIF28 modified with two disialosugar chains, S1-3C(disialo)-SRIF28 modified with three disialosugar chains, and S1-4C(disialo)-SRIF28 modified with four disialosugar chains on SRIF28 each extended $t_{1/2}$ by 13, 21, 30, and 48-folds and increased AUC by 11, 12, 12, and 15-folds compared to the non-glycosylated form when administered intravenously. In either of SRIF14 and SRIF28, it became clear that stability in blood is improved according to the number of modifying disialosugar chain.

TABLE 5E

| Example | | Intravenous administration | | | | Subcutaneous administration | | | | |
|---|---|---|---|---|---|---|---|---|---|---|
| | | $T_{1/2}$ | AUC | MRT | $C_0$ | $T_{1/2}$ | AUC | MRT | Cmax | BA |
| — | SRIF28 | 1.32 | 467 | 2.46 | 518 | 2.38 | 22 | 4.18 | 4.65 | 5 |
| 27 | S1C(asialo)-SRIF28 | 13.4 | 4602 | 12.5 | 749 | 19.7 | 710 | 29.0 | 17.2 | 16 |
| 28 | S1-2C(asialo)-SRIF28 | 8.30 | 2664 | 9.60 | 741 | 19.2 | 1049 | 36.4 | 19.8 | 39 |
| 29 | S1-3C(asialo)-SRIF28 | 6.60 | 2733 | 6.50 | 1147 | 26.4 | 885 | 42.1 | 15.0 | 32 |

As is clear from the results shown in Table 5E, S1C(asialo)-SRIF28 modified with one asialosugar chain, S1-2C(asialo)-SRIF28 modified with two asialosugar chains, and S1-3C(asialo)-SRIF28 modified with three asialosugar chains on SRIF28 each extended $t_{1/2}$ by 10, 6, and 5-folds and increased AUC by 10, 6, and 6-folds compared to the non-glycosylated form when administered intravenously. It became clear that stability in blood is also improved when the modifying sugar chain is an asialosugar chain.

TABLE 5F

| Example | | Intravenous administration | | | | Subcutaneous administration | | | | |
|---|---|---|---|---|---|---|---|---|---|---|
| | | $T_{1/2}$ | AUC | MRT | $C_0$ | $T_{1/2}$ | AUC | MRT | Cmax | BA |
| — | SRIF28 | 1.32 | 467 | 2.46 | 518 | 2.38 | 22 | 4.18 | 4.65 | 5 |
| 1 | S1C(disialo)-SRIF28 | 17.7 | 5190 | 19.1 | 633 | 31.2 | 1946 | 49.2 | 30.1 | 38 |
| 20 | S1-2C(disialo)-SRIF28 | 28.2 | 5804 | 23.0 | 950 | 40.8 | 3091 | 65.3 | 34.6 | 53 |
| 28 | S1-2C(asialo)-SRIF28 | 8.30 | 2664 | 9.60 | 741 | 19.2 | 1049 | 36.4 | 19.8 | 39 |
| 63 | S1-2C(disialo(amide))-SRIF28 | 23.8 | 5268 | 20.5 | 737 | 33.1 | 1297 | 55.8 | 16.3 | 25 |
| 64 | S1-2C(disialo(Bn))-SRIF28 | 25.6 | 5525 | 20.7 | 807 | 33.9 | 1843 | 59.4 | 21.5 | 33 |
| 67 | C(disialo(aminoethylamide))•S1C(disialo)-SRIF28 | 22.5 | 3742 | 20.5 | 518 | 42.3 | 1289 | 64.7 | 16.2 | 34 |

As is clear from the results shown in Table 5F, S1-2C(disialo)-SRIF28, S1-2C(asialo)-SRIF28, C(disialo(aminoethylamide))/S1C(disialo)-SRIF28, S1-2C(disialo(Bn))-SRIF28, and S1-2C(disialo(amide))-SRIF28 each extended $t_{1/2}$ by 6-21-folds and increased AUC by 6-12-folds compared to the non-glycosylated form when administered intravenously. In other words, stability in blood improved by modifying a sugar chain onto SRIF28. Moreover, $t_{1/2}$ AUC, Cmax, and BA increased in both intravenous and subcutaneous administrations according to the increase in the number of sialic acid sugar chains. On the other hand, when the negative charge of the carboxy group of the sialic acid was removed (2C(disialo(Bn))/2C(disialo(amide))), or when a positive charge was adjacently added (C(disialo(aminoethylamide))/S1C(disialo)), although $t_{1/2}$ was extended when administered subcutaneously, AUC or Cmax did not increase. Since the carboxy group of the sialic acid has a large influence on retentivity in blood or blood migration, this shows the possibility for (usage in) blood clearance or body distribution control by conversion of charge at the sugar chain terminal.

Example 88 Plasma Stability Test with Rat Plasma 88-1 Preparation of Compound Solution, Reagent, and Rat Plasma The glycosylated form and the non-glycosylated SRIF28 were dissolved in PBS solution to prepare 2 µM solutions as treatment solutions. 10% TFA was prepared by dissolving trifluoroacetic acid (208-02746 from Wako Pure Chemical Industries, Ltd.) in water to 10 v/v %. Rat plasma was prepared from Wistar rats (Crlj: Wistar, male, Charles River Japan, 7 weeks-old) as heparin-added plasma (heparin: Japanese Pharmacopeia heparin sodium injectable solution (Mochida Pharmaceutical Co., Ltd.)).

88-2 Preparation of Plasma-Added Sample

To 0.27 mL of rat plasma (n=3), 0.03 mL of the glycosylated compound solution prepared in the above 88-1 was promptly mixed as plasma-added sample, and kept warm in a 37° C. thermostat bath. After mixing, 0.04 mL of plasma-added sample was taken at 0 minute and over time at 1-24 hours, and then promptly mixed with 0.01 mL of 10% TFA. After centrifugal separation (20,000×g, 4° C., 10 minutes), 0.04 mL of the supernatant was taken as plasma stability measurement samples. Sampling time was 0, 1, 2, and 4 hours, or 0, 4, 8, and 24 hours. As blank plasma, plasma obtained from a similar treatment except that PBS solution was employed as the treatment solution was employed. Plasma samples were frozen in storage until employed for measurement. For each experiment run, non-glycosylated SRIF28 was employed as the positive control.

Figure 20:
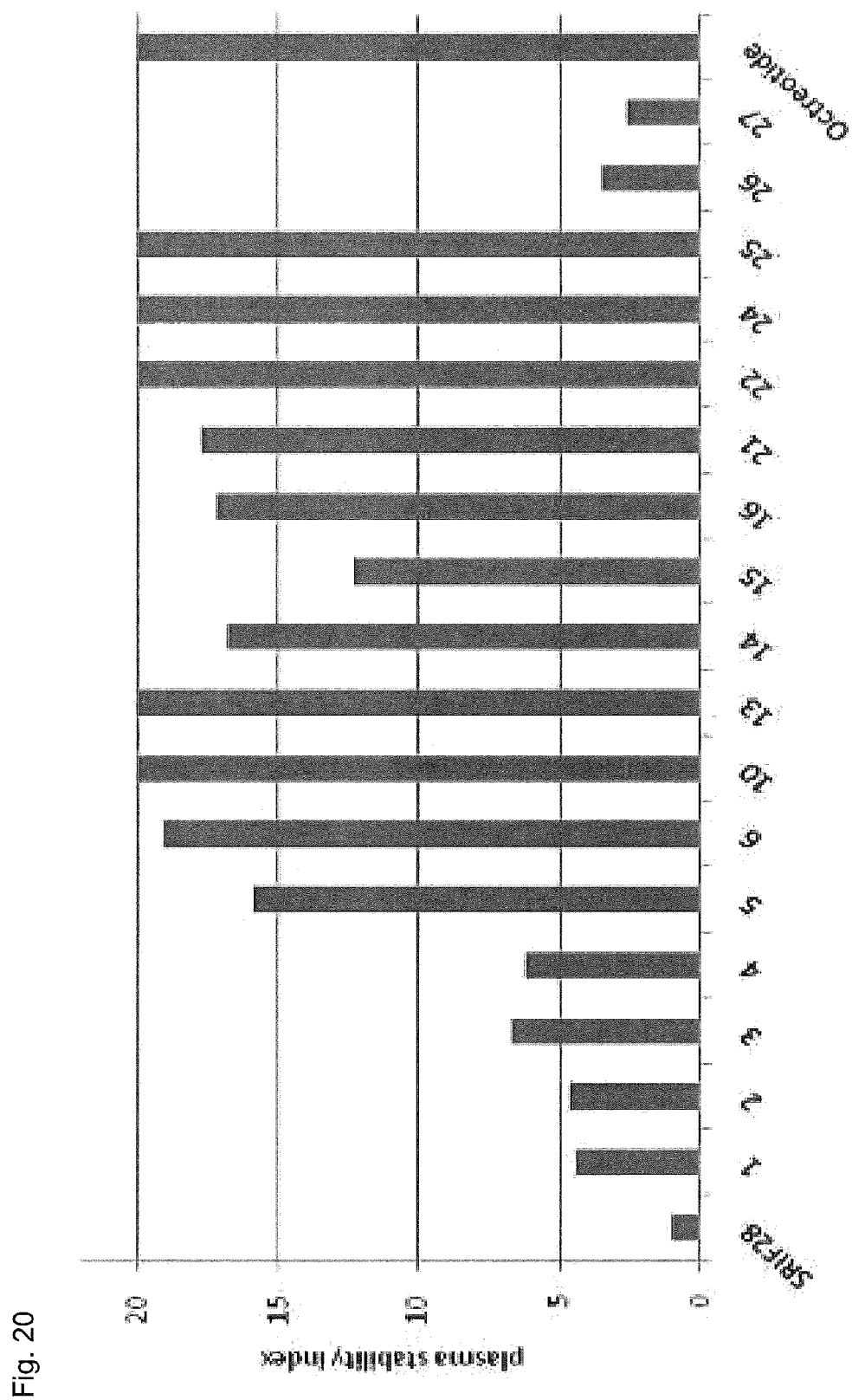
FIG. 20 is a graph showing the result of plasma stability test employing rat plasma for the glycosylated polypeptides of an embodiment of the present invention.

88-3 Measurement of Concentration in Sample and Calculation of Plasma Stability Index In a method similar to plasma concentration measurement of Example 70-3, the concentration of the glycosylated form remaining in the plasma stability measurement samples obtained in the above 88-2 was measured. The concentration of the glycosylated form at 0 minute after mixing was set as 100%, the residual rate over time was represented in percentage (%), and the half-life was calculated from the elimination rate constant of the following exponential formula (1) employing the calculation formula (2). Then, the half-life of the non-glycosylated SRIF28 for each experiment run was set as 1, and the plasma stability index (PS index) of the glycosylated form Was calculated. The results are shown in Table 6 and FIG. 20. Moreover, those having a plasma stability index of 20 or higher are shown as >20. In FIG. 20, those having a plasma stability index of higher than 20 are also shown with 20 as the upper limit.

$$\text{Residual rate (\%)} = 100 \cdot e^{(k \cdot t)} \quad (1)$$

e: Base of natural logarithm
k: elimination rate constant
t: Time (hours)

Half-life (hours)=0.693/k     (2)

TABLE 6

| Example | | PS index |
|---|---|---|
| 1 | S1C(disialo)-SRIF28 | 4.5 |
| 2 | N5C(disialo)-SRIF28 | 4.7 |
| 3 | A9C(disialo)-SRIF28 | 6.7 |
| 4 | E12C(disialo)-SRIF28 | 6.2 |
| 5 | R13C(disialo)-SRIF28 | 15.9 |
| 6 | K14C(disialo)-SRIF28 | 19.1 |
| 10 | N19C(disialo)-SRIF28 | >20 |
| 13 | 29C(disialo)-SRIF28 | >20 |
| 14 | 30C(disialo)-SRIF28 | 16.8 |
| 15 | S1C(disialo)-D-Trp-SRIF28 | 12.3 |
| 16 | A9C(disialo)-D-Trp-SRIF28 | 17.2 |
| 21 | S1C(disialo)-N5C(disialo)-SRIF28 | 17.8 |
| 22 | S1C(disialo)-R13C(disialo)-SRIF28 | >20 |
| 24 | S1-3C(disialo)-SRIF28 | >20 |
| 25 | S1C(disialo)-N5C(disialo)-A9C(disialo)-SRIF28 | >20 |
| 26 | S1C(monosialo)-SRIF28 | 3.5 |
| 27 | S1C(asialo)-SRIF28 | 2.6 |
| — | Octreotide | >20 |
| — | SRIF28 | 1 |

As is clear from the results shown in FIG. 20, the glycosylated polypeptide of the present invention was increased in plasma stability compared to SRIF28. In other words, this was 4.5-6.7-folds in those having one sugar chain added at positions 1, 5, 9, and 12 (the compounds of Examples 1, 2, 3, and 4), 15.9-folds for those having a sugar chain added at position 13 (the compound of Example 5), 19.1-folds for those having a sugar chain added at position 14 (the compound of Example 6), and 16.8-folds for those having a sugar chain added at position 30 (the compound of Example 14), compared to that of SRIF28. Moreover, this was 20-folds or more for those having one glycosylated amino acid further added at position 19 which is the C-terminal side (the compounds of Examples 10 and 13). It was shown that in regards to the position for glycosylation, plasma stability increases from position 1 towards the C-terminal.

Example 89 GH Production Suppression Test with Rats

As shown in Example 69, the glycosylated polypeptide of the present invention had affinity towards each receptor of SSTR. On the other hand, some were seen to have attenuated affinity towards each SSTR, but in order to prove that even in such cases pharmacologically effective action is shown towards receptors in vivo by e.g. extension of half-life in blood or increase in bioavailability as shown in Examples 70-88, a test for evaluating the administration effect of the glycosylated polypeptide of the present invention on growth hormone (GH) production was carried out as an in vivo test employing rats. Increase of GH production amount into the blood is thought to cause proliferation or differentiation of cells and activation or suppression of the biosynthetic system in various organs via the paracrine effect of GH, and thereby influence biological reactions. Somatostatin released from the hypothalamus suppresses GH secretion from the anterior pituitary gland into the blood. This experimental line was carried out as a test line that can evaluate the pharmacological action of the glycosylated form on SSTR and its residence in blood after administration, with blood GH production amount as an indicator.

89-1 Preparation of Administration Solution and Reagent

Employing S1C(disialo)-SRIF28, N19C(disialo)-SRIF28, 29C(disialo)-SRIF28, S1C(disialo)•N5C(disialo)-SRIF28, and S1C(disialo)•N5C(disialo)•A9C(disialo)-SRIF28 as the glycosylated forms, these were dissolved in Japanese Pharmacopeia saline (from Otsuka Pharmaceutical factory, Inc.) to prepare 1-100 μM solutions as the administration solution. Moreover, GRF (GH releasing hormone, Growth hormone releasing factor) was used as the GH release enhancer. GRF was prepared by dissolving GRF injectable solution (GRF Sumitomo 50 for injection, Lot. 2006C, from Dainippon Sumitomo Pharma Co., Ltd.) in 1 mL of water for injection (Lot. 09H18C, from Fuso Pharmaceutical Industries, Ltd.), and then diluting to 25-folds with saline to obtain 2 μg/mL. As heparin employed as the anticoagulant when collecting blood, Japanese Pharmacopeia heparin sodium injectable solution (Lot. B084, from Mochida Pharmaceutical Co., Ltd.) was used directly as stock solution.

89-2 Preparation of Plasma Sample

To the dorsal subcutaneous of male SD rats (Crl: CD (SD), Charles River Japan, 6 weeks-old, n=3, body weight 145.2-163.9 g), the administration solution prepared in the above 89-1 was administered under nonfasting condition at a dosage of 1 mL/kg with a glass syringe and a 26 G injection needle (all from Terumo Corporation). As the control group, saline without glycosylated polypeptide was similarly administered (vehicle group). Then, i.e. between 5-6 minutes after the administration of the glycosylated form, pentobarbital sodium (somnopentyl, Lot. 0608101, from Kyoritsuseiyaku Corporation) was intraperitoneally administered as a general anesthetic with a glass syringe and an injection needle to give 50 mg/kg. One hour after administration of the glycosylated form, i.e. after 50 minutes or more had passed under anesthesia, GRF was administered as the GH release enhancer to the tail vain at a dosage of 1 mL/kg with a glass syringe and an injection needle. Five minutes after administration of GRF, blood was collected from the rat cervical vein with a glass syringe containing heparin and an injection needle. 0.4 mL of the collected blood was left on ice for 20 minutes or more, then centrifuged (1,870×g, 4° C., 10 minutes), and 100 μL of the supernatant was taken as the plasma sample. As blank plasma, plasma obtained by similarly treating the blood collected from untreated rat cervical vein was employed. Plasma samples were frozen in storage until employed for measurement.

89-3 Measurement of GH Concentration in Plasma

Measurement of GH concentration in the plasma sample obtained in the above 89-2 was performed with rat Growth Hormone EIA kit from SPI-Bio (SPI-Bio, A05104). The plasma sample was diluted with the assay buffer supplied in the EIA kit to 20, 100, and 500-folds as measurement samples. The standard solution for creating a standard curve followed the attached instructions by preparing a 40 ng/mL solution with distilled water, and then subjecting to serial dilution with the assay buffer to prepare 20 ng/mL, 10 ng/mL, 5 ng/mL, 2.5 ng/mL, 1.25 ng/mL, 0.63 ng/mL, and 0.31 ng/mL. By multiplying the results obtained and the dilution ratio, the GH concentration was calculated. The GH concentration in the plasma sample obtained is shown in Table 7.

TABLE 7

| Example | | Dose | GH (ng/mL) |
|---|---|---|---|
| 1 | S1C(disialo)-SRIF28 | 1 nmol/kg | 490 |
| 1 | S1C(disialo)-SRIF28 | 10 nmol/kg | 17.1 |
| 10 | N19C(disialo)-SRIF28 | 10 nmol/kg | 563 |
| 10 | N19C(disialo)-SRIF28 | 100 nmol/kg | 1.5 |
| 13 | 29C(disialo)-SRIF28 | 10 nmol/kg | 497 |
| 13 | 29C(disialo)-SRIF28 | 100 nmol/kg | 88.5 |
| 21 | S1C(disialo)-N5C(disialo)-SRIF28 | 1 nmol/kg | 776 |
| 21 | S1C(disialo)-N5C(disialo)-SRIF28 | 10 nmol/kg | 181 |
| 25 | S1C(disialo)-N5C(disialo)-A9C(disialo)-SRIF28 | 10 nmol/kg | 833 |
| 25 | S1C(disialo)-N5C(disialo)-A9C(disialo)-SRIF28 | 100 nmol/kg | 151 |
| — | vehicle | — | 861 |

As is clear from the results shown in Table 7, the glycosylated form of the present invention suppressed GH production in rats. The ratio between the Ki value of glycosylated forms of Examples 21 and 25 against each receptor and the Ki value of unglycosylated SRIF14 is shown to be in the range of 15.7:1-1.2:1 (the compound of Example 21) and 158:1-7.1:1 (the compound of Example 25), respectively, as measured in the method of Example 69-1. Moreover, the glycosylated forms of Examples 21 and 25 are shown to have 25-folds or more (the compound of Example 21) or 30-folds or more (the compound of Example 25) increase in half-life in blood, respectively, as measured in the method of Example 70. On the other hand, from the present Example having two sugar chains, it was shown that the glycosylated form effectively exerts pharmacological action even in vivo.

Moreover, the glycosylated form of the present invention had GH production suppressing action even when administered 1 hour before GRF administration.

It was shown that the effective administration dose for rat GH production ability between the glycosylated forms of Examples 1 and 21 and Example 25 was different by approximately 10-folds. This is similar to the receptor affinities thereof having a difference of approximately 10-folds in terms of Ki value, as measured in the method of Example 69-1. It was shown that they have pharmacological activity even when the affinity of the glycosylated form was somewhat attenuated.

Example 90 GH Production Suppression Test with Rats 2

Similarly to Examples 89-1-89-3, rat GH production suppression tests of the glycosylated compounds shown below were carried out. S1C(disialo)-SRIF28, N5C(disialo)-SRIF28, A9C(disialo)-SRIF28, E12C(disialo)-SRIF28, R13C(disialo)-SRIF28, K14C(disialo)-SRIF28, S1C(disialo)-D-Trp22-SRIF28, S1C(disialo(Bn))-SRIF28, S1C(disialo(amide))-SRIF28, S1C(disialo(aminoethylamide))-SRIF28, S1C(monosialo)-SRIF28, S1C(asialo)-SRIF28, C(disialo)-R-K-SRIF14, S1-2C(asialo)-SRIF28, S1C(disialo) N5C(disialo)-SRIF28, S1C(disialo)•N5C(disialo)-A9C(disialo)-SRIF28, and S1-5C(disialo)-SRIF28 were employed as the glycosylated forms. The GH concentration in the plasma sample obtained is shown in Table 8.

TABLE 8

| Example | | Dose | GH (ng/mL) | The number of runs |
|---|---|---|---|---|
| 1 | S1C(disialo)-SRIF28 | 1 nmol/kg | 787 | 4 |
| | | 3 nmol/kg | 182 | 3 |
| | | 10 nmol/kg | 15 | 5 |
| | | 30 nmol/kg | 8 | 1 |
| | | 100 nmol/kg | 7 | 2 |
| 2 | N5C(disialo)-SRIF28 | 1 nmol/kg | 969 | 1 |
| | | 10 nmol/kg | 12 | 1 |
| 3 | A9C(disialo)-SRIF28 | 1 nmol/kg | 577 | 1 |
| | | 10 nmol/kg | 20 | 1 |
| 4 | E12G(disialo)-SRIF28 | 10 nmol/kg | 10 | 1 |
| 5 | R13C(disialo)-SRIF28 | 10 nmol/kg | 136 | 1 |
| 6 | K14C(disialo)-SRIF28 | 10 nmol/kg | 55 | 1 |
| 15 | S1C(disialo)-D-Trp22-SRIF28 | 0.3 nmol/kg | 986 | 3 |
| | | 1 nmol/kg | 335 | 3 |
| | | 3 nmol/kg | 50 | 1 |
| | | 10 nmol/kg | 6 | 2 |
| | | 30 nmol/kg | 2 | 1 |
| 18 | C(disialo)-R-K-SRIF14 | 1 nmol/kg | 912 | 4 |
| | | 3 nmol/kg | 291 | 4 |
| | | 10 nmol/kg | 30 | 4 |
| | | 30 nmol/kg | 12 | 1 |
| 21 | S1C(disialo)-N5C(disialo)-SRIF28 | 1 nmol/kg | 776 | 1 |
| | | 10 nmol/kg | 181 | 1 |
| 25 | S1C(disialo)-N5C(disialo)-A9C(disialo)-SRIF28 | 100 nmol/kg | 151 | 1 |
| 26 | S1C(monosialo)-SRIF28 | 10 nmol/kg | 47 | 1 |
| 27 | S1C(asialo)-SRIF28 | 1 nmol/kg | 879 | 4 |
| | | 3 nmol/kg | 515 | 4 |
| | | 10 nmol/kg | 146 | 4 |
| 28 | S1-2C(asialo)-SRIF28 | 3 nmol/kg | 997 | 3 |
| | | 10 nmol/kg | 175 | 3 |
| 34 | S1-5C(disialo)-SRIF28 | 10 nmol/kg | 842 | 1 |
| 59 | S1C(disialo(aminoethylamide))-SRIF28 | 10 nmol/kg | 314 | 1 |
| 60 | S1C(disialo(amide))-SRIF28 | 10 nmol/kg | 14 | 1 |
| 61 | S1C(disialo(Bn))-SRIF28 | 10 nmol/kg | 49 | 1 |
| — | vehicle | — | 1012 | 19 |

As is clear from the results shown in Table 8, the glycosylated polypeptide of the present invention suppressed GH production in rats. In the present test line, S1C(disialo)-SRIF28 suppressed GH production from 1 nmol/kg, and showed 82-99% of the GH production suppression effect at 3-10 nmol/kg. This is thought to be due to the gain in affinity towards SSTR1-SSTR5 and improvement in the retentivity in blood as shown in Examples 69-1, 69-2, and 70-87.

In Examples 69-1 and 69-2, N5C(disialo)-SRIF28, A9C(disialo)-SRIF28, E12C(disialo)-SRIF28, S1C(disialo)-D-Trp-SRIF28, S1C(disialo(Bn))-SRIF28, and C(disialo)-R-K-SRIF14 showing affinity equivalent to S1C(disialo)-SRIF28 showed 95-99% of the GH production suppression effect at 10 nmol/kg, showing an effect equivalent to S1C(disialo)-SRIF28.

From the results shown in the methods of Examples 70-87, S1C(monosialo)-SRIF28, S1C(asialo)-SRIF28, S1-2C(asialo)-SRIF28, and S1C(disialo(amide))-SRIF28 had an AUC for subcutaneous administration which was ⅓-½ of S1C(disialo)-SRIF28, and S1C(disialo(aminoethylamide))-SRIF28 was ⅐. Meanwhile, all of these showed higher affinity than S1C(disialo)-SRIF28 by the methods shown in Examples 69-1 and 69-2. Accordingly, in this experimental line, S1C(monosialo)-SRIF28, S1C(asialo)-SRIF28, S1-2C(asialo)-SRIF28, S1C(disialo(aminoethylamide))-SRIF28, and S1C(disialo(amide))-SRIF28 suppressed 70-99% of the GH production at 10 nmol/kg, and is thought to have shown an effect equivalent to S1C(disialo)-SRIF28.

R13C(disialo)-SRIF28, K14C(disialo)-SRIF28, S1C(disialo) N5C(disialo)-SRIF28, S1C(disialo) N5C(disialo) A9C(disialo)-SRIF28, and S1-5C(disialo)-SRIF28 showed a lower affinity than S1C(disialo)-SRIF28 by the methods shown in Examples 69-1 and 69-2. Meanwhile, from the results shown in the methods of Examples 70-87, these compounds have AUC for subcutaneous administration that was improved to 1.8-3.1-folds of S1C(disialo)-SRIF28. In this experimental line, R13C(disialo)-SRIF28, K14C(disialo)-SRIF28, S1C(disialo) N5C(disialo)-SRIF28, S1C(disialo) N5C(disialo) A9C(disialo)-SRIF28, and S1-5C(disialo)-SRIF28 showed GH production suppression activity by administration of 10 or 100 nmol/kg. These results show that somatostatin activity can be compensated or increased by the increase in stability in blood even when receptor affinity is reduced.

Example 91 Drug Effect Test in Gastrointestinal Obstruction Model

As shown in Examples 89 and 90, the glycosylated polypeptides of the present invention proved to have effective action as agonists even in rats in vivo. Next, in order to prove that they also show efficacy in disease models, an evaluation in rat gastrointestinal obstruction model was carried out. In gastrointestinal obstructions such as ileus, gastrointestinal symptoms such as sense of abdominal fullness, vomiting, and abdominal pain are shown by gastrointestinal tract tissue disorder and reduction in absorption ability of e.g. water or electrolyte. Their pathologies are known to be caused by obstruction of gastrointestinal content or release of digestive juice or biologically active material into the gastrointestinal tract. Somatostatin show the effect of decreasing the gastrointestinal content by secretory suppression of various digestive juices or promotion of water and electrolytes absorption via SSTR expressed in the gastrointestinal system, and is thought to be effective for improvement of the symptoms. This experimental line was carried out as a test line to evaluate the promotion of intestinal fluid absorption or the secretory suppressing action, using the change in the intestinal fluid weight in the jejunum after bowel obstruction as an indicator. Moreover, blood parameters of deviation enzymes amylase (pancreas), lactate dehydrogenase (LDH, liver), and creatine phosphokinase (CPK, skeletal muscle, cardiac muscle etc.) were measured as indicators of tissue disorders.

Example 91-1 Production of Gastrointestinal Obstruction Model

The present test was consigned to Mitsubishi Chemical Medience Corporation and carried out. Male SD rats (Crl: CD (SD), Charles River Japan, 8 weeks-old, n=5 or more, body weight 251.1-278.1 g) were fasted for 12 hours or more. Anesthesia was introduced with inhalation of 2% isoflurane and laughing gas:oxygen=7:3, and this was maintained throughout the surgery. A median incision was made in the abdomen, and the jejunum at about 10 cm from the musculus suspensorius duodeni was ligated with a surgical suture. Then, the incision site was promptly sutured, and the rats were fasted until compound administration. In the sham treatment group, ligation of the jejunum was not performed, but the treatment of suturing the incision site after a median incision was made in the abdomen was performed.

Example 91-2 Preparation of Compound and Administration

Employing S1C(disialo)-SRIF28, C(disialo)-R-K-SRIF14, and S1-2C(asialo)-SRIF28 as the glycosylated forms, these were dissolved in Japanese Pharmacopeia saline (from Otsuka Pharmaceutical factory, Inc.) to prepare a 40 μM solution as the administration solution. Eighteen hours after the gastrointestinal obstruction surgery, this was subcutaneously administered into the dorsal cervix at a dosage of 1 mL/kg with a glass syringe and a 25 G injection needle (all from Terumo Corporation). As the vehicle group, saline without glycosylated polypeptide was similarly administered. Moreover, octreotide was administered as the control group.

Example 91-3 Measurement of Intestinal Fluid Weight

One hour after compound administration, a median incision was made in the abdomen under inhalation anesthesia, and 1.5 mL of blood was collected from the abdominal vena cava. Then, the ligated jejunum on the musculus suspensorius duodeni side was resected. The fluid and blood on the jejunum surface were removed with a paper towel, nerves, blood vessels, and fat attached to the jejunum was removed, this was cut into 6 cm lengths, and wet weight was measured. This was then dried at 36 degrees for 24 hours, and dry weight was measured. The intestinal fluid weight (mg) was calculated by wet weight-dry weight. The intestinal fluid weight of the jejunum obtained is shown in Table 9.

TABLE 9

| | Intestinal fluid weight (mg) |
|---|---|
| Sham treatment | 285 ± 27 |
| vehicle | 481 ± 31 |

TABLE 9-continued

|  | Intestinal fluid weight (mg) |
| --- | --- |
| octreotide | 693 ± 48 |
| S1C(disialo)-SRIF28 | 630 ± 83 |
| C(disialo)-R-K-SRIF14 | 584 ± 95 |
| S1-2C(asialo)-SRIF28 | 566 ± 34 |

As apparent from Table 9, the vehicle had significantly increased intestinal fluid weight compared to the sham treatment, and it was recognized that enhancement of intestinal fluid secretion accompanying gastrointestinal obstruction due to ligation was caused. Somatostatin or octreotide are shown to have the secretory suppression effect of the intestinal fluid into the intestinal tract and the promotional effect of intestinal fluid absorption into the bowel tissue side in such gastrointestinal obstruction models (Scand. J. Gastroenterol. 1995 May; 30 (5): 464-9), and octreotide was confirmed to have this effect also in this experimental line. S1C(disialo)-SRIF28, C(disialo)-R-K-SRIF14, and S1-2C (asialo)-SRIF28 were all recognized to have increase in the intestinal fluid weight compared to the vehicle, and it became clear that the glycosylated forms of the present invention also show efficacy such as secretory suppression of the intestinal fluid and promotion of water and electrolyte absorption. Moreover, it has become clear that in Examples 86 and 87, the AUC for subcutaneous administration of S1-2C(asialo)-SRIF28 was ½ compared to S1C(disialo)-SRIF28, but in Example 69-1, the affinity towards SSTR1-SSTR5 is approximately 1.7-2.9-folds higher than S1C(disialo)-SRIF28. This is thought to be the reason why improvement of receptor affinity causes the drug effects in the present model to be similar even when plasma concentration is low. Similarly, this is thought to be the reason why drug effects are similar because receptor affinity is approximately 0.7-2.4-folds higher even though C(disialo)-R-K-SRIF14 has a slightly low AUC for subcutaneous administration compared to that of S1C(disialo)-SRIF28.

Example 91-4 Measurement of Blood Parameter

Employing the blood collected in Example 91-3, amylase (IU/L), LDH (IU/L) and CPK concentrations (IU/L) were measured with an autoanalyzer 7170 (Hitachi, Ltd.). The measuring methods employed were BG5B, UV-rate, and JSCC methods, respectively. The results obtained are shown in Table 10.

TABLE 10

|  | Amylase (IU/L) | LDH (IU/L) | CPK (IU/L) |
| --- | --- | --- | --- |
| Sham treatment | 669 ± 164 | 168 ± 82 | 353 ± 68 |
| vehicle | 1672 ± 743 | 341 ± 68 | 377 ± 57 |
| octreotide | 1732 ± 774 | 269 ± 141 | 472 ± 215 |
| S1C(disialo)-SRIF28 | 1164 ± 224 | 338 ± 97 | 455 ± 202 |
| C(disialo)-R-K-SRIF14 | 985 ± 238 | 228 ± 155 | 415 ± 137 |
| S1-2C(asialo)-SRF28 | 1594 ± 573 | 318 ± 44 | 728 ± 665 |

As apparent from Table 10, the vehicle had increased amylase activity and LDH activity compared to the sham treatment, and it was speculated that tissue disorder of the gastrointestinal system had developed accompanying gastrointestinal obstruction. In S1C(disialo)-SRIF28 and C(disialo)-R-K-SRIF14, the amylase activity had a low value compared to the vehicle. On the other hand, the amylase activity of octreotide was equivalent to the vehicle. As apparent from Examples 69-1 and 69-2, S1C(disialo)-SRIF28, C(disialo)-R-K-SRIF14, and S1-2C(asialo)-SRIF28 had binding affinity toward all the receptors from SSTR1-SSTR5, whereas octreotide is a compound having specific affinity towards SSTR2, SSTR3, and SSTR5. In rat pancreas, since there is a report that all the receptors SSTR1-SSTR5 are expressed (J. Histochem. Cytochem. 2004 March; 52 (3): 391-400), the possibility that the glycosylated form alleviated the tissue disorder by acting on a receptor different from that of octreotide was conceived. Moreover, in octreotide and C(disialo)-R-K-SRIF14, the LDH activity had a low value compared to the vehicle. There were no others that reduced each parameter by administration of the glycosylated form.

The invention claimed is:

1. A polypeptide selected from the group consisting of:
   (A) a SRIF14 consisting of the amino acid sequence represented by SEQ ID NO:1;
   (B) a polypeptide having one amino acid deleted from, substituted with, or added to SRIF14, SRIF14 consisting of the amino acid sequence represented by SEQ ID NO:1; and
   (C) a polypeptide having 90% or more homology with SRIF14 consisting of the amino acid sequence represented by SEQ ID NO:1;
   wherein said polypeptide further comprises N amino acids at the N-terminal side, wherein N is an integer from 1 or more to 20 or less; and/or
   said polypeptide further comprises M amino acids at the C-terminal side, wherein M is an integer from 1 or more to 6 or less;
   wherein at least two amino acids of the N and/or M amino acids are substituted with a glycosylated amino acid, and the polypeptide has affinity towards somatostatin receptors.

2. The glycosylated polypeptide of claim 1, comprising any one of the following features:
   at least two of the amino acids substituted with said glycosylated amino acid is present in said N amino acids; or
   at least two of the amino acids substituted with said glycosylated amino acid is present in said M amino acids.

3. The glycosylated polypeptide of claim 1, wherein at least two amino acids are substituted with glycosylated amino acids in said polypeptide, and further
   the sequence of said N amino acids added onto the N-terminal is represented by X—Y—,
   wherein X is a sequence of any L amino acids and L is an integer from 1 or more to 6 or less; and Y is a sequence selected from the group consisting of:
   (1) Lys,
   (2) Arg-Lys,
   (3) Glu-Arg-Lys,
   (4) Arg-Glu-Arg-Lys, SEQ ID NO:171
   (5) Pro-Arg-Glu-Arg-Lys, SEQ ID NO:172
   (6) Ala-Pro-Arg-Glu-Arg-Lys, SEQ ID NO:173
   (7) Met-Ala-Pro-Arg-Glu-Arg-Lys, SEQ ID NO:174
   (8) Ala-Met-Ala-Pro-Arg-Glu-Arg-Lys, SEQ ID NO:175
   (9) Pro-Ala-Met-Ala-Pro-Arg-Glu-Arg-Lys, SEQ ID NO:176
   (10) Asn-Pro-Ala-Met-Ala-Pro-Arg-Glu-Arg-Lys, SEQ ID NO:177
   (11) Ser-Asn-Pro-Ala-Met-Ala-Pro-Arg-Glu-Arg-Lys, SEQ ID NO:178
   (12) Asn-Ser-Asn-Pro-Ala-Met-Ala-Pro-Arg-Glu-Arg-Lys, SEQ ID NO:179
   (13) Ala-Asn-Ser-Asn-Pro-Ala-Met-Ala-Pro-Arg-Glu-Arg-Lys, SEQ ID NO:180
   (14) Ser-Ala-Asn-Ser-Asn-Pro-Ala-Met-Ala-Pro-Arg-Glu-Arg-Lys, SEQ ID NO:181 and
   (15) a sequence having one or a few amino acids deleted from, substituted with, or added to the above sequences (2)-(14).

4. The glycosylated polypeptide according to claim 3, wherein at least one amino acid substituted with said glycosylated amino acid is present in any of L amino acids.

5. The glycosylated polypeptide of claim 1, wherein said glycosylated peptide has increased stability in blood compared to SRIF28; and said affinity towards somatostatin receptors is an affinity towards at least two or more receptors selected from the group consisting of SSTR1, SSTR2, SSTR3, SSTR4, and SSTR5.

6. The glycosylated polypeptide of claim 1, wherein each of said glycosylated amino acids is glycosylated Asn or glycosylated Cys.

7. The glycosylated polypeptide of claim 1, wherein in each of said glycosylated amino acids, the sugar chain consists of 4 or more sugars.

8. A pharmaceutical composition comprising a glycosylated polypeptide of claim 1 and/or a pharmaceutically acceptable salt thereof, and a pharmaceutically acceptable carrier.

9. A method for treating or preventing a somatostatin-related disease, comprising administering an effective amount of a glycosylated polypeptide of claim 1.

10. The method of claim 9, wherein said somatostatin-related disease is at least one disease selected from the group consisting of acromegaly, gigantism, Alzheimer's disease and other forms of dementia, cancer, hormone-producing tumor, endocrine tumor, carcinoid, VIPoma, insulinoma, glucagonoma, Cushing's disease, hormone secretion defect, diabetes and complications thereof, pains, arthritis, diarrhea, gastric ulcer, inflammatory bowel disease, irritable bowel syndrome, gastrointestinal obstruction, ileus, postoperative restenosis, radiation damage, eye disease, dry eye, glaucoma, interstitial keratitis, iritis, cataract, and conjunctivitis.

11. A polypeptide selected from the group consisting of:
(A) a SRIF28 consisting of the amino acid sequence of SEQ ID NO:2;
(B) a polypeptide having one or two amino acids deleted from, substituted with, or added to SRIF28, SRIF28 consisting of the amino acid sequence of SEQ ID NO:2;
(C) a polypeptide having 90% or more homology with SRIF28 consisting of the amino acid sequence of SEQ ID NO:2;
(D) a polypeptide further comprising J amino acids at the N-terminal side of (A)-(C), wherein J is an integer from 1 or more to 6 or less; and
(E) a polypeptide further comprising K amino acids at the C-terminal side of (A)-(C), wherein K is an integer from 1 or more to 6 or less;
wherein at least two amino acids are substituted with a glycosylated amino acid, and the polypeptide has affinity towards somatostatin receptors.

12. The glycosylated polypeptide of claim 11, further comprising any one of the following features:
at least one of the amino acids substituted with said glycosylated amino acid is an amino acid selected from the group consisting of the amino acid corresponding to position 1, the amino acid corresponding to position 5, the amino acid corresponding to position 9, the amino acid corresponding to position 12, the amino acid corresponding to position 13, the amino acid corresponding to position 14, and the amino acid corresponding to position 19 of SRIF28;
at least two amino acids are substituted with glycosylated amino acids in said polypeptide D, wherein, at least one of the amino acids substituted with said glycosylated amino acid is present in said J amino acids at the N-terminal side of said polypeptide (D); or
at least two amino acids are substituted with glycosylated amino acids in said polypeptide E, wherein at least one of the amino acids substituted with said glycosylated amino acid is present in said K amino, acids of the C-terminal side of said polypeptide (E).

13. The glycosylated polypeptide of claim 11, wherein said glycosylated peptide has increased stability in blood compared to SRIF28; and said affinity towards somatostatin receptors is an affinity towards at least two or more receptors selected from the group consisting of SSTR1, SSTR2, SSTR3, SSTR4, SSTR5.

14. The glycosylated polypeptide of claim 11, wherein each of said glycosylated amino acids is glycosylated Asn or glycosylated Cys.

15. The glycosylated polypeptide of claim 11, Wherein each of said glycosylated amino acids comprise a sugar chain consisting of 4 or more sugars.

16. A pharmaceutical composition comprising a glycosylated polypeptide according to claim 11 and/or a pharmaceutically acceptable salt thereof, and a pharmaceutically acceptable carrier.

17. A method for treating or preventing a somatostatin-related disease, comprising administering to a patient in need thereof an effective amount of a glycosylated polypeptide according to claim 11.

18. The method of claim 17, wherein said somatostatin-related disease is at least one disease selected from the group consisting of acromegaly, gigantism, Alzheimer's disease and other forms of dementia, cancer, hormone-producing tumor, endocrine tumor, carcinoid, VIPoma, insulinoma, glucagonoma, Cushing's disease, hormone secretion defect, diabetes and complications thereof, pains, arthritis, diarrhea, gastric ulcer, inflammatory bowel disease, irritable bowel syndrome, gastrointestinal obstruction, ileus, postoperative restenosis, radiation damage, eye disease, dry eye, glaucoma, interstitial keratitis, iritis, cataract, and conjunctivitis.

\* \* \* \* \*

UNITED STATES PATENT AND TRADEMARK OFFICE
CERTIFICATE OF CORRECTION

| | |
|---|---|
| PATENT NO. | : 9,802,996 B2 |
| APPLICATION NO. | : 15/213872 |
| DATED | : October 31, 2017 |
| INVENTOR(S) | : Ochiai et al. |

It is certified that error appears in the above-identified patent and that said Letters Patent is hereby corrected as shown below:

In the Specification

Column 1, Statement of Priority: Please delete in entirety and insert the following:
-- This application is a continuation application of U.S. Patent Application No. 14/342,360, filed on May 28, 2014, which is a 35 U.S.C. § 371 national phase application of International Application Serial No. PCT/JP2012/072383, filed September 3, 2012, which claims the benefit, under 35 U.S.C. § 119 (a) of Japanese Patent Application No. 2011-192203, filed September 4, 2011, the entire contents of each of which are incorporated by reference herein. --

Column 19, Line 63: Please correct "position of" to read -- position 1 of --

Column 63, Formula 15, 2$^{nd}$ formula on the page: Please delete the 2$^{nd}$ formula as it is a duplicate of formula 33

Column 63, above formula 34: Please insert -- [Chemical Formula 16] --

Column 89, Line 36: Please correct "[Chemical Formula 432]" to read -- [Chemical Formula 42] --

Column 96, Line 51: Please correct "920×250" to read -- φ20×250 --

Column 125, Line 32: Please correct "T6" to read -- 76 --

Column 135, Line 18: Please correct "$N_{30}$" to read -- $N_{80}$ --

Column 159, Line 16: Please correct "Cys-Cys-Cys-Arg-Lys-Ala-Gly-Cys" to read -- Cys-Cys-Cys-Arg-Lys-Ala-Gly --

Column 162, Line 47: Please correct "S1C(diG1NAc)" to read -- S1C(diG1cNAc) --

Signed and Sealed this
Tenth Day of July, 2018

Andrei Iancu
*Director of the United States Patent and Trademark Office*

CERTIFICATE OF CORRECTION (continued)
U.S. Pat. No. 9,802,996 B2

Column 165, Chemical Formula 160, 3rd branch:

Please correct " 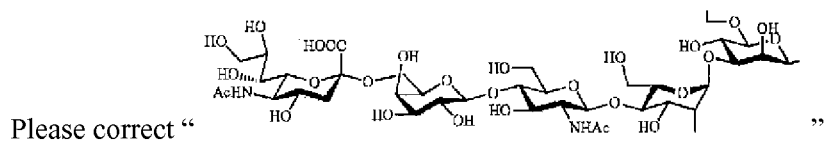 "

to read -- 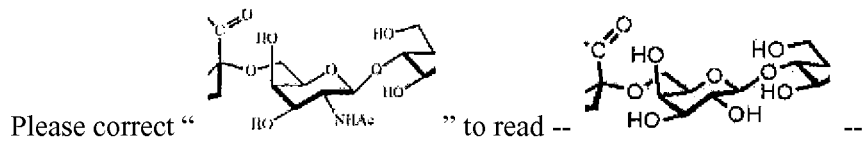 --

Column 174, Line 5: Please correct "minutes" to read -- 14 minutes --

Column 175, Line 1: Please correct "[Chemical Formula 164]" to read -- [Chemical Formula 169] --

Column 193, Chemical Formula 191:

Please correct " " to read -- --

Column 224, Line 40, Table 5B, last line: Please correct "43" to read -- 45 --

Column 228, Line 67: Please correct "$100 \cdot e^{(k \cdot t)}$" to read -- $100 \cdot e^{(k \cdot t)}$ ... --

Column 229, Line 5: Please correct "0.693/k" to read -- 0.693/k ... --

Column 232, Line 28: Please correct "·N5C(disialo)-A9C(disialo)" to read -- ·N5C(disialo)·A9C(disialo) --

Column 233, Lines 40-41: Please correct "S1C(disialo) N5C(disialo)" to read -- S1C(disialo·N5C(disialo) --

In the Claims

Column 372, Claim 12, Line 4: Please correct "amino, acids" to read -- amino acids --

Column 372, Claim 15, Line 16: Please correct "Wherein" to read -- wherein --

SEQUENCE LISTING

```
<160> NUMBER OF SEQ ID NOS: 183

<210> SEQ ID NO 1
<211> LENGTH: 14
<212> TYPE: PRT
<213> ORGANISM: Homo sapiens
<220> FEATURE:
<221> NAME/KEY: DISULFID
<222> LOCATION: (3)..(14)

<400> SEQUENCE: 1

Ala Gly Cys Lys Asn Phe Phe Trp Lys Thr Phe Thr Ser Cys
1               5                   10

<210> SEQ ID NO 2
<211> LENGTH: 28
<212> TYPE: PRT
<213> ORGANISM: Homo sapiens
<220> FEATURE:
<221> NAME/KEY: DISULFID
<222> LOCATION: (17)..(28)

<400> SEQUENCE: 2
```

```
Ser Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 3
<211> LENGTH: 14
<212> TYPE: PRT
<213> ORGANISM: Artificial
<220> FEATURE:
<223> OTHER INFORMATION: Synthetic peptide
<220> FEATURE:
<221> NAME/KEY: DISULFID
<222> LOCATION: (3)..(14)
<220> FEATURE:
<221> NAME/KEY: MOD_RES
<222> LOCATION: (14)..(14)
<223> OTHER INFORMATION: AMIDATION

<400> SEQUENCE: 3

Ala Gly Cys Lys Asn Phe Phe Trp Lys Thr Phe Thr Ser Cys
1               5                   10

<210> SEQ ID NO 4
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: DISULFID
<222> LOCATION: (17)..(28)
<220> FEATURE:
<221> NAME/KEY: MOD_RES
<222> LOCATION: (28)..(28)
<223> OTHER INFORMATION: AMIDATION

<400> SEQUENCE: 4

Ser Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 5
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: DISULFID
<222> LOCATION: (17)..(28)

<400> SEQUENCE: 5

Cys Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 6
<211> LENGTH: 28
<212> TYPE: PRT
<213> ORGANISM: Artificial
<220> FEATURE:
<223> OTHER INFORMATION: Synthetic peptide
```

```
<220> FEATURE:
<221> NAME/KEY: CARBOHYD
<222> LOCATION: (5)..(5)
<223> OTHER INFORMATION: Disialo sugar chain added
<220> FEATURE:
<221> NAME/KEY: DISULFID
<222> LOCATION: (17)..(28)

<400> SEQUENCE: 6

Ser Ala Asn Ser Cys Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 7
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (9)..(9)
<223> OTHER INFORMATION: Disialo sugar chain added
<220> FEATURE:
<221> NAME/KEY: DISULFID
<222> LOCATION: (17)..(28)

<400> SEQUENCE: 7

Ser Ala Asn Ser Asn Pro Ala Met Cys Pro Arg Glu Arg Lys Ala Gly
1               5                   10                  15

Cys Lys Asn Phe Phe Trp Lys Thr Phe Thr Ser Cys
            20                  25

<210> SEQ ID NO 8
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (12)..(12)
<223> OTHER INFORMATION: Disialo sugar chain added
<220> FEATURE:
<221> NAME/KEY: DISULFID
<222> LOCATION: (17)..(28)

<400> SEQUENCE: 8

Ser Ala Asn Ser Asn Pro Ala Met Ala Pro Arg Cys Arg Lys Ala Gly
1               5                   10                  15

Cys Lys Asn Phe Phe Trp Lys Thr Phe Thr Ser Cys
            20                  25

<210> SEQ ID NO 9
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (13)..(13)
<223> OTHER INFORMATION: Disialo sugar chain added
<220> FEATURE:
<221> NAME/KEY: DISULFID
<222> LOCATION: (17)..(28)

<400> SEQUENCE: 9
```

```
Ser Ala Asn Ser Asn Pro Ala Met Ala Pro Arg Glu Cys Lys Ala Gly
1               5                   10                  15

Cys Lys Asn Phe Phe Trp Lys Thr Phe Thr Ser Cys
            20                  25
```

<210> SEQ ID NO 10
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (14)..(14)
<223> OTHER INFORMATION: Disialo sugar chain added
<220> FEATURE:
<221> NAME/KEY: DISULFID
<222> LOCATION: (17)..(28)

<400> SEQUENCE: 10

```
Ser Ala Asn Ser Asn Pro Ala Met Ala Pro Arg Glu Arg Cys Ala Gly
1               5                   10                  15

Cys Lys Asn Phe Phe Trp Lys Thr Phe Thr Ser Cys
            20                  25
```

<210> SEQ ID NO 11
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (15)..(15)
<223> OTHER INFORMATION: Disialo sugar chain added
<220> FEATURE:
<221> NAME/KEY: DISULFID
<222> LOCATION: (17)..(28)

<400> SEQUENCE: 11

```
Ser Ala Asn Ser Asn Pro Ala Met Ala Pro Arg Glu Arg Lys Cys Gly
1               5                   10                  15

Cys Lys Asn Phe Phe Trp Lys Thr Phe Thr Ser Cys
            20                  25
```

<210> SEQ ID NO 12
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (16)..(16)
<223> OTHER INFORMATION: Disialo sugar chain added
<220> FEATURE:
<221> NAME/KEY: DISULFID
<222> LOCATION: (17)..(28)

<400> SEQUENCE: 12

```
Ser Ala Asn Ser Asn Pro Ala Met Ala Pro Arg Glu Arg Lys Ala Cys
1               5                   10                  15

Cys Lys Asn Phe Phe Trp Lys Thr Phe Thr Ser Cys
            20                  25
```

<210> SEQ ID NO 13
<211> LENGTH: 28
<212> TYPE: PRT

-continued

```
<213> ORGANISM: Artificial
<220> FEATURE:
<223> OTHER INFORMATION: Synthetic peptide
<220> FEATURE:
<221> NAME/KEY: DISULFID
<222> LOCATION: (17)..(28)
<220> FEATURE:
<221> NAME/KEY: CARBOHYD
<222> LOCATION: (18)..(18)
<223> OTHER INFORMATION: Disialo sugar chain added

<400> SEQUENCE: 13

Ser Ala Asn Ser Asn Pro Ala Met Ala Pro Arg Glu Arg Lys Ala Gly
1               5                   10                  15

Cys Cys Asn Phe Phe Trp Lys Thr Phe Thr Ser Cys
            20                  25

<210> SEQ ID NO 14
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: DISULFID
<222> LOCATION: (17)..(28)
<220> FEATURE:
<221> NAME/KEY: CARBOHYD
<222> LOCATION: (19)..(19)
<223> OTHER INFORMATION: Disialo sugar chain added

<400> SEQUENCE: 14

Ser Ala Asn Ser Asn Pro Ala Met Ala Pro Arg Glu Arg Lys Ala Gly
1               5                   10                  15

Cys Lys Cys Phe Phe Trp Lys Thr Phe Thr Ser Cys
            20                  25

<210> SEQ ID NO 15
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: DISULFID
<222> LOCATION: (17)..(28)
<220> FEATURE:
<221> NAME/KEY: CARBOHYD
<222> LOCATION: (21)..(21)
<223> OTHER INFORMATION: Disialo sugar chain added

<400> SEQUENCE: 15

Ser Ala Asn Ser Asn Pro Ala Met Ala Pro Arg Glu Arg Lys Ala Gly
1               5                   10                  15

Cys Lys Asn Phe Cys Trp Lys Thr Phe Thr Ser Cys
            20                  25

<210> SEQ ID NO 16
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: DISULFID
<222> LOCATION: (17)..(28)
<220> FEATURE:
<221> NAME/KEY: CARBOHYD
<222> LOCATION: (26)..(26)
<223> OTHER INFORMATION: Disialo sugar chain added
```

```
<400> SEQUENCE: 16

Ser Ala Asn Ser Asn Pro Ala Met Ala Pro Arg Glu Arg Lys Ala Gly
1               5                   10                  15

Cys Lys Asn Phe Phe Trp Lys Thr Phe Cys Ser Cys
            20                  25

<210> SEQ ID NO 17
<211> LENGTH: 29
<212> TYPE: PRT
<213> ORGANISM: Artificial
<220> FEATURE:
<223> OTHER INFORMATION: Synthetic peptide
<220> FEATURE:
<221> NAME/KEY: DISULFID
<222> LOCATION: (17)..(28)
<220> FEATURE:
<221> NAME/KEY: CARBOHYD
<222> LOCATION: (29)..(29)
<223> OTHER INFORMATION: Disialo sugar chain added

<400> SEQUENCE: 17

Ser Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys Cys
            20                  25

<210> SEQ ID NO 18
<211> LENGTH: 30
<212> TYPE: PRT
<213> ORGANISM: Artificial
<220> FEATURE:
<223> OTHER INFORMATION: Synthetic peptide
<220> FEATURE:
<221> NAME/KEY: DISULFID
<222> LOCATION: (17)..(28)
<220> FEATURE:
<221> NAME/KEY: CARBOHYD
<222> LOCATION: (30)..(30)
<223> OTHER INFORMATION: Disialo sugar chain added

<400> SEQUENCE: 18

Ser Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys Thr Cys
            20                  25                  30

<210> SEQ ID NO 19
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<220> FEATURE:
<221> NAME/KEY: DISULFID
<222> LOCATION: (17)..(28)
<220> FEATURE:
<221> NAME/KEY: MISC_FEATURE
<222> LOCATION: (22)..(22)
<223> OTHER INFORMATION: D-Trp

<400> SEQUENCE: 19

Cys Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
```

<210> SEQ ID NO 20
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (9)..(9)
<220> FEATURE:
<221> NAME/KEY: DISULFID
<222> LOCATION: (17)..(28)
<220> FEATURE:
<221> NAME/KEY: MISC_FEATURE
<222> LOCATION: (22)..(22)
<223> OTHER INFORMATION: D-Trp

<400> SEQUENCE: 20

Ser Ala Asn Ser Asn Pro Ala Met Cys Pro Arg Glu Arg Lys Ala Gly
1               5                   10                  15

Cys Lys Asn Phe Phe Trp Lys Thr Phe Thr Ser Cys
            20                  25

<210> SEQ ID NO 21
<211> LENGTH: 29
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: CARBOHYD
<222> LOCATION: (2)..(2)
<223> OTHER INFORMATION: Disialo sugar chain added
<220> FEATURE:
<221> NAME/KEY: DISULFID
<222> LOCATION: (18)..(29)

<400> SEQUENCE: 21

Cys Cys Ala Asn Ser Asn Pro Ala Met Ala Pro Arg Glu Arg Lys Ala
1               5                   10                  15

Gly Cys Lys Asn Phe Phe Trp Lys Thr Phe Thr Ser Cys
            20                  25

<210> SEQ ID NO 22
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: CARBOHYD
<222> LOCATION: (5)..(5)
<223> OTHER INFORMATION: Disialo sugar chain added
<220> FEATURE:
<221> NAME/KEY: DISULFID
<222> LOCATION: (17)..(28)

<400> SEQUENCE: 22

Cys Ala Asn Ser Cys Pro Ala Met Ala Pro Arg Glu Arg Lys Ala Gly
1               5                   10                  15

```
Cys Lys Asn Phe Phe Trp Lys Thr Phe Thr Ser Cys
            20                  25
```

<210> SEQ ID NO 23
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: CARBOHYD
<222> LOCATION: (13)..(13)
<223> OTHER INFORMATION: Disialo sugar chain added
<220> FEATURE:
<221> NAME/KEY: DISULFID
<222> LOCATION: (17)..(28)

<400> SEQUENCE: 23

```
Cys Ala Asn Ser Asn Pro Ala Met Ala Pro Arg Glu Cys Lys Ala Gly
1               5                   10                  15
Cys Lys Asn Phe Phe Trp Lys Thr Phe Thr Ser Cys
            20                  25
```

<210> SEQ ID NO 24
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (5)..(5)
<223> OTHER INFORMATION: Disialo sugar chain added
<220> FEATURE:
<221> NAME/KEY: CARBOHYD
<222> LOCATION: (9)..(9)
<223> OTHER INFORMATION: Disialo sugar chain added
<220> FEATURE:
<221> NAME/KEY: DISULFID
<222> LOCATION: (17)..(28)

<400> SEQUENCE: 24

```
Ser Ala Asn Ser Cys Pro Ala Met Cys Pro Arg Glu Arg Lys Ala Gly
1               5                   10                  15
Cys Lys Asn Phe Phe Trp Lys Thr Phe Thr Ser Cys
            20                  25
```

<210> SEQ ID NO 25
<211> LENGTH: 30
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: CARBOHYD
<222> LOCATION: (2)..(2)
<223> OTHER INFORMATION: Disialo sugar chain added
<220> FEATURE:
<221> NAME/KEY: CARBOHYD
<222> LOCATION: (3)..(3)
<223> OTHER INFORMATION: Disialo sugar chain added
<220> FEATURE:
<221> NAME/KEY: DISULFID
<222> LOCATION: (19)..(30)

```
<400> SEQUENCE: 25

Cys Cys Cys Ala Asn Ser Asn Pro Ala Met Ala Pro Arg Glu Arg Lys
1               5                   10                  15

Ala Gly Cys Lys Asn Phe Phe Trp Lys Thr Phe Thr Ser Cys
            20                  25                  30

<210> SEQ ID NO 26
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: CARBOHYD
<222> LOCATION: (5)..(5)
<223> OTHER INFORMATION: Disialo sugar chain added
<220> FEATURE:
<221> NAME/KEY: CARBOHYD
<222> LOCATION: (9)..(9)
<223> OTHER INFORMATION: Disialo sugar chain added
<220> FEATURE:
<221> NAME/KEY: DISULFID
<222> LOCATION: (17)..(28)

<400> SEQUENCE: 26

Cys Ala Asn Ser Cys Pro Ala Met Cys Pro Arg Glu Arg Lys Ala Gly
1               5                   10                  15

Cys Lys Asn Phe Phe Trp Lys Thr Phe Thr Ser Cys
            20                  25

<210> SEQ ID NO 27
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: monosialo sugar chain  added
<220> FEATURE:
<221> NAME/KEY: DISULFID
<222> LOCATION: (17)..(28)

<400> SEQUENCE: 27

Cys Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 28
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: asialo sugar chain added
<220> FEATURE:
<221> NAME/KEY: DISULFID
<222> LOCATION: (17)..(28)

<400> SEQUENCE: 28
```

Cys Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 29
<211> LENGTH: 29
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: asialo sugar chain added
<220> FEATURE:
<221> NAME/KEY: CARBOHYD
<222> LOCATION: (2)..(2)
<223> OTHER INFORMATION: asialo sugar chain added
<220> FEATURE:
<221> NAME/KEY: DISULFID
<222> LOCATION: (18)..(29)

<400> SEQUENCE: 29

Cys Cys Ala Asn Ser Asn Pro Ala Met Ala Pro Arg Glu Arg Lys Ala
1               5                   10                  15

Gly Cys Lys Asn Phe Phe Trp Lys Thr Phe Thr Ser Cys
            20                  25

<210> SEQ ID NO 30
<211> LENGTH: 30
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: asialo suger chain added
<220> FEATURE:
<221> NAME/KEY: CARBOHYD
<222> LOCATION: (2)..(2)
<223> OTHER INFORMATION: asialo suger chain added
<220> FEATURE:
<221> NAME/KEY: CARBOHYD
<222> LOCATION: (3)..(3)
<223> OTHER INFORMATION: asialo suger chain added
<220> FEATURE:
<221> NAME/KEY: DISULFID
<222> LOCATION: (19)..(30)

<400> SEQUENCE: 30

Cys Cys Cys Ala Asn Ser Asn Pro Ala Met Ala Pro Arg Glu Arg Lys
1               5                   10                  15

Ala Gly Cys Lys Asn Phe Phe Trp Lys Thr Phe Thr Ser Cys
            20                  25                  30

<210> SEQ ID NO 31
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (5)..(5)
<223> OTHER INFORMATION: Disialo sugar chain added
<220> FEATURE:
<221> NAME/KEY: DISULFID
<222> LOCATION: (17)..(28)

<400> SEQUENCE: 31

Ser Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 32
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: DISULFID
<222> LOCATION: (17)..(28)

<400> SEQUENCE: 32

Asn Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 33
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: DISULFID
<222> LOCATION: (17)..(28)
<220> FEATURE:
<221> NAME/KEY: CARBOHYD
<222> LOCATION: (19)..(19)
<223> OTHER INFORMATION: GlcNAc added

<400> SEQUENCE: 33

Cys Ala Asn Ser Asn Pro Ala Met Ala Pro Arg Glu Arg Lys Ala Gly
1               5                   10                  15

Cys Lys Cys Phe Phe Trp Lys Thr Phe Thr Ser Cys
            20                  25

<210> SEQ ID NO 34
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: DISULFID
<222> LOCATION: (17)..(28)
<220> FEATURE:
<221> NAME/KEY: CARBOHYD
<222> LOCATION: (19)..(19)
<223> OTHER INFORMATION: diMan sugar chain added

<400> SEQUENCE: 34

-continued

```
Cys Ala Asn Ser Asn Pro Ala Met Ala Pro Arg Glu Arg Lys Ala Gly
1               5                   10                  15

Cys Lys Cys Phe Phe Trp Lys Thr Phe Thr Ser Cys
            20                  25

<210> SEQ ID NO 35
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: DISULFID
<222> LOCATION: (4)..(15)

<400> SEQUENCE: 35

Cys Ala Gly Cys Lys Asn Phe Phe Trp Lys Thr Phe Thr Ser Cys
1               5                   10                  15

<210> SEQ ID NO 36
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: DISULFID
<222> LOCATION: (6)..(17)

<400> SEQUENCE: 36

Cys Arg Lys Ala Gly Cys Lys Asn Phe Phe Trp Lys Thr Phe Thr Ser
1               5                   10                  15

Cys

<210> SEQ ID NO 37
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: NON_CONS
<222> LOCATION: (1)..(2)
<223> OTHER INFORMATION: Cys and Ala are bonded through C12linker
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: DISULFID
<222> LOCATION: (4)..(15)

<400> SEQUENCE: 37

Cys Ala Gly Cys Lys Asn Phe Phe Trp Lys Thr Phe Thr Ser Cys
1               5                   10                  15

<210> SEQ ID NO 38
<211> LENGTH: 28
<212> TYPE: PRT
<213> ORGANISM: Artificial
<220> FEATURE:
```

```
<223> OTHER INFORMATION: Synthetic peptide
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 38

Cys Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 39
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 39

Cys Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 40
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added

<400> SEQUENCE: 40

Cys Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 41
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (17)..(17)
<223> OTHER INFORMATION: Acm
<220> FEATURE:
<221> NAME/KEY: BINDING
```

<222> LOCATION: (28)..(28)
<223> OTHER INFORMATION: Acm

<400> SEQUENCE: 41

Ser Ala Asn Ser Cys Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 42
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 42

Ser Ala Asn Ser Asn Pro Ala Met Cys Pro Arg Glu Arg Lys Ala Gly
1               5                   10                  15

Cys Lys Asn Phe Phe Trp Lys Thr Phe Thr Ser Cys
            20                  25

<210> SEQ ID NO 43
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 43

Ser Ala Asn Ser Asn Pro Ala Met Ala Pro Arg Cys Arg Lys Ala Gly
1               5                   10                  15

Cys Lys Asn Phe Phe Trp Lys Thr Phe Thr Ser Cys
            20                  25

<210> SEQ ID NO 44
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 44

Ser Ala Asn Ser Asn Pro Ala Met Ala Pro Arg Glu Cys Lys Ala Gly
1               5                   10                  15

Cys Lys Asn Phe Phe Trp Lys Thr Phe Thr Ser Cys
            20                  25

<210> SEQ ID NO 45
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 45

Ser Ala Asn Ser Asn Pro Ala Met Ala Pro Arg Glu Arg Cys Ala Gly
1               5                   10                  15

Cys Lys Asn Phe Phe Trp Lys Thr Phe Thr Ser Cys
            20                  25

<210> SEQ ID NO 46
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 46

Ser Ala Asn Ser Asn Pro Ala Met Ala Pro Arg Glu Arg Lys Cys Gly
1               5                   10                  15

Cys Lys Asn Phe Phe Trp Lys Thr Phe Thr Ser Cys
            20                  25

<210> SEQ ID NO 47
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 47

Ser Ala Asn Ser Asn Pro Ala Met Ala Pro Arg Glu Arg Lys Ala Cys
1               5                   10                  15

Cys Lys Asn Phe Phe Trp Lys Thr Phe Thr Ser Cys
            20                  25

<210> SEQ ID NO 48
<211> LENGTH: 28

```
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 48

Ser Ala Asn Ser Asn Pro Ala Met Ala Pro Arg Glu Arg Lys Ala Gly
1               5                   10                  15

Cys Cys Asn Phe Phe Trp Lys Thr Phe Thr Ser Cys
            20                  25

<210> SEQ ID NO 49
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 49

Ser Ala Asn Ser Asn Pro Ala Met Ala Pro Arg Glu Arg Lys Ala Gly
1               5                   10                  15

Cys Lys Cys Phe Phe Trp Lys Thr Phe Thr Ser Cys
            20                  25

<210> SEQ ID NO 50
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 50

Ser Ala Asn Ser Asn Pro Ala Met Ala Pro Arg Glu Arg Lys Ala Gly
1               5                   10                  15

Cys Lys Asn Phe Cys Trp Lys Thr Phe Thr Ser Cys
            20                  25

<210> SEQ ID NO 51
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (17)..(17)
```

```
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 51

Ser Ala Asn Ser Asn Pro Ala Met Ala Pro Arg Glu Arg Lys Ala Gly
1               5                   10                  15

Cys Lys Asn Phe Phe Trp Lys Thr Phe Cys Ser Cys
            20                  25

<210> SEQ ID NO 52
<211> LENGTH: 29
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 52

Ser Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys Cys
            20                  25

<210> SEQ ID NO 53
<211> LENGTH: 30
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 53

Ser Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys Thr Cys
            20                  25                  30

<210> SEQ ID NO 54
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (17)..(17)
<223> OTHER INFORMATION: Acm
<220> FEATURE:
<221> NAME/KEY: MISC_FEATURE
<222> LOCATION: (22)..(22)
<223> OTHER INFORMATION: D-Trp
<220> FEATURE:
<221> NAME/KEY: BINDING
```

-continued

```
<222> LOCATION: (28)..(28)
<223> OTHER INFORMATION: Acm

<400> SEQUENCE: 54

Cys Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 55
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (17)..(17)
<223> OTHER INFORMATION: Acm
<220> FEATURE:
<221> NAME/KEY: MISC_FEATURE
<222> LOCATION: (22)..(22)
<223> OTHER INFORMATION: D-Trp
<220> FEATURE:
<221> NAME/KEY: BINDING
<222> LOCATION: (28)..(28)
<223> OTHER INFORMATION: Acm

<400> SEQUENCE: 55

Ser Ala Asn Ser Asn Pro Ala Met Cys Pro Arg Glu Arg Lys Ala Gly
1               5                   10                  15

Cys Lys Asn Phe Phe Trp Lys Thr Phe Thr Ser Cys
            20                  25

<210> SEQ ID NO 56
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (4)..(4)
<223> OTHER INFORMATION: Acm
<220> FEATURE:
<221> NAME/KEY: BINDING
<222> LOCATION: (15)..(15)
<223> OTHER INFORMATION: Acm

<400> SEQUENCE: 56

Cys Ala Gly Cys Lys Asn Phe Phe Trp Lys Thr Phe Thr Ser Cys
1               5                   10                  15

<210> SEQ ID NO 57
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (6)..(6)
<223> OTHER INFORMATION: Acm
<220> FEATURE:
<221> NAME/KEY: BINDING
<222> LOCATION: (17)..(17)
<223> OTHER INFORMATION: Acm

<400> SEQUENCE: 57

Cys Arg Lys Ala Gly Cys Lys Asn Phe Phe Trp Lys Thr Phe Thr Ser
```

```
1               5                  10                  15

Cys

<210> SEQ ID NO 58
<211> LENGTH: 14
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (1)..(1)
<223> OTHER INFORMATION: Fmoc
<220> FEATURE:
<221> NAME/KEY: BINDING
<222> LOCATION: (3)..(3)
<223> OTHER INFORMATION: Acm
<220> FEATURE:
<221> NAME/KEY: BINDING
<222> LOCATION: (4)..(4)
<223> OTHER INFORMATION: Boc
<220> FEATURE:
<221> NAME/KEY: BINDING
<222> LOCATION: (5)..(5)
<223> OTHER INFORMATION: Trt
<220> FEATURE:
<221> NAME/KEY: BINDING
<222> LOCATION: (8)..(8)
<223> OTHER INFORMATION: Boc
<220> FEATURE:
<221> NAME/KEY: BINDING
<222> LOCATION: (9)..(9)
<223> OTHER INFORMATION: Boc
<220> FEATURE:
<221> NAME/KEY: BINDING
<222> LOCATION: (10)..(10)
<223> OTHER INFORMATION: tBu
<220> FEATURE:
<221> NAME/KEY: BINDING
<222> LOCATION: (12)..(12)
<223> OTHER INFORMATION: tBu
<220> FEATURE:
<221> NAME/KEY: BINDING
<222> LOCATION: (13)..(13)
<223> OTHER INFORMATION: tBu
<220> FEATURE:
<221> NAME/KEY: BINDING
<222> LOCATION: (14)..(14)
<223> OTHER INFORMATION: Acm
<220> FEATURE:
<221> NAME/KEY: BINDING
<222> LOCATION: (14)..(14)
<223> OTHER INFORMATION: Resin

<400> SEQUENCE: 58

Ala Gly Cys Lys Asn Phe Phe Trp Lys Thr Phe Thr Ser Cys
1               5                  10

<210> SEQ ID NO 59
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: NON_CONS
<222> LOCATION: (1)..(2)
<223> OTHER INFORMATION: Cys and Ala are bonded through C12linker
<220> FEATURE:
<221> NAME/KEY: BINDING
<222> LOCATION: (4)..(4)
<223> OTHER INFORMATION: Acm
<220> FEATURE:
<221> NAME/KEY: BINDING
<222> LOCATION: (15)..(15)
```

<223> OTHER INFORMATION: Acm

<400> SEQUENCE: 59

Cys Ala Gly Cys Lys Asn Phe Phe Trp Lys Thr Phe Thr Ser Cys
1               5                   10                  15

<210> SEQ ID NO 60
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: NON_CONS
<222> LOCATION: (1)..(2)
<223> OTHER INFORMATION: Cys and Ala are bonded through C12linker
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: BINDING
<222> LOCATION: (4)..(4)
<223> OTHER INFORMATION: Acm
<220> FEATURE:
<221> NAME/KEY: BINDING
<222> LOCATION: (15)..(15)
<223> OTHER INFORMATION: Acm

<400> SEQUENCE: 60

Cys Ala Gly Cys Lys Asn Phe Phe Trp Lys Thr Phe Thr Ser Cys
1               5                   10                  15

<210> SEQ ID NO 61
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: NON_CONS
<222> LOCATION: (1)..(2)
<223> OTHER INFORMATION: Cys and Ala are bonded through C12linker
<220> FEATURE:
<221> NAME/KEY: CARBOHYD
<222> LOCATION: (1)..(1)
<223> OTHER INFORMATION: Disialo sugar chain added

<400> SEQUENCE: 61

Cys Ala Gly Cys Lys Asn Phe Phe Trp Lys Thr Phe Thr Ser Cys
1               5                   10                  15

<210> SEQ ID NO 62
<211> LENGTH: 29
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (18)..(18)
<223> OTHER INFORMATION: Acm
<220> FEATURE:
<221> NAME/KEY: BINDING
<222> LOCATION: (29)..(29)
<223> OTHER INFORMATION: Acm

<400> SEQUENCE: 62

Cys Cys Ala Asn Ser Asn Pro Ala Met Ala Pro Arg Glu Arg Lys Ala
1               5                   10                  15

Gly Cys Lys Asn Phe Phe Trp Lys Thr Phe Thr Ser Cys

<210> SEQ ID NO 63
<211> LENGTH: 29
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: CARBOHYD
<222> LOCATION: (2)..(2)
<223> OTHER INFORMATION: Disialo sugar chain added
<220> FEATURE:
<221> NAME/KEY: BINDING
<222> LOCATION: (18)..(18)
<223> OTHER INFORMATION: Acm
<220> FEATURE:
<221> NAME/KEY: BINDING
<222> LOCATION: (29)..(29)
<223> OTHER INFORMATION: Acm

<400> SEQUENCE: 63

Cys Cys Ala Asn Ser Asn Pro Ala Met Ala Pro Arg Glu Arg Lys Ala
 1               5                  10                  15

Gly Cys Lys Asn Phe Phe Trp Lys Thr Phe Thr Ser Cys
            20                  25

<210> SEQ ID NO 64
<211> LENGTH: 29
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: CARBOHYD
<222> LOCATION: (2)..(2)
<223> OTHER INFORMATION: Disialo sugar chain added

<400> SEQUENCE: 64

Cys Cys Ala Asn Ser Asn Pro Ala Met Ala Pro Arg Glu Arg Lys Ala
 1               5                  10                  15

Gly Cys Lys Asn Phe Phe Trp Lys Thr Phe Thr Ser Cys
            20                  25

<210> SEQ ID NO 65
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 65

Cys Ala Asn Ser Cys Pro Ala Met Ala Pro Arg Glu Arg Lys Ala Gly
 1               5                  10                  15

Cys Lys Asn Phe Phe Trp Lys Thr Phe Thr Ser Cys
            20                  25

<210> SEQ ID NO 66
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 66

Cys Ala Asn Ser Asn Pro Ala Met Ala Pro Arg Glu Cys Lys Ala Gly
1               5                   10                  15

Cys Lys Asn Phe Phe Trp Lys Thr Phe Thr Ser Cys
            20                  25

<210> SEQ ID NO 67
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 67

Ser Ala Asn Ser Cys Pro Ala Met Cys Pro Arg Glu Arg Lys Ala Gly
1               5                   10                  15

Cys Lys Asn Phe Phe Trp Lys Thr Phe Thr Ser Cys
            20                  25

<210> SEQ ID NO 68
<211> LENGTH: 30
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (19)..(19)
<223> OTHER INFORMATION: Acm
<220> FEATURE:
<221> NAME/KEY: BINDING
<222> LOCATION: (30)..(30)
<223> OTHER INFORMATION: Acm

<400> SEQUENCE: 68

Cys Cys Cys Ala Asn Ser Asn Pro Ala Met Ala Pro Arg Glu Arg Lys
1               5                   10                  15

Ala Gly Cys Lys Asn Phe Phe Trp Lys Thr Phe Thr Ser Cys
            20                  25                  30

<210> SEQ ID NO 69
<211> LENGTH: 30
<212> TYPE: PRT

```
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: CARBOHYD
<222> LOCATION: (2)..(2)
<223> OTHER INFORMATION: Disialo sugar chain added
<220> FEATURE:
<221> NAME/KEY: CARBOHYD
<222> LOCATION: (3)..(3)
<223> OTHER INFORMATION: Disialo sugar chain added
<220> FEATURE:
<221> NAME/KEY: BINDING
<222> LOCATION: (19)..(19)
<223> OTHER INFORMATION: Acm
<220> FEATURE:
<221> NAME/KEY: BINDING
<222> LOCATION: (30)..(30)
<223> OTHER INFORMATION: Acm

<400> SEQUENCE: 69

Cys Cys Cys Ala Asn Ser Asn Pro Ala Met Ala Pro Arg Glu Arg Lys
1               5                   10                  15

Ala Gly Cys Lys Asn Phe Phe Trp Lys Thr Phe Thr Ser Cys
            20                  25                  30

<210> SEQ ID NO 70
<211> LENGTH: 30
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: CARBOHYD
<222> LOCATION: (2)..(2)
<223> OTHER INFORMATION: Disialo sugar chain added
<220> FEATURE:
<221> NAME/KEY: CARBOHYD
<222> LOCATION: (3)..(3)
<223> OTHER INFORMATION: Disialo sugar chain added

<400> SEQUENCE: 70

Cys Cys Cys Ala Asn Ser Asn Pro Ala Met Ala Pro Arg Glu Arg Lys
1               5                   10                  15

Ala Gly Cys Lys Asn Phe Phe Trp Lys Thr Phe Thr Ser Cys
            20                  25                  30

<210> SEQ ID NO 71
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 71

Cys Ala Asn Ser Cys Pro Ala Met Cys Pro Arg Glu Arg Lys Ala Gly
```

```
1               5                   10                  15
Cys Lys Asn Phe Phe Trp Lys Thr Phe Thr Ser Cys
            20                  25
```

<210> SEQ ID NO 72
<211> LENGTH: 29
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: asialo sugar chain added
<220> FEATURE:
<221> NAME/KEY: CARBOHYD
<222> LOCATION: (2)..(2)
<223> OTHER INFORMATION: asialo sugar chain added
<220> FEATURE:
<221> NAME/KEY: BINDING
<222> LOCATION: (18)..(18)
<223> OTHER INFORMATION: Acm
<220> FEATURE:
<221> NAME/KEY: BINDING
<222> LOCATION: (29)..(29)
<223> OTHER INFORMATION: Acm

<400> SEQUENCE: 72

```
Cys Cys Ala Asn Ser Asn Pro Ala Met Ala Pro Arg Glu Arg Lys Ala
1               5                   10                  15

Gly Cys Lys Asn Phe Phe Trp Lys Thr Phe Thr Ser Cys
            20                  25
```

<210> SEQ ID NO 73
<211> LENGTH: 29
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: asialo sugar chain added
<220> FEATURE:
<221> NAME/KEY: CARBOHYD
<222> LOCATION: (2)..(2)
<223> OTHER INFORMATION: asialo sugar chain added

<400> SEQUENCE: 73

```
Cys Cys Ala Asn Ser Asn Pro Ala Met Ala Pro Arg Glu Arg Lys Ala
1               5                   10                  15

Gly Cys Lys Asn Phe Phe Trp Lys Thr Phe Thr Ser Cys
            20                  25
```

<210> SEQ ID NO 74
<211> LENGTH: 30
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: asialo sugar chain added
<220> FEATURE:
<221> NAME/KEY: CARBOHYD
<222> LOCATION: (2)..(2)
<223> OTHER INFORMATION: asialo sugar chain added
<220> FEATURE:
<221> NAME/KEY: CARBOHYD
<222> LOCATION: (3)..(3)

<223> OTHER INFORMATION: asialo sugar chain added
<220> FEATURE:
<221> NAME/KEY: BINDING
<222> LOCATION: (19)..(19)
<223> OTHER INFORMATION: Acm
<220> FEATURE:
<221> NAME/KEY: BINDING
<222> LOCATION: (30)..(30)
<223> OTHER INFORMATION: Acm

<400> SEQUENCE: 74

Cys Cys Cys Ala Asn Ser Asn Pro Ala Met Ala Pro Arg Glu Arg Lys
1               5                   10                  15

Ala Gly Cys Lys Asn Phe Phe Trp Lys Thr Phe Thr Ser Cys
            20                  25                  30

<210> SEQ ID NO 75
<211> LENGTH: 30
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: asialo sugar chain added
<220> FEATURE:
<221> NAME/KEY: CARBOHYD
<222> LOCATION: (2)..(2)
<223> OTHER INFORMATION: asialo sugar chain added
<220> FEATURE:
<221> NAME/KEY: CARBOHYD
<222> LOCATION: (3)..(3)
<223> OTHER INFORMATION: asialo sugar chain added

<400> SEQUENCE: 75

Cys Cys Cys Ala Asn Ser Asn Pro Ala Met Ala Pro Arg Glu Arg Lys
1               5                   10                  15

Ala Gly Cys Lys Asn Phe Phe Trp Lys Thr Phe Thr Ser Cys
            20                  25                  30

<210> SEQ ID NO 76
<211> LENGTH: 23
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (1)..(1)
<223> OTHER INFORMATION: Fmoc
<220> FEATURE:
<221> NAME/KEY: BINDING
<222> LOCATION: (6)..(6)
<223> OTHER INFORMATION: Pbf
<220> FEATURE:
<221> NAME/KEY: BINDING
<222> LOCATION: (7)..(7)
<223> OTHER INFORMATION: OtBu
<220> FEATURE:
<221> NAME/KEY: BINDING
<222> LOCATION: (8)..(8)
<223> OTHER INFORMATION: Pbf
<220> FEATURE:
<221> NAME/KEY: BINDING
<222> LOCATION: (9)..(9)
<223> OTHER INFORMATION: Boc
<220> FEATURE:
<221> NAME/KEY: BINDING
<222> LOCATION: (12)..(12)
<223> OTHER INFORMATION: Trt
<220> FEATURE:
<221> NAME/KEY: BINDING

```
<222> LOCATION: (13)..(13)
<223> OTHER INFORMATION: Boc
<220> FEATURE:
<221> NAME/KEY: BINDING
<222> LOCATION: (14)..(14)
<223> OTHER INFORMATION: Trt
<220> FEATURE:
<221> NAME/KEY: BINDING
<222> LOCATION: (17)..(17)
<223> OTHER INFORMATION: Boc
<220> FEATURE:
<221> NAME/KEY: BINDING
<222> LOCATION: (18)..(18)
<223> OTHER INFORMATION: Boc
<220> FEATURE:
<221> NAME/KEY: BINDING
<222> LOCATION: (19)..(19)
<223> OTHER INFORMATION: tBu
<220> FEATURE:
<221> NAME/KEY: BINDING
<222> LOCATION: (21)..(21)
<223> OTHER INFORMATION: tBu
<220> FEATURE:
<221> NAME/KEY: BINDING
<222> LOCATION: (22)..(22)
<223> OTHER INFORMATION: tBu
<220> FEATURE:
<221> NAME/KEY: BINDING
<222> LOCATION: (23)..(23)
<223> OTHER INFORMATION: Trt
<220> FEATURE:
<221> NAME/KEY: BINDING
<222> LOCATION: (23)..(23)
<223> OTHER INFORMATION: Resin

<400> SEQUENCE: 76

Pro Ala Met Ala Pro Arg Glu Arg Lys Ala Gly Cys Lys Asn Phe Phe
1               5                   10                  15

Trp Lys Thr Phe Thr Ser Cys
            20

<210> SEQ ID NO 77
<211> LENGTH: 24
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain protected with benzyl
      group added
<220> FEATURE:
<221> NAME/KEY: BINDING
<222> LOCATION: (7)..(7)
<223> OTHER INFORMATION: Pbf
<220> FEATURE:
<221> NAME/KEY: BINDING
<222> LOCATION: (8)..(8)
<223> OTHER INFORMATION: OtBu
<220> FEATURE:
<221> NAME/KEY: BINDING
<222> LOCATION: (9)..(9)
<223> OTHER INFORMATION: Pbf
<220> FEATURE:
<221> NAME/KEY: BINDING
<222> LOCATION: (10)..(10)
<223> OTHER INFORMATION: Boc
<220> FEATURE:
<221> NAME/KEY: BINDING
<222> LOCATION: (13)..(13)
<223> OTHER INFORMATION: Trt
<220> FEATURE:
<221> NAME/KEY: BINDING
<222> LOCATION: (14)..(14)
<223> OTHER INFORMATION: Boc
```

```
<220> FEATURE:
<221> NAME/KEY: BINDING
<222> LOCATION: (15)..(15)
<223> OTHER INFORMATION: Trt
<220> FEATURE:
<221> NAME/KEY: BINDING
<222> LOCATION: (18)..(18)
<223> OTHER INFORMATION: Boc
<220> FEATURE:
<221> NAME/KEY: BINDING
<222> LOCATION: (19)..(19)
<223> OTHER INFORMATION: Boc
<220> FEATURE:
<221> NAME/KEY: BINDING
<222> LOCATION: (20)..(20)
<223> OTHER INFORMATION: tBu
<220> FEATURE:
<221> NAME/KEY: BINDING
<222> LOCATION: (22)..(22)
<223> OTHER INFORMATION: tBu
<220> FEATURE:
<221> NAME/KEY: BINDING
<222> LOCATION: (23)..(23)
<223> OTHER INFORMATION: tBu
<220> FEATURE:
<221> NAME/KEY: BINDING
<222> LOCATION: (24)..(24)
<223> OTHER INFORMATION: Trt
<220> FEATURE:
<221> NAME/KEY: BINDING
<222> LOCATION: (24)..(24)
<223> OTHER INFORMATION: Resin

<400> SEQUENCE: 77

Asn Pro Ala Met Ala Pro Arg Glu Arg Lys Ala Gly Cys Lys Asn Phe
1               5                   10                  15

Phe Trp Lys Thr Phe Thr Ser Cys
            20

<210> SEQ ID NO 78
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (5)..(5)
<223> OTHER INFORMATION: Disialo sugar chain protected with benzyl
      group added

<400> SEQUENCE: 78

Ser Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 79
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (5)..(5)
<223> OTHER INFORMATION: Disialo sugar chain protected with benzyl
      group added
<220> FEATURE:
<221> NAME/KEY: DISULFID
<222> LOCATION: (17)..(28)

<400> SEQUENCE: 79
```

```
Ser Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 80
<211> LENGTH: 27
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (1)..(1)
<223> OTHER INFORMATION: Fmoc
<220> FEATURE:
<221> NAME/KEY: BINDING
<222> LOCATION: (2)..(2)
<223> OTHER INFORMATION: Trt
<220> FEATURE:
<221> NAME/KEY: BINDING
<222> LOCATION: (3)..(3)
<223> OTHER INFORMATION: tBu
<220> FEATURE:
<221> NAME/KEY: BINDING
<222> LOCATION: (4)..(4)
<223> OTHER INFORMATION: Trt
<220> FEATURE:
<221> NAME/KEY: BINDING
<222> LOCATION: (10)..(10)
<223> OTHER INFORMATION: Pbf
<220> FEATURE:
<221> NAME/KEY: BINDING
<222> LOCATION: (11)..(11)
<223> OTHER INFORMATION: OtBu
<220> FEATURE:
<221> NAME/KEY: BINDING
<222> LOCATION: (12)..(12)
<223> OTHER INFORMATION: Pbf
<220> FEATURE:
<221> NAME/KEY: BINDING
<222> LOCATION: (13)..(13)
<223> OTHER INFORMATION: Boc
<220> FEATURE:
<221> NAME/KEY: BINDING
<222> LOCATION: (16)..(16)
<223> OTHER INFORMATION: Trt
<220> FEATURE:
<221> NAME/KEY: BINDING
<222> LOCATION: (17)..(17)
<223> OTHER INFORMATION: Boc
<220> FEATURE:
<221> NAME/KEY: BINDING
<222> LOCATION: (18)..(18)
<223> OTHER INFORMATION: Trt
<220> FEATURE:
<221> NAME/KEY: BINDING
<222> LOCATION: (21)..(21)
<223> OTHER INFORMATION: Boc
<220> FEATURE:
<221> NAME/KEY: BINDING
<222> LOCATION: (22)..(22)
<223> OTHER INFORMATION: Boc
<220> FEATURE:
<221> NAME/KEY: BINDING
<222> LOCATION: (23)..(23)
<223> OTHER INFORMATION: tBu
<220> FEATURE:
<221> NAME/KEY: BINDING
<222> LOCATION: (25)..(25)
<223> OTHER INFORMATION: tBu
<220> FEATURE:
<221> NAME/KEY: BINDING
<222> LOCATION: (26)..(26)
<223> OTHER INFORMATION: tBu
<220> FEATURE:
```

```
<221> NAME/KEY: BINDING
<222> LOCATION: (27)..(27)
<223> OTHER INFORMATION: Trt
<220> FEATURE:
<221> NAME/KEY: BINDING
<222> LOCATION: (27)..(27)
<223> OTHER INFORMATION: Resin

<400> SEQUENCE: 80

Ala Asn Ser Asn Pro Ala Met Ala Pro Arg Glu Arg Lys Ala Gly Cys
1               5                   10                  15

Lys Asn Phe Phe Trp Lys Thr Phe Thr Ser Cys
            20                  25

<210> SEQ ID NO 81
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain protected with benzyl
      group added
<220> FEATURE:
<221> NAME/KEY: BINDING
<222> LOCATION: (3)..(3)
<223> OTHER INFORMATION: Trt
<220> FEATURE:
<221> NAME/KEY: BINDING
<222> LOCATION: (4)..(4)
<223> OTHER INFORMATION: tBu
<220> FEATURE:
<221> NAME/KEY: BINDING
<222> LOCATION: (5)..(5)
<223> OTHER INFORMATION: Trt
<220> FEATURE:
<221> NAME/KEY: BINDING
<222> LOCATION: (11)..(11)
<223> OTHER INFORMATION: Pbf
<220> FEATURE:
<221> NAME/KEY: BINDING
<222> LOCATION: (12)..(12)
<223> OTHER INFORMATION: OtBu
<220> FEATURE:
<221> NAME/KEY: BINDING
<222> LOCATION: (13)..(13)
<223> OTHER INFORMATION: Pbf
<220> FEATURE:
<221> NAME/KEY: BINDING
<222> LOCATION: (14)..(14)
<223> OTHER INFORMATION: Boc
<220> FEATURE:
<221> NAME/KEY: BINDING
<222> LOCATION: (17)..(17)
<223> OTHER INFORMATION: Trt
<220> FEATURE:
<221> NAME/KEY: BINDING
<222> LOCATION: (18)..(18)
<223> OTHER INFORMATION: Boc
<220> FEATURE:
<221> NAME/KEY: BINDING
<222> LOCATION: (19)..(19)
<223> OTHER INFORMATION: Trt
<220> FEATURE:
<221> NAME/KEY: BINDING
<222> LOCATION: (22)..(22)
<223> OTHER INFORMATION: Boc
<220> FEATURE:
<221> NAME/KEY: BINDING
<222> LOCATION: (23)..(23)
<223> OTHER INFORMATION: Boc
<220> FEATURE:
<221> NAME/KEY: BINDING
<222> LOCATION: (24)..(24)
```

```
<223> OTHER INFORMATION: tBu
<220> FEATURE:
<221> NAME/KEY: BINDING
<222> LOCATION: (26)..(26)
<223> OTHER INFORMATION: tBu
<220> FEATURE:
<221> NAME/KEY: BINDING
<222> LOCATION: (27)..(27)
<223> OTHER INFORMATION: tBu
<220> FEATURE:
<221> NAME/KEY: BINDING
<222> LOCATION: (28)..(28)
<223> OTHER INFORMATION: Trt
<220> FEATURE:
<221> NAME/KEY: BINDING
<222> LOCATION: (28)..(28)
<223> OTHER INFORMATION: Resin

<400> SEQUENCE: 81

Asn Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 82
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain protected with benzyl
      group added

<400> SEQUENCE: 82

Asn Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 83
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain protected with benzyl
      group added
<220> FEATURE:
<221> NAME/KEY: DISULFID
<222> LOCATION: (17)..(28)

<400> SEQUENCE: 83

Asn Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 84
<211> LENGTH: 28
<212> TYPE: PRT
<213> ORGANISM: Artificial
<220> FEATURE:
<223> OTHER INFORMATION: Synthetic peptide
<220> FEATURE:
```

```
<221> NAME/KEY: BINDING
<222> LOCATION: (1)..(1)
<223> OTHER INFORMATION: StBu
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 84

Cys Ala Asn Ser Asn Pro Ala Met Ala Pro Arg Glu Arg Lys Ala Gly
1               5                   10                  15

Cys Lys Cys Phe Phe Trp Lys Thr Phe Thr Ser Cys
            20                  25

<210> SEQ ID NO 85
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (17)..(17)
<223> OTHER INFORMATION: Acm
<220> FEATURE:
<221> NAME/KEY: CARBOHYD
<222> LOCATION: (19)..(19)
<223> OTHER INFORMATION: GlcNAc added
<220> FEATURE:
<221> NAME/KEY: BINDING
<222> LOCATION: (28)..(28)
<223> OTHER INFORMATION: Acm

<400> SEQUENCE: 85

Cys Ala Asn Ser Asn Pro Ala Met Ala Pro Arg Glu Arg Lys Ala Gly
1               5                   10                  15

Cys Lys Cys Phe Phe Trp Lys Thr Phe Thr Ser Cys
            20                  25

<210> SEQ ID NO 86
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: BINDING
<222> LOCATION: (17)..(17)
<223> OTHER INFORMATION: Acm
<220> FEATURE:
<221> NAME/KEY: CARBOHYD
<222> LOCATION: (19)..(19)
<223> OTHER INFORMATION: GlcNAc added
<220> FEATURE:
<221> NAME/KEY: BINDING
<222> LOCATION: (28)..(28)
<223> OTHER INFORMATION: Acm

<400> SEQUENCE: 86

Cys Ala Asn Ser Asn Pro Ala Met Ala Pro Arg Glu Arg Lys Ala Gly
1               5                   10                  15

Cys Lys Cys Phe Phe Trp Lys Thr Phe Thr Ser Cys
            20                  25
```

<210> SEQ ID NO 87
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: CARBOHYD
<222> LOCATION: (19)..(19)
<223> OTHER INFORMATION: GlcNAc added

<400> SEQUENCE: 87

Cys Ala Asn Ser Asn Pro Ala Met Ala Pro Arg Glu Arg Lys Ala Gly
1               5                   10                  15

Cys Lys Cys Phe Phe Trp Lys Thr Phe Thr Ser Cys
            20                  25

<210> SEQ ID NO 88
<211> LENGTH: 32
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: CARBOHYD
<222> LOCATION: (2)..(2)
<223> OTHER INFORMATION: Disialo sugar chain added
<220> FEATURE:
<221> NAME/KEY: CARBOHYD
<222> LOCATION: (3)..(3)
<223> OTHER INFORMATION: Disialo sugar chain added
<220> FEATURE:
<221> NAME/KEY: CARBOHYD
<222> LOCATION: (4)..(4)
<223> OTHER INFORMATION: Disialo sugar chain added
<220> FEATURE:
<221> NAME/KEY: CARBOHYD
<222> LOCATION: (5)..(5)
<223> OTHER INFORMATION: Disialo sugar chain added
<220> FEATURE:
<221> NAME/KEY: DISULFID
<222> LOCATION: (21)..(32)

<400> SEQUENCE: 88

Cys Cys Cys Cys Cys Ala Asn Ser Asn Pro Ala Met Ala Pro Arg Glu
1               5                   10                  15

Arg Lys Ala Gly Cys Lys Asn Phe Phe Trp Lys Thr Phe Thr Ser Cys
            20                  25                  30

<210> SEQ ID NO 89
<211> LENGTH: 37
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: CARBOHYD
<222> LOCATION: (2)..(2)
<223> OTHER INFORMATION: Disialo sugar chain added

```
<220> FEATURE:
<221> NAME/KEY: CARBOHYD
<222> LOCATION: (3)..(3)
<223> OTHER INFORMATION: Disialo sugar chain added
<220> FEATURE:
<221> NAME/KEY: CARBOHYD
<222> LOCATION: (4)..(4)
<223> OTHER INFORMATION: Disialo sugar chain added
<220> FEATURE:
<221> NAME/KEY: CARBOHYD
<222> LOCATION: (5)..(5)
<223> OTHER INFORMATION: Disialo sugar chain added
<220> FEATURE:
<221> NAME/KEY: CARBOHYD
<222> LOCATION: (6)..(6)
<223> OTHER INFORMATION: Disialo sugar chain added
<220> FEATURE:
<221> NAME/KEY: CARBOHYD
<222> LOCATION: (7)..(7)
<223> OTHER INFORMATION: Disialo sugar chain added
<220> FEATURE:
<221> NAME/KEY: CARBOHYD
<222> LOCATION: (8)..(8)
<223> OTHER INFORMATION: Disialo sugar chain added
<220> FEATURE:
<221> NAME/KEY: CARBOHYD
<222> LOCATION: (9)..(9)
<223> OTHER INFORMATION: Disialo sugar chain added
<220> FEATURE:
<221> NAME/KEY: CARBOHYD
<222> LOCATION: (10)..(10)
<223> OTHER INFORMATION: Disialo sugar chain added
<220> FEATURE:
<221> NAME/KEY: DISULFID
<222> LOCATION: (26)..(37)

<400> SEQUENCE: 89

Cys Cys Cys Cys Cys Cys Cys Cys Cys Cys Ala Asn Ser Asn Pro Ala
1               5                   10                  15

Met Ala Pro Arg Glu Arg Lys Ala Gly Cys Lys Asn Phe Phe Trp Lys
            20                  25                  30

Thr Phe Thr Ser Cys
        35

<210> SEQ ID NO 90
<211> LENGTH: 32
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (21)..(21)
<223> OTHER INFORMATION: Acm
<220> FEATURE:
<221> NAME/KEY: BINDING
<222> LOCATION: (32)..(32)
<223> OTHER INFORMATION: Acm

<400> SEQUENCE: 90

Cys Cys Cys Cys Cys Ala Asn Ser Asn Pro Ala Met Ala Pro Arg Glu
1               5                   10                  15

Arg Lys Ala Gly Cys Lys Asn Phe Phe Trp Lys Thr Phe Thr Ser Cys
            20                  25                  30

<210> SEQ ID NO 91
<211> LENGTH: 32
<212> TYPE: PRT
<213> ORGANISM: Artificial
<220> FEATURE:
<223> OTHER INFORMATION: Synthetic peptide
<220> FEATURE:
```

```
<221> NAME/KEY: CARBOHYD
<222> LOCATION: (1)..(1)
<223> OTHER INFORMATION: Disialo sugar chain added
<220> FEATURE:
<221> NAME/KEY: CARBOHYD
<222> LOCATION: (2)..(2)
<223> OTHER INFORMATION: Disialo sugar chain added
<220> FEATURE:
<221> NAME/KEY: CARBOHYD
<222> LOCATION: (3)..(3)
<223> OTHER INFORMATION: Disialo sugar chain added
<220> FEATURE:
<221> NAME/KEY: CARBOHYD
<222> LOCATION: (4)..(4)
<223> OTHER INFORMATION: Disialo sugar chain added
<220> FEATURE:
<221> NAME/KEY: CARBOHYD
<222> LOCATION: (5)..(5)
<223> OTHER INFORMATION: Disialo sugar chain added
<220> FEATURE:
<221> NAME/KEY: BINDING
<222> LOCATION: (21)..(21)
<223> OTHER INFORMATION: Acm
<220> FEATURE:
<221> NAME/KEY: BINDING
<222> LOCATION: (32)..(32)
<223> OTHER INFORMATION: Acm

<400> SEQUENCE: 91

Cys Cys Cys Cys Cys Ala Asn Ser Asn Pro Ala Met Ala Pro Arg Glu
1               5                   10                  15

Arg Lys Ala Gly Cys Lys Asn Phe Phe Trp Lys Thr Phe Thr Ser Cys
            20                  25                  30

<210> SEQ ID NO 92
<211> LENGTH: 32
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: CARBOHYD
<222> LOCATION: (2)..(2)
<223> OTHER INFORMATION: Disialo sugar chain added
<220> FEATURE:
<221> NAME/KEY: CARBOHYD
<222> LOCATION: (3)..(3)
<223> OTHER INFORMATION: Disialo sugar chain added
<220> FEATURE:
<221> NAME/KEY: CARBOHYD
<222> LOCATION: (4)..(4)
<223> OTHER INFORMATION: Disialo sugar chain added
<220> FEATURE:
<221> NAME/KEY: CARBOHYD
<222> LOCATION: (5)..(5)
<223> OTHER INFORMATION: Disialo sugar chain added

<400> SEQUENCE: 92

Cys Cys Cys Cys Cys Ala Asn Ser Asn Pro Ala Met Ala Pro Arg Glu
1               5                   10                  15

Arg Lys Ala Gly Cys Lys Asn Phe Phe Trp Lys Thr Phe Thr Ser Cys
            20                  25                  30

<210> SEQ ID NO 93
<211> LENGTH: 37
<212> TYPE: PRT
<213> ORGANISM: Artificial
<220> FEATURE:
<223> OTHER INFORMATION: Synthetic peptide
```

```
<220> FEATURE:
<221> NAME/KEY: BINDING
<222> LOCATION: (26)..(26)
<223> OTHER INFORMATION: Acm
<220> FEATURE:
<221> NAME/KEY: BINDING
<222> LOCATION: (37)..(37)
<223> OTHER INFORMATION: Acm

<400> SEQUENCE: 93

Cys Cys Cys Cys Cys Cys Cys Cys Cys Cys Ala Asn Ser Asn Pro Ala
1               5                   10                  15

Met Ala Pro Arg Glu Arg Lys Ala Gly Cys Lys Asn Phe Phe Trp Lys
            20                  25                  30

Thr Phe Thr Ser Cys
            35

<210> SEQ ID NO 94
<211> LENGTH: 37
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain protected with benzyl
      group added
<220> FEATURE:
<221> NAME/KEY: CARBOHYD
<222> LOCATION: (2)..(2)
<223> OTHER INFORMATION: Disialo sugar chain protected with benzyl
      group added
<220> FEATURE:
<221> NAME/KEY: CARBOHYD
<222> LOCATION: (3)..(3)
<223> OTHER INFORMATION: Disialo sugar chain protected with benzyl
      group added
<220> FEATURE:
<221> NAME/KEY: CARBOHYD
<222> LOCATION: (4)..(4)
<223> OTHER INFORMATION: Disialo sugar chain protected with benzyl
      group added
<220> FEATURE:
<221> NAME/KEY: CARBOHYD
<222> LOCATION: (5)..(5)
<223> OTHER INFORMATION: Disialo sugar chain protected with benzyl
      group added
<220> FEATURE:
<221> NAME/KEY: CARBOHYD
<222> LOCATION: (6)..(6)
<223> OTHER INFORMATION: Disialo sugar chain protected with benzyl
      group added
<220> FEATURE:
<221> NAME/KEY: CARBOHYD
<222> LOCATION: (7)..(7)
<223> OTHER INFORMATION: Disialo sugar chain protected with benzyl
      group added
<220> FEATURE:
<221> NAME/KEY: CARBOHYD
<222> LOCATION: (8)..(8)
<223> OTHER INFORMATION: Disialo sugar chain protected with benzyl
      group added
<220> FEATURE:
<221> NAME/KEY: CARBOHYD
<222> LOCATION: (9)..(9)
<223> OTHER INFORMATION: Disialo sugar chain protected with benzyl
      group added
<220> FEATURE:
<221> NAME/KEY: CARBOHYD
<222> LOCATION: (10)..(10)
<223> OTHER INFORMATION: Disialo sugar chain protected with benzyl
      group added
<220> FEATURE:
<221> NAME/KEY: BINDING
```

```
<222> LOCATION: (26)..(26)
<223> OTHER INFORMATION: Acm
<220> FEATURE:
<221> NAME/KEY: BINDING
<222> LOCATION: (37)..(37)
<223> OTHER INFORMATION: Acm

<400> SEQUENCE: 94

Cys Cys Cys Cys Cys Cys Cys Cys Cys Cys Ala Asn Ser Asn Pro Ala
1               5                   10                  15

Met Ala Pro Arg Glu Arg Lys Ala Gly Cys Lys Asn Phe Phe Trp Lys
            20                  25                  30

Thr Phe Thr Ser Cys
            35

<210> SEQ ID NO 95
<211> LENGTH: 37
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain protected with benzyl
      group added
<220> FEATURE:
<221> NAME/KEY: CARBOHYD
<222> LOCATION: (2)..(2)
<223> OTHER INFORMATION: Disialo sugar chain protected with benzyl
      group added
<220> FEATURE:
<221> NAME/KEY: CARBOHYD
<222> LOCATION: (3)..(3)
<223> OTHER INFORMATION: Disialo sugar chain protected with benzyl
      group added
<220> FEATURE:
<221> NAME/KEY: CARBOHYD
<222> LOCATION: (4)..(4)
<223> OTHER INFORMATION: Disialo sugar chain protected with benzyl
      group added
<220> FEATURE:
<221> NAME/KEY: CARBOHYD
<222> LOCATION: (5)..(5)
<223> OTHER INFORMATION: Disialo sugar chain protected with benzyl
      group added
<220> FEATURE:
<221> NAME/KEY: CARBOHYD
<222> LOCATION: (6)..(6)
<223> OTHER INFORMATION: Disialo sugar chain protected with benzyl
      group added
<220> FEATURE:
<221> NAME/KEY: CARBOHYD
<222> LOCATION: (7)..(7)
<223> OTHER INFORMATION: Disialo sugar chain protected with benzyl
      group added
<220> FEATURE:
<221> NAME/KEY: CARBOHYD
<222> LOCATION: (8)..(8)
<223> OTHER INFORMATION: Disialo sugar chain protected with benzyl
      group added
<220> FEATURE:
<221> NAME/KEY: CARBOHYD
<222> LOCATION: (9)..(9)
<223> OTHER INFORMATION: Disialo sugar chain protected with benzyl
      group added
<220> FEATURE:
<221> NAME/KEY: CARBOHYD
<222> LOCATION: (10)..(10)
<223> OTHER INFORMATION: Disialo sugar chain protected with benzyl
      group added

<400> SEQUENCE: 95

Cys Cys Cys Cys Cys Cys Cys Cys Cys Cys Ala Asn Ser Asn Pro Ala
```

```
                1               5                      10                      15
            Met Ala Pro Arg Glu Arg Lys Ala Gly Cys Lys Asn Phe Phe Trp Lys
                                20                      25                      30
            Thr Phe Thr Ser Cys
                        35
```

<210> SEQ ID NO 96
<211> LENGTH: 37
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain protected with benzyl
      group added
<220> FEATURE:
<221> NAME/KEY: CARBOHYD
<222> LOCATION: (2)..(2)
<223> OTHER INFORMATION: Disialo sugar chain protected with benzyl
      group added
<220> FEATURE:
<221> NAME/KEY: CARBOHYD
<222> LOCATION: (3)..(3)
<223> OTHER INFORMATION: Disialo sugar chain protected with benzyl
      group added
<220> FEATURE:
<221> NAME/KEY: CARBOHYD
<222> LOCATION: (4)..(4)
<223> OTHER INFORMATION: Disialo sugar chain protected with benzyl
      group added
<220> FEATURE:
<221> NAME/KEY: CARBOHYD
<222> LOCATION: (5)..(5)
<223> OTHER INFORMATION: Disialo sugar chain protected with benzyl
      group added
<220> FEATURE:
<221> NAME/KEY: CARBOHYD
<222> LOCATION: (6)..(6)
<223> OTHER INFORMATION: Disialo sugar chain protected with benzyl
      group added
<220> FEATURE:
<221> NAME/KEY: CARBOHYD
<222> LOCATION: (7)..(7)
<223> OTHER INFORMATION: Disialo sugar chain protected with benzyl
      group added
<220> FEATURE:
<221> NAME/KEY: CARBOHYD
<222> LOCATION: (8)..(8)
<223> OTHER INFORMATION: Disialo sugar chain protected with benzyl
      group added
<220> FEATURE:
<221> NAME/KEY: CARBOHYD
<222> LOCATION: (9)..(9)
<223> OTHER INFORMATION: Disialo sugar chain protected with benzyl
      group added
<220> FEATURE:
<221> NAME/KEY: CARBOHYD
<222> LOCATION: (10)..(10)
<223> OTHER INFORMATION: Disialo sugar chain protected with benzyl
      group added
<220> FEATURE:
<221> NAME/KEY: DISULFID
<222> LOCATION: (26)..(37)

<400> SEQUENCE: 96

```
            Cys Cys Cys Cys Cys Cys Cys Cys Cys Cys Ala Asn Ser Asn Pro Ala
            1               5                       10                      15

Met Ala Pro Arg Glu Arg Lys Ala Gly Cys Lys Asn Phe Phe Trp Lys
                                20                      25                      30

Thr Phe Thr Ser Cys
                        35
```

<210> SEQ ID NO 97
<211> LENGTH: 29
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (18)..(18)
<223> OTHER INFORMATION: Acm
<220> FEATURE:
<221> NAME/KEY: BINDING
<222> LOCATION: (29)..(29)
<223> OTHER INFORMATION: Acm

<400> SEQUENCE: 97

Cys Ser Ala Asn Ser Asn Pro Ala Met Ala Pro Arg Glu Arg Lys Ala
1               5                   10                  15

Gly Cys Lys Asn Phe Phe Trp Lys Thr Phe Thr Ser Cys
            20                  25

<210> SEQ ID NO 98
<211> LENGTH: 29
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: DISULFID
<222> LOCATION: (18)..(29)

<400> SEQUENCE: 98

Cys Ser Ala Asn Ser Asn Pro Ala Met Ala Pro Arg Glu Arg Lys Ala
1               5                   10                  15

Gly Cys Lys Asn Phe Phe Trp Lys Thr Phe Thr Ser Cys
            20                  25

<210> SEQ ID NO 99
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 99

Ser Ala Asn Ser Asn Pro Ala Met Ala Pro Cys Glu Arg Lys Ala Gly
1               5                   10                  15

Cys Lys Asn Phe Phe Trp Lys Thr Phe Thr Ser Cys
            20                  25

<210> SEQ ID NO 100
<211> LENGTH: 28
<212> TYPE: PRT
<213> ORGANISM: Artificial
<220> FEATURE:
<223> OTHER INFORMATION: Synthetic peptide

```
<220> FEATURE:
<221> NAME/KEY: CARBOHYD
<222> LOCATION: (11)..(11)
<223> OTHER INFORMATION: Disialo sugar chain added
<220> FEATURE:
<221> NAME/KEY: DISULFID
<222> LOCATION: (17)..(28)

<400> SEQUENCE: 100

Ser Ala Asn Ser Asn Pro Ala Met Ala Pro Cys Glu Arg Lys Ala Gly
1               5                   10                  15

Cys Lys Asn Phe Phe Trp Lys Thr Phe Thr Ser Cys
            20                  25

<210> SEQ ID NO 101
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 101

Ser Ala Asn Ser Asn Pro Ala Met Ala Pro Arg Glu Arg Lys Ala Gly
1               5                   10                  15

Cys Lys Asn Cys Phe Trp Lys Thr Phe Thr Ser Cys
            20                  25

<210> SEQ ID NO 102
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: DISULFID
<222> LOCATION: (17)..(28)
<220> FEATURE:
<221> NAME/KEY: CARBOHYD
<222> LOCATION: (20)..(20)
<223> OTHER INFORMATION: Disialo sugar chain added

<400> SEQUENCE: 102

Ser Ala Asn Ser Asn Pro Ala Met Ala Pro Arg Glu Arg Lys Ala Gly
1               5                   10                  15

Cys Lys Asn Cys Phe Trp Lys Thr Phe Thr Ser Cys
            20                  25

<210> SEQ ID NO 103
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm
```

-continued

<400> SEQUENCE: 103

Ser Ala Asn Ser Asn Pro Ala Met Ala Pro Arg Glu Arg Lys Ala Gly
1               5                   10                  15

Cys Lys Asn Phe Phe Trp Lys Cys Phe Thr Ser Cys
            20                  25

<210> SEQ ID NO 104
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: DISULFID
<222> LOCATION: (17)..(28)
<220> FEATURE:
<221> NAME/KEY: CARBOHYD
<222> LOCATION: (24)..(24)
<223> OTHER INFORMATION: Disialo sugar chain added

<400> SEQUENCE: 104

Ser Ala Asn Ser Asn Pro Ala Met Ala Pro Arg Glu Arg Lys Ala Gly
1               5                   10                  15

Cys Lys Asn Phe Phe Trp Lys Cys Phe Thr Ser Cys
            20                  25

<210> SEQ ID NO 105
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 105

Ser Ala Asn Ser Asn Pro Ala Met Ala Pro Arg Glu Arg Lys Ala Gly
1               5                   10                  15

Cys Lys Asn Phe Phe Trp Lys Thr Cys Thr Ser Cys
            20                  25

<210> SEQ ID NO 106
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: DISULFID
<222> LOCATION: (17)..(28)
<220> FEATURE:
<221> NAME/KEY: CARBOHYD
<222> LOCATION: (25)..(25)
<223> OTHER INFORMATION: Disialo sugar chain added

<400> SEQUENCE: 106

Ser Ala Asn Ser Asn Pro Ala Met Ala Pro Arg Glu Arg Lys Ala Gly
1               5                   10                  15

Cys Lys Asn Phe Phe Trp Lys Thr Cys Thr Ser Cys
            20                  25

```
<210> SEQ ID NO 107
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 107

Ser Ala Asn Ser Asn Pro Ala Met Ala Pro Arg Glu Arg Lys Ala Gly
1               5                   10                  15

Cys Lys Asn Phe Phe Trp Lys Thr Phe Thr Cys Cys
            20                  25

<210> SEQ ID NO 108
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: DISULFID
<222> LOCATION: (17)..(28)
<220> FEATURE:
<221> NAME/KEY: CARBOHYD
<222> LOCATION: (27)..(27)
<223> OTHER INFORMATION: Disialo sugar chain added

<400> SEQUENCE: 108

Ser Ala Asn Ser Asn Pro Ala Met Ala Pro Arg Glu Arg Lys Ala Gly
1               5                   10                  15

Cys Lys Asn Phe Phe Trp Lys Thr Phe Thr Cys Cys
            20                  25

<210> SEQ ID NO 109
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (5)..(5)
<223> OTHER INFORMATION: Acm
<220> FEATURE:
<221> NAME/KEY: BINDING
<222> LOCATION: (16)..(16)
<223> OTHER INFORMATION: Acm

<400> SEQUENCE: 109

Cys Lys Ala Gly Cys Lys Asn Phe Phe Trp Lys Thr Phe Thr Ser Cys
1               5                   10                  15

<210> SEQ ID NO 110
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
```

```
<221> NAME/KEY: DISULFID
<222> LOCATION: (5)..(16)

<400> SEQUENCE: 110

Cys Lys Ala Gly Cys Lys Asn Phe Phe Trp Lys Thr Phe Thr Ser Cys
1               5                   10                  15

<210> SEQ ID NO 111
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 111

Cys Ala Asn Ser Asn Pro Ala Met Ala Pro Arg Glu Arg Lys Ala Gly
1               5                   10                  15

Cys Lys Asn Phe Phe Trp Lys Thr Tyr Thr Ser Cys
            20                  25

<210> SEQ ID NO 112
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: DISULFID
<222> LOCATION: (17)..(28)

<400> SEQUENCE: 112

Cys Ala Asn Ser Asn Pro Ala Met Ala Pro Arg Glu Arg Lys Ala Gly
1               5                   10                  15

Cys Lys Asn Phe Phe Trp Lys Thr Tyr Thr Ser Cys
            20                  25

<210> SEQ ID NO 113
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm
<220> FEATURE:
<221> NAME/KEY: MOD_RES
<222> LOCATION: (28)..(28)
<223> OTHER INFORMATION: AMIDATION

<400> SEQUENCE: 113

Cys Ala Asn Ser Asn Pro Ala Met Ala Pro Arg Glu Arg Lys Ala Gly
1               5                   10                  15
```

```
Cys Lys Asn Phe Phe Trp Lys Thr Phe Thr Ser Cys
            20                  25

<210> SEQ ID NO 114
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: DISULFID
<222> LOCATION: (17)..(28)
<220> FEATURE:
<221> NAME/KEY: MOD_RES
<222> LOCATION: (28)..(28)
<223> OTHER INFORMATION: AMIDATION

<400> SEQUENCE: 114

Cys Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 115
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: NON_CONS
<222> LOCATION: (1)..(2)
<223> OTHER INFORMATION: Cys and Ala are bonded through PEGlinker
<220> FEATURE:
<221> NAME/KEY: BINDING
<222> LOCATION: (4)..(4)
<223> OTHER INFORMATION: Acm
<220> FEATURE:
<221> NAME/KEY: BINDING
<222> LOCATION: (15)..(15)
<223> OTHER INFORMATION: Acm

<400> SEQUENCE: 115

Cys Ala Gly Cys Lys Asn Phe Phe Trp Lys Thr Phe Thr Ser Cys
1               5                   10                  15

<210> SEQ ID NO 116
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: NON_CONS
<222> LOCATION: (1)..(2)
<223> OTHER INFORMATION: Cys and Ala are bonded through PEGlinker
<220> FEATURE:
<221> NAME/KEY: DISULFID
<222> LOCATION: (4)..(15)

<400> SEQUENCE: 116

Cys Ala Gly Cys Lys Asn Phe Phe Trp Lys Thr Phe Thr Ser Cys
1               5                   10                  15
```

```
<210> SEQ ID NO 117
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (1)..(1)
<223> OTHER INFORMATION: Fmoc
<220> FEATURE:
<221> NAME/KEY: BINDING
<222> LOCATION: (1)..(1)
<223> OTHER INFORMATION: Trt
<220> FEATURE:
<221> NAME/KEY: BINDING
<222> LOCATION: (3)..(3)
<223> OTHER INFORMATION: Trt
<220> FEATURE:
<221> NAME/KEY: BINDING
<222> LOCATION: (4)..(4)
<223> OTHER INFORMATION: tBu
<220> FEATURE:
<221> NAME/KEY: BINDING
<222> LOCATION: (5)..(5)
<223> OTHER INFORMATION: Trt
<220> FEATURE:
<221> NAME/KEY: BINDING
<222> LOCATION: (11)..(11)
<223> OTHER INFORMATION: Pbf
<220> FEATURE:
<221> NAME/KEY: BINDING
<222> LOCATION: (12)..(12)
<223> OTHER INFORMATION: OtBu
<220> FEATURE:
<221> NAME/KEY: BINDING
<222> LOCATION: (13)..(13)
<223> OTHER INFORMATION: Pbf
<220> FEATURE:
<221> NAME/KEY: BINDING
<222> LOCATION: (14)..(14)
<223> OTHER INFORMATION: Boc
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (18)..(18)
<223> OTHER INFORMATION: Boc
<220> FEATURE:
<221> NAME/KEY: BINDING
<222> LOCATION: (19)..(19)
<223> OTHER INFORMATION: Trt
<220> FEATURE:
<221> NAME/KEY: BINDING
<222> LOCATION: (22)..(22)
<223> OTHER INFORMATION: Boc
<220> FEATURE:
<221> NAME/KEY: BINDING
<222> LOCATION: (23)..(23)
<223> OTHER INFORMATION: Boc
<220> FEATURE:
<221> NAME/KEY: BINDING
<222> LOCATION: (24)..(24)
<223> OTHER INFORMATION: tBu
<220> FEATURE:
<221> NAME/KEY: BINDING
<222> LOCATION: (26)..(26)
<223> OTHER INFORMATION: tBu
<220> FEATURE:
<221> NAME/KEY: BINDING
<222> LOCATION: (27)..(27)
<223> OTHER INFORMATION: tBu
<220> FEATURE:
<221> NAME/KEY: BINDING
<222> LOCATION: (28)..(28)
```

```
<223> OTHER INFORMATION: Acm
<220> FEATURE:
<221> NAME/KEY: BINDING
<222> LOCATION: (28)..(28)
<223> OTHER INFORMATION: Resin

<400> SEQUENCE: 117

Cys Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 118
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (1)..(1)
<223> OTHER INFORMATION: Biotin
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 118

Cys Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 119
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: BINDING
<222> LOCATION: (1)..(1)
<223> OTHER INFORMATION: Biotin
<220> FEATURE:
<221> NAME/KEY: DISULFID
<222> LOCATION: (17)..(28)

<400> SEQUENCE: 119

Cys Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 120
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (1)..(1)
```

```
<223> OTHER INFORMATION: Biotin is bonded to Cys through PEGlinker
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 120

Cys Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 121
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: BINDING
<222> LOCATION: (1)..(1)
<223> OTHER INFORMATION: Biotin is bonded to Cys through PEGlinker
<220> FEATURE:
<221> NAME/KEY: DISULFID
<222> LOCATION: (17)..(28)

<400> SEQUENCE: 121

Cys Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 122
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (1)..(1)
<223> OTHER INFORMATION: Azido pentanoyl is bonded to Cys
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 122

Cys Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 123
<211> LENGTH: 28
<212> TYPE: PRT
<213> ORGANISM: Artificial
<220> FEATURE:
```

```
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: BINDING
<222> LOCATION: (1)..(1)
<223> OTHER INFORMATION: Azido pentanoyl is bonded to Cys
<220> FEATURE:
<221> NAME/KEY: DISULFID
<222> LOCATION: (17)..(28)

<400> SEQUENCE: 123

Cys Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 124
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 124

Cys Ala Asn Ser Asn Pro Ala Met Ala Pro Arg Cys Arg Lys Ala Gly
1               5                   10                  15

Cys Lys Asn Phe Phe Trp Lys Thr Phe Thr Ser Cys
            20                  25

<210> SEQ ID NO 125
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: CARBOHYD
<222> LOCATION: (12)..(12)
<223> OTHER INFORMATION: Disialo sugar chain added
<220> FEATURE:
<221> NAME/KEY: DISULFID
<222> LOCATION: (17)..(28)

<400> SEQUENCE: 125

Cys Ala Asn Ser Asn Pro Ala Met Ala Pro Arg Cys Arg Lys Ala Gly
1               5                   10                  15

Cys Lys Asn Phe Phe Trp Lys Thr Phe Thr Ser Cys
            20                  25

<210> SEQ ID NO 126
<211> LENGTH: 18
<212> TYPE: PRT
<213> ORGANISM: Artificial
<220> FEATURE:
<223> OTHER INFORMATION: Synthetic peptide
```

<220> FEATURE:
<221> NAME/KEY: BINDING
<222> LOCATION: (7)..(7)
<223> OTHER INFORMATION: Acm
<220> FEATURE:
<221> NAME/KEY: BINDING
<222> LOCATION: (18)..(18)
<223> OTHER INFORMATION: Acm

<400> SEQUENCE: 126

Cys Cys Arg Lys Ala Gly Cys Lys Asn Phe Phe Trp Lys Thr Phe Thr
1               5                   10                  15

Ser Cys

<210> SEQ ID NO 127
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: CARBOHYD
<222> LOCATION: (2)..(2)
<223> OTHER INFORMATION: Disialo sugar chain added
<220> FEATURE:
<221> NAME/KEY: DISULFID
<222> LOCATION: (7)..(18)

<400> SEQUENCE: 127

Cys Cys Arg Lys Ala Gly Cys Lys Asn Phe Phe Trp Lys Thr Phe Thr
1               5                   10                  15

Ser Cys

<210> SEQ ID NO 128
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (8)..(8)
<223> OTHER INFORMATION: Acm
<220> FEATURE:
<221> NAME/KEY: BINDING
<222> LOCATION: (19)..(19)
<223> OTHER INFORMATION: Acm

<400> SEQUENCE: 128

Cys Cys Cys Arg Lys Ala Gly Cys Lys Asn Phe Phe Trp Lys Thr Phe
1               5                   10                  15

Thr Ser Cys

<210> SEQ ID NO 129
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: CARBOHYD
<222> LOCATION: (2)..(2)

-continued

<223> OTHER INFORMATION: Disialo sugar chain added
<220> FEATURE:
<221> NAME/KEY: CARBOHYD
<222> LOCATION: (3)..(3)
<223> OTHER INFORMATION: Disialo sugar chain added
<220> FEATURE:
<221> NAME/KEY: DISULFID
<222> LOCATION: (8)..(19)

<400> SEQUENCE: 129

Cys Cys Cys Arg Lys Ala Gly Cys Lys Asn Phe Phe Trp Lys Thr Phe
1               5                   10                  15

Thr Ser Cys

<210> SEQ ID NO 130
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: diGlcNAc sugar chain added
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 130

Cys Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 131
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: diGlcNAc sugar chain added

<400> SEQUENCE: 131

Cys Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 132
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: diGlcNAc sugar chain added
<220> FEATURE:
<221> NAME/KEY: DISULFID
<222> LOCATION: (17)..(28)

-continued

```
<400> SEQUENCE: 132

Cys Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 133
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: diMan sugar chain added
<220> FEATURE:
<221> NAME/KEY: DISULFID
<222> LOCATION: (17)..(28)

<400> SEQUENCE: 133

Cys Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 134
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: DISULFID
<222> LOCATION: (17)..(28)
<220> FEATURE:
<221> NAME/KEY: CARBOHYD
<222> LOCATION: (19)..(19)
<223> OTHER INFORMATION: diMan sugar chain added

<400> SEQUENCE: 134

Ser Ala Asn Ser Asn Pro Ala Met Ala Pro Arg Glu Arg Lys Ala Gly
1               5                   10                  15

Cys Lys Cys Phe Phe Trp Lys Thr Phe Thr Ser Cys
            20                  25

<210> SEQ ID NO 135
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: GlcNAc added
<220> FEATURE:
<221> NAME/KEY: DISULFID
<222> LOCATION: (17)..(28)

<400> SEQUENCE: 135

Cys Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 136
```

```
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: DISULFID
<222> LOCATION: (17)..(28)
<220> FEATURE:
<221> NAME/KEY: CARBOHYD
<222> LOCATION: (19)..(19)
<223> OTHER INFORMATION: GlcNAc added

<400> SEQUENCE: 136

Ser Ala Asn Ser Asn Pro Ala Met Ala Pro Arg Glu Arg Lys Ala Gly
1               5                   10                  15

Cys Lys Cys Phe Phe Trp Lys Thr Phe Thr Ser Cys
            20                  25

<210> SEQ ID NO 137
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Trisialo sugar chain added
<220> FEATURE:
<221> NAME/KEY: DISULFID
<222> LOCATION: (17)..(28)

<400> SEQUENCE: 137

Cys Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 138
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Tetrasialo sugar chain added
<220> FEATURE:
<221> NAME/KEY: DISULFID
<222> LOCATION: (17)..(28)

<400> SEQUENCE: 138

Cys Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 139
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo(Boc-aminoethylamide) sugar chain added
<220> FEATURE:
```

```
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 139

Cys Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 140
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo(aminoethylamide) sugar chain added
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 140

Cys Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 141
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo(aminoethylamide) sugar chain added

<400> SEQUENCE: 141

Cys Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 142
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo(aminoethylamide) sugar chain added
<220> FEATURE:
<221> NAME/KEY: DISULFID
<222> LOCATION: (17)..(28)
```

```
<400> SEQUENCE: 142

Cys Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 143
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo(amide) sugar chain added
<220> FEATURE:
<221> NAME/KEY: DISULFID
<222> LOCATION: (17)..(28)

<400> SEQUENCE: 143

Cys Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 144
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain protected with benzyl
      group added
<220> FEATURE:
<221> NAME/KEY: DISULFID
<222> LOCATION: (17)..(28)

<400> SEQUENCE: 144

Cys Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 145
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo(hexadecylamide) sugar chain added
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 145

Cys Ala Asn Ser Asn Pro Ala Met Ala Pro Arg Glu Arg Lys Ala Gly
1               5                   10                  15
```

Cys Lys Asn Phe Phe Trp Lys Thr Phe Thr Ser Cys
            20                  25

<210> SEQ ID NO 146
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo(hexadecylamide) sugar chain added

<400> SEQUENCE: 146

Cys Ala Asn Ser Asn Pro Ala Met Ala Pro Arg Glu Arg Lys Ala Gly
1               5                   10                  15
Cys Lys Asn Phe Phe Trp Lys Thr Phe Thr Ser Cys
            20                  25

<210> SEQ ID NO 147
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo(hexadecylamide) sugar chain added
<220> FEATURE:
<221> NAME/KEY: DISULFID
<222> LOCATION: (17)..(28)

<400> SEQUENCE: 147

Cys Ala Asn Ser Asn Pro Ala Met Ala Pro Arg Glu Arg Lys Ala Gly
1               5                   10                  15
Cys Lys Asn Phe Phe Trp Lys Thr Phe Thr Ser Cys
            20                  25

<210> SEQ ID NO 148
<211> LENGTH: 29
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo(amide) sugar chain added
<220> FEATURE:
<221> NAME/KEY: CARBOHYD
<222> LOCATION: (2)..(2)
<223> OTHER INFORMATION: Disialo(amide) sugar chain added
<220> FEATURE:
<221> NAME/KEY: DISULFID
<222> LOCATION: (18)..(29)

<400> SEQUENCE: 148

Cys Cys Ala Asn Ser Asn Pro Ala Met Ala Pro Arg Glu Arg Lys Ala
1               5                   10                  15
Gly Cys Lys Asn Phe Phe Trp Lys Thr Phe Thr Ser Cys
            20                  25

<210> SEQ ID NO 149
<211> LENGTH: 29
<212> TYPE: PRT
<213> ORGANISM: Artificial

<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain protected with benzyl
      group added
<220> FEATURE:
<221> NAME/KEY: CARBOHYD
<222> LOCATION: (2)..(2)
<223> OTHER INFORMATION: Disialo sugar chain protected with benzyl
      group added
<220> FEATURE:
<221> NAME/KEY: DISULFID
<222> LOCATION: (18)..(29)

<400> SEQUENCE: 149

Cys Cys Ala Asn Ser Asn Pro Ala Met Ala Pro Arg Glu Arg Lys Ala
1               5                   10                  15

Gly Cys Lys Asn Phe Phe Trp Lys Thr Phe Thr Ser Cys
            20                  25

<210> SEQ ID NO 150
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Asn(disialo) added
<220> FEATURE:
<221> NAME/KEY: DISULFID
<222> LOCATION: (17)..(28)

<400> SEQUENCE: 150

Cys Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 151
<211> LENGTH: 27
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (1)..(1)
<223> OTHER INFORMATION: Fmoc
<220> FEATURE:
<221> NAME/KEY: BINDING
<222> LOCATION: (2)..(2)
<223> OTHER INFORMATION: Trt
<220> FEATURE:
<221> NAME/KEY: BINDING
<222> LOCATION: (3)..(3)
<223> OTHER INFORMATION: tBu
<220> FEATURE:
<221> NAME/KEY: BINDING
<222> LOCATION: (4)..(4)
<223> OTHER INFORMATION: Trt
<220> FEATURE:
<221> NAME/KEY: BINDING
<222> LOCATION: (10)..(10)
<223> OTHER INFORMATION: Pbf
<220> FEATURE:
<221> NAME/KEY: BINDING
<222> LOCATION: (11)..(11)
<223> OTHER INFORMATION: OtBu
<220> FEATURE:

```
<221> NAME/KEY: BINDING
<222> LOCATION: (12)..(12)
<223> OTHER INFORMATION: Pbf
<220> FEATURE:
<221> NAME/KEY: BINDING
<222> LOCATION: (13)..(13)
<223> OTHER INFORMATION: Boc
<220> FEATURE:
<221> NAME/KEY: BINDING
<222> LOCATION: (16)..(16)
<223> OTHER INFORMATION: Acm
<220> FEATURE:
<221> NAME/KEY: BINDING
<222> LOCATION: (17)..(17)
<223> OTHER INFORMATION: Boc
<220> FEATURE:
<221> NAME/KEY: BINDING
<222> LOCATION: (18)..(18)
<223> OTHER INFORMATION: Trt
<220> FEATURE:
<221> NAME/KEY: BINDING
<222> LOCATION: (21)..(21)
<223> OTHER INFORMATION: Boc
<220> FEATURE:
<221> NAME/KEY: BINDING
<222> LOCATION: (22)..(22)
<223> OTHER INFORMATION: Boc
<220> FEATURE:
<221> NAME/KEY: BINDING
<222> LOCATION: (23)..(23)
<223> OTHER INFORMATION: tBu
<220> FEATURE:
<221> NAME/KEY: BINDING
<222> LOCATION: (25)..(25)
<223> OTHER INFORMATION: tBu
<220> FEATURE:
<221> NAME/KEY: BINDING
<222> LOCATION: (26)..(26)
<223> OTHER INFORMATION: tBu
<220> FEATURE:
<221> NAME/KEY: BINDING
<222> LOCATION: (27)..(27)
<223> OTHER INFORMATION: Acm
<220> FEATURE:
<221> NAME/KEY: BINDING
<222> LOCATION: (27)..(27)
<223> OTHER INFORMATION: Resin

<400> SEQUENCE: 151

Ala Asn Ser Asn Pro Ala Met Ala Pro Arg Glu Arg Lys Ala Gly Cys
1               5                   10                  15
Lys Cys Phe Phe Trp Lys Thr Phe Thr Ser Cys
            20                  25

<210> SEQ ID NO 152
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain protected with benzyl
      group added
<220> FEATURE:
<221> NAME/KEY: BINDING
<222> LOCATION: (3)..(3)
<223> OTHER INFORMATION: Trt
<220> FEATURE:
<221> NAME/KEY: BINDING
<222> LOCATION: (4)..(4)
<223> OTHER INFORMATION: tBu
<220> FEATURE:
<221> NAME/KEY: BINDING
<222> LOCATION: (5)..(5)
```

```
<223> OTHER INFORMATION: Trt
<220> FEATURE:
<221> NAME/KEY: BINDING
<222> LOCATION: (11)..(11)
<223> OTHER INFORMATION: Pbf
<220> FEATURE:
<221> NAME/KEY: BINDING
<222> LOCATION: (12)..(12)
<223> OTHER INFORMATION: OtBu
<220> FEATURE:
<221> NAME/KEY: BINDING
<222> LOCATION: (13)..(13)
<223> OTHER INFORMATION: Pbf
<220> FEATURE:
<221> NAME/KEY: BINDING
<222> LOCATION: (14)..(14)
<223> OTHER INFORMATION: Boc
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (18)..(18)
<223> OTHER INFORMATION: Boc
<220> FEATURE:
<221> NAME/KEY: BINDING
<222> LOCATION: (19)..(19)
<223> OTHER INFORMATION: Trt
<220> FEATURE:
<221> NAME/KEY: BINDING
<222> LOCATION: (22)..(22)
<223> OTHER INFORMATION: Boc
<220> FEATURE:
<221> NAME/KEY: BINDING
<222> LOCATION: (23)..(23)
<223> OTHER INFORMATION: Boc
<220> FEATURE:
<221> NAME/KEY: BINDING
<222> LOCATION: (24)..(24)
<223> OTHER INFORMATION: tBu
<220> FEATURE:
<221> NAME/KEY: BINDING
<222> LOCATION: (26)..(26)
<223> OTHER INFORMATION: tBu
<220> FEATURE:
<221> NAME/KEY: BINDING
<222> LOCATION: (27)..(27)
<223> OTHER INFORMATION: tBu
<220> FEATURE:
<221> NAME/KEY: BINDING
<222> LOCATION: (28)..(28)
<223> OTHER INFORMATION: Acm
<220> FEATURE:
<221> NAME/KEY: BINDING
<222> LOCATION: (28)..(28)
<223> OTHER INFORMATION: Resin

<400> SEQUENCE: 152

Asn Ala Asn Ser Asn Pro Ala Met Ala Pro Arg Glu Arg Lys Ala Gly
1               5                   10                  15
Cys Lys Cys Phe Phe Trp Lys Thr Phe Thr Ser Cys
            20                  25

<210> SEQ ID NO 153
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain protected with benzyl
      group added
<220> FEATURE:
```

<221> NAME/KEY: BINDING
<222> LOCATION: (17)..(17)
<223> OTHER INFORMATION: Acm
<220> FEATURE:
<221> NAME/KEY: BINDING
<222> LOCATION: (28)..(28)
<223> OTHER INFORMATION: Acm

<400> SEQUENCE: 153

Asn Ala Asn Ser Asn Pro Ala Met Ala Pro Arg Glu Arg Lys Ala Gly
1               5                   10                  15

Cys Lys Cys Phe Phe Trp Lys Thr Phe Thr Ser Cys
            20                  25

<210> SEQ ID NO 154
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain protected with benzyl
      group added
<220> FEATURE:
<221> NAME/KEY: BINDING
<222> LOCATION: (17)..(17)
<223> OTHER INFORMATION: Acm
<220> FEATURE:
<221> NAME/KEY: CARBOHYD
<222> LOCATION: (19)..(19)
<223> OTHER INFORMATION: diMan sugar chain added
<220> FEATURE:
<221> NAME/KEY: BINDING
<222> LOCATION: (28)..(28)
<223> OTHER INFORMATION: Acm

<400> SEQUENCE: 154

Asn Ala Asn Ser Asn Pro Ala Met Ala Pro Arg Glu Arg Lys Ala Gly
1               5                   10                  15

Cys Lys Cys Phe Phe Trp Lys Thr Phe Thr Ser Cys
            20                  25

<210> SEQ ID NO 155
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain protected with benzyl
      group added
<220> FEATURE:
<221> NAME/KEY: CARBOHYD
<222> LOCATION: (19)..(19)
<223> OTHER INFORMATION: diMan sugar chain added

<400> SEQUENCE: 155

Asn Ala Asn Ser Asn Pro Ala Met Ala Pro Arg Glu Arg Lys Ala Gly
1               5                   10                  15

Cys Lys Cys Phe Phe Trp Lys Thr Phe Thr Ser Cys
            20                  25

<210> SEQ ID NO 156
<211> LENGTH: 28
<212> TYPE: PRT
<213> ORGANISM: Artificial

```
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain protected with benzyl
      group added
<220> FEATURE:
<221> NAME/KEY: DISULFID
<222> LOCATION: (17)..(28)
<220> FEATURE:
<221> NAME/KEY: CARBOHYD
<222> LOCATION: (19)..(19)
<223> OTHER INFORMATION: diMan sugar chain added

<400> SEQUENCE: 156

Asn Ala Asn Ser Asn Pro Ala Met Ala Pro Arg Glu Arg Lys Ala Gly
1               5                   10                  15

Cys Lys Cys Phe Phe Trp Lys Thr Phe Thr Ser Cys
            20                  25

<210> SEQ ID NO 157
<211> LENGTH: 28
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: DISULFID
<222> LOCATION: (17)..(28)
<220> FEATURE:
<221> NAME/KEY: CARBOHYD
<222> LOCATION: (19)..(19)
<223> OTHER INFORMATION: diMan sugar chain added

<400> SEQUENCE: 157

Asn Ala Asn Ser Asn Pro Ala Met Ala Pro Arg Glu Arg Lys Ala Gly
1               5                   10                  15

Cys Lys Cys Phe Phe Trp Lys Thr Phe Thr Ser Cys
            20                  25

<210> SEQ ID NO 158
<211> LENGTH: 29
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (1)..(1)
<223> OTHER INFORMATION: Fmoc
<220> FEATURE:
<221> NAME/KEY: BINDING
<222> LOCATION: (1)..(1)
<223> OTHER INFORMATION: Trt
<220> FEATURE:
<221> NAME/KEY: BINDING
<222> LOCATION: (2)..(2)
<223> OTHER INFORMATION: StBu
<220> FEATURE:
<221> NAME/KEY: BINDING
<222> LOCATION: (4)..(4)
<223> OTHER INFORMATION: Trt
<220> FEATURE:
<221> NAME/KEY: BINDING
<222> LOCATION: (5)..(5)
<223> OTHER INFORMATION: tBu
<220> FEATURE:
<221> NAME/KEY: BINDING
```

```
<222> LOCATION: (6)..(6)
<223> OTHER INFORMATION: Trt
<220> FEATURE:
<221> NAME/KEY: BINDING
<222> LOCATION: (12)..(12)
<223> OTHER INFORMATION: Pbf
<220> FEATURE:
<221> NAME/KEY: BINDING
<222> LOCATION: (13)..(13)
<223> OTHER INFORMATION: OtBu
<220> FEATURE:
<221> NAME/KEY: BINDING
<222> LOCATION: (14)..(14)
<223> OTHER INFORMATION: Pbf
<220> FEATURE:
<221> NAME/KEY: BINDING
<222> LOCATION: (15)..(15)
<223> OTHER INFORMATION: Boc
<220> FEATURE:
<221> NAME/KEY: BINDING
<222> LOCATION: (18)..(18)
<223> OTHER INFORMATION: Acm
<220> FEATURE:
<221> NAME/KEY: BINDING
<222> LOCATION: (19)..(19)
<223> OTHER INFORMATION: Boc
<220> FEATURE:
<221> NAME/KEY: BINDING
<222> LOCATION: (20)..(20)
<223> OTHER INFORMATION: Trt
<220> FEATURE:
<221> NAME/KEY: BINDING
<222> LOCATION: (23)..(23)
<223> OTHER INFORMATION: Boc
<220> FEATURE:
<221> NAME/KEY: BINDING
<222> LOCATION: (24)..(24)
<223> OTHER INFORMATION: Boc
<220> FEATURE:
<221> NAME/KEY: BINDING
<222> LOCATION: (25)..(25)
<223> OTHER INFORMATION: tBu
<220> FEATURE:
<221> NAME/KEY: BINDING
<222> LOCATION: (27)..(27)
<223> OTHER INFORMATION: tBu
<220> FEATURE:
<221> NAME/KEY: BINDING
<222> LOCATION: (28)..(28)
<223> OTHER INFORMATION: tBu
<220> FEATURE:
<221> NAME/KEY: BINDING
<222> LOCATION: (29)..(29)
<223> OTHER INFORMATION: Acm
<220> FEATURE:
<221> NAME/KEY: BINDING
<222> LOCATION: (29)..(29)
<223> OTHER INFORMATION: Resin

<400> SEQUENCE: 158

Cys Cys Ala Asn Ser Asn Pro Ala Met Ala Pro Arg Glu Arg Lys Ala
1               5                   10                  15

Gly Cys Lys Asn Phe Phe Trp Lys Thr Phe Thr Ser Cys
            20                  25

<210> SEQ ID NO 159
<211> LENGTH: 29
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (2)..(2)
<223> OTHER INFORMATION: StBu
<220> FEATURE:
```

```
<221> NAME/KEY: BINDING
<222> LOCATION: (18)..(18)
<223> OTHER INFORMATION: Acm
<220> FEATURE:
<221> NAME/KEY: BINDING
<222> LOCATION: (29)..(29)
<223> OTHER INFORMATION: Acm

<400> SEQUENCE: 159

Cys Cys Ala Asn Ser Asn Pro Ala Met Ala Pro Arg Glu Arg Lys Ala
1               5                   10                  15

Gly Cys Lys Asn Phe Phe Trp Lys Thr Phe Thr Ser Cys
            20                  25

<210> SEQ ID NO 160
<211> LENGTH: 29
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo(aminoethylamide) sugar chain added
<220> FEATURE:
<221> NAME/KEY: BINDING
<222> LOCATION: (2)..(2)
<223> OTHER INFORMATION: StBu
<220> FEATURE:
<221> NAME/KEY: BINDING
<222> LOCATION: (18)..(18)
<223> OTHER INFORMATION: Acm
<220> FEATURE:
<221> NAME/KEY: BINDING
<222> LOCATION: (29)..(29)
<223> OTHER INFORMATION: Acm

<400> SEQUENCE: 160

Cys Cys Ala Asn Ser Asn Pro Ala Met Ala Pro Arg Glu Arg Lys Ala
1               5                   10                  15

Gly Cys Lys Asn Phe Phe Trp Lys Thr Phe Thr Ser Cys
            20                  25

<210> SEQ ID NO 161
<211> LENGTH: 29
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo(aminoethylamide) sugar chain added
<220> FEATURE:
<221> NAME/KEY: BINDING
<222> LOCATION: (18)..(18)
<223> OTHER INFORMATION: Acm
<220> FEATURE:
<221> NAME/KEY: BINDING
<222> LOCATION: (29)..(29)
<223> OTHER INFORMATION: Acm

<400> SEQUENCE: 161

Cys Cys Ala Asn Ser Asn Pro Ala Met Ala Pro Arg Glu Arg Lys Ala
1               5                   10                  15

Gly Cys Lys Asn Phe Phe Trp Lys Thr Phe Thr Ser Cys
            20                  25

<210> SEQ ID NO 162
<211> LENGTH: 29
```

```
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo(aminoethylamide) sugar chain added
<220> FEATURE:
<221> NAME/KEY: CARBOHYD
<222> LOCATION: (2)..(2)
<223> OTHER INFORMATION: Disialo sugar chain added
<220> FEATURE:
<221> NAME/KEY: BINDING
<222> LOCATION: (18)..(18)
<223> OTHER INFORMATION: Acm
<220> FEATURE:
<221> NAME/KEY: BINDING
<222> LOCATION: (29)..(29)
<223> OTHER INFORMATION: Acm

<400> SEQUENCE: 162

Cys Cys Ala Asn Ser Asn Pro Ala Met Ala Pro Arg Glu Arg Lys Ala
1               5                   10                  15

Gly Cys Lys Asn Phe Phe Trp Lys Thr Phe Thr Ser Cys
            20                  25

<210> SEQ ID NO 163
<211> LENGTH: 29
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo(aminoethylamide) sugar chain added
<220> FEATURE:
<221> NAME/KEY: CARBOHYD
<222> LOCATION: (2)..(2)
<223> OTHER INFORMATION: Disialo sugar chain added

<400> SEQUENCE: 163

Cys Cys Ala Asn Ser Asn Pro Ala Met Ala Pro Arg Glu Arg Lys Ala
1               5                   10                  15

Gly Cys Lys Asn Phe Phe Trp Lys Thr Phe Thr Ser Cys
            20                  25

<210> SEQ ID NO 164
<211> LENGTH: 29
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo(aminoethylamide) sugar chain added
<220> FEATURE:
<221> NAME/KEY: CARBOHYD
<222> LOCATION: (2)..(2)
<223> OTHER INFORMATION: Disialo sugar chain added
<220> FEATURE:
<221> NAME/KEY: DISULFID
<222> LOCATION: (18)..(29)

<400> SEQUENCE: 164

Cys Cys Ala Asn Ser Asn Pro Ala Met Ala Pro Arg Glu Arg Lys Ala
1               5                   10                  15

Gly Cys Lys Asn Phe Phe Trp Lys Thr Phe Thr Ser Cys
            20                  25
```

```
<210> SEQ ID NO 165
<211> LENGTH: 31
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (1)..(1)
<223> OTHER INFORMATION: Fmoc
<220> FEATURE:
<221> NAME/KEY: BINDING
<222> LOCATION: (1)..(1)
<223> OTHER INFORMATION: Trt
<220> FEATURE:
<221> NAME/KEY: BINDING
<222> LOCATION: (2)..(2)
<223> OTHER INFORMATION: Trt
<220> FEATURE:
<221> NAME/KEY: BINDING
<222> LOCATION: (3)..(3)
<223> OTHER INFORMATION: Trt
<220> FEATURE:
<221> NAME/KEY: BINDING
<222> LOCATION: (4)..(4)
<223> OTHER INFORMATION: Trt
<220> FEATURE:
<221> NAME/KEY: BINDING
<222> LOCATION: (6)..(6)
<223> OTHER INFORMATION: Trt
<220> FEATURE:
<221> NAME/KEY: BINDING
<222> LOCATION: (7)..(7)
<223> OTHER INFORMATION: tBu
<220> FEATURE:
<221> NAME/KEY: BINDING
<222> LOCATION: (8)..(8)
<223> OTHER INFORMATION: Trt
<220> FEATURE:
<221> NAME/KEY: BINDING
<222> LOCATION: (14)..(14)
<223> OTHER INFORMATION: Pbf
<220> FEATURE:
<221> NAME/KEY: BINDING
<222> LOCATION: (15)..(15)
<223> OTHER INFORMATION: OtBu
<220> FEATURE:
<221> NAME/KEY: BINDING
<222> LOCATION: (16)..(16)
<223> OTHER INFORMATION: Pbf
<220> FEATURE:
<221> NAME/KEY: BINDING
<222> LOCATION: (17)..(17)
<223> OTHER INFORMATION: Boc
<220> FEATURE:
<221> NAME/KEY: BINDING
<222> LOCATION: (20)..(20)
<223> OTHER INFORMATION: Acm
<220> FEATURE:
<221> NAME/KEY: BINDING
<222> LOCATION: (21)..(21)
<223> OTHER INFORMATION: Boc
<220> FEATURE:
<221> NAME/KEY: BINDING
<222> LOCATION: (22)..(22)
<223> OTHER INFORMATION: Trt
<220> FEATURE:
<221> NAME/KEY: BINDING
<222> LOCATION: (25)..(25)
<223> OTHER INFORMATION: Boc
<220> FEATURE:
<221> NAME/KEY: BINDING
<222> LOCATION: (26)..(26)
<223> OTHER INFORMATION: Boc
<220> FEATURE:
<221> NAME/KEY: BINDING
<222> LOCATION: (27)..(27)
```

```
<223> OTHER INFORMATION: tBu
<220> FEATURE:
<221> NAME/KEY: BINDING
<222> LOCATION: (29)..(29)
<223> OTHER INFORMATION: tBu
<220> FEATURE:
<221> NAME/KEY: BINDING
<222> LOCATION: (30)..(30)
<223> OTHER INFORMATION: tBu
<220> FEATURE:
<221> NAME/KEY: BINDING
<222> LOCATION: (31)..(31)
<223> OTHER INFORMATION: Acm
<220> FEATURE:
<221> NAME/KEY: BINDING
<222> LOCATION: (31)..(31)
<223> OTHER INFORMATION: Resin

<400> SEQUENCE: 165

Cys Cys Cys Cys Ala Asn Ser Asn Pro Ala Met Ala Pro Arg Glu Arg
1               5                   10                  15

Lys Ala Gly Cys Lys Asn Phe Phe Trp Lys Thr Phe Thr Ser Cys
            20                  25                  30

<210> SEQ ID NO 166
<211> LENGTH: 31
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (20)..(20)
<223> OTHER INFORMATION: Acm
<220> FEATURE:
<221> NAME/KEY: BINDING
<222> LOCATION: (31)..(31)
<223> OTHER INFORMATION: Acm

<400> SEQUENCE: 166

Cys Cys Cys Cys Ala Asn Ser Asn Pro Ala Met Ala Pro Arg Glu Arg
1               5                   10                  15

Lys Ala Gly Cys Lys Asn Phe Phe Trp Lys Thr Phe Thr Ser Cys
            20                  25                  30

<210> SEQ ID NO 167
<211> LENGTH: 31
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: CARBOHYD
<222> LOCATION: (2)..(2)
<223> OTHER INFORMATION: Disialo sugar chain added
<220> FEATURE:
<221> NAME/KEY: CARBOHYD
<222> LOCATION: (3)..(3)
<223> OTHER INFORMATION: Disialo sugar chain added
<220> FEATURE:
<221> NAME/KEY: CARBOHYD
<222> LOCATION: (4)..(4)
<223> OTHER INFORMATION: Disialo sugar chain added
<220> FEATURE:
<221> NAME/KEY: BINDING
<222> LOCATION: (20)..(20)
<223> OTHER INFORMATION: Acm
<220> FEATURE:
<221> NAME/KEY: BINDING
```

<222> LOCATION: (31)..(31)
<223> OTHER INFORMATION: Acm

<400> SEQUENCE: 167

Cys Cys Cys Cys Ala Asn Ser Asn Pro Ala Met Ala Pro Arg Glu Arg
1               5                   10                  15

Lys Ala Gly Cys Lys Asn Phe Phe Trp Lys Thr Phe Thr Ser Cys
            20                  25                  30

<210> SEQ ID NO 168
<211> LENGTH: 31
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: CARBOHYD
<222> LOCATION: (2)..(2)
<223> OTHER INFORMATION: Disialo sugar chain added
<220> FEATURE:
<221> NAME/KEY: CARBOHYD
<222> LOCATION: (3)..(3)
<223> OTHER INFORMATION: Disialo sugar chain added
<220> FEATURE:
<221> NAME/KEY: CARBOHYD
<222> LOCATION: (4)..(4)
<223> OTHER INFORMATION: Disialo sugar chain added

<400> SEQUENCE: 168

Cys Cys Cys Cys Ala Asn Ser Asn Pro Ala Met Ala Pro Arg Glu Arg
1               5                   10                  15

Lys Ala Gly Cys Lys Asn Phe Phe Trp Lys Thr Phe Thr Ser Cys
            20                  25                  30

<210> SEQ ID NO 169
<211> LENGTH: 31
<212> TYPE: PRT
<213> ORGANISM: Artificial
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Disialo sugar chain added
<220> FEATURE:
<221> NAME/KEY: CARBOHYD
<222> LOCATION: (2)..(2)
<223> OTHER INFORMATION: Disialo sugar chain added
<220> FEATURE:
<221> NAME/KEY: CARBOHYD
<222> LOCATION: (3)..(3)
<223> OTHER INFORMATION: Disialo sugar chain added
<220> FEATURE:
<221> NAME/KEY: CARBOHYD
<222> LOCATION: (4)..(4)
<223> OTHER INFORMATION: Disialo sugar chain added
<220> FEATURE:
<221> NAME/KEY: DISULFID
<222> LOCATION: (20)..(31)

<400> SEQUENCE: 169

Cys Cys Cys Cys Ala Asn Ser Asn Pro Ala Met Ala Pro Arg Glu Arg
1               5                   10                  15

Lys Ala Gly Cys Lys Asn Phe Phe Trp Lys Thr Phe Thr Ser Cys
            20                  25                  30

```
<210> SEQ ID NO 170
<211> LENGTH: 4
<212> TYPE: PRT
<213> ORGANISM: Artificial
<220> FEATURE:
<223> OTHER INFORMATION: Octreotide peptide sequence

<400> SEQUENCE: 170

Phe Trp Lys Thr
1

<210> SEQ ID NO 171
<211> LENGTH: 4
<212> TYPE: PRT
<213> ORGANISM: Artificial
<220> FEATURE:
<223> OTHER INFORMATION: SRIF14 N-terminal peptide sequence

<400> SEQUENCE: 171

Arg Glu Arg Lys
1

<210> SEQ ID NO 172
<211> LENGTH: 5
<212> TYPE: PRT
<213> ORGANISM: Artificial
<220> FEATURE:
<223> OTHER INFORMATION: SRIF14 N-terminal peptide sequence

<400> SEQUENCE: 172

Pro Arg Glu Arg Lys
1               5

<210> SEQ ID NO 173
<211> LENGTH: 6
<212> TYPE: PRT
<213> ORGANISM: Artificial
<220> FEATURE:
<223> OTHER INFORMATION: SRIF14 N-terminal peptide sequence

<400> SEQUENCE: 173

Ala Pro Arg Glu Arg Lys
1               5

<210> SEQ ID NO 174
<211> LENGTH: 7
<212> TYPE: PRT
<213> ORGANISM: Artificial
<220> FEATURE:
<223> OTHER INFORMATION: SRIF14 N-terminal peptide sequence

<400> SEQUENCE: 174

Met Ala Pro Arg Glu Arg Lys
1               5

<210> SEQ ID NO 175
<211> LENGTH: 8
<212> TYPE: PRT
<213> ORGANISM: Artificial
<220> FEATURE:
<223> OTHER INFORMATION: SRIF14 N-terminal peptide sequence

<400> SEQUENCE: 175

Ala Met Ala Pro Arg Glu Arg Lys
1               5

<210> SEQ ID NO 176
```

```
<211> LENGTH: 9
<212> TYPE: PRT
<213> ORGANISM: Artificial
<220> FEATURE:
<223> OTHER INFORMATION: SRIF14 N-terminal peptide sequence

<400> SEQUENCE: 176

Pro Ala Met Ala Pro Arg Glu Arg Lys
1               5

<210> SEQ ID NO 177
<211> LENGTH: 10
<212> TYPE: PRT
<213> ORGANISM: Artificial
<220> FEATURE:
<223> OTHER INFORMATION: SRIF14 N-terminal peptide sequence

<400> SEQUENCE: 177

Asn Pro Ala Met Ala Pro Arg Glu Arg Lys
1               5                   10

<210> SEQ ID NO 178
<211> LENGTH: 11
<212> TYPE: PRT
<213> ORGANISM: Artificial
<220> FEATURE:
<223> OTHER INFORMATION: SRIF14 N-terminal peptide sequence

<400> SEQUENCE: 178

Ser Asn Pro Ala Met Ala Pro Arg Glu Arg Lys
1               5                   10

<210> SEQ ID NO 179
<211> LENGTH: 12
<212> TYPE: PRT
<213> ORGANISM: Artificial
<220> FEATURE:
<223> OTHER INFORMATION: SRIF14 N-terminal peptide sequence

<400> SEQUENCE: 179

Asn Ser Asn Pro Ala Met Ala Pro Arg Glu Arg Lys
1               5                   10

<210> SEQ ID NO 180
<211> LENGTH: 13
<212> TYPE: PRT
<213> ORGANISM: Artificial
<220> FEATURE:
<223> OTHER INFORMATION: SRIF14 N-terminal peptide sequence

<400> SEQUENCE: 180

Ala Asn Ser Asn Pro Ala Met Ala Pro Arg Glu Arg Lys
1               5                   10

<210> SEQ ID NO 181
<211> LENGTH: 14
<212> TYPE: PRT
<213> ORGANISM: Artificial
<220> FEATURE:
<223> OTHER INFORMATION: SRIF14 N-terminal peptide sequence

<400> SEQUENCE: 181

Ser Ala Asn Ser Asn Pro Ala Met Ala Pro Arg Glu Arg Lys
1               5                   10

<210> SEQ ID NO 182
<211> LENGTH: 4
```

```
<212> TYPE: PRT
<213> ORGANISM: Artificial
<220> FEATURE:
<223> OTHER INFORMATION: Exemplary glycosylated polypeptide sequence

<400> SEQUENCE: 182

Ser Ala Asn Ser
1

<210> SEQ ID NO 183
<211> LENGTH: 5
<212> TYPE: PRT
<213> ORGANISM: Artificial
<220> FEATURE:
<223> OTHER INFORMATION: Exemplary glycosylated polypeptide sequence

<400> SEQUENCE: 183

Ser Ala Thr Asn Ser
1               5
```